United States Patent
Hesson et al.

(10) Patent No.: US 7,705,127 B1
(45) Date of Patent: Apr. 27, 2010

(54) HDM2 POLYPEPTIDES

(75) Inventors: Thomas E. Hesson, Burlington, NJ (US); Hung V. Le, Rockaway, NJ (US); Yao Ma, Lexington, MA (US); Vincent S. Madison, Mountain Lakes, NJ (US); Anthony F. Mannarino, Melrose, MA (US); Paul Reichert, Montville, NJ (US); Gerald W. Shipps, Jr., Stoneham, MA (US); Corey O. Strickland, Martinsville, NJ (US); Shahriar Shane Taremi, Upper Montclair, NJ (US); Yaolin Wang, Edison, NJ (US); Rumin Zhang, Edison, NJ (US); Jose Duca, Cranford, NJ (US)

(73) Assignee: Schering Corporation, Kenilworth, NJ (US)

( * ) Notice: Subject to any disclaimer, the term of this patent is extended or adjusted under 35 U.S.C. 154(b) by 1 day.

(21) Appl. No.: 12/249,314

(22) Filed: Oct. 10, 2008

Related U.S. Application Data

(60) Provisional application No. 60/979,575, filed on Oct. 12, 2007.

(51) Int. Cl.
*C07K 14/00* (2006.01)
(52) U.S. Cl. .................................................. 530/350
(58) Field of Classification Search ........................ None
See application file for complete search history.

(56) References Cited

U.S. PATENT DOCUMENTS

| | | | |
|---|---|---|---|
| 2004/0197893 | A1 | 10/2004 | Schubert et al. |
| 2005/0037383 | A1 | 2/2005 | Taremi et al. |

OTHER PUBLICATIONS

Fotouhi et al. (Current Topics in Medicinal Chemistry, 2005, 5, pp. 159-165).*
Kussie, Paul H., et al.; "Structure of the MDM2 Oncoprotein Bound to the p53 Tumor Suppressor Transactivation Domain"; Science; 274:948-953 (1996).

* cited by examiner

*Primary Examiner*—Suzanne M. Noakes
*Assistant Examiner*—Jae W Lee

(57) ABSTRACT

The present invention relates to HDM2 polypeptides and mutants thereof which are complexed with various compounds, e.g., HDM2 inhibitors.

8 Claims, 6 Drawing Sheets

SEQUENCE LISTING

<160> NUMBER OF SEQ ID NOS: 8

<210> SEQ ID NO 1
<211> LENGTH: 492
<212> TYPE: PRT
<213> ORGANISM: Homo sapiens

<400> SEQUENCE: 1

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro

-continued

```
                20                  25                  30
Leu Leu Leu Lys Leu Leu Lys Ser Val Gly Ala Gln Lys Asp Thr Tyr
            35                  40                  45
Thr Met Lys Glu Val Leu Phe Tyr Leu Gly Gln Tyr Ile Met Thr Lys
        50                  55                  60
Arg Leu Tyr Asp Glu Lys Gln Gln His Ile Val Tyr Cys Ser Asn Asp
65                  70                  75                  80
Leu Leu Gly Asp Leu Phe Gly Val Pro Ser Phe Ser Val Lys Glu His
                85                  90                  95
Arg Lys Ile Tyr Thr Met Ile Tyr Arg Asn Leu Val Val Asn Gln
            100                 105                 110
Gln Glu Ser Ser Asp Ser Gly Thr Ser Val Ser Glu Asn Arg Cys His
        115                 120                 125
Leu Glu Gly Gly Ser Asp Gln Lys Asp Leu Val Gln Glu Leu Gln Glu
        130                 135                 140
Glu Lys Pro Ser Ser His Leu Val Ser Arg Pro Ser Thr Ser Ser
145                 150                 155                 160
Arg Arg Arg Ala Ile Ser Glu Thr Glu Glu Asn Ser Asp Glu Leu Ser
                165                 170                 175
Gly Glu Arg Gln Arg Lys Arg His Lys Ser Asp Ser Ile Ser Leu Ser
            180                 185                 190
Phe Asp Glu Ser Leu Ala Leu Cys Val Ile Arg Glu Ile Cys Cys Glu
        195                 200                 205
Arg Ser Ser Ser Glu Ser Thr Gly Thr Pro Ser Asn Pro Asp Leu
210                 215                 220
Asp Ala Gly Val Ser Glu His Ser Gly Asp Trp Leu Asp Gln Asp Ser
225                 230                 235                 240
Val Ser Asp Gln Phe Ser Val Glu Phe Glu Val Glu Ser Leu Asp Ser
                245                 250                 255
Glu Asp Tyr Ser Leu Ser Glu Glu Gly Gln Glu Leu Ser Asp Glu Asp
            260                 265                 270
Asp Glu Val Tyr Gln Val Thr Val Tyr Gln Ala Gly Glu Ser Asp Thr
        275                 280                 285
Asp Ser Phe Glu Glu Asp Pro Glu Ile Ser Leu Ala Asp Tyr Trp Lys
        290                 295                 300
Cys Thr Ser Cys Asn Glu Met Asn Pro Pro Leu Pro Ser His Cys Asn
305                 310                 315                 320
Arg Cys Trp Ala Leu Arg Glu Asn Trp Leu Pro Glu Asp Lys Gly Lys
                325                 330                 335
Asp Lys Gly Glu Ile Ser Glu Lys Ala Lys Leu Glu Asn Ser Thr Gln
            340                 345                 350
Ala Glu Glu Gly Phe Asp Val Pro Asp Cys Lys Lys Thr Ile Val Asn
        355                 360                 365
Asp Ser Arg Glu Ser Cys Val Glu Asn Asp Asp Lys Ile Thr Gln
        370                 375                 380
Ala Ser Gln Ser Gln Glu Ser Glu Asp Tyr Ser Gln Pro Ser Thr Ser
385                 390                 395                 400
Ser Ser Ile Ile Tyr Ser Ser Gln Glu Asp Val Lys Glu Phe Glu Arg
                405                 410                 415
Glu Glu Thr Gln Asp Lys Glu Glu Ser Val Glu Ser Ser Leu Pro Leu
            420                 425                 430
Asn Ala Ile Glu Pro Cys Val Ile Cys Gln Gly Arg Pro Lys Asn Gly
        435                 440                 445
```

```
Cys Ile Val His Gly Lys Thr Gly His Leu Met Ala Cys Phe Thr Cys
    450                 455                 460
Ala Lys Lys Leu Lys Lys Arg Asn Lys Pro Cys Pro Val Cys Arg Gln
465                 470                 475                 480
Pro Ile Gln Met Ile Val Leu Thr Tyr Phe Pro Leu
                485                 490

<210> SEQ ID NO 2
<211> LENGTH: 109
<212> TYPE: PRT
<213> ORGANISM: Artificial Sequence
<220> FEATURE:
<223> OTHER INFORMATION: HDM2 (17-125) F55Y and Y76H

<400> SEQUENCE: 2

Ser Gln Ile Pro Ala Ser Glu Gln Glu Thr Leu Val Arg Pro Lys Pro
1               5                   10                  15
Leu Leu Leu Lys Leu Leu Lys Ser Val Gly Ala Gln Lys Asp Thr Tyr
                20                  25                  30
Thr Met Lys Glu Val Leu Tyr Tyr Leu Gly Gln Tyr Ile Met Thr Lys
            35                  40                  45
Arg Leu Tyr Asp Glu Lys Gln Gln His Ile Val His Cys Ser Asn Asp
        50                  55                  60
Leu Leu Gly Asp Leu Phe Gly Val Pro Ser Phe Ser Val Lys Glu His
65                  70                  75                  80
Arg Lys Ile Tyr Thr Met Ile Tyr Arg Asn Leu Val Val Val Asn Gln
                85                  90                  95
Gln Glu Ser Ser Asp Ser Gly Thr Ser Val Ser Glu Asn
            100                 105

<210> SEQ ID NO 3
<211> LENGTH: 43
<212> TYPE: DNA
<213> ORGANISM: Artificial Sequence
<220> FEATURE:
<223> OTHER INFORMATION: hdm2F55Y primer

<400> SEQUENCE: 3
ctatgaaaga ggttctttat tatcttggcc agtatattat gac                   43

<210> SEQ ID NO 4
<211> LENGTH: 43
<212> TYPE: DNA
<213> ORGANISM: Artificial Sequence
<220> FEATURE:
<223> OTHER INFORMATION: RChdm2F55Y primer

<400> SEQUENCE: 4
gtcataatat actggccaag ataataaaga acctctttca tag                   43

<210> SEQ ID NO 5
<211> LENGTH: 44
<212> TYPE: DNA
<213> ORGANISM: Artificial Sequence
<220> FEATURE:
<223> OTHER INFORMATION: hdm2Y76H primer

<400> SEQUENCE: 5
gagaagcaac aacatattgt acattgttca aatgatcttc tagg                  44

<210> SEQ ID NO 6
```

```
<211> LENGTH: 44
<212> TYPE: DNA
<213> ORGANISM: Artificial Sequence
<220> FEATURE:
<223> OTHER INFORMATION: RChdm2Y76H primer

<400> SEQUENCE: 6
cctagaagat catttgaaca atgtacaata tgttgttgct tctc            44

<210> SEQ ID NO 7
<211> LENGTH: 29
<212> TYPE: DNA
<213> ORGANISM: Artificial Sequence
<220> FEATURE:
<223> OTHER INFORMATION: Y104S-GTAILOR-F primer

<400> SEQUENCE: 7
caggaacttg gtagtagtca atcagcagg                              29

<210> SEQ ID NO 8
<211> LENGTH: 30
<212> TYPE: DNA
<213> ORGANISM: Artificial Sequence
<220> FEATURE:
<223> OTHER INFORMATION: Y104-GTAILOR-R primer

<400> SEQUENCE: 8
gactactacc aagttcctgg agatcatggt                             30
```

HDM2 POLYPEPTIDES

This application claims the benefit of U.S. provisional patent application No. 60/979,575, filed Oct. 12, 2007; which is herein incorporated by reference in its entirety.

FIELD OF THE INVENTION

The present invention relates, generally, to HDM2 polypeptides complexed with a small molecule.

BACKGROUND OF THE INVENTION

Human double minute 2 (HDM2) oncoprotein is a negative regulator of the tumor suppressor protein p53. The p53 protein is a transcription factor which signals the activation of several protective genes when a cell encounters stress. The importance of p53 in this signaling process is evident in a number of solid tumors that contain defective forms of the p53 that are unable to stop cells from proliferating. In addition to inactivating mutations in p53, HDM2 may, in some cases, act as a negative regulator of p53.

There is evidence for a physical interaction between HDM2 and p53. First, cellular stress results in increased p53 activation, which in turn switches on the HDM2 gene. The resulting HDM2 protein represses p53 by inducing its degradation. The degradation is initiated by formation of an HDM2-p53 complex that results in proteosomal destruction of p53. This suggests that a HDM2-antagonist could restore p53's normal signaling functions for cell death and apoptosis.

Purification of this enzyme for structural and biochemical studies has been critical for the initiation of a structure-based drug design program. Crystals of MDM2 suitable for structure based drug design were reported by Kussie, P., et al., Science 274 (1996) 948-953. Taremi et al. (US2005/0037383) also reported crystals of HDM2 p53 binding domain. Schubert et al. (US2004/0197893) describe crystalline complexes. An effective technique in structure based drug design is the analysis of the ability of a certain inhibitor compound to dock into the binding site of the target protein and, using molecular modeling techniques, discern what modified compounds may also fit into the pocket and, thereby, inhibit activity of the target. There has been a need in the art for such crystalline complexes which can be used, for example, for the design of therapeutic inhibitors of the HDM2/p53 interaction. Such inhibitors are useful, for example, for the treatment of cancer.

SUMMARY OF THE INVENTION

The crystals of the present invention address this need, in part, by providing crystalline complexes between HDM2 (17-125) and inhibitors (e.g., small molecule inhibitors) of the HDM2/p53 interaction. The three dimensional structure of such complexes have been generated. Molecular modeling techniques are used to determine modifications to the inhibitors which may be made in an effort to improve the strength of the inhibitor/HDM2 interaction and, thereby, lead to the development of superior therapeutic inhibitors of HDM2-mediated p53 inactivation.

The present invention provides a complex comprising an isolated polypeptide comprising amino acids 17-125 of human HDM2; amino acids 17-125 of human HDM2 comprising an F55Y mutation; amino acids 17-125 of human HDM2 comprising a Y76H mutation; or amino acids 17-125 of human HDM2 comprising an F55Y/Y76H double mutation; complexed with a compound selected from the group consisting of

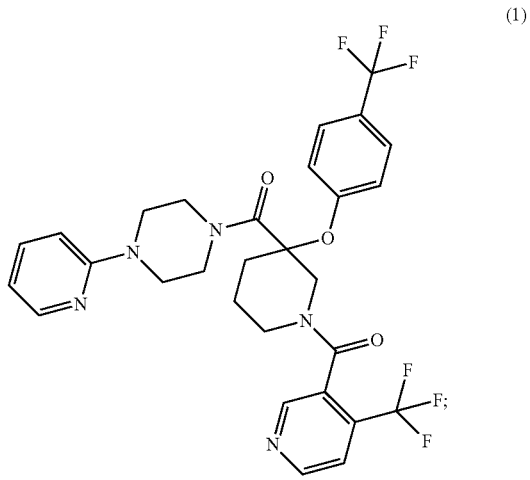

and

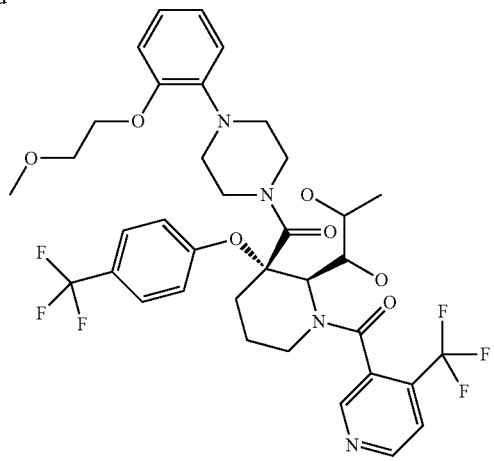

(3)

(crystalline complexes or non-crystalline/soluble complexes). The present invention further comprises crystalline complexes comprising such polypeptides and compounds (including complexes which are arranged in a three-dimensional lattice comprising repeating units of one or more of said complexes). In an embodiment of the invention, said amino acids 17-125 are SQIPASEQETLVRPK-PLLLKLLKSVGAQKDTYTMKEV-LYYLGQYIMTKRLYDEKQQHIVHC-SNDLLGDLFGVPSFSVKEHRKI YTMIYRNLVVVNQQESSDSGTSVSEN (SEQ ID NO: 2). The present invention also provides a soluble, non-crystalline complex, as set forth above, whose atoms are situated and oriented as represented by a three dimensional structure which is represented by the structural coordinates set forth in a member selected from the group consisting of Tables 1-4. An embodiment of the invention includes complexes which are arranged in a three-dimensional lattice comprising repeating units of one or more of said complexes. The scope of the present invention also encompasses a method for making the complex comprising contacting said polypeptide and said compound.

The present invention provides a composition comprising ammonium sulfate and an isolated polypeptide comprising amino acids 17-125 of human HDM2; amino acids 17-125 of human HDM2 comprising an F55Y mutation; amino acids 17-125 of human HDM2 comprising a Y76H mutation; or amino acids 17-125 of human HDM2 comprising an F55Y/Y76H double mutation; and a compound selected from the group consisting of

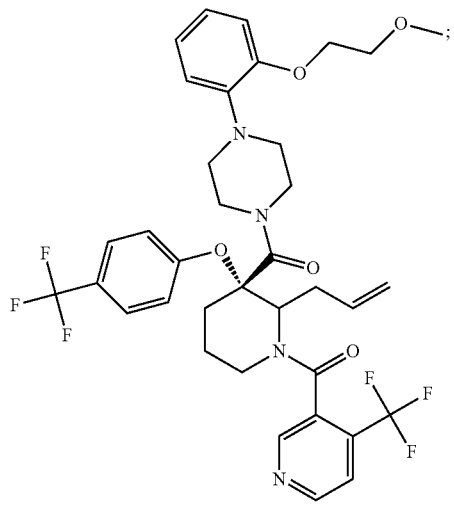

(2)

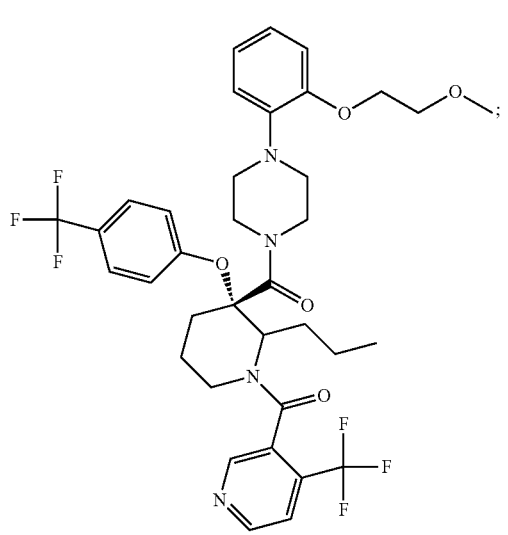

(3)

and

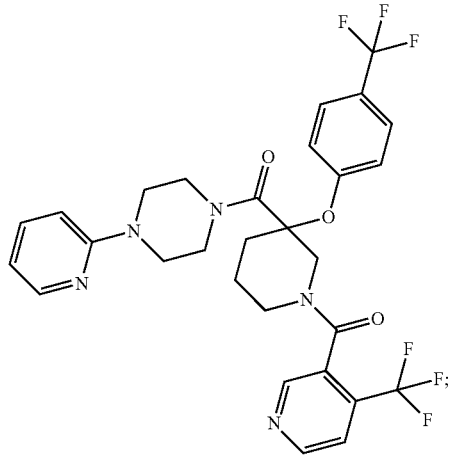

(1)

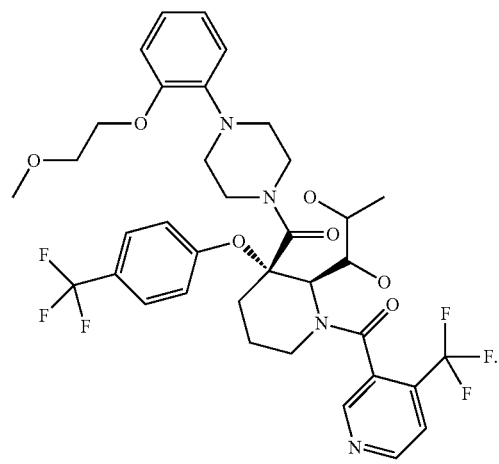

(4)

In an embodiment of the invention, said amino acids 17-125 are SQIPASEQETLVRPKPLLLKLLKSVGAQKDTYTM-KEVLYYLGQYIMTKRLYDEKQQHIVHCSNDLLGDL-FGVPSFSVKEHRKI YTMIYRNLVVVNQQESSDSGTS-VSEN (SEQ ID NO: 2). In an embodiment of the invention, the polypeptide is present at a concentration of at least about 10 mg/ml. In an embodiment of the invention, the temperature of the composition is about 22° C. or about 4° C. In an embodiment of the invention, the ammonium sulfate is at a concentration of about 0.9M. In an embodiment of the invention, said complexes are arranged in a three-dimensional lattice comprising repeating units of one or more of said complexes. In an embodiment of the invention, the composition is a crystallization condition as set forth below in the examples section.

The present invention also provides a crystalline composition comprising a polypeptide comprising the amino acid sequence of SEQ ID NO: 2; complexed with

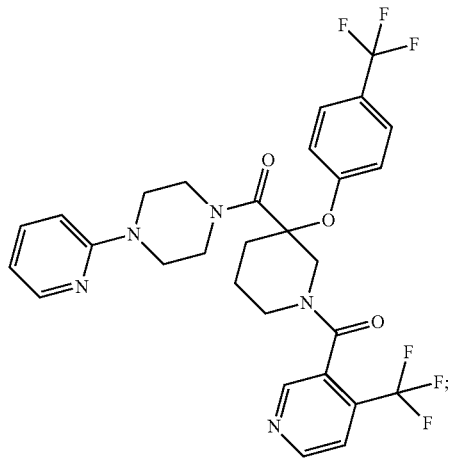

(1)

characterized by unit cell dimensions: a=90.9 Å, b=90.9 Å, c=90.8 Å, α=β=γ=90°; and in space group P6₁22. In an embodiment of the invention, the complex is characterized by the structural coordinates set forth in Table 1. The scope of the present invention also includes a method for making the crystalline composition comprising combining about 30 mg/ml of said polypeptide complexed with

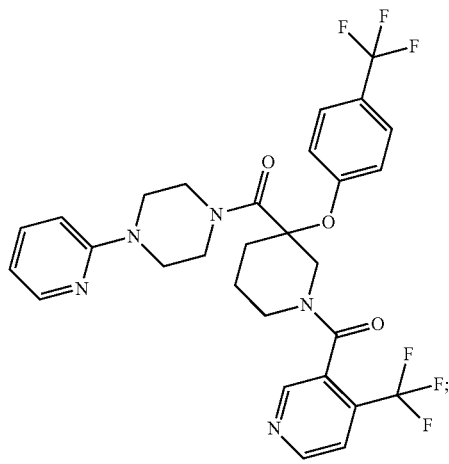

(1)

and an equal volume of precipitant solution which comprises about 0.9 M ammonium sulfate, into a mixture, and incubating said mixture in the presence of precipitant solution, in a sealed container, at about 4° C. In an embodiment of the invention, said mixture is in the form of a droplet when incubated.

The present invention also provides a crystalline composition comprising a polypeptide comprising the amino acid sequence of SEQ ID NO: 2; complexed with

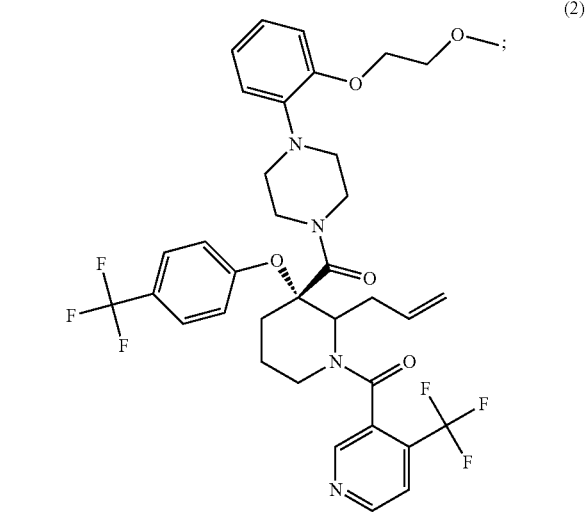

(2)

characterized by unit cell dimensions a=39.3 Å, b=38.9, c=131.3 Å, α=β=γ=90°; and in space group P2₁2₁2₁. In an embodiment of the invention, the complex is characterized by the structural coordinates set forth in Table 2. The present invention further comprises a method for making the crystalline composition comprising combining, at opposite ends of a vessel, a mixture comprising about 14 mg/ml of said polypeptide complexed with

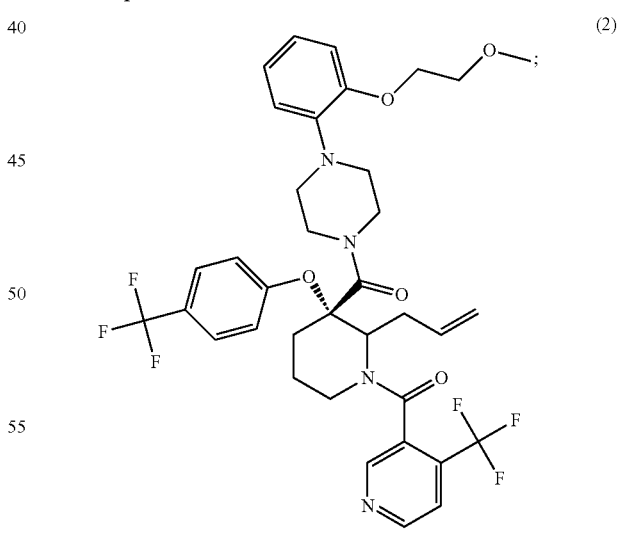

(2)

and a precipitant solution which comprises about 2.2 M ammonium sulfate; and allowing said mixture and said precipitant solution to diffusively combine within said vessel at about 22° C. The present invention further provides a method for making the crystalline composition comprising combining about 14 mg/ml of said polypeptide complexed with (2)

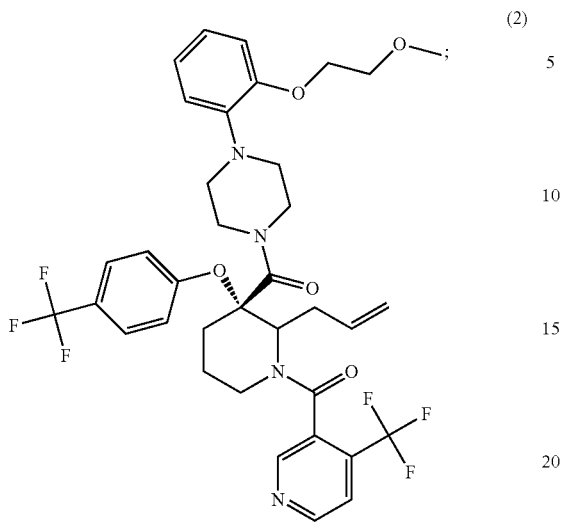

and an equal volume of precipitant solution which comprises about 1.1 M ammonium sulfate, into a mixture, and incubating said mixture in the presence of precipitant solution, in a sealed container, at about 4° C. In an embodiment of the invention, the vessel is a capillary-type tube.

The present invention also provides a crystalline composition comprising a polypeptide comprising the amino acid sequence of SEQ ID NO: 2; complexed with

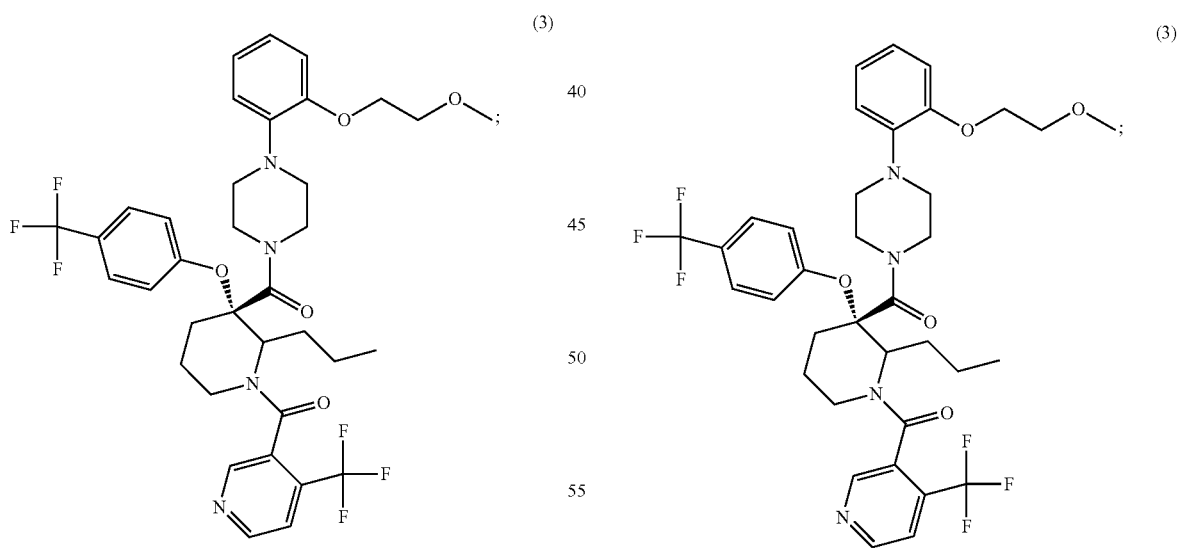

characterized by unit cell dimensions a=39.9 Å, b=39.8 Å, c=134.5 Å, α=β=γ=90°; and in space group P2$_1$2$_1$2$_1$. In an embodiment of the invention, the complex is characterized by the structural coordinates set forth in Table 3. The scope of the present invention also includes a method for making the crystalline composition comprising combining about 11 mg/ml of said polypeptide complexed with (3)

and an equal volume of precipitant solution which comprises about 0.98 M ammonium sulfate, into a mixture, and incubating said mixture in the presence of precipitant solution, in a sealed container, at about 22° C. In an embodiment of the invention, said mixture is in the form of a droplet when incubated. The present invention further comprises a method for making the crystalline composition comprising combining, at opposite ends of a vessel, a mixture comprising about 11 mg/ml of said polypeptide complexed with (3)

and a precipitant solution which comprises about 2.2 M ammonium sulfate; and allowing said mixture and said precipitant solution to diffusively combine within said vessel at about 22° C.

The present invention also provides a crystalline composition comprising a polypeptide comprising the amino acid sequence of SEQ ID NO: 2; complexed with

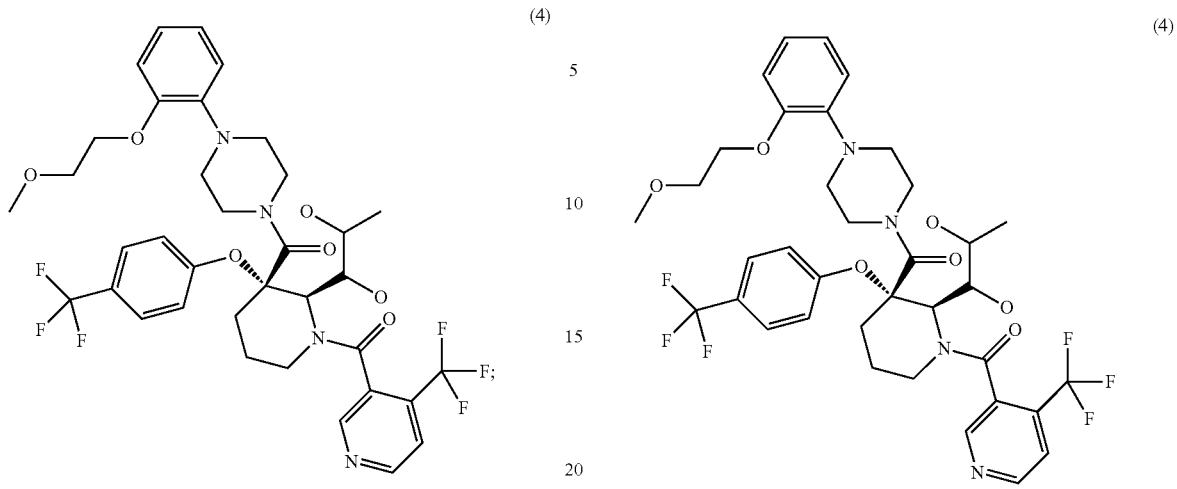

(4)

characterized by unit cell dimensions a=38.7 Å, b=38.7 Å, c=121.1 Å, α=β=γ=90°; and in space group P4₃2₁2. In an embodiment of the invention, the complex is characterized by the structural coordinates set forth in Table 4. The present invention also provides a method for making the crystalline composition comprising combining about 11 mg/ml of said polypeptide complexed with a precipitant solution which comprises about 2.4 M ammonium sulfate; and allowing said mixture and said precipitant solution to diffusively combine at about 22° C. In an embodiment of the invention, the vessel is a capillary-type tube.

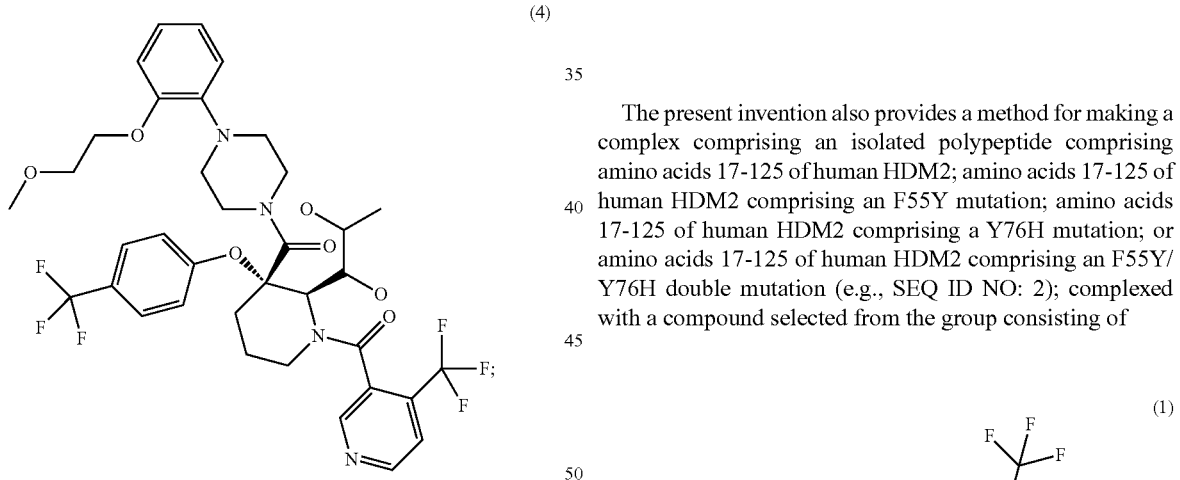

(4)

and an equal volume of precipitant solution which comprises about 1.45 M ammonium sulfate, into a mixture, and incubating mixture in the presence of precipitant solution, in a sealed container, at about 22° C. In an embodiment of the invention, said mixture is in the form of a droplet when incubated.

The present invention provides a method for making the crystalline composition comprising combining, at opposite ends of a vessel, a mixture comprising about 11 mg/ml of said polypeptide complexed with The present invention also provides a method for making a complex comprising an isolated polypeptide comprising amino acids 17-125 of human HDM2; amino acids 17-125 of human HDM2 comprising an F55Y mutation; amino acids 17-125 of human HDM2 comprising a Y76H mutation; or amino acids 17-125 of human HDM2 comprising an F55Y/Y76H double mutation (e.g., SEQ ID NO: 2); complexed with a compound selected from the group consisting of

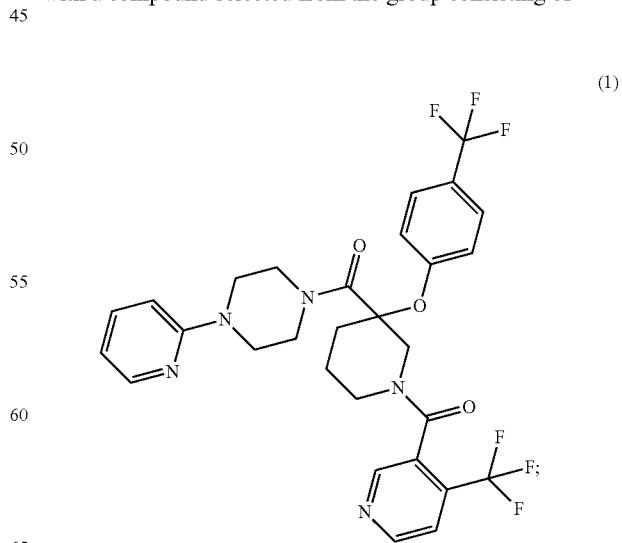

(1)

11

-continued

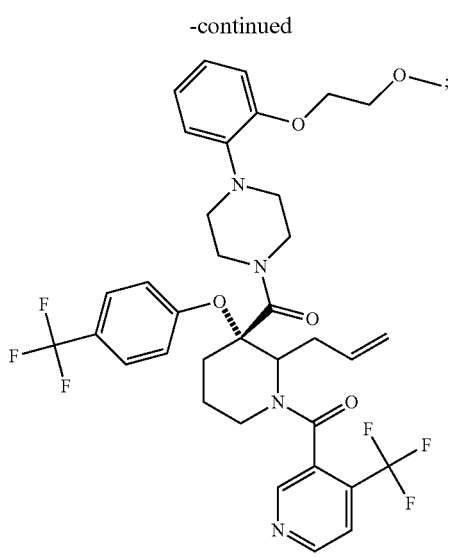

(2)

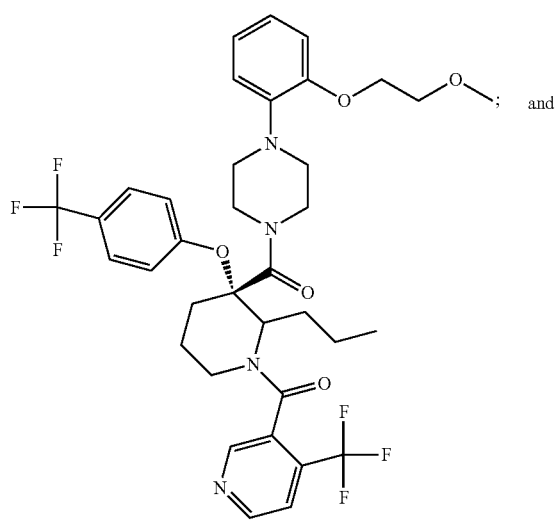

(3) and

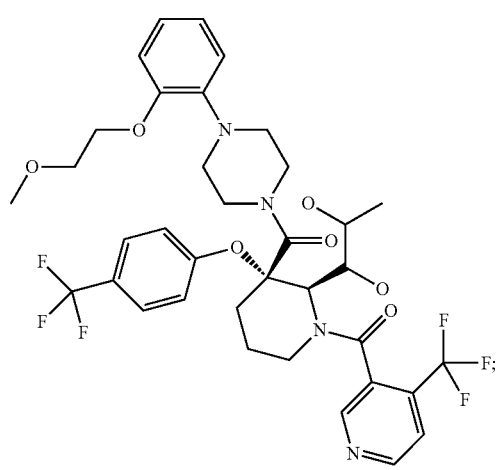

comprising contacting said polypeptide with said compound.

12

DETAILED DESCRIPTION OF THE INVENTION

Figure 1:
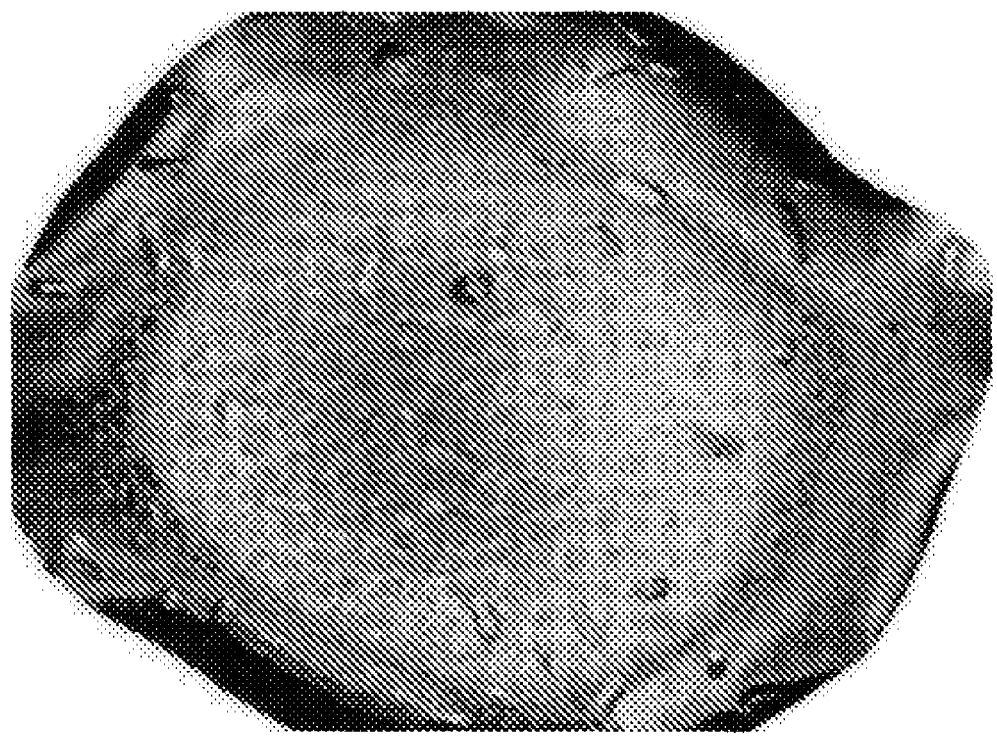
FIG. 1. Photomicrograph of double mutant HDM2 (17-125) F55Y/Y76H-cpd.1 complex crystals.

The present invention includes both soluble and crystalline complexes between a fragment of HDM2 comprising the p53 binding pocket (e.g., SEQ ID NO: 2) and comprising a mutation in solvent-exposed, surface residues which mutations confer enhanced solubility on the polypeptide. The crystalline complexes are useful, e.g., for analysis of the characteristics the molecular interactions between the HDM2 p53 binding pocket and various organic compounds set forth herein. Methods for generating the crystalline complexes are also covered.

HDM2 Polypeptides

The present invention comprises crystalline and soluble HDM2 polypeptides (full length or fragments such as residues 17-125) complexed with any of compounds 1, 2, 3 or 4

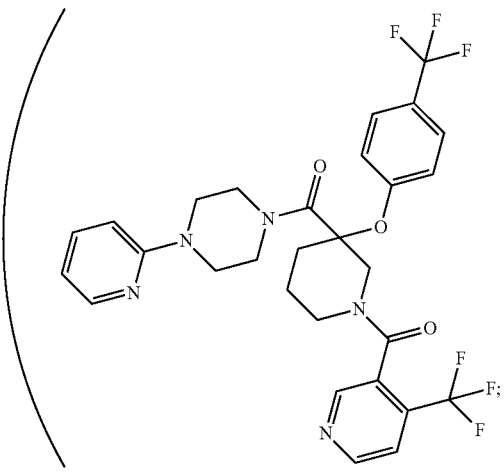

-continued

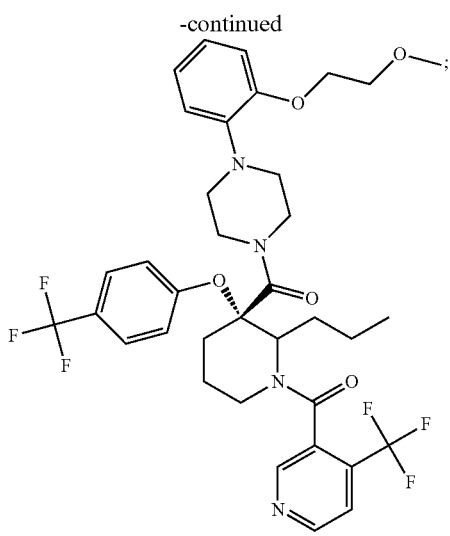

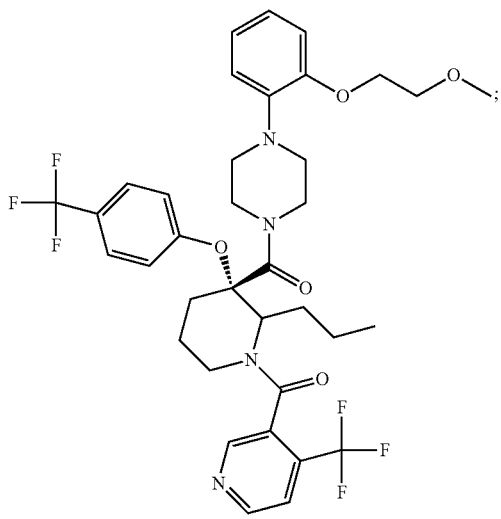

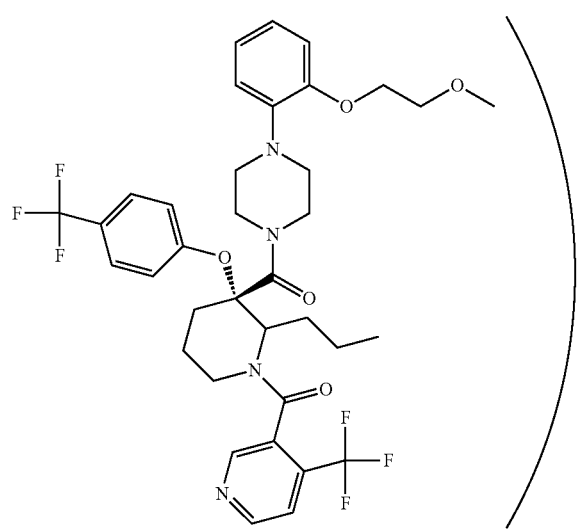

In an embodiment of the invention, HDM2 is a wild-type polypeptide or HDM2 is a mutant polypeptide. In an embodiment of the invention, a mutant HDM2 polypeptide comprises the mutation F55Y or Y76H or both F55Y and Y76H.

In an embodiment of the invention, wild-type full length HDM2 comprises the amino acid sequence:

mcntnmsvpt dgavttsqip aseqetlvrp kplllkllks vgaqkdtytm kevlfylgqy imtkrlydek qqhivycsnd llgdlfgvps fsvkehrkiy tmiyrnlvvv nqqessdsgt svsenrchle ggsdqkdlvq elqeekpsss hlvsrpstss rrraisetee nsdelsgerq rkrhksdsis lsfdeslalc vireiccers sssestgtps npdldagvse hsgdwldqds vsdqfsvefe vesldsedys lseegqelsd eddevyqvtv yqagesdtds feedpeisla dywkctscne mnpplpshcn rcwalrenwl pedkgkdkge isekaklens tqaeegfdvp dckktivnds rescveendd kitqasqsqe sedysqpsts ssi-iyssqed vkefereetq dkeesvessl plnaiepcvi cqgrpkngci vhgktghlma cftcakklkk rnkpcpvcrq piqmivltyf pl(SEQ ID NO: 1)

The HDM2 polypeptide sequence is known in the art; see e.g., Genbank accession nos. AAP36607 and AAX29588. Residues 17-125, which include the p53 binding pocket, are underscored. Residues 55 and 76 are in bold font. The amino acid sequence of HDM2 (17-125), which forms a part of the present invention, comprising the F55Y and Y76H mutations is set forth below:

SQIPASEQETLVRPKPLLLKLLKSVGAQKDTYTMKE-VLYYLGQYIMTKRLYDEKQQHIVHCSNDLLGDLFG-VPSFSVKEHRKI YTMIYRNLVVVNQQESSDSGTS-VSEN (SEQ ID NO: 2).

The present invention further includes any HDM2 polypeptide or fragment thereof comprising any one of the following mutations:

L27K, L33K, F55H, Y76K, L81K, P89K, Y104S and V109S (i.e., comprising 1, 2, 3, 4, 5, 6, 7, or all 8 of said mutations in any combination whatsoever).

Compounds 1-4 are as follows:

Compound 1:

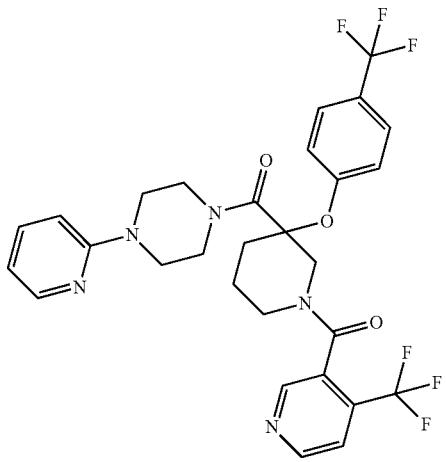

Compound 2:

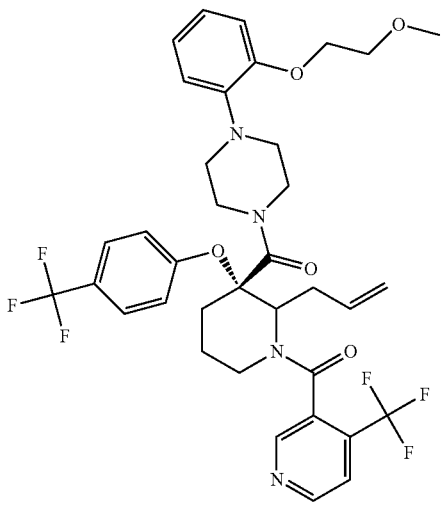

Compound 3:

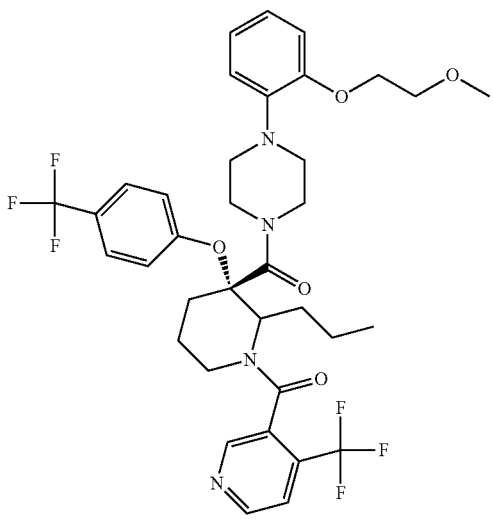

Compound 4:

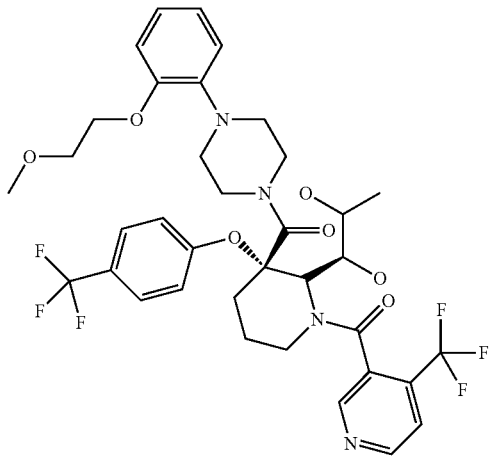

The present invention includes compositions comprising any of the HDM2 polypeptide complexes of the present invention in any medium. In an embodiment of the invention, the complex is in a crystallizable composition, for example, in a composition comprising any concentration of ammonium sulfate or any other precipitant.

The present invention also comprises any of compounds 1, 2, 3 and 4 or a pharmaceutical composition thereof which comprises a pharmaceutically acceptable carrier. See e.g., Remington's Pharmaceutical Sciences, Mack Publishing Company, Easter, Pa., 19th Edition (1995).

Crystals The crystals of the present invention have a wide range of uses. For example, high quality crystals are suitable for X-ray or neutron diffraction analysis to determine the three dimensional structure of HDM2, or a fragment, variant or a complex thereof and in particular to assist in the identification of the inhibitors of the protein.

In addition, crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing high-quality crystals which are useful for diffraction analysis. Such a method forms part of the present invention.

Once a crystalline complex of the present invention is grown, X-ray diffraction data can be collected. One method for determining structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of a HDM2 or a fragment, variant or complex thereof. The present invention includes crystals which effectively diffract X-rays for the determination of the atomic coordinates of HDM2 or a fragment, variant or complex thereof to a resolution of greater than about 5.0 Ångströms (e.g., about 4.5 Å, about 4.0 Å, about 3 Å, about 2.5 Å, about 2 Å, about 1 Å), preferably greater than about 4.0 Ångströms (e.g., about 3 Å, about 2.5 Å, about 2 Å, about 1 Å), more preferably greater than about 2.8 Ångströms (e.g., about 2.5 Å, about 2 Å, about 1 Å).

The present invention includes crystals of HDM2 or a fragment, variant or complex thereof whose three-dimensional structure is described by the structure coordinates set forth herein, e.g., in any of Tables 1-4. The scope of the present invention also includes crystals that possess structural coordinates which are similar, but not identical, to those set forth herein, e.g., in any of Tables 1-4. In an embodiment of the invention, the crystals include a polypeptide which includes the amino acid sequence of SEQ ID NO: 2. Structural similarity between crystals is discussed in detail below.

The term "structure coordinates" includes Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates for a protein or a protein complex or a portion thereof, is a relative set of points that define a shape in three dimensions. Thus, it is possible that an entirely different set of coordinates could define a similar or identical shape. Moreover, slight variations in the individual coordinates may have little effect on overall shape.

The present invention includes crystals exhibiting structural coordinates which are similar to those set forth herein, e.g., in any of Tables 1-4 but for crystallographic permutations of the structure coordinates, fractionalization of the structure coordinates, additions, subtractions, rotations or translations to sets of the structure coordinates or any combinations of the above.

Modifications in the crystal structure due to mutations, additions, substitutions, and/or deletions of amino acids, or other changes in any of the components that make up the crystal may account for variations in structure coordinates. If such variations are within an acceptable standard error as compared to the coordinates of any of Tables 1-4, the resulting three-dimensional shape is considered to be the same and, accordingly, the modified crystal is considered to be within the scope of the present invention.

Various computational analyses may be necessary to determine whether a crystal is sufficiently similar to the crystals whose structural coordinates are set forth in any of Tables 1-4 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation; and 4) analyze the results. Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) or alpha carbon atoms only for all conserved or common residues between the two structures being compared.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Ångströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

For the purpose of this invention, any crystalline molecule characterized by a set of structure coordinates that has a RMSD of conserved or common residue backbone atoms (N, Cα, C, O) or of only alpha carbon atoms of less than about 1.5 Å when superimposed—using backbone atoms or alpha carbon atoms (Cα)—on the relevant structure coordinates of any of Tables 1-4 are considered identical and are within the scope of the present invention. In an embodiment, the root mean square deviation is less than about 1.0 Å (e.g., 0.9 Å, 0.8 Å, 0.7 Å, 0.6 Å), less than about 0.5 (e.g., 0.4 Å, 0.3 Å), less than about 0.25 Å (e.g., 0.2 Å, 0.15 Å) or less than about 0.1 Å.

The term "least squares" refers to a method based on the principle that the best estimate of a value is that in which the sum of the squares of the deviations of observed values is a minimum.

Crystallization

Crystallization may be accomplished by using a number of methods (See e.g., Giegé, et al., (1994) *Acta Crystallogr.* D50: 339-350; McPherson, (1990) *Eur. J. Biochem.* 189: 1-23). Such techniques include microbatch, hanging drop, standing drop, free interface diffusion, seeding and dialysis. It is important to promote continued crystal growth after nucleation by maintaining a supersaturated solution. In the microbatch method, polypeptide or a complex thereof is mixed with precipitants to achieve supersaturation, the vessel is sealed and is set aside until crystals appear. In the dialysis method, polypeptide is retained in a sealed dialysis membrane which is placed into a solution containing precipitant. Equilibration across the membrane increases the precipitant concentration thereby causing the polypeptide to reach supersaturation levels.

An embodiment of the invention includes methods for generating a crystal of the present invention using free interface diffusion (FID) crystallization. Using the FID method one actually places the sample to be crystallized in liquid contact with precipitant. For example, in an embodiment of the invention, the sample and precipitant are placed at opposite sides of a vessel, such as a cylindrical vessel, e.g., a capillary-type vessel such as a capillary tube; and the two components are then gradually allowed to combine diffusively. A capillary-type vessel is a vessel which is generally tubular or cylindrical in shape. A clearly defined interface between the sample and the precipitant is thus created. Over time, the sample and precipitant diffuse into one another and crystallization occurs at the interface, or on the side of high sample/low precipitant or low sample/high precipitant. The FID technique allows one to screen a gradient of sample precipitant concentration combinations. FID may also be performed in a low volume (nanocrystallization) chip format. When a chip is used, the sample and reagent solutions are automatically loaded into diffusion chambers within the chip. When interface valves open, the two solutions mix by diffusion. The result is a gradual increase of reagent concentration that causes crystal nucleation and growth. This slow diffusive mixing samples a wide swath of chemical space and often produces a crystallization gradient. In addition, because the chip material is typically gas-permeable, the mixture also undergoes a controlled process of evaporative concentration (Ng et al., (2003) J. Structural Biol. 142: 219231; Salemme (1972) Arch. Biochem. Biophys. 151: 533-539).

The present invention includes a free interface diffusion method for making a crystalline composition comprising combining, in a vessel, e.g., a cylindrical or capillary-type vessel, a mixture comprising HDM2 polypeptide or a fragment or sequence variant thereof (e.g., SEQ ID NO: 2) and; any one of compounds 1-4: (1)

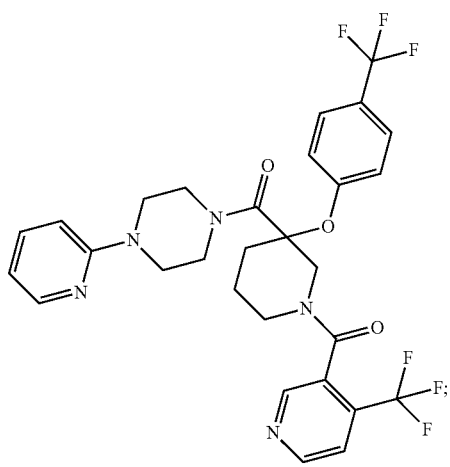

(2)

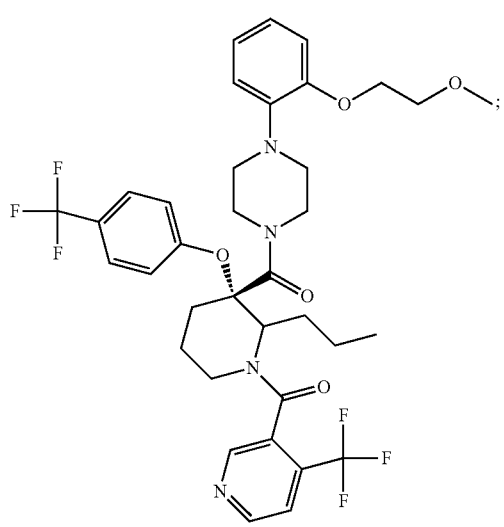

(3)

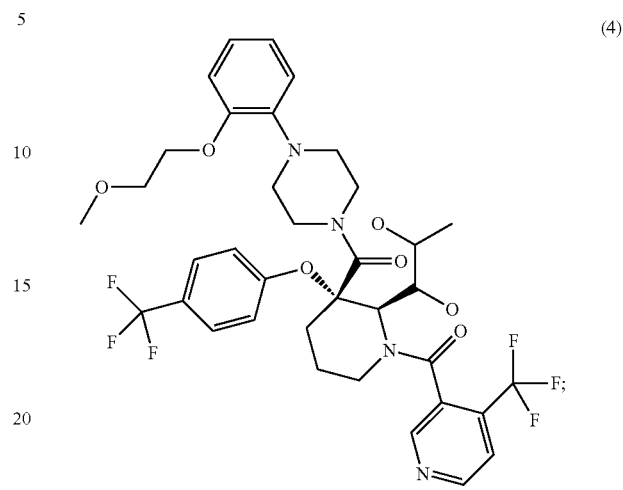

(4)

with a precipitant solution which comprises ammonium sulfate; and allowing said mixture and said precipitant solution to diffusively combine. For example, the two components may be placed at opposite ends of the vessel and allowed to combine through the liquid interface between said components. After a period of incubation, crystals of HDM2/compound complexes are formed.

An embodiment of the invention includes a method for making any crystalline composition of the invention by a hanging drop- or standing drop-vapor diffusion technique. In such a technique, a drop composed of a mixture of HDM2 polypeptide of fragment or sequence variant thereof and said compound 1, 2, 3, or 4 and a precipitant reagent is placed in a sealed chamber for vapor equilibration with a liquid reservoir. The reservoir contains precipitant reagent. For example, the drop can be suspended in the equilibration chamber or placed atop a platform within the chamber. Typically, the drop contains a lower precipitant concentration (e.g., 50%) than the reservoir. To achieve equilibrium, water vapor leaves the drop and eventually ends up in the reservoir. As water leaves the drop, the sample undergoes an increase in relative supersaturation. Both the sample and precipitant reagent increase in concentration as water leaves the drop for the reservoir. Equilibration is reached when the reagent concentration in the drop is approximately the same as that in the reservoir.

For example, an embodiment of the invention comprises a method for making a crystalline composition comprising combining HDM2 polypeptide or a fragment or sequence variant thereof; along with any one of compounds 1-4:

(1)

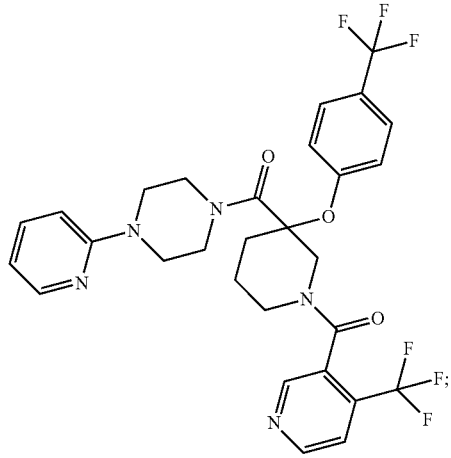

(2)

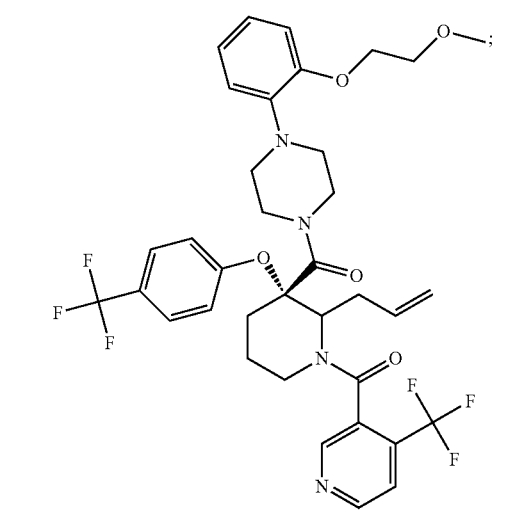

(3)

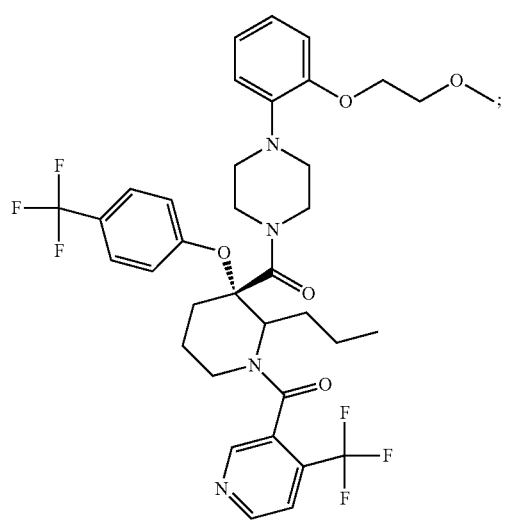

-continued (4)

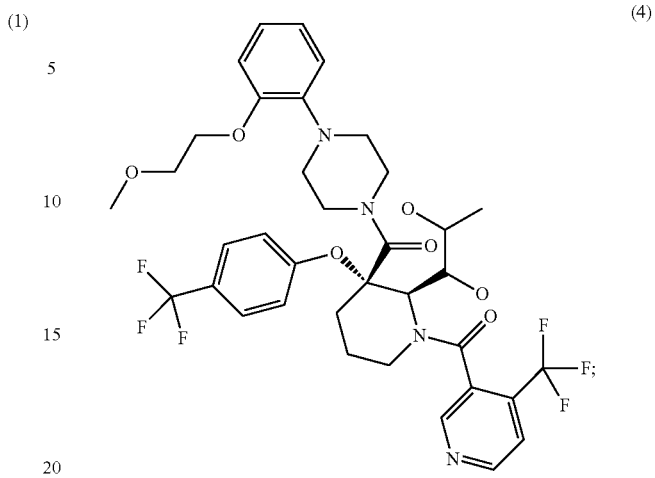

and precipitant solution (e.g., an equal volume thereof) which comprises ammonium sulfate, into a mixture, and incubating a drop (e.g., a hanging drop or standing drop) of said mixture in the presence of precipitant solution (not in physical contact), in a sealed container, such that water may equilibrate, via vapor diffusion, between the drop and the precipitant solution. After an incubation, crystals of HDM2/compound complexes form.

In an embodiment of the invention, incubation is performed at about 4° C. to about 22° C. (e.g., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C. or 22° C.). In an embodiment of the invention, the precipitant solution comprises about 1.8 M to about 2.9 M ammonium sulfate (e.g., 1.96 M or 2.2 M).

Computers and Molecular Modeling

In accordance with the present invention, the structure coordinates of the HDM2 complex of the invention may be stored in a machine-readable storage medium. Such data may be used for a variety of purposes, such as drug discovery and X-ray crystallographic analysis of a protein crystal. Accordingly, one aspect of this invention provides a machine-readable data storage medium comprising a data storage material encoded with the structure coordinates set forth in Table 1, 2, 3 or 4. The machine-readable data storage medium may also include any set of structure coordinates of a molecule that has a root mean square deviation of conserved residue backbone atoms (N, Cα, C, O) or alpha carbon atoms only of less than about 1.5 Å when superimposed—using backbone atoms—on the relevant structure coordinates of Table 1, 2, 3 or 4.

A computer system, useful in reading the machine readable data storage medium, includes a computer comprising a central processing unit ("CPU") and a memory storage device and is also within the scope of the present invention. In general, the computer system may be any computer with an operating system such as MS-DOS, PC-DOS, Windows, OS/2, Unix, Unix variant or MacOS. Examples of computer systems are the Silicon Graphics Octane workstation or Compaq AlphaServer DS20. Other hardware systems and software packages will be known to those skilled in the art.

Input hardware coupled to the computer system by input line, may be implemented in a variety of ways. Machine-readable data of this invention may be input via the use of a modem or modems connected by a telephone line or a dedicated data line. Alternatively or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal (e.g., a cathode ray tube (CRT)) for displaying a graphical representation of the three dimensional structure of an HDM2 complex of the invention or a portion thereof using a program such as INSIGHT (Molecular Simulations Inc., San Diego, Calif.) or QUANTA as described herein. Output hardware might also include a printer, so that hard copy output may be produced, or a disk drive, to store system output for later use. In embodiments of the invention, the computer possesses a display that is displaying a three dimensional representation of an HDM2 complex of the invention or a homologue thereof.

In operation, the central processing unit (CPU) coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a manner which may be conventional, machine readable data, such as that described herein, for execution by a system as described herein. Storage medium may also have an opening for receiving the spindle of a disk drive or other data storage device. Alternatively, an optically-readable data storage medium can be encoded with such machine-readable data, or a set of instructions. Medium can be a conventional compact disk read only memory (CD-ROM) or a rewritable medium such as a magneto-optical disk which is optically readable and magneto-optically writable.

In general, in the case of CD-ROM, as is well known, disk coating is reflective and is impressed with a plurality of pits to encode the machine-readable data. The arrangement of the pits is read by reflecting laser light off the surface of the coating. A protective coating, which in an embodiment of the invention is substantially transparent, is provided on top of the coating.

In general, in the case of a magneto-optical disk, as is well known, disk coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Computers of the present invention, e.g., as discussed herein are particularly useful tools for the process of molecular modeling, structure based drug design or computer assisted drug design (CADD).

The p53 protein is known to bind to HDM2 at its hydrophobic binding pocket. Binding occurs via the hydrophobic Phe19, Trp23, and Leu26 residues of p53. The hydrophobic binding pocket of HDM2 is known to exist within amino acids 17-125. Compounds 1-4 were shown herein to bind to HDM2 within the hydrophobic binding pocket. These inhibitors thus inhibit the ability of p53 to bind to HDM2. Accordingly, variants of compounds 1-4 may also be shown, via molecular modeling techniques to bind to HDM2 via the hydrophobic pocket.

The present invention permits the use of structure-assisted drug design techniques to design, select, and synthesize chemical entities, including inhibitory compounds that are capable of binding to a HDM2 or a fragment or variant thereof. Also, de novo and iterative drug design methods can be used to develop drugs from the structure of the HDM2 crystals of this invention.

The present method comprises a method by which the three-dimensional structure of any HDM2 crystal of the invention can be used to identify an HDM2 antagonist or substance that binds to HDM2. For example, the present invention comprises a method for identifying an HDM2 antagonist comprising the steps of: a) crystallizing a complex between HDM2 or a fragment or variant thereof (e.g., SEQ ID NO: 2) and compound 1, 2, 3, or 4 to form at least one crystal; b) irradiating the crystal produced by step (a) to obtain a diffraction pattern of said crystal; c) determining the atomic coordinates of the three-dimensional structure of the complex from the diffraction pattern; d) using the atomic coordinates (e.g., as set forth herein) and one or more molecular modeling techniques to identify points wherein the compound may be modified and exhibit an acceptably low binding energy for binding to the binding pocket; and, optionally, e) determining, experimentally, if the compound does, in fact, bind to the HDM2 p53 binding pocket and/or if the compound antagonizes the interaction between p53 and HDM2; wherein the substance is selected if such binding and/or antagonism is observed or wherein the substance is selected if acceptable binding characteristics are identified by way of the molecular modeling techniques.

Several factors are considered when determining if there will be a sufficiently low binding energy between a compound and the HDM2 p53 binding pocket. Factors considered when performing a computer evaluation of the binding between a compound and a protein include electrostatic forces involving the compound and the binding pocket amino acids, the proximity of hydrogen bond donors and acceptors in the compound and the binding site amino acids, solvation energy required to move the compound from its soluble, unbound medium and dock it in the binding site, solvent effects (e.g., the effect of displacing an ordered water molecule on the binding site by compound binding), the conformational flexibility of the compound and the binding pocket amino acids, and the steric interactions between the binding pocket and compound (e.g., the ability of the compound to physically fit into the binding pocket and the ability of the compound and the binding pocket amino acids to assume low energy conformations upon binding). These factors and others contribute to the estimation of the binding energy of a given compound/binding pocket interaction. Each of these factors may be calculated or otherwise evaluated using conventional computer assisted drug design techniques and experimentation commonly known in the art.

In an embodiment of the invention, the compound analyzed is evaluated for the likelihood that it will be bioavailable. Bioavailability of a compound may be evaluated using the "rule of 5" which states that a compound is likely to be bioavailable if it contains less than five hydrogen bond donors, less than ten hydrogen bond acceptors, a molecular weight less than 500 g/mole, and a calculated log of the partition coefficient (clogP) of less than five (Lipinski et al., Adv. Drug Deliv. (1997) 23:3-25). Generally, the number of rotational bonds should be kept low, e.g., less than 10, in order to increase the potential of bioavailability (Veber et al., J. Med. Chem. (2002) 45:2615-2623).

The ability of p53 and HDM2 or a fragment or variant thereof to bind in the presence of an inhibitor can be determined by any number of assays known in the art (See e.g., Lundholt et al., Assay Drug Dev. Technol. (2006) 4(6):679-88 or the assays described herein).

EXAMPLES

The following information is provided for more clearly describing the present invention and should not be construed to limit the present invention. Any and all of the compositions and methods described below fall within the scope of the present invention.

Example 1

Mutation Strategy for HDM2 Constructs

Surface mutants were proposed to interrupt hydrophobic patches, thereby increasing the solubility of Hdm2 and creating new crystal contact sites. Using the program Clustalw, amino acid sequences were aligned for hdm2 and hdm4 analogs from the following species: *Brachydanio Rerio* (Zebrafish), *Canis Familiaris* (Dog), *Equus Caballus* (Horse), *Homo Sapiens* (Human), *Mesocricetus Auratus* (Golden Hamster), *Mus Musculus* (Mouse), *Xenopus Laevis* (African Clawed Frog) and *Gallus Gallus* (Chicken). For six Hdm2 surface residues in hydrophobic patches, the corresponding hydrophilic residues from a species homolog were substituted, viz.: L27K, L33K, F55H, Y76K, L81K and P89K.

An additional protein surface analysis was performed to identify all of the surface, solvent exposed, human residues that have hydrophobic side chains versus amino acid residues at the same location for *Xenopus Laevis* that are known to have hydrophilic side chains. From this analysis it was determined that the following mutations should be introduced (Human Residue: *Xenopus Laevis*): F55Y, Y76H, Y104S, V109S.

Example 2

Cloning of Thioredoxin/His Tag Fused HDM2 (17-125) and Mutant HDM2 (17-125) Constructs The hdm2(17-125) mutants (single mutant F55Y and Y76H, double mutant F55Y/Y76H) were generated using the QuickChange kit (Stratagene, La Jolla, Calif., USA) using the pET32 Xa/LIC-hdm2 (17-125) vector as a template; the triple mutant F55Y/Y76H/Y104S was generated using GeneTailor Site-directed Mutagenesis system (Invitrogen, Carlsbad, Calif., USA) using the vector mentioned above as the template. The following mutagenic primers were used to generate the above mutants:

1) hdm2F55Y:
  5' CTATGAAAGAGGTTCTTTATTATCTTG-GCCAGTATATTATGAC 3' (SEQ ID NO: 3)

2) RChdm2F55Y:
  5' GTCATAATATACTGGCCAAGATAATAAA-GAACCTCTTTCATAG 3' (SEQ ID NO: 4)

3) hdm2Y76H:
  5' GAGAAGCAACAACATATTGTACATTGT-TCAAATGATCTTCTAGG 3' (SEQ ID NO: 5)

4) RChdm2Y76H:
  5' CCTAGAAGATCATTTGAACAATGTA-CAATATGTTGTTGCTTCTC 3' (SEQ ID NO: 6)

5) Y104S-GTAILOR-F:
  5'CAGGAACTTGGTAGTAGTCAATCAGCAGG 3' (SEQ ID NO: 7)

6) Y104-GTAILOR—R:
  5' GACTACTACCAAGTTCCTGGAGATCATGGT 3' (SEQ ID NO: 8)

The QuickChange mutagenesis was performed in two steps as previously described (Wang, W., Malcolm B. A., (1999) BioTechniques 26:680-682). In the first stage, two extension reactions were performed in separate tubes; one containing the forward primer and the other containing the reverse primer. After two cycles, the two reactions were mixed and the standard QuickChange mutagenesis procedure was carried out for an additional 18 cycles. Following amplification, the parental strand was digested with 1 U of Dpn1 for 2 hours and an aliquot was transformed into DH5-α cells. The GeneTailor mutagenesis was performed according to the manufacture's instruction manual except the pfu turbo DNA polymerase was used instead of the one recommended by manufacture. All constructs were sequence confirmed (GeneWiz, New York, N.Y.).

The double mutant F55Y/Y76H was selected for further experimentation.

Example 3

Amino Acid Sequence of Double Mutant HDM2 (17-125) F55Y/Y76H

SQIPASEQETLVRPKPLLLKLLKSVGAQKDTYTMKE-VLYYLGQYIMTKRLYDEKQQHIVHCSNDLLGDLFG-VPSFSVKEHRKI YTMIYRNLVVVNQQESSDSGTS-VSEN (SEQ ID NO: 2)

Example 4

Expression of HDM2 Mutants

A colony from freshly transformed cells was grown in 10 ml terrific broth (Mediatech, Inc.) with 100 ug/ml carbenicilin and 1% glucose at 37° C. to OD of 2.0; the 10 ml of culture was then used to inoculate a 1 liter culture with the same medium composition, and it was grown to a OD of 2.0 at 37° C. The 1 L culture was then stored at 4° C. overnight for inoculation of a 10 L tank (terrific broth and 100 ug/ml carbenicilin); The 10 L culture was grown to a OD of 1.5-2.0 at 37° C., and temperature was then lowered to 16° C. The 10 L culture was then induced with 1 mM IPTG, and cells were harvested 18 hours post-induction.

Example 5

Purification of Double Mutant HDM2 (17-125) F55Y/Y76H

The following protocol described specifically for purification of double mutant HDM2 (17-125) F55Y/Y76H) was applied to all HDM2 forms generated herein. The cell pellets from a 10 liter fermentation were suspended in 500 ml of 50 mM Tris-Cl Buffer, pH $8.0_{rt}$, 0.3 M NaCl, 10% (v/v) glycerol, 5 mM β-mercaptoethanol, 25 mM imidazole, 18,000 Units/liter endonuclease (ultra pure benzonase; SIGMA), and 6 ml/liter of CALBIOCHEM Protease Inhibitor Cocktail III. All processing was done at 4° C.

The cell suspension was homogenized by 3 passages through a large OMNI Mixer probe, for 45 seconds each. The cell suspension was kept on ice for 2 minutes between each pass. The cells were then broken by three passages of the homogenized cell suspension through a Microfluidizer. The extract was recovered by centrifugation at 205,000×g at 4° C. for 80 minutes.

The extract (645 ml) was mixed end-over-end for 50 minutes, with 28 ml of QIAGEN Ni-NTA Superflow resin, equilibrated with 50 mM Tris-Cl, pH $8.0_{rt}$, 0.3 M NaCl, 5 mM β-mercaptoethanol and 25 mM imidazole (equilibration buffer). The supernatant was decanted, and the resin was then washed with 600 ml of the same buffer. The resin was poured into a 2.6×5.3 cm column, washed with an additional 200 ml of equilibration buffer at 3.6 ml/min, and then eluted with 50 mM Tris-Cl, pH $8.0_{rt}$, 0.1 M NaCl, 250 mM imidazole, 5 mM β-mercaptoethanol and 20% glycerol.

A 0.64 ml volume of 0.5 M $CaCl_2$ was added to the eluted fusion protein pool (195 mg of protein in 63 ml of elution buffer). The pool was then diluted to a protein concentration of 1 mg/ml with 50 mM Tris-Cl, pH $8.0_{rt}$, 0.1 M NaCl, 10% glycerol, 5 mM $CaCl_2$ and 5 mM β-mercaptoethanol. A 1.95 ml volume of 2000 Units/ml Factor Xa protease (NOVAGEN) was added, and the pool was dialyzed overnight versus 3.87 liters of the same buffer.

A 4.33 ml volume of 1 M imidazole, pH 8.0, was added to the 200 ml cleaved fusion protein pool, to bring the imidazole concentration up to 24 mM. The pool was applied to a 50 ml (2.6×9.4 cm) column of QIAGEN Ni-NTA Superflow resin in equilibration buffer at 3.6 ml/min, and washed with the same.

The 230 ml flow through was dialyzed versus 3 changes (6 liters, 5 liters and 5 liters) of Buffer A: 25 mM Hepes-KOH, pH 7.5, 0.15 M KCl, 1 mM $Na_2$-EDTA, 0.03% sodium azide and 5 mM dithiothreitol. All manipulations of double mutant HDM2 (17-125) F55Y/Y76H were in Buffer A from this point on. The dialyzed pool was concentrated to 8.5 ml on an Amicon YM10 membrane, centrifuged at 205,000×g for 15 minutes, and then applied to a 2.6×60 cm column of PHARMACIA Superdex-75 at a flow rate of 0.8 ml/min. 3.2 ml fractions were collected. The purified double mutant HDM2 (17-125) F55Y/Y76H monomer fractions (66-75) were pooled.

The protein concentration of 3.6 mg/ml was determined using $E\epsilon_{276}=10,150$ $M^{-1}$ $cm^{-1}$ in 20 mM sodium phosphate, pH 6.5, 6 M guanidine hydrochloride (ExPASy-ProtParam Tool). These values were correlated with the protein concentrations of the purified protein measured by the Bradford dye binding method (BIORAD), using BSA as a standard.

Example 6

Structure and Activity of HDM2 Inhibitor Compound 1

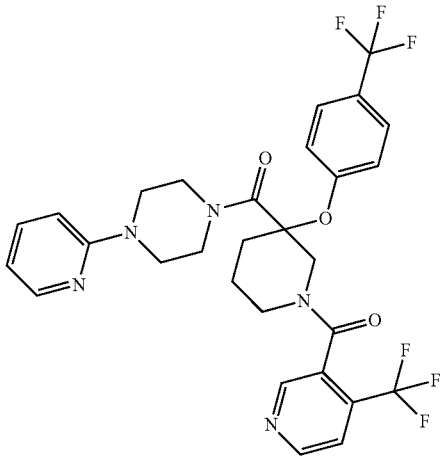

Compound 1

In vitro binding assays were performed to assess the affinity of compound 1 to HDM2 using both Fluorescent polarization assay (Zhang R, Mayhood T, Lipari P, Wang Y, Durkin J, Syto R, Gesell J, McNemar C, Windsor W. (2004) Fluorescence polarization assay and inhibitor design for MDM2/p53 interaction. Analytical Biochemistry 331(1):138-146) and TdF assay.

Fluorescence polarization assays include equilibrating a serially diluted compound solution with 10 nM HDM2 protein in the presence of 1 nM 6-carboxyfluorescein (FAM)-labeled p53 peptide ligand in PBS buffer, followed by detection of fluorescence polarization signals and non-linear regression analysis to derive IC50 and Ki values. TdF assays include melting a 6 uM HDM2 solution in 10 mM HEPES buffer (pH 7.4) containing 150 mM NaCl, 1 mM DTT and Sypro Orange (5×), in the absence and presence of 10 and 20 uM compound, followed by non-linear regression analysis to derive melting points and Kd values.

The values calculated using these assays are set forth below:

Fluorescent polarization assay IC50 (nM): <5000
Fluorescent polarization assay Ki (nM): <2000
*TdF Kd (nM): <2000

*Michael W. Pantoliano et al. (2001) "High-Density Miniaturized Thermal Shift Assays as a General Strategy for Drug Discovery", Journal of Biomolecular Screening, 6(6), 429-440; Mei-Chu Lo et al (2004) "Evaluation of fluorescence-based thermal shift assays for hit identification in drug discovery", Analytical Biochemistry 332, 153-159; Daumantas Matulis et al. (2005) "Thermodynamic Stability of Carbonic Anhydrase: Measurements of Binding Affinity and Stoichiometry Using ThermoFluor", Biochemistry, 44, 5258-5266; Todd W. Mayhood and William T. Windsor (2005) "Ligand binding affinity determined by temperature-dependent circu-

Example 7

Preparation of Double Mutant HDM2 (17-125) F55Y/Y76H-cpd.1 Complex

The HDM2 (17-125) F55Y/Y76H-cpd.1 complex was prepared by adding 400 ul of a 20 mM DMSO stock of cpd.1, to 43 ml of 1 mg/ml HDM2 (17-125) F55Y/Y76H in 25 mM Hepes-KOH, pH 7.5, 0.15 M KCl, 1 mM EDTA, 0.03% sodium azide and 5 mM DTT. The complex was incubated for 32 minutes with mixing at 4° C. and concentrated to 1 ml using a 5000 molecular weight cut off Ultrafree micro concentrator (catalog #UFC3LGC25, Millipore Corporation, Bedford, Mass., USA). The complex was centrifuged at 98,000×g for 30 minutes at 4° C. and the supernatant used for crystallization studies in example 8.

Example 8

Crystallization of Double Mutant HDM2 (17-125) F55Y/Y76H-cpd.1 Complex

The double mutant HDM2 (17-125) F55Y/Y76H-cpd.1 complex as described in example 7 was crystallized using a hanging-drop vapor diffusion method. The protein (0.5 μl; 30.6 mg/ml) in 50 mM Hepes-potassium hydroxide, pH7.5, 0.15 M potassium chloride, 1 mM EDTA, 0.03% sodium azide, 5 mM DTT buffer was mixed with an equal volume of precipitant solution containing 1.8 M ammonium sulfate, 0.1 M sodium acetate, pH 4.1 placed on the underside of a siliconized Teflon coverslip and sealed in close proximity to 0.08 ml of the precipitant solution. Crystallization plates were incubated at 4° C. Hexagonal rod crystals (0.01×0.05 mm) grew over 13-23 days.

Example 9

Photomicrograph of Double Mutant HDM2 (17-125) F55Y/Y76H-cpd.1 Complex Crystals A photomicrographic image of the crystal was prepared (FIG. 1). A description of the crystal is set forth below:

70× Magnification 1.8 M ammonium sulfate, 0.1 M sodium acetate, pH 4.1

23 days@4° C.

Example 10

Crystallographic Analysis of Double Mutant HDM2 (17-125)F55Y/Y76H-cpd.1

Prior to data collection, crystals were harvested at 4° C. and transferred into cryo-protectant; 1.8 M ammonium sulfate, 0.1 M sodium acetate, pH 4.1, 25% glycerol for 2 minutes and frozen in liquid nitrogen. The frozen crystals were then mounted onto the X-ray detector in a nitrogen cooled stream. X-ray diffraction was collected at the Advanced Photon Source sector 32 on the ID beamline. This beamline was equipped with a Mar165 CCD detector. Data were integrated and scaled using the HKL package.

| Data collection statistics: | |
| --- | --- |
| Resolution | 20.0-1.89 Å |
| No. of collected reflections | 269244 |
| No. of unique reflections (F >= 0) | 17709 |
| R-sym | 8.4% |
| Percent of theoretical (I/s >= 1) | 97.4% |
| Unit Cell | a = 90.9 Å, b = 90.9 Å, c = 90.8 Å, α = β = γ = 90° |
| Space Group | P6$_1$22 |
| Asymmetric unit | 2 molecules |

Example 11

Double Mutant HDM2 (17-125) F55Y/Y76H-cpd.1 Complex Structure Determination

The crystal structure was solved using molecular replacement using the search model 1RV1. Refinement was done using the program CNX2002 (Accelrys Inc.; San Diego, Calif.).

| | |
| --- | --- |
| Theoretical number of reflections | 18021 |
| Resolution Limits | 50.0-1.90 Å |
| Number of unobserved reflections | 458 (2.5%) |
| Number of reflections in working set | 16663 (92.5%) |
| Number of reflections in test set | 900 (5.0%) |
| Number of protein residues | 183 |
| Number of solvent atoms | 55 |
| R-factor | 0.28 |
| R-free | 0.34 |
| RMSD bond length | 0.0085 Å |
| RMSD bond angles | 1.29° |

Example 12

Structure and Activity of HDM2 Inhibitor cpd.2

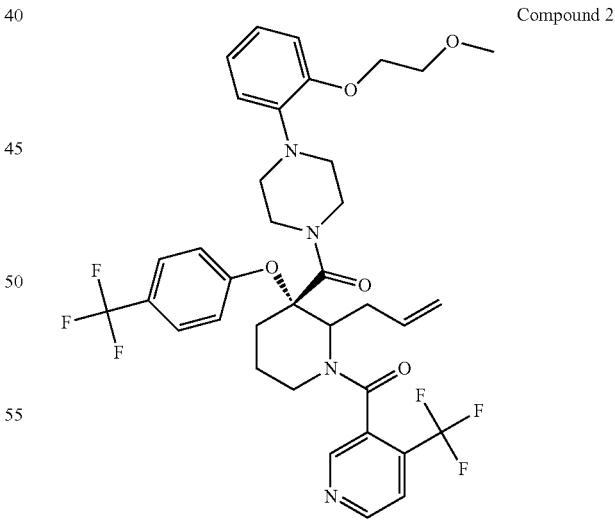

Compound 2

In vitro binding assays were performed to assess the affinity of cpd.2 to HDM2 using both Fluorescent polarization assay (Zhang R, Mayhood T, Lipari P, Wang Y, Durkin J, Syto R, Gesell J, McNemar C, Windsor W. (2004) Fluorescence polarization assay and inhibitor design for MDM2/p53 interaction. Analytical Biochemistry 331(1):138-146) and TdF assay. The results of these assays are set forth below:

Fluorescent polarization assay IC50 (nM): <5000
Fluorescent polarization assay Ki (nM): <2000
*TdF Kd (nM): <2000

Example 13

Preparation of Double Mutant HDM2 (17-125) F55Y/Y76H-cpd.2 Complex 1.1 mM cpd.2 (20 mM cpd.2 (DMSO)) was added to HDM2 (17-125) F55Y/Y76H (14 mg/ml; 1.1 mM). The complex was incubated at 2° C. for 45 minutes. The sample was clarified by low speed centrifugation (5 minutes×1000 g), concentrated using a 5000 Molecular Weight Cut Off Millipore Ultrafree micro concentrator (catalog #UFC3LGC25, Millipore corporation, Bedford, Mass., USA) to prepare a 42 mg/ml; 3.5 mM HDM2 (17-125) F55Y/Y76H-cpd.2 complex in 33 ul of 50 mM Hepes-potassium hydroxide, pH 7.5, 0.15 M potassium chloride, 1 mM EDTA, 0.03% sodium azide, 5 mM DTT, 5% DMSO. This complex was used in examples 14 and 16.

Example 14

Nano-Crystallization of Double Mutant HDM2 (17-125) F55Y/Y76H-cpd.2 Complex

HDM2/cpd.2 complex (1.6 ul) as described in example 13 was screened in a Topaz 1.96 Screening Chip (Catalog# TPZ-M-1.96, Fluidigm Corporation, South San Francisco, Calif., USA; Hansen C. L., Skoardalakes, Berger, J. M. and Quake, S. R. (2002) A Robust and Scalable Microfluidic metering method that allows protein crystal growth by free interface diffusion. PNAS 99 (26) 16531-16536) versus the 96 crystallization screen; Ammonium Sulfate Suite (Catalog #06082-WD-1D-1, Qiagen Canada Inc.; Montreal, Canada). The free interface diffusion experiment was performed for 1 hour at 22° C. in a Topaz FID Crystallizer (Catalog #41000002, Fluidigm Corporation, South San Francisco, Calif., USA). Small crystals were observed microscopically within 15 hours at 22° C. from the reagent condition # 42: 0.2 M sodium phosphate, 2.2 M ammonium sulfate, pH 4.2.

Example 15

Figure 2:
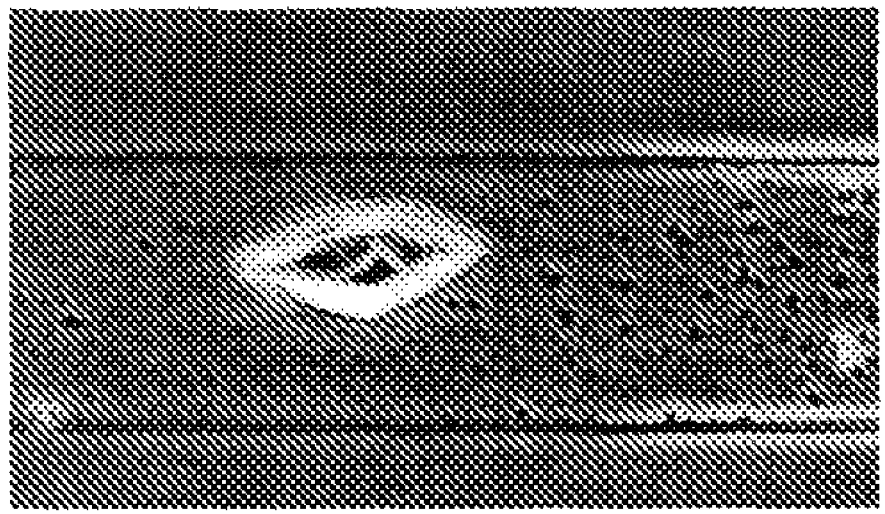
FIG. 2. Photomicrograph of double mutant HDM2 (17-125) F55Y/Y76H-cpd.2 complex nano-crystals.

Photomicrograph of Double Mutant HDM2 (17-125) F55Y/Y76H-cpd.2 Complex Nano-Crystals A photomicrographic image of the crystal as prepared (FIG. 2). A description of the crystal is set forth below:

200× magnification

Fluidigm Chip 1-96 (example 14)

0.2 M sodium phosphate 2.2 M ammonium sulfate, pH 4.2

18 hours at 22° C.

Example 16

Vapor Diffusion-Crystallization of Double Mutant HDM2 (17-125) F55Y/Y76H-cpd.2 Complex The double mutant HDM2 (17-125) F55Y/Y76H-cpd.2 complex as described in example 13 was crystallized using a hanging-drop vapor diffusion method. 1 ul of HDM2 (17-125) F55Y/Y76H-cpd.2 complex (3.5 mM) in 50 mM Hepes-potassium hydroxide, pH 7.5, 0.15 M potassium chloride, 1 mM EDTA, 0.03% sodium azide, 5 mM DTT, 5% DMSO was mixed with 1 ul of precipitant solution containing 0.2 M sodium phosphate, 2.2 M ammonium sulfate, pH 4.2 placed on the underside of a siliconized Teflon coverslip and sealed in close proximity to 80 ul of the precipitant solution. Crystallization plates were incubated at 22° C.; X-ray diffraction quality crystals grew within 18 hours (0.05×0.05×0.15 mm).

Example 17

Photomicrograph of Double Mutant HDM2 (17-125) F55Y/Y76H-cpd.2 Complex Crystals

Figure 3:
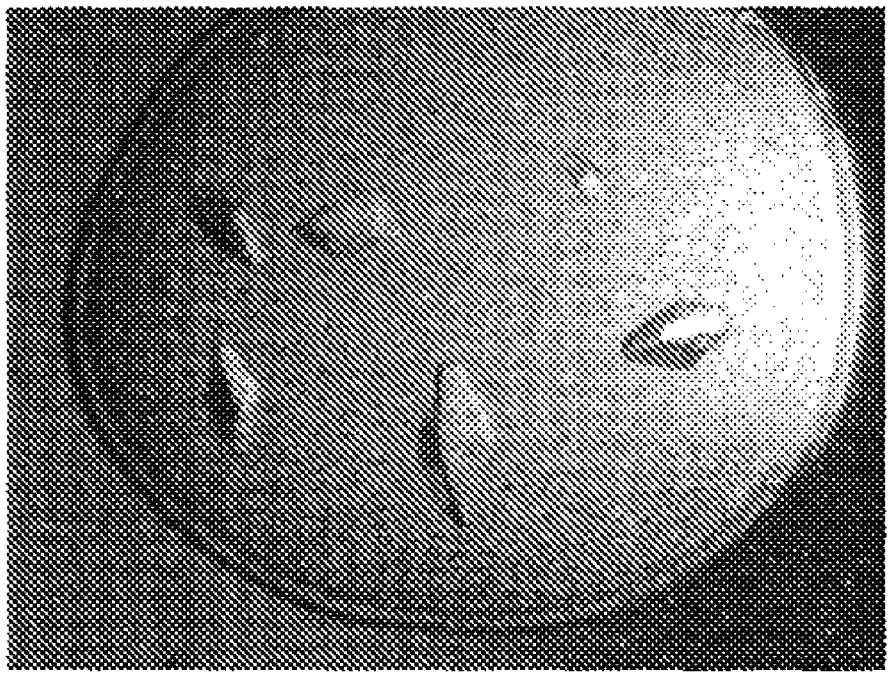
FIG. 3. Photomicrograph of double mutant HDM2 (17-125) F55Y/Y76H-cpd.2 complex crystals.

A photographic image of the crystal as prepared (FIG. 3). A description of the crystal is set forth below:

80× magnification vapor diffusion experiment (example 16)

0.2 M sodium phosphate 2.2 M ammonium sulfate, pH 4.2

15 hours at 22° C.

Example 18

Crystallographic Analysis of Single of Double Mutant HDM2 (17-125) F55Y/Y76H-cpd.2 Complex Prior to data collection, crystals were harvested and cryo-protected for 15 seconds in the crystallization solution containing 25% glycerol. The crystals were then frozen directly into liquid nitrogen. X-ray diffraction was collected using a Rigaku generator equipped with a Raxis 4 detector.

Data were integrated and scaled using the HKL package.

| Data collection statistics: | |
|---|---|
| Resolution | 50.0-2.05 Å |
| No. of collected reflections | 40930 |
| No. of unique reflections (F >= 0) | 12843 |
| R-sym | 5.3% |
| Percent of theoretical (I/s >= 1) | 98.2% |
| Unit Cell | a = 39.3 Å, b = 38.9, |
| | c = 131.3 Å, $\alpha = \beta = \gamma = 90°$ |
| Space Group | $P2_12_12_1$ |
| Asymmetric unit | 2 molecule |

Example 19

Structure Determination of Double Mutant HDM2 (17-125) F55Y/Y76H-cpd.2 Complex

The crystal structure was solved using molecular replacement using, as a search model, the structure from example 23. Refinement was done using the program CNX2002 (Accelrys, Inc.).

| | |
|---|---|
| Theoretical number of reflections | 12931 |
| Resolution Limits | 50.0-2.1 Å |
| Number of unobserved reflections | 230 (1.9%) |
| Number of reflections in working set | 11576 (93.4%) |

-continued

| | |
|---|---|
| Number of reflections in test set | 585 (4.7%) |
| Number of protein residues | 182 |
| Number of solvent atoms | 7 |
| R-factor | 0.294 |
| R-free | 0.359 |
| RMSD bond length | 0.008 Å |
| RMSD bond angles | 1.21° |

Example 20

Structure and Activity of HDM2 Inhibitor Compound 3

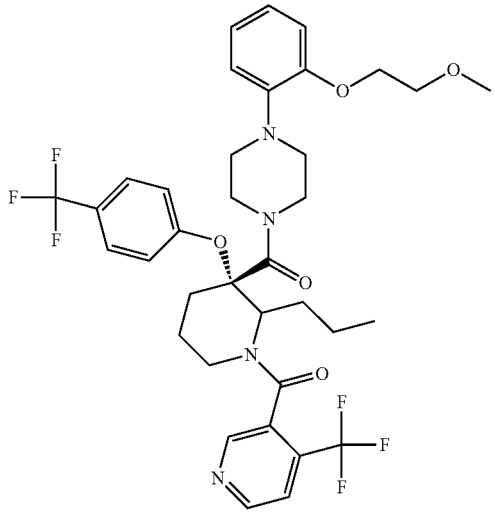

Compound 3

In vitro binding assays were performed to assess the affinity of cpd.3 to HDM2 using both Fluorescent polarization assay (Zhang R, Mayhood T, Lipari P, Wang Y, Durkin J, Syto R, Gesell J, McNemar C, Windsor W. (2004) Fluorescence polarization assay and inhibitor design for MDM2/p53 interaction. Analytical Biochemistry 331(1):138-146) and TdF assay. The results of these experiments are set forth below:

Fluorescent polarization assay IC50 (nM): <5000

Fluorescent polarization assay Ki (nM): <2000

*TdF Kd (nM): <2000

Example 21

Preparation of Double Mutant HDM2 (17-125) F55Y/Y76H-cpd.3 Complex

A 100 mM cpd.3 (DMSO) solution was added to 1 mM final concentration to 11 mg/ml; 887 mM HDM2 and incubated on ice for 45 minutes to form the complex. The centrifuged clarified double mutant HDM2 (17-125) F55Y/Y76H-cpd.3 complex in 50 mM Hepes-potassium hydroxide, pH 7.5, 0.15 M potassium chloride, 1 mM EDTA, 0.03% sodium azide, 5 mM DTT, 1% DMSO. This complex was used in examples 22 and 23.

Example 22

Nano-Crystallization of Double Mutant HDM2 (17-125) F55Y/Y76H-cpd.3 Complex

HDM2-cpd.3 complex (1.6 ul) as described in example 21 was screened in a Topaz 1.96 Screening Chip (Catalog# TPZ-M-1.96, Fluidigm Corporation, South San Francisco, Calif., USA; Hansen C. L., Skoardalakes, Berger, J. M. and Quake, S. R. (2002) A Robust and Scalable Microfluidic metering method that allows protein crystal growth by free interface diffusion PNAS 99(26): 16531-16536) versus the 96 crystallization screen; Ammonium Sulfate Suite (Catalog #06082-WD-1D-1, Qiagen Canada Inc., Montreal, Canada). The free interface diffusion experiment was performed for 1 hour at 22° C. in a Topaz FID Crystallizer (Catalog #41000002, Fluidigm Corporation, South San Francisco, Calif., USA). Small crystals were observed microscopically after 4 days at 22° C. from the reagent condition #42: 0.2 M sodium phosphate, 2.2 M ammonium sulfate, pH 4.2.

Example 23

Vapor-Diffusion Crystallization of Double Mutant HDM2 (17-125) F55Y/Y76H-cpd.3 Complex The double mutant HDM2 (17-125) F55Y/Y76H-cpd.3 complex as described in example 20 was crystallized using a hanging-drop vapor diffusion method. 1 ul of HDM2 (17-125) F55Y/Y76H-cpd.3 complex in 50 mM Hepes-potassium hydroxide, pH 7.5, 0.15 M potassium chloride, 1 mM EDTA, 0.03% sodium azide, 5 mM DTT, 5% DMSO was mixed with 1 ul of precipitant solution containing 0.2 M sodium phosphate, 1.96 M ammonium sulfate, pH 4.2 placed on the underside of a siliconized Teflon coverslip and sealed in close proximity to 80 ul of the precipitant solution. Crystallization plates were incubated at 22° C.; X-ray diffraction quality crystals grew within 2-5 days (0.05×0.05×0.075 mm).

Example 24

Figure 4:
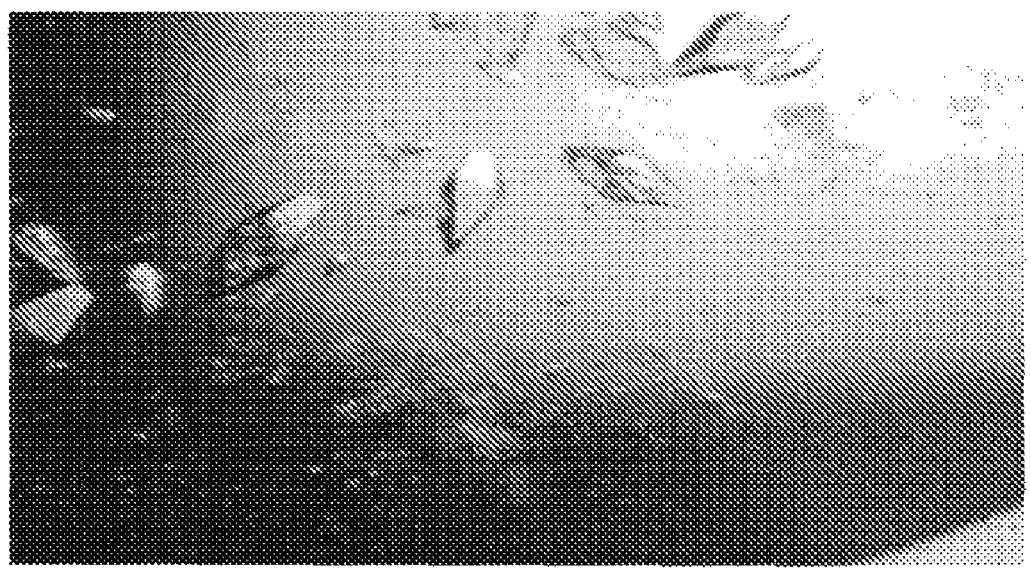
FIG. 4. Photomicrograph of double mutant HDM2 (17-125) F55Y/Y76H-cpd.3 complex crystals from vapor-diffusion experiment.

Photomicrograph of Double Mutant HDM2 (17-125) F55Y/Y76H-cpd.3 Complex Crystals Form Vapor-Diffusion Experiment A photomicrographic image of the crystal as prepared (FIG. 4). A description of the crystal is set forth below:

70× Magnification

Vapor diffusion experiment 0.2 M sodium phosphate 1.96 M ammonium sulfate 5 days at 22° C.

Example 25

Crystallographic Analysis of Single of Double Mutant HDM2 (17-125) F55Y/Y76H-cpd.3 Complex Prior to data collection, crystals were harvested and cryo-protected for 1-3 minutes in the crystallization solution containing 25% glycerol. The crystals were then frozen directly into liquid nitrogen. X-ray diffraction was collected using a Rigaku generator equipped with a Raxis 4++ detector. Data were integrated and scaled using the HKL package.

| Data collection statistics: | |
|---|---|
| Resolution | 50.0-2.3 Å |
| No. of collected reflections | 69479 |
| No. of unique reflections (F >= 0) | 9558 |
| R-sym | 7.9% |
| Percent of theoretical (I/s >= 1) | 99.9% |
| Unit Cell | a = 39.9 Å, b = 39.8 Å, c = 134.5 Å, $\alpha = \beta = \gamma = 90°$ |
| Space Group | $P2_12_12_1$ |
| Asymmetric unit | 2 molecules |

Example 26

Structure Determination of Double Mutant HDM2 (17-125) F55Y/Y76H-cpd.3 Complex

The crystal structure was solved using molecular replacement using the search models 1YCR from the PDB. Refinement was done using the program CNX2002 (Accelrys Inc.).

| | |
|---|---|
| Theoretical number of reflections | 9452 |
| Resolution Limits | 50.0-2.35 Å |
| Number of unobserved reflections | 23 (0.2%) |
| Number of reflections in working set | 8973 (94.9%) |
| Number of reflections in test set | 456 (4.8%) |
| Number of protein residues | 182 |
| Number of solvent atoms | 25 |
| R-factor | 0.255 |
| R-free | 0.316 |
| RMSD bond length | 0.009 Å |
| RMSD bond angles | 1.24° |

Example 27

Structure and Activity of HDM2 Inhibitor Compound 4

Compound 4

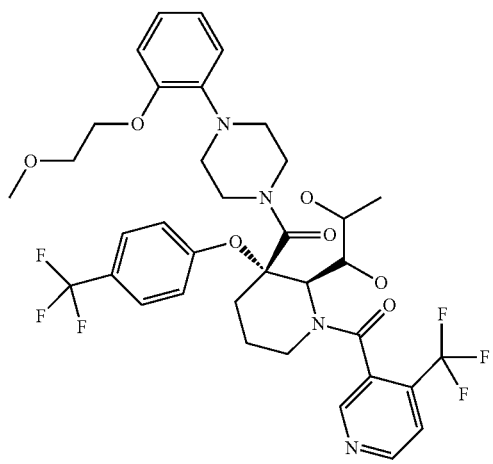

In vitro binding assays were performed to assess the affinity of cpd.4 to HDM2 using both Fluorescent polarization assay (Zhang R, Mayhood T, Lipari P, Wang Y, Durkin J, Syto R, Gesell J, McNemar C, Windsor W. (2004) Fluorescence polarization assay and inhibitor design for MDM2/p53 interaction. Analytical Biochemistry 331(1):138-146) and TdF assay.

Fluorescent polarization assay IC50 (nM): <5000
Fluorescent polarization assay Ki (nM): <2000
*TdF Kd (nM): <2000

Example 28

Preparation of Double Mutant HDM2 (17-125) F55Y/Y76H-cpd.4 Complex

A 100 mM cpd.4 (DMSO) solution was added to 1 mM final concentration to 11 mg/ml; 887 µM HDM2 (17-125) F55Y/Y76H-cpd.4 and incubated on ice for 45 minutes to form the complex. The centrifuged clarified double mutant HDM2 (17-125) F55Y/Y76H-cpd.3 complex in 50 mM Hepes-potassium hydroxide, pH 7.5, 0.15 M potassium chloride, 1 mM EDTA, 0.03% sodium azide, 5 mM DTT, 10% DMSO was used in examples 29 and 31.

Example 29

Nano-Crystallization of Double Mutant HDM2 (17-125) F55Y/Y76H-cpd.4 Complex

HDM2-cpd.4 complex (1.6 ul) as described in example 28 was screened in a Topaz 1.96 Screening Chip (Catalog# TPZ-M-1.96, Fluidigm Corporation, South San Francisco, Calif., USA; Hansen C. L., Skoardalakes, Berger, J. M. and Quake, S. R. (2002) A Robust and Scalable Microfluidic metering method that allows protein crystal growth by free interface diffusion. PNAS 99 (26) 16531-16536) versus the 96 crystallization screen; Ammonium Sulfate Suite (Catalog #06082-WD-1D-1, Qiagen Canada Inc., Montreal, Canada). The free interface diffusion experiment was performed for 1 hour at 22° C. in a Topaz FID Crystallizer (Catalog #41000002, Fluidigm Corporation, South San Francisco, Calif., USA). Small crystals were observed microscopically after 1 day at 22° C. from the reagent condition # 61: 0.1 M citric acid, 2.4 M ammonium sulfate, pH 4.0.

Example 30

Figure 5:
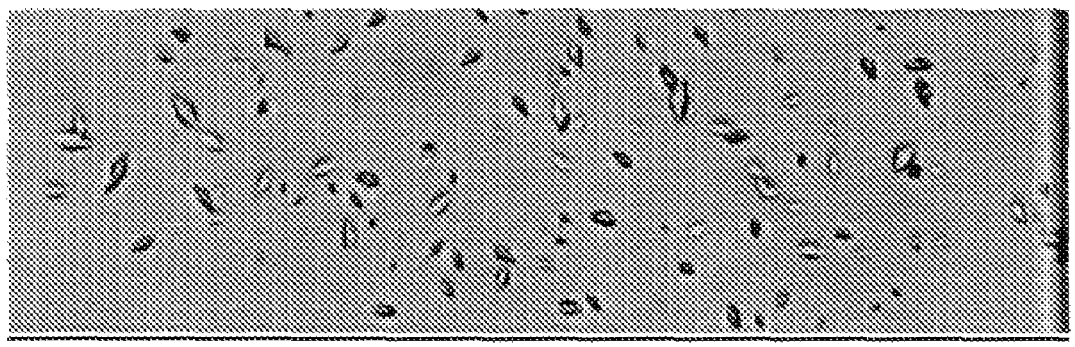
FIG. 5. Photomicrograph of double mutant HDM2 (17-125) F55Y/Y76H-cpd.4 complex nano-crystals.

Photomicrograph of Double Mutant HDM2 (17-125) F55Y/Y76H-cpd.4 Complex Nano-Crystals A photomicrographic image of the crystal as prepared (FIG. 5). A description of the crystal is set forth below:

200× magnification

Fluidigm Chip 1-96 (example 29)

0.1 M citric acid, 2.4 M ammonium sulfate, pH 4.0

18 hours at 22° C.

Example 31

Vapor Diffusion Crystallization of Double Mutant HDM2 (17-125) F55Y/Y76H-cpd.4 Complex The double mutant HDM2 (17-125) F55Y/Y76H-cpd.4 complex as described in example 28 was crystallized using a hanging-drop vapor diffusion method. 1 ul of HDM2 (17-125) F55Y/Y76H-cpd.4 complex in 50 mM Hepes-potassium hydroxide, pH 7.5, 0.15 M potassium chloride, 1 mM EDTA, 0.03% sodium azide, 5 mM DTT, 10% DMSO was mixed with 1 ul of precipitant solution containing 0.1 M citric acid, pH 4.0, 2.9 M ammonium sulfate placed on the underside of a siliconized Teflon coverslip and sealed in close proximity to 80 ul of the precipitant solution. Crystallization plates were incubated at 22° C.; X-ray diffraction quality crystals grew within 3 days (0.05×0.05×0.075 mm).

Example 32

Photomicrograph of Double Mutant HDM2 (17-125) F55Y/Y76H-cpd.4 Complex Crystals

Figure 6:
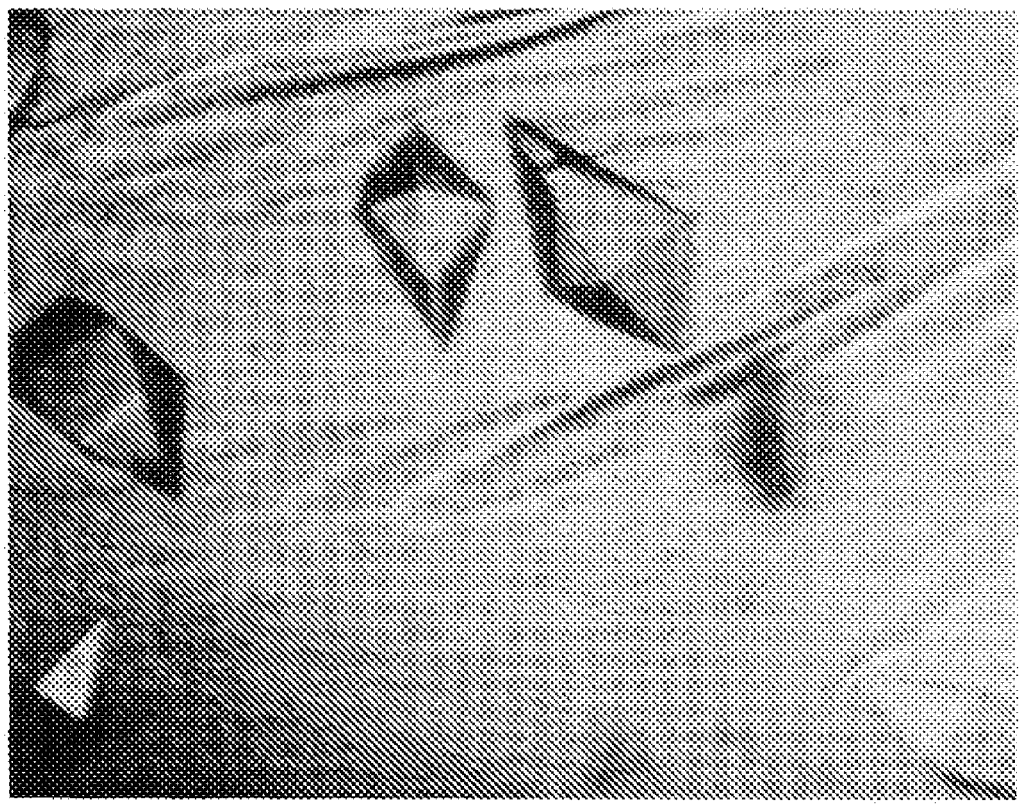
FIG. 6. Photomicrograph of double mutant HDM2 (17-125) F55Y/Y76H-cpd.4 complex crystals.

A photomicrographic image of the crystal as prepared (FIG. 6). A description of the crystal is set forth below:

70× Magnification

Vapor diffusion experiment 0.1 M citric acid, pH 4.0

2.29 M ammonium sulfate 4 days at 22° C.

Example 33

Crystallographic Analysis of Single of Double Mutant HDM2 (17-125) F55Y/Y76H-cpd.4 Complex Prior to data collection, crystals were harvested and cryoprotected for 5 seconds in the crystallization solution containing 25% glycerol. The crystals were then frozen directly into liquid nitrogen. X-ray diffraction was collected using a Rigaku generator equipped with a Raxis 4++detector. Data were integrated and scaled using the HKL package.

| Data collection statistics: | |
| --- | --- |
| Resolution | 50.0-2.14 Å |
| No. of collected reflections | 38239 |
| No. of unique reflections (F >= 0) | 5414 |
| R-sym | 7.3% |
| Percent of theoretical (I/s >= 1) | 96.6% |
| Unit Cell | a = 38.7 Å, b = 38.7 Å, c = 121.1 Å, $\alpha = \beta = \gamma = 90°$ |
| Space Group | $P4_32_12$ |
| Asymmetric unit | 1 molecules |

Example 34

Structure Determination of Double Mutant HDM2 (17-125) F55Y/Y76H-cpd.4 Complex

The crystal structure was solved using molecular replacement using the search model of the refined structure in example 26. Refinement was done using the program Auto-Buster (Global Phasing, Ltd.; Cambridge, UK).

| | |
| --- | --- |
| Resolution Limits | 50.0-2.14 Å |
| Number of protein residues | 96 |
| Number of solvent atoms | 23 |
| R-factor | 0.208 |
| R-free | 0.278 |
| RMSD bond length | 0.011 Å |
| RMSD bond angles | 1.22° |

Published U.S. patent application no. US2005/0037383 is herein incorporated by reference in its entirety.

TABLE 1

Structural coordinates of HDM2 (17-125; F55Y/Y76H) (SEQ ID NO: 2) complexed with compound 1.

SER, CB, 22, 16.7, 5.5, 39.7, 25, A
SER, OG, 22, 17.4, 5.3, 40.9, 26, A
SER, C, 22, 18.6, 6.9, 39.0, 24, A
SER, O, 22, 19.2, 7.5, 39.9, 26, A
SER, N, 22, 16.6, 6.8, 37.6, 13, A
SER, CA, 22, 17.1, 6.8, 39.0, 20, A
GLU, N, 23, 19.3, 6.2, 38.1, 23, A
GLU, CA, 23, 20.7, 6.3, 38.0, 19, A
GLU, CB, 23, 21.4, 4.9, 38.1, 17, A
GLU, CG, 23, 20.9, 4.1, 39.3, 22, A
GLU, CD, 23, 21.6, 2.7, 39.3, 17, A
GLU, OE1, 23, 21.7, 2.1, 38.3, 18, A
GLU, OE2, 23, 21.9, 2.3, 40.4, 25, A
GLU, C, 23, 21.0, 6.9, 36.6, 17, A
GLU, O, 23, 22.0, 6.7, 36.0, 18, A
GLN, N, 24, 19.9, 7.5, 36.0, 18, A
GLN, CA, 24, 20.0, 8.0, 34.7, 21, A
GLN, CB, 24, 18.8, 7.6, 33.9, 25, A
GLN, CG, 24, 18.8, 8.1, 32.5, 33, A
GLN, CD, 24, 17.6, 7.8, 31.7, 37, A
GLN, OE1, 24, 17.0, 6.7, 31.9, 36, A
GLN, NE2, 24, 17.2, 8.7, 30.8, 37, A
GLN, C, 24, 20.2, 9.5, 34.7, 21, A
GLN, O, 24, 19.3, 10.2, 35.2, 23, A
GLU, N, 25, 21.2, 10.0, 34.1, 19, A
GLU, CA, 25, 21.5, 11.4, 34.1, 25, A
GLU, CB, 25, 22.9, 11.7, 34.3, 29, A
GLU, CG, 25, 23.2, 13.0, 35.0, 37, A
GLU, CD, 25, 24.6, 13.2, 35.5, 40, A
GLU, OE1, 25, 25.5, 13.5, 34.6, 43, A
GLU, OE2, 25, 24.9, 13.0, 36.7, 41, A
GLU, C, 25, 21.0, 11.9, 32.7, 24, A
GLU, O, 25, 21.8, 11.7, 31.7, 26, A
THR, N, 26, 19.8, 12.4, 32.5, 23, A
THR, CA, 26, 19.3, 12.8, 31.2, 23, A
THR, CB, 26, 17.8, 12.8, 31.2, 24, A
THR, OG1, 26, 17.4, 11.4, 31.5, 26, A
THR, CG2, 26, 17.4, 13.2, 29.8, 22, A
THR, C, 26, 19.8, 14.2, 30.8, 22, A
THR, O, 26, 19.4, 15.2, 31.4, 23, A
LEU, N, 27, 20.4, 14.3, 29.6, 21, A
LEU, CA, 27, 20.9, 15.6, 29.1, 24, A
LEU, CB, 27, 22.4, 15.5, 28.9, 22, A
LEU, CG, 27, 23.1, 15.1, 30.2, 22, A
LEU, CD1, 27, 24.6, 15.2, 29.9, 21, A
LEU, CD2, 27, 22.7, 16.0, 31.3, 25, A
LEU, C, 27, 20.2, 16.0, 27.8, 25, A
LEU, O, 27, 19.6, 15.1, 27.1, 31, A
VAL, N, 28, 20.3, 17.2, 27.4, 23, A
VAL, CA, 28, 19.8, 17.8, 26.2, 23, A
VAL, CB, 28, 18.5, 18.6, 26.4, 21, A
VAL, CG1, 28, 17.5, 17.8, 27.0, 19, A
VAL, CG2, 28, 18.8, 19.8, 27.3, 22, A
VAL, C, 28, 20.9, 18.6, 25.5, 26, A
VAL, O, 28, 21.7, 19.3, 26.2, 28, A
ARG, N, 29, 20.9, 18.6, 24.2, 23, A
ARG, CA, 29, 21.9, 19.3, 23.4, 24, A
ARG, CB, 29, 22.6, 18.4, 22.4, 24, A
ARG, CG, 29, 23.5, 19.0, 21.4, 25, A
ARG, CD, 29, 24.1, 18.0, 20.5, 25, A
ARG, NE, 29, 24.9, 17.1, 21.3, 28, A
ARG, CZ, 29, 26.1, 17.4, 21.9, 30, A
ARG, NH1, 29, 26.5, 18.6, 21.8, 34, A
ARG, NH2, 29, 26.7, 16.5, 22.6, 31, A
ARG, C, 29, 21.3, 20.4, 22.7, 20, A
ARG, O, 29, 20.8, 20.3, 21.5, 21, A
PRO, N, 30, 21.2, 21.6, 23.3, 18, A
PRO, CD, 30, 21.9, 22.0, 24.5, 19, A
PRO, CA, 30, 20.7, 22.8, 22.7, 18, A
PRO, CB, 30, 21.1, 23.9, 23.6, 19, A
PRO, CG, 30, 21.2, 23.2, 24.9, 20, A
PRO, C, 30, 21.1, 23.1, 21.2, 20, A
PRO, O, 30, 22.2, 22.9, 20.9, 17, A
LYS, N, 31, 20.2, 23.6, 20.4, 25, A
LYS, CA, 31, 20.5, 23.9, 19.0, 25, A
LYS, CB, 31, 19.3, 24.2, 18.2, 24, A

TABLE 1-continued

Structural coordinates of HDM2 (17-125; F55Y/Y76H) (SEQ ID NO: 2) complexed with compound 1.

| | | | | | | |
|---|---|---|---|---|---|---|
| LYS, | CG, | 31, | 18.5, | 22.9, | 17.8, | 27, A |
| LYS, | CD, | 31, | 17.3, | 23.1, | 17.0, | 29, A |
| LYS, | CE, | 31, | 16.7, | 21.8, | 16.6, | 30, A |
| LYS, | NZ, | 31, | 15.5, | 22.0, | 15.8, | 27, A |
| LYS, | C, | 31, | 21.4, | 25.1, | 19.0, | 26, A |
| LYS, | O, | 31, | 21.4, | 25.9, | 19.9, | 29, A |
| PRO, | N, | 32, | 22.3, | 25.3, | 18.0, | 27, A |
| PRO, | CD, | 32, | 22.2, | 24.5, | 16.7, | 23, A |
| PRO, | CA, | 32, | 23.2, | 26.4, | 17.8, | 25, A |
| PRO, | CB, | 32, | 23.4, | 26.5, | 16.3, | 23, A |
| PRO, | CG, | 32, | 23.4, | 25.0, | 15.9, | 25, A |
| PRO, | C, | 32, | 22.8, | 27.7, | 18.4, | 21, A |
| PRO, | O, | 32, | 23.6, | 28.3, | 19.2, | 22, A |
| LEU, | N, | 33, | 21.6, | 28.2, | 18.1, | 18, A |
| LEU, | CA, | 33, | 21.2, | 29.5, | 18.6, | 20, A |
| LEU, | CB, | 33, | 20.1, | 30.1, | 17.7, | 22, A |
| LEU, | CG, | 33, | 20.5, | 30.6, | 16.3, | 24, A |
| LEU, | CD1, | 33, | 19.3, | 31.4, | 15.8, | 25, A |
| LEU, | CD2, | 33, | 21.7, | 31.6, | 16.5, | 19, A |
| LEU, | C, | 33, | 20.7, | 29.5, | 20.1, | 19, A |
| LEU, | O, | 33, | 20.7, | 30.6, | 20.7, | 18, A |
| LEU, | N, | 34, | 20.3, | 28.4, | 20.6, | 21, A |
| LEU, | CA, | 34, | 19.9, | 28.3, | 22.0, | 20, A |
| LEU, | CB, | 34, | 19.1, | 27.1, | 22.3, | 19, A |
| LEU, | CG, | 34, | 18.7, | 27.0, | 23.7, | 21, A |
| LEU, | CD1, | 34, | 18.0, | 28.3, | 24.2, | 21, A |
| LEU, | CD2, | 34, | 17.7, | 25.8, | 23.9, | 19, A |
| LEU, | C, | 34, | 21.2, | 28.3, | 22.8, | 19, A |
| LEU, | O, | 34, | 21.2, | 28.9, | 23.9, | 20, A |
| LEU, | N, | 35, | 22.2, | 27.6, | 22.3, | 22, A |
| LEU, | CA, | 35, | 23.4, | 27.5, | 23.0, | 24, A |
| LEU, | CB, | 35, | 24.4, | 26.5, | 22.2, | 21, A |
| LEU, | CG, | 35, | 25.6, | 26.1, | 23.0, | 25, A |
| LEU, | CD1, | 35, | 25.3, | 25.3, | 24.3, | 24, A |
| LEU, | CD2, | 35, | 26.5, | 25.2, | 22.1, | 23, A |
| LEU, | C, | 35, | 24.1, | 28.9, | 23.1, | 27, A |
| LEU, | O, | 35, | 24.6, | 29.2, | 24.2, | 28, A |
| LYS, | N, | 36, | 24.0, | 29.6, | 22.1, | 28, A |
| LYS, | CA, | 36, | 24.5, | 31.0, | 22.0, | 27, A |
| LYS, | CB, | 36, | 24.4, | 31.6, | 20.6, | 30, A |
| LYS, | CG, | 36, | 24.9, | 33.0, | 20.5, | 36, A |
| LYS, | CD, | 36, | 24.9, | 33.4, | 19.0, | 40, A |
| LYS, | CE, | 36, | 25.6, | 34.7, | 18.7, | 42, A |
| LYS, | NZ, | 36, | 25.7, | 35.1, | 17.3, | 46, A |
| LYS, | C, | 36, | 23.8, | 31.9, | 23.1, | 27, A |
| LYS, | O, | 36, | 24.3, | 32.7, | 23.7, | 25, A |
| LEU, | N, | 37, | 22.5, | 31.6, | 23.2, | 26, A |
| LEU, | CA, | 37, | 21.7, | 32.4, | 24.1, | 25, A |
| LEU, | CB, | 37, | 20.2, | 32.2, | 23.9, | 25, A |
| LEU, | CG, | 37, | 19.2, | 33.0, | 24.7, | 26, A |
| LEU, | CD1, | 37, | 17.8, | 32.8, | 24.2, | 30, A |
| LEU, | CD2, | 37, | 19.2, | 32.7, | 26.2, | 25, A |
| LEU, | C, | 37, | 22.2, | 32.0, | 25.5, | 25, A |
| LEU, | O, | 37, | 22.3, | 32.9, | 26.4, | 20, A |
| LEU, | N, | 38, | 22.4, | 30.7, | 25.7, | 23, A |
| LEU, | CA, | 38, | 22.8, | 30.2, | 27.1, | 26, A |
| LEU, | CB, | 38, | 22.7, | 28.7, | 27.1, | 25, A |
| LEU, | CG, | 38, | 21.3, | 28.1, | 26.7, | 23, A |
| LEU, | CD1, | 38, | 21.4, | 26.6, | 26.8, | 21, A |
| LEU, | CD2, | 38, | 20.3, | 28.6, | 27.7, | 25, A |
| LEU, | C, | 38, | 24.2, | 30.7, | 27.4, | 28, A |
| LEU, | O, | 38, | 24.5, | 31.2, | 28.5, | 28, A |
| LYS, | N, | 39, | 25.2, | 30.5, | 26.5, | 25, A |
| LYS, | CA, | 39, | 26.5, | 30.9, | 26.7, | 26, A |
| LYS, | CB, | 39, | 27.4, | 30.4, | 25.5, | 23, A |
| LYS, | CG, | 39, | 27.9, | 29.0, | 25.7, | 23, A |
| LYS, | CD, | 39, | 28.7, | 28.5, | 24.5, | 22, A |
| LYS, | CE, | 39, | 29.1, | 27.1, | 24.8, | 20, A |
| LYS, | NZ, | 39, | 29.9, | 26.4, | 23.7, | 27, A |
| LYS, | C, | 39, | 26.7, | 32.4, | 26.9, | 23, A |
| LYS, | O, | 39, | 27.7, | 32.8, | 27.5, | 22, A |
| SER, | N, | 40, | 25.7, | 33.1, | 26.5, | 23, A |
| SER, | CA, | 40, | 25.7, | 34.6, | 26.6, | 20, A |
| SER, | CB, | 40, | 24.6, | 35.3, | 25.8, | 24, A |
| SER, | OG, | 40, | 23.4, | 35.1, | 26.4, | 26, A |
| SER, | C, | 40, | 25.6, | 35.0, | 28.1, | 22, A |
| SER, | O, | 40, | 25.9, | 36.2, | 28.5, | 25, A |
| VAL, | N, | 41, | 25.0, | 34.1, | 28.9, | 19, A |
| VAL, | CA, | 41, | 24.8, | 34.5, | 30.4, | 18, A |
| VAL, | CB, | 41, | 23.4, | 34.4, | 30.8, | 17, A |
| VAL, | CG1, | 41, | 22.7, | 35.7, | 30.5, | 14, A |
| VAL, | CG2, | 41, | 22.7, | 33.2, | 30.1, | 20, A |
| VAL, | C, | 41, | 25.7, | 33.6, | 31.3, | 20, A |
| VAL, | O, | 41, | 25.3, | 33.4, | 32.5, | 20, A |
| GLY, | N, | 42, | 26.8, | 33.1, | 30.7, | 23, A |
| GLY, | CA, | 42, | 27.7, | 32.3, | 31.6, | 22, A |
| GLY, | C, | 42, | 27.9, | 30.8, | 31.2, | 24, A |
| GLY, | O, | 42, | 29.0, | 30.3, | 31.4, | 22, A |
| ALA, | N, | 43, | 26.8, | 30.1, | 30.7, | 25, A |
| ALA, | CA, | 43, | 26.9, | 28.7, | 30.3, | 25, A |
| ALA, | CB, | 43, | 25.7, | 28.3, | 29.5, | 22, A |
| ALA, | C, | 43, | 28.2, | 28.5, | 29.6, | 26, A |
| ALA, | O, | 43, | 28.6, | 29.3, | 28.8, | 24, A |
| GLN, | N, | 44, | 28.8, | 27.3, | 29.8, | 29, A |
| GLN, | CA, | 44, | 30.0, | 26.9, | 29.1, | 31, A |
| GLN, | CB, | 44, | 31.2, | 27.1, | 30.1, | 34, A |
| GLN, | CG, | 44, | 31.5, | 28.5, | 30.4, | 38, A |
| GLN, | CD, | 44, | 32.8, | 28.6, | 31.3, | 41, A |
| GLN, | OE1, | 44, | 32.8, | 28.1, | 32.5, | 42, A |
| GLN, | NE2, | 44, | 33.8, | 29.2, | 30.8, | 42, A |
| GLN, | C, | 44, | 30.1, | 25.5, | 28.6, | 31, A |
| GLN, | O, | 44, | 31.1, | 24.9, | 28.4, | 31, A |
| LYS, | N, | 45, | 28.9, | 24.8, | 28.5, | 29, A |
| LYS, | CA, | 45, | 28.8, | 23.4, | 28.1, | 29, A |
| LYS, | CB, | 45, | 28.1, | 22.6, | 29.1, | 31, A |
| LYS, | CG, | 45, | 28.9, | 22.5, | 30.5, | 34, A |
| LYS, | CD, | 45, | 28.4, | 21.4, | 31.4, | 34, A |
| LYS, | CE, | 45, | 26.9, | 21.7, | 31.8, | 38, A |
| LYS, | NZ, | 45, | 26.4, | 20.6, | 32.6, | 40, A |
| LYS, | C, | 45, | 28.0, | 23.3, | 26.8, | 27, A |
| LYS, | O, | 45, | 27.5, | 24.3, | 26.3, | 28, A |
| ASP, | N, | 46, | 28.0, | 22.2, | 26.2, | 30, A |
| ASP, | CA, | 46, | 27.2, | 21.9, | 25.0, | 30, A |
| ASP, | CB, | 46, | 28.0, | 21.2, | 23.9, | 34, A |
| ASP, | CG, | 46, | 29.2, | 22.0, | 23.5, | 38, A |
| ASP, | OD1, | 46, | 29.0, | 23.2, | 23.1, | 39, A |
| ASP, | OD2, | 46, | 30.4, | 21.5, | 23.5, | 43, A |
| ASP, | C, | 46, | 25.9, | 21.1, | 25.3, | 26, A |
| ASP, | O, | 46, | 25.0, | 21.1, | 24.6, | 23, A |
| THR, | N, | 47, | 26.0, | 20.4, | 26.5, | 24, A |
| THR, | CA, | 47, | 24.9, | 19.6, | 26.9, | 23, A |
| THR, | CB, | 47, | 25.3, | 18.1, | 26.9, | 23, A |
| THR, | OG1, | 47, | 26.3, | 17.8, | 27.8, | 26, A |
| THR, | CG2, | 47, | 25.7, | 17.7, | 25.5, | 22, A |
| THR, | C, | 47, | 24.5, | 20.0, | 28.4, | 21, A |
| THR, | O, | 47, | 25.4, | 20.3, | 29.2, | 20, A |
| TYR, | N, | 48, | 23.2, | 20.1, | 28.6, | 19, A |
| TYR, | CA, | 48, | 22.8, | 20.5, | 30.0, | 20, A |
| TYR, | CB, | 48, | 22.3, | 21.9, | 29.9, | 15, A |
| TYR, | CG, | 48, | 23.3, | 22.9, | 29.4, | 19, A |
| TYR, | CD1, | 48, | 23.6, | 23.0, | 28.1, | 18, A |
| TYR, | CE1, | 48, | 24.5, | 23.9, | 27.6, | 21, A |
| TYR, | CD2, | 48, | 23.9, | 23.8, | 30.3, | 20, A |
| TYR, | CE2, | 48, | 24.9, | 24.7, | 29.9, | 20, A |
| TYR, | CZ, | 48, | 25.2, | 24.7, | 28.5, | 20, A |
| TYR, | OH, | 48, | 26.1, | 25.6, | 28.0, | 22, A |
| TYR, | C, | 48, | 21.6, | 19.6, | 30.4, | 18, A |
| TYR, | O, | 48, | 21.0, | 18.9, | 29.6, | 20, A |
| THR, | N, | 49, | 21.2, | 19.7, | 31.7, | 19, A |
| THR, | CA, | 49, | 20.1, | 19.0, | 32.1, | 15, A |
| THR, | CB, | 49, | 20.1, | 18.6, | 33.6, | 14, A |
| THR, | OG1, | 49, | 20.1, | 19.8, | 34.4, | 17, A |
| THR, | CG2, | 49, | 21.4, | 17.9, | 33.9, | 15, A |
| THR, | C, | 49, | 19.0, | 20.1, | 31.9, | 15, A |
| THR, | O, | 49, | 19.3, | 21.2, | 31.8, | 15, A |
| MET, | N, | 50, | 17.8, | 19.7, | 31.8, | 10, A |
| MET, | CA, | 50, | 16.7, | 20.6, | 31.6, | 15, A |
| MET, | CB, | 50, | 15.3, | 19.9, | 31.5, | 16, A |
| MET, | CG, | 50, | 15.0, | 19.4, | 30.1, | 24, A |
| MET, | SD, | 50, | 14.6, | 20.7, | 28.9, | 26, A |
| MET, | CE, | 50, | 13.7, | 21.8, | 29.9, | 21, A |
| MET, | C, | 50, | 16.7, | 21.7, | 32.6, | 13, A |

TABLE 1-continued

Structural coordinates of HDM2 (17-125; F55Y/Y76H) (SEQ ID NO: 2) complexed with compound 1.

MET, O, 50, 16.4, 22.8, 32.3, 11, A
LYS, N, 51, 17.0, 21.3, 33.9, 13, A
LYS, CA, 51, 17.0, 22.3, 35.0, 16, A
LYS, CB, 51, 17.2, 21.6, 36.3, 16, A
LYS, CG, 51, 15.9, 21.0, 36.9, 17, A
LYS, CD, 51, 16.1, 20.5, 38.3, 17, A
LYS, CE, 51, 14.8, 19.9, 38.9, 20, A
LYS, NZ, 51, 14.4, 18.7, 38.2, 21, A
LYS, C, 51, 18.0, 23.4, 34.7, 14, A
LYS, O, 51, 17.8, 24.5, 35.1, 15, A
GLU, N, 52, 19.2, 22.9, 34.2, 10, A
GLU, CA, 52, 20.2, 23.9, 33.9, 15, A
GLU, CB, 52, 21.5, 23.2, 33.5, 13, A
GLU, CG, 52, 22.0, 22.1, 34.5, 18, A
GLU, CD, 52, 23.3, 21.5, 34.2, 21, A
GLU, OE1, 52, 24.3, 22.0, 34.8, 26, A
GLU, OE2, 52, 23.3, 20.6, 33.4, 21, A
GLU, C, 52, 19.8, 24.8, 32.8, 13, A
GLU, O, 52, 20.1, 26.0, 32.8, 13, A
VAL, N, 53, 19.1, 24.2, 31.8, 11, A
VAL, CA, 53, 18.7, 25.1, 30.7, 13, A
VAL, CB, 53, 17.9, 24.2, 29.6, 8, A
VAL, CG1, 53, 17.3, 25.2, 28.6, 11, A
VAL, CG2, 53, 18.9, 23.3, 29.0, 13, A
VAL, C, 53, 17.7, 26.1, 31.2, 10, A
VAL, O, 53, 17.8, 27.3, 31.0, 16, A
LEU, N, 54, 16.8, 25.6, 32.1, 11, A
LEU, CA, 54, 15.8, 26.5, 32.7, 5, A
LEU, CB, 54, 14.9, 25.7, 33.6, 11, A
LEU, CG, 54, 13.9, 24.8, 32.9, 9, A
LEU, CD1, 54, 13.1, 24.0, 33.9, 11, A
LEU, CD2, 54, 13.0, 25.6, 32.0, 10, A
LEU, C, 54, 16.6, 27.5, 33.6, 10, A
LEU, O, 54, 16.2, 28.7, 33.6, 8, A
TYR, N, 55, 17.7, 27.1, 34.2, 9, A
TYR, CA, 55, 18.4, 28.1, 35.0, 11, A
TYR, CB, 55, 19.6, 27.4, 35.7, 10, A
TYR, CG, 55, 20.6, 28.3, 36.4, 12, A
TYR, CD1, 55, 20.3, 28.8, 37.7, 11, A
TYR, CE1, 55, 21.2, 29.7, 38.3, 13, A
TYR, CD2, 55, 21.8, 28.7, 35.8, 13, A
TYR, CE2, 55, 22.7, 29.5, 36.5, 13, A
TYR, CZ, 55, 22.3, 30.0, 37.7, 14, A
TYR, OH, 55, 23.3, 30.7, 38.4, 16, A
TYR, C, 55, 19.0, 29.2, 34.1, 12, A
TYR, O, 55, 18.8, 30.4, 34.4, 13, A
TYR, N, 56, 19.7, 28.8, 33.1, 7, A
TYR, CA, 56, 20.4, 29.8, 32.2, 13, A
TYR, CB, 56, 21.4, 29.1, 31.3, 11, A
TYR, CG, 56, 22.6, 28.7, 32.0, 14, A
TYR, CD1, 56, 23.4, 29.7, 32.5, 15, A
TYR, CE1, 56, 24.6, 29.5, 33.3, 17, A
TYR, CD2, 56, 23.0, 27.4, 32.2, 11, A
TYR, CE2, 56, 24.2, 27.1, 32.9, 13, A
TYR, CZ, 56, 24.9, 28.1, 33.4, 15, A
TYR, OH, 56, 26.1, 27.8, 34.2, 21, A
TYR, C, 56, 19.4, 30.6, 31.5, 14, A
TYR, O, 56, 19.7, 31.8, 31.2, 16, A
LEU, N, 57, 18.3, 30.1, 31.1, 14, A
LEU, CA, 57, 17.2, 30.8, 30.4, 14, A
LEU, CB, 57, 16.1, 30.0, 29.9, 17, A
LEU, CG, 57, 16.2, 29.3, 28.5, 14, A
LEU, CD1, 57, 15.1, 28.3, 28.4, 16, A
LEU, CD2, 57, 16.1, 30.4, 27.4, 15, A
LEU, C, 57, 16.7, 31.8, 31.4, 15, A
LEU, O, 57, 16.3, 32.9, 31.1, 16, A
GLY, N, 58, 16.7, 31.4, 32.7, 15, A
GLY, CA, 58, 16.3, 32.2, 33.7, 15, A
GLY, C, 58, 17.2, 33.5, 33.9, 11, A
GLY, O, 58, 16.7, 34.6, 34.1, 7, A
GLN, N, 59, 18.5, 33.2, 34.0, 10, A
GLN, CA, 59, 19.4, 34.3, 34.2, 15, A
GLN, CB, 59, 20.8, 33.8, 34.2, 19, A
GLN, CG, 59, 21.1, 32.9, 35.4, 25, A
GLN, CD, 59, 21.1, 33.6, 36.7, 29, A
GLN, OE1, 59, 21.6, 34.7, 36.8, 30, A
GLN, NE2, 59, 20.6, 32.9, 37.8, 25, A
GLN, C, 59, 19.3, 35.3, 33.0, 20, A
GLN, O, 59, 19.4, 36.5, 33.1, 15, A
TYR, N, 60, 19.1, 34.8, 31.8, 16, A
TYR, CA, 60, 18.9, 35.6, 30.6, 15
TYR, CB, 60, 18.7, 34.7, 29.4, 15, A
TYR, CG, 60, 18.6, 35.4, 28.0, 12, A
TYR, CD1, 60, 19.7, 35.9, 27.3, 13, A
TYR, CE1, 60, 19.6, 36.5, 26.1, 14, A
TYR, CD2, 60, 17.4, 35.6, 27.5, 13, A
TYR, CE2, 60, 17.2, 36.2, 26.3, 15, A
TYR, CZ, 60, 18.3, 36.6, 25.6, 15, A
TYR, OH, 60, 18.1, 37.2, 24.3, 16, A
TYR, C, 60, 17.8, 36.6, 30.7, 16, A
TYR, O, 60, 18.0, 37.8, 30.5, 18, A
ILE, N, 61, 16.6, 36.1, 31.1, 12, A
ILE, CA, 61, 15.4, 36.9, 31.2, 16, A
ILE, CB, 61, 14.2, 36.1, 31.5, 16, A
ILE, CG2, 61, 13.1, 36.9, 32.3, 18, A
ILE, CG1, 61, 13.7, 35.4, 30.2, 14, A
ILE, CD1, 61, 12.9, 34.2, 30.5, 17, A
ILE, C, 61, 15.6, 37.9, 32.4, 18, A
ILE, O, 61, 15.1, 39.1, 32.3, 19, A
MET, N, 62, 16.3, 37.5, 33.4, 19, A
MET, CA, 62, 16.5, 38.5, 34.6, 19, A
MET, CB, 62, 16.9, 37.7, 35.8, 16, A
MET, CG, 62, 15.8, 36.9, 36.4, 18, A
MET, SD, 62, 14.3, 37.8, 36.5, 17, A
MET, CE, 62, 14.5, 38.5, 38.1, 17, A
MET, C, 62, 17.5, 39.5, 34.2, 22, A
MET, O, 62, 17.4, 40.7, 34.6, 20, A
THR, N, 63, 18.5, 39.1, 33.5, 20, A
THR, CA, 63, 19.6, 40.1, 33.1, 23, A
THR, CB, 63, 20.7, 39.3, 32.4, 22, A
THR, OG1, 63, 21.4, 38.6, 33.4, 22, A
THR, CG2, 63, 21.6, 40.3, 31.8, 25, A
THR, C, 63, 19.0, 41.1, 32.2, 26, A
THR, O, 63, 19.0, 42.3, 32.5, 27, A
LYS, N, 64, 18.5, 40.7, 31.1, 25, A
LYS, CA, 64, 17.9, 41.6, 30.1, 25, A
LYS, CB, 64, 17.8, 40.9, 28.7, 24, A
LYS, CG, 64, 19.1, 40.2, 28.3, 23, A
LYS, CD, 64, 19.0, 39.9, 26.8, 23, A
LYS, CE, 64, 18.6, 41.1, 26.0, 22, A
LYS, NZ, 64, 18.7, 40.9, 24.5, 21, A
LYS, C, 64, 16.6, 42.2, 30.5, 26, A
LYS, O, 64, 16.0, 43.0, 29.8, 31, A
ARG, N, 65, 16.1, 41.7, 31.6, 25, A
ARG, CA, 65, 14.8, 42.1, 32.1, 27, A
ARG, CB, 65, 14.9, 43.5, 32.8, 29, A
ARG, CG, 65, 15.8, 43.4, 34.0, 33, A
ARG, CD, 65, 16.6, 44.7, 34.3, 36, A
ARG, NE, 65, 15.7, 45.8, 34.6, 40, A
ARG, CZ, 65, 16.2, 47.1, 34.7, 42, A
ARG, NH1, 65, 17.4, 47.4, 34.4, 41, A
ARG, NH2, 65, 15.3, 48.0, 35.0, 42, A
ARG, C, 65, 13.7, 42.1, 31.0, 26, A
ARG, O, 65, 13.1, 43.2, 30.8, 28, A
LEU, N, 66, 13.5, 41.0, 30.4, 25
LEU, CA, 66, 12.6, 40.8, 29.3, 28, A
LEU, CB, 66, 13.0, 39.6, 28.5, 25, A
LEU, CG, 66, 14.4, 39.7, 27.9, 23, A
LEU, CD1, 66, 14.7, 38.4, 27.0, 23, A
LEU, CD2, 66, 14.5, 40.9, 27.0, 23, A
LEU, C, 66, 11.2, 40.6, 29.9, 31, A
LEU, O, 66, 10.3, 40.1, 29.2, 34, A
TYR, N, 67, 11.0, 41.0, 31.1, 35, A
TYR, CA, 67, 9.7, 40.8, 31.8, 40, A
TYR, CB, 67, 9.8, 40.1, 33.1, 38, A
TYR, CG, 67, 10.7, 40.8, 34.1, 35, A
TYR, CD1, 67, 10.2, 41.6, 35.1, 34, A
TYR, CE1, 67, 11.0, 42.2, 36.0, 32, A
TYR, CD2, 67, 12.0, 40.5, 34.1, 34, A
TYR, CE2, 67, 12.9, 41.1, 35.1, 34, A
TYR, CZ, 67, 12.3, 41.9, 36.0, 32, A
TYR, OH, 67, 13.2, 42.5, 37.0, 32, A

TABLE 1-continued

Structural coordinates of HDM2 (17-125; F55Y/Y76H) (SEQ ID NO: 2) complexed with compound 1.

TYR, C, 67, 8.9, 42.2, 32.0, 44, A
TYR, O, 67, 9.6, 43.2, 32.1, 45, A
ASP, N, 68, 7.6, 42.1, 32.1, 49, A
ASP, CA, 68, 6.8, 43.2, 32.2, 55, A
ASP, CB, 68, 5.4, 42.9, 31.9, 59, A
ASP, CG, 68, 4.5, 44.1, 31.8, 62, A
ASP, OD1, 68, 4.9, 45.1, 31.1, 64, A
ASP, OD2, 68, 3.5, 44.2, 32.5, 65, A
ASP, C, 68, 6.9, 43.8, 33.7, 58, A
ASP, O, 68, 6.5, 43.0, 34.6, 57, A
GLU, N, 69, 7.3, 45.0, 33.8, 62
GLU, CA, 69, 7.4, 45.7, 35.1, 66, A
GLU, CB, 69, 8.2, 47.0, 34.9, 68, A
GLU, CG, 69, 7.7, 47.8, 33.6, 72, A
GLU, CD, 69, 8.7, 48.9, 33.3, 73, A
GLU, OE1, 69, 9.8, 48.6, 33.0, 73, A
GLU, OE2, 69, 8.2, 50.1, 33.3, 74, A
GLU, C, 69, 6.0, 46.0, 35.7, 66
GLU, O, 69, 5.5, 47.1, 35.6, 69, A
LYS, N, 70, 5.5, 45.0, 36.4, 66, A
LYS, CA, 70, 4.1, 45.0, 37.0, 66, A
LYS, CB, 70, 3.1, 45.8, 36.2, 67, A
LYS, CG, 70, 1.7, 45.7, 36.8, 69, A
LYS, CD, 70, 0.7, 46.5, 35.9, 70, A
LYS, CE, 70, −0.7, 46.4, 36.4, 71, A
LYS, NZ, 70, −1.6, 47.3, 35.7, 70, A
LYS, C, 70, 3.7, 43.6, 37.1, 65, A
LYS, O, 70, 3.6, 43.0, 38.2, 65, A
GLN, N, 71, 3.4, 43.0, 35.9, 62, A
GLN, CA, 71, 3.0, 41.6, 35.8, 59, A
GLN, CB, 71, 2.0, 41.4, 34.7, 61, A
GLN, CG, 71, 0.6, 41.9, 35.1, 62, A
GLN, CD, 71, −0.5, 41.1, 34.4, 64, A
GLN, OE1, 71, −0.5, 41.2, 33.2, 66, A
GLN, NE2, 71, −1.3, 40.4, 35.1, 64, A
GLN, C, 71, 4.3, 40.8, 35.5, 54, A
GLN, O, 71, 4.5, 40.4, 34.4, 53, A
GLN, N, 72, 5.1, 40.7, 36.5, 49, A
GLN, CA, 72, 6.4, 40.1, 36.4, 44, A
GLN, CB, 72, 7.2, 40.2, 37.7, 42, A
GLN, CG, 72, 7.5, 41.6, 38.1, 40, A
GLN, CD, 72, 8.1, 41.7, 39.4, 39, A
GLN, OE1, 72, 7.5, 41.4, 40.5, 41, A
GLN, NE2, 72, 9.4, 42.1, 39.5, 38, A
GLN, C, 72, 6.3, 38.6, 36.0, 43, A
GLN, O, 72, 7.4, 37.9, 35.8, 44, A
HIS, N, 73, 5.1, 38.1, 35.8, 41, A
HIS, CA, 73, 5.0, 36.7, 35.4, 38, A
HIS, CB, 73, 3.8, 36.0, 36.0, 43, A
HIS, CG, 73, 2.5, 36.6, 35.7, 46, A
HIS, CD2, 73, 2.1, 37.9, 35.6, 48, A
HIS, ND1, 73, 1.4, 35.8, 35.4, 47, A
HIS, CE1, 73, 0.3, 36.6, 35.2, 47, A
HIS, NE2, 73, 0.7, 37.9, 35.3, 47, A
HIS, C, 73, 5.0, 36.6, 33.8, 36, A
HIS, O, 73, 5.1, 35.5, 33.3, 33, A
ILE, N, 74, 4.8, 37.7, 33.2, 32, A
ILE, CA, 74, 4.7, 37.7, 31.7, 30, A
ILE, CB, 74, 3.5, 38.7, 31.3, 29, A
ILE, CG2, 74, 3.5, 38.7, 29.8, 27, A
ILE, CG1, 74, 2.2, 38.1, 31.8, 30, A
ILE, CD1, 74, 1.0, 39.0, 31.4, 32, A
ILE, C, 74, 6.0, 38.2, 31.1, 28, A
ILE, O, 74, 6.5, 39.3, 31.4, 29, A
VAL, N, 75, 6.5, 37.4, 30.2, 26, A
VAL, CA, 75, 7.8, 37.7, 29.5, 26, A
VAL, CB, 75, 8.7, 36.4, 29.4, 22, A
VAL, CG1, 75, 9.9, 36.7, 28.6, 24, A
VAL, CG2, 75, 9.1, 35.9, 30.8, 23, A
VAL, C, 75, 7.6, 38.2, 28.1, 26, A
VAL, O, 75, 7.0, 37.6, 27.3, 24, A
HIS, N, 76, 8.0, 39.4, 27.9, 30, A
HIS, CA, 76, 7.9, 40.1, 26.6, 34, A
HIS, CB, 76, 7.6, 41.6, 26.8, 34, A
HIS, CG, 76, 6.3, 41.8, 27.4, 36, A
HIS, CD2, 76, 6.0, 42.4, 28.6, 35, A
HIS, ND1, 76, 5.1, 41.5, 26.9, 37, A
HIS, CE1, 76, 4.1, 41.8, 27.7, 35, A
HIS, NE2, 76, 4.6, 42.4, 28.8, 37, A
HIS, C, 76, 9.2, 39.9, 25.8, 35, A
HIS, O, 76, 10.3, 40.4, 26.2, 36, A
CYS, N, 77, 9.2, 39.1, 24.8, 34, A
CYS, CA, 77, 10.4, 38.8, 24.0, 36, A
CYS, CB, 77, 10.7, 37.3, 24.1, 38, A
CYS, SG, 77, 9.2, 36.3, 24.3, 37, A
CYS, C, 77, 10.4, 39.2, 22.5, 39, A
CYS, O, 77, 11.4, 38.9, 21.8, 39, A
SER, N, 78, 9.4, 39.9, 22.1, 41, A
SER, CA, 78, 9.3, 40.3, 20.7, 46
SER, CB, 78, 8.1, 41.1, 20.4, 47, A
SER, OG, 78, 6.9, 40.4, 20.8, 50, A
SER, C, 78, 10.6, 41.2, 20.5, 46, A
SER, O, 78, 10.8, 42.1, 21.3, 47, A
ASN, N, 79, 11.3, 41.0, 19.4, 47, A
ASN, CA, 79, 12.5, 41.8, 19.1, 46, A
ASN, CB, 79, 12.3, 43.3, 19.4, 50, A
ASN, CG, 79, 11.1, 43.8, 18.6, 54, A
ASN, OD1, 79, 11.1, 43.7, 17.3, 56, A
ASN, ND2, 79, 10.1, 44.3, 19.3, 55, A
ASN, C, 79, 13.6, 41.3, 20.1, 44, A
ASN, O, 79, 14.3, 42.1, 20.7, 44, A
ASP, N, 80, 13.7, 40.0, 20.2, 40, A
ASP, CA, 80, 14.7, 39.4, 21.0, 35, A
ASP, CB, 80, 14.2, 39.3, 22.5, 36, A
ASP, CG, 80, 15.3, 39.1, 23.5, 39, A
ASP, OD1, 80, 16.1, 40.1, 23.7, 39, A
ASP, OD2, 80, 15.4, 38.0, 24.0, 40, A
ASP, C, 80, 15.0, 38.0, 20.5, 31, A
ASP, O, 80, 14.1, 37.3, 20.1, 31, A
LEU, N, 81, 16.2, 37.5, 20.6, 27
LEU, CA, 81, 16.6, 36.2, 20.1, 21, A
LEU, CB, 81, 18.0, 35.8, 20.5, 23, A
LEU, CG, 81, 18.4, 34.4, 20.0, 20, A
LEU, CD1, 81, 18.2, 34.4, 18.5, 25, A
LEU, CD2, 81, 19.8, 34.1, 20.4, 25, A
LEU, C, 81, 15.6, 35.2, 20.7, 22, A
LEU, O, 81, 15.2, 34.2, 20.0, 20, A
LEU, N, 82, 15.3, 35.4, 22.0, 20, A
LEU, CA, 82, 14.4, 34.5, 22.7, 22
LEU, CB, 82, 14.1, 35.0, 24.1, 23, A
LEU, CG, 82, 13.2, 34.2, 25.0, 22, A
LEU, CD1, 82, 14.0, 33.0, 25.5, 24, A
LEU, CD2, 82, 12.8, 35.0, 26.2, 23, A
LEU, C, 82, 13.1, 34.3, 21.9, 24, A
LEU, O, 82, 12.6, 33.2, 21.7, 25, A
GLY, N, 83, 12.5, 35.4, 21.5, 22, A
GLY, CA, 83, 11.2, 35.4, 20.8, 26, A
GLY, C, 83, 11.2, 34.7, 19.5, 27, A
GLY, O, 83, 10.2, 34.2, 19.0, 24, A
ASP, N, 84, 12.4, 34.7, 18.8, 26, A
ASP, CA, 84, 12.5, 34.0, 17.5, 29, A
ASP, CB, 84, 13.8, 34.5, 16.8, 34, A
ASP, CG, 84, 13.7, 36.0, 16.4, 38
ASP, OD1, 84, 14.8, 36.5, 16.1, 40, A
ASP, OD2, 84, 12.6, 36.6, 16.5, 39, A
ASP, C, 84, 12.7, 32.6, 17.7, 29, A
ASP, O, 84, 12.2, 31.7, 16.9, 30, A
LEU, N, 85, 13.3, 32.2, 18.9, 29, A
LEU, CA, 85, 13.6, 30.9, 19.2, 28, A
LEU, CB, 85, 14.7, 30.8, 20.2, 29, A
LEU, CG, 85, 16.0, 31.5, 19.6, 29, A
LEU, CD1, 85, 17.1, 31.4, 20.6, 31, A
LEU, CD2, 85, 16.4, 30.8, 18.4, 28, A
LEU, C, 85, 12.3, 30.2, 19.8, 26, A
LEU, O, 85, 12.1, 29.0, 19.7, 31, A
PHE, N, 86, 11.5, 31.1, 20.4, 23, A
PHE, CA, 86, 10.2, 30.6, 21.1, 20, A
PHE, CB, 86, 10.0, 31.3, 22.4, 17, A
PHE, CG, 86, 10.6, 30.7, 23.6, 16, A
PHE, CD1, 86, 11.6, 29.7, 23.4, 17, A
PHE, CD2, 86, 10.3, 31.1, 24.8, 16, A
PHE, CE1, 86, 12.2, 29.1, 24.5, 18, A

TABLE 1-continued

Structural coordinates of HDM2 (17-125; F55Y/Y76H) (SEQ ID NO: 2) complexed with compound 1.

PHE, CE2, 86, 10.9, 30.5, 25.9, 20
PHE, CZ, 86, 11.8, 29.5, 25.8, 13, A
PHE, C, 86, 9.1, 30.8, 20.1, 22, A
PHE, O, 86, 8.0, 30.3, 20.4, 21, A
GLY, N, 87, 9.3, 31.4, 19.0, 23, A
GLY, CA, 87, 8.2, 31.6, 18.1, 23, A
GLY, C, 87, 7.0, 32.3, 18.6, 26, A
GLY, O, 87, 5.9, 32.2, 18.1, 28, A
VAL, N, 88, 7.2, 33.1, 19.7, 27, A
VAL, CA, 88, 6.1, 33.8, 20.3, 28, A
VAL, CB, 88, 5.5, 33.1, 21.5, 27, A
VAL, CG1, 88, 5.1, 31.6, 21.1, 27, A
VAL, CG2, 88, 6.6, 33.0, 22.6, 26, A
VAL, C, 88, 6.5, 35.2, 20.8, 30, A
VAL, O, 88, 7.7, 35.4, 21.0, 30, A
PRO, N, 89, 5.6, 36.1, 20.8, 31, A
PRO, CD, 89, 4.2, 35.9, 20.3, 28, A
PRO, CA, 89, 5.8, 37.5, 21.2, 31, A
PRO, CB, 89, 4.6, 38.2, 20.7, 29, A
PRO, CG, 89, 3.5, 37.2, 20.8, 30, A
PRO, C, 89, 6.0, 37.7, 22.7, 32, A
PRO, O, 89, 6.5, 38.7, 23.2, 30, A
SER, N, 90, 5.5, 36.7, 23.5, 29, A
SER, CA, 90, 5.5, 36.8, 24.9, 27, A
SER, CB, 90, 4.8, 38.1, 25.4, 30, A
SER, OG, 90, 3.5, 38.1, 25.1, 29, A
SER, C, 90, 4.7, 35.6, 25.5, 27, A
SER, O, 90, 4.0, 35.0, 24.8, 25, A
PHE, N, 91, 4.9, 35.4, 26.8, 26, A
PHE, CA, 91, 4.3, 34.3, 27.4, 28, A
PHE, CB, 91, 5.0, 33.0, 27.1, 27, A
PHE, CG, 91, 6.4, 32.9, 27.5, 28, A
PHE, CD1, 91, 6.8, 32.4, 28.7, 25, A
PHE, CD2, 91, 7.4, 33.3, 26.6, 27, A
PHE, CE1, 91, 8.1, 32.3, 29.1, 25, A
PHE, CE2, 91, 8.7, 33.3, 27.0, 24, A
PHE, CZ, 91, 9.1, 32.8, 28.3, 24, A
PHE, C, 91, 4.3, 34.4, 29.0, 29, A
PHE, O, 91, 4.9, 35.3, 29.5, 27, A
SER, N, 92, 3.6, 33.6, 29.6, 31, A
SER, CA, 92, 3.5, 33.6, 31.1, 33, A
SER, CB, 92, 2.1, 33.3, 31.6, 35, A
SER, OG, 92, 2.1, 32.8, 32.9, 37
SER, C, 92, 4.5, 32.5, 31.6, 33, A
SER, O, 92, 4.3, 31.3, 31.1, 35, A
VAL, N, 93, 5.4, 32.8, 32.5, 32, A
VAL, CA, 93, 6.3, 31.8, 33.0, 30, A
VAL, CB, 93, 7.3, 32.5, 33.9, 28, A
VAL, CG1, 93, 7.9, 33.7, 33.2, 27, A
VAL, CG2, 93, 6.7, 32.9, 35.2, 29, A
VAL, C, 93, 5.5, 30.7, 33.8, 29, A
VAL, O, 93, 6.0, 29.7, 34.2, 30, A
LYS, N, 94, 4.2, 31.9, 34.0, 30, A
LYS, CA, 94, 3.3, 30.1, 34.7, 32, A
LYS, CB, 94, 2.2, 30.8, 35.4, 32, A
LYS, CG, 94, 2.6, 31.9, 36.4, 34, A
LYS, CD, 94, 3.1, 31.3, 37.7, 35, A
LYS, CE, 94, 3.4, 32.4, 38.7, 38, A
LYS, NZ, 94, 3.8, 31.9, 40.0, 38, A
LYS, C, 94, 2.7, 29.0, 33.7, 32, A
LYS, O, 94, 2.0, 28.1, 34.1, 30, A
GLU, N, 95, 3.1, 29.2, 32.4, 31, A
GLU, CA, 95, 2.6, 28.3, 31.4, 28, A
GLU, CB, 95, 2.2, 29.1, 30.1, 29, A
GLU, CG, 95, 1.3, 30.2, 30.4, 33, A
GLU, CD, 95, 1.0, 31.1, 29.1, 37, A
GLU, OE1, 95, 1.9, 31.7, 28.6, 35, A
GLU, OE2, 95, −0.2, 31.1, 28.7, 38, A
GLU, C, 95, 3.7, 27.2, 31.0, 24, A
GLU, O, 95, 4.2, 27.3, 30.0, 21, A
HIS, N, 96, 3.9, 26.3, 32.0, 26, A
HIS, CA, 96, 5.0, 25.3, 31.8, 23, A
HIS, CB, 96, 5.1, 24.5, 33.1, 23, A
HIS, CG, 96, 5.4, 25.3, 34.3, 20, A
HIS, CD2, 96, 5.5, 26.7, 34.5, 18, A
HIS, ND1, 96, 5.7, 24.8, 35.6, 20, A
HIS, CE1, 96, 6.0, 25.8, 36.4, 22, A
HIS, NE2, 96, 5.9, 26.9, 35.8, 19, A
HIS, C, 96, 4.9, 24.4, 30.7, 23, A
HIS, O, 96, 5.9, 24.1, 30.0, 22, A
ARG, N, 97, 3.7, 23.8, 30.4, 25, A
ARG, CA, 97, 3.6, 22.9, 29.3, 23, A
ARG, CB, 97, 2.1, 22.3, 29.3, 28, A
ARG, CG, 97, 1.9, 21.3, 28.2, 36, A
ARG, CD, 97, 0.5, 20.6, 28.3, 39, A
ARG, NE, 97, −0.5, 21.6, 28.4, 43, A
ARG, CZ, 97, −1.8, 21.3, 28.5, 45, A
ARG, NH1, 97, −2.2, 20.1, 28.6, 48, A
ARG, NH2, 97, −2.7, 22.3, 28.5, 46, A
ARG, C, 97, 3.9, 23.6, 28.0, 20, A
ARG, O, 97, 4.6, 23.0, 27.2, 22, A
LYS, N, 98, 3.6, 24.8, 27.9, 22, A
LYS, CA, 98, 3.9, 25.5, 26.6, 24, A
LYS, CB, 98, 3.1, 26.9, 26.6, 25, A
LYS, CG, 98, 3.5, 27.8, 25.4, 29, A
LYS, CD, 98, 2.6, 29.0, 25.3, 35, A
LYS, CE, 98, 1.2, 28.6, 25.0, 39, A
LYS, NZ, 98, 0.3, 29.8, 24.7, 41, A
LYS, C, 98, 5.4, 25.9, 26.5, 20, A
LYS, O, 98, 6.0, 25.6, 25.5, 21, A
ILE, N, 99, 6.0, 26.3, 27.6, 22, A
ILE, CA, 99, 7.4, 26.6, 27.7, 19, A
ILE, CB, 99, 7.8, 27.2, 29.1, 20, A
ILE, CG2, 99, 9.3, 27.1, 29.3, 19, A
ILE, CG1, 99, 7.3, 28.6, 29.3, 18, A
ILE, CD1, 99, 7.4, 29.1, 30.7, 18, A
ILE, C, 99, 8.2, 25.4, 27.4, 21, A
ILE, O, 99, 9.2, 25.5, 26.7, 20, A
TYR, N, 100, 7.8, 24.3, 27.9, 20, A
TYR, CA, 100, 8.6, 23.0, 27.7, 15, A
TYR, CB, 100, 8.0, 21.9, 28.5, 14, A
TYR, CG, 100, 8.5, 21.8, 29.9, 16, A
TYR, CD1, 100, 7.7, 21.6, 31.0, 15, A
TYR, CE1, 100, 8.3, 21.4, 32.2, 16, A
TYR, CD2, 100, 9.9, 21.8, 30.1, 17, A
TYR, CE2, 100, 10.4, 21.7, 31.3, 18, A
TYR, CZ, 100, 9.6, 21.5, 32.4, 18, A
TYR, OH, 100, 10.2, 21.4, 33.7, 22, A
TYR, C, 100, 8.6, 22.7, 26.2, 17, A
TYR, O, 100, 9.6, 22.3, 25.6, 18, A
THR, N, 101, 7.4, 22.9, 25.6, 17, A
THR, CA, 101, 7.3, 22.6, 24.2, 20, A
THR, CB, 101, 5.8, 22.7, 23.7, 23, A
THR, OG1, 101, 5.1, 21.6, 24.3, 21, A
THR, CG2, 101, 5.8, 22.6, 22.2, 23, A
THR, C, 101, 8.2, 23.5, 23.4, 19, A
THR, O, 101, 8.9, 23.0, 22.5, 21, A
MET, N, 102, 8.2, 24.8, 23.7, 21, A
MET, CA, 102, 9.1, 25.7, 23.0, 19, A
MET, CB, 102, 8.8, 27.1, 23.5, 20, A
MET, CG, 102, 7.4, 27.6, 23.3, 17, A
MET, SD, 102, 7.0, 29.3, 23.6, 24, A
MET, CE, 102, 7.3, 29.5, 25.3, 18, A
MET, C, 102, 10.6, 25.3, 23.1, 19, A
MET, O, 102, 11.3, 25.4, 22.2, 21, A
ILE, N, 103, 11.0, 24.9, 24.3, 17, A
ILE, CA, 103, 12.4, 24.6, 24.6, 16, A
ILE, CB, 103, 12.6, 24.2, 26.0, 13, A
ILE, CG2, 103, 14.0, 23.7, 26.2, 13, A
ILE, CG1, 103, 12.5, 25.5, 26.9, 10, A
ILE, CD1, 103, 12.6, 25.2, 28.4, 12, A
ILE, C, 103, 12.7, 23.4, 23.7, 14, A
ILE, O, 103, 13.7, 23.4, 23.0, 16, A
TYR, N, 104, 12.0, 22.3, 23.8, 16, A
TYR, CA, 104, 12.2, 21.0, 23.1, 18, A
TYR, CB, 104, 11.1, 20.0, 23.2, 20, A
TYR, CG, 104, 10.7, 19.6, 24.6, 21, A
TYR, CD1, 104, 11.6, 19.3, 25.6, 20, A
TYR, CE1, 104, 11.2, 18.9, 26.8, 20, A
TYR, CD2, 104, 9.3, 19.4, 24.9, 22, A
TYR, CE2, 104, 9.0, 19.0, 26.2, 21, A
TYR, CZ, 104, 9.9, 18.7, 27.1, 21, A

TABLE 1-continued

Structural coordinates of HDM2 (17-125; F55Y/Y76H) (SEQ ID NO: 2) complexed with compound 1.

| | | | | | | |
|---|---|---|---|---|---|---|
| TYR, | OH, | 104, | 9.5, | 18.2, | 28.4, | 24, A |
| TYR, | C, | 104, | 12.4, | 21.3, | 21.6, | 20, A |
| TYR, | O, | 104, | 13.1, | 20.6, | 20.9, | 18, A |
| ARG, | N, | 105, | 11.8, | 22.3, | 21.2, | 21, A |
| ARG, | CA, | 105, | 11.8, | 22.8, | 19.8, | 25, A |
| ARG, | CB, | 105, | 10.7, | 23.8, | 19.6, | 26, A |
| ARG, | CG, | 105, | 10.1, | 24.0, | 18.2, | 30, A |
| ARG, | CD, | 105, | 8.7, | 24.7, | 18.3, | 33, A |
| ARG, | NE, | 105, | 7.7, | 23.7, | 18.5, | 34, A |
| ARG, | CZ, | 105, | 6.4, | 24.0, | 18.9, | 36, A |
| ARG, | NH1, | 105, | 6.1, | 25.3, | 19.2, | 36, A |
| ARG, | NH2, | 105, | 5.5, | 23.1, | 19.0, | 35, A |
| ARG, | C, | 105, | 13.1, | 23.3, | 19.4, | 26, A |
| ARG, | O, | 105, | 13.4, | 23.6, | 18.2, | 26, A |
| ASN, | N, | 106, | 14.0, | 23.4, | 20.4, | 21, A |
| ASN, | CA, | 106, | 15.3, | 23.9, | 20.2, | 20, A |
| ASN, | CB, | 106, | 15.5, | 25.3, | 20.9, | 21, A |
| ASN, | CG, | 106, | 14.9, | 26.4, | 20.1, | 21, A |
| ASN, | OD1, | 106, | 15.4, | 26.8, | 19.1, | 25, A |
| ASN, | ND2, | 106, | 13.7, | 26.9, | 20.6, | 18, A |
| ASN, | C, | 106, | 16.4, | 23.0, | 20.7, | 22, A |
| ASN, | O, | 106, | 17.5, | 23.4, | 21.0, | 14, A |
| LEU, | N, | 107, | 16.1, | 21.7, | 20.8, | 15, A |
| LEU, | CA, | 107, | 17.1, | 20.7, | 21.2, | 22, A |
| LEU, | CB, | 107, | 16.5, | 19.9, | 22.3, | 21, A |
| LEU, | CG, | 107, | 16.1, | 20.5, | 23.6, | 16, A |
| LEU, | CD1, | 107, | 15.7, | 19.5, | 24.6, | 14, A |
| LEU, | CD2, | 107, | 17.3, | 21.4, | 24.2, | 19, A |
| LEU, | C, | 107, | 17.4, | 19.9, | 20.0, | 25, A |
| LEU, | O, | 107, | 16.5, | 19.7, | 19.1, | 29, A |
| VAL, | N, | 108, | 18.6, | 19.3, | 19.9, | 29, A |
| VAL, | CA, | 108, | 19.0, | 18.5, | 18.8, | 28, A |
| VAL, | CB, | 108, | 20.6, | 18.4, | 18.8, | 28, A |
| VAL, | CG1, | 108, | 21.0, | 17.5, | 17.6, | 30, A |
| VAL, | CG2, | 108, | 21.2, | 19.7, | 18.7, | 30, A |
| VAL, | C, | 108, | 18.5, | 17.1, | 19.0, | 30, A |
| VAL, | O, | 108, | 18.5, | 16.5, | 20.1, | 27, A |
| VAL, | N, | 109, | 18.0, | 16.5, | 17.8, | 29, A |
| VAL, | CA, | 109, | 17.5, | 15.2, | 17.8, | 27, A |
| VAL, | CB, | 109, | 16.7, | 14.9, | 16.6, | 26, A |
| VAL, | CG1, | 109, | 16.8, | 13.4, | 16.3, | 25, A |
| VAL, | CG2, | 109, | 15.3, | 15.3, | 16.8, | 21, A |
| VAL, | C, | 109, | 18.8, | 14.3, | 17.8, | 29, A |
| VAL, | O, | 109, | 19.6, | 14.4, | 16.9, | 31, A |
| VAL, | N, | 110, | 19.0, | 13.5, | 18.9, | 28, A |
| VAL, | CA, | 110, | 20.2, | 12.7, | 19.0, | 32, A |
| VAL, | CB, | 110, | 20.9, | 12.9, | 20.4, | 31, A |
| VAL, | CG1, | 110, | 22.3, | 12.4, | 20.3, | 34, A |
| VAL, | CG2, | 110, | 20.9, | 14.4, | 20.7, | 30, A |
| VAL, | C, | 110, | 19.8, | 11.2, | 19.0, | 31, A |
| VAL, | O, | 110, | 20.6, | 10.4, | 18.6, | 35, A |
| ASN, | N, | 111, | 18.6, | 10.9, | 19.4, | 36, A |
| ASN, | CA, | 111, | 18.1, | 9.5, | 19.4, | 36, A |
| ASN, | CB, | 111, | 18.4, | 8.8, | 18.2, | 37, A |
| ASN, | CG, | 111, | 17.3, | 8.7, | 17.1, | 36, A |
| ASN, | OD1, | 111, | 16.7, | 9.8, | 16.9, | 35, A |
| ASN, | ND2, | 111, | 17.1, | 7.6, | 16.5, | 37, A |
| ASN, | C, | 111, | 18.6, | 8.8, | 20.6, | 39, A |
| ASN, | O, | 111, | 18.5, | 9.3, | 21.8, | 41, A |
| PRO, | N, | 20, | −7.2, | 17.0, | 40.0, | 27, B |
| PRO, | CD, | 20, | −8.5, | 17.6, | 39.7, | 23, B |
| PRO, | CA, | 20, | −6.4, | 16.8, | 38.7, | 27, B |
| PRO, | CB, | 20, | −7.2, | 17.5, | 37.7, | 26, B |
| PRO, | CG, | 20, | −8.6, | 17.3, | 38.2, | 24, B |
| PRO, | C, | 20, | −4.9, | 17.2, | 38.8, | 31, B |
| PRO, | O, | 20, | −4.7, | 18.4, | 38.9, | 32, B |
| ALA, | N, | 21, | −4.0, | 16.3, | 38.7, | 30, B |
| ALA, | CA, | 21, | −2.6, | 16.6, | 38.8, | 30, B |
| ALA, | CB, | 21, | −1.8, | 15.3, | 38.5, | 30, B |
| ALA, | C, | 21, | −2.2, | 17.6, | 37.7, | 29, B |
| ALA, | O, | 21, | −1.4, | 18.5, | 38.0, | 32, B |
| SER, | N, | 22, | −2.9, | 17.6, | 36.6, | 31, B |
| SER, | CA, | 22, | −2.6, | 18.5, | 35.5, | 33, B |
| SER, | CB, | 22, | −3.3, | 18.1, | 34.2, | 34, B |
| SER, | OG, | 22, | −4.7, | 17.9, | 34.5, | 38, B |
| SER, | C, | 22, | −3.1, | 19.9, | 35.8, | 34, B |
| SER, | O, | 22, | −3.0, | 20.9, | 35.0, | 35, B |
| GLU, | N, | 23, | −3.7, | 20.1, | 37.0, | 32, B |
| GLU, | CA, | 23, | −4.3, | 21.4, | 37.4, | 30, B |
| GLU, | CB, | 23, | −5.8, | 21.4, | 37.4, | 32, B |
| GLU, | CG, | 23, | −6.5, | 21.0, | 36.1, | 35, B |
| GLU, | CD, | 23, | −8.0, | 21.0, | 36.2, | 37, B |
| GLU, | OE1, | 23, | −8.6, | 20.4, | 37.1, | 38, B |
| GLU, | OE2, | 23, | −8.6, | 21.7, | 35.3, | 39, B |
| GLU, | C, | 23, | −3.7, | 21.9, | 38.7, | 29, B |
| GLU, | O, | 23, | −4.1, | 22.9, | 39.2, | 28, B |
| GLN, | N, | 24, | −2.7, | 21.2, | 39.3, | 27, B |
| GLN, | CA, | 24, | −2.1, | 21.5, | 40.5, | 25, B |
| GLN, | CB, | 24, | −1.7, | 20.3, | 41.3, | 23, B |
| GLN, | CG, | 24, | −2.9, | 19.5, | 41.8, | 22, B |
| GLN, | CD, | 24, | −2.5, | 18.2, | 42.6, | 22, B |
| GLN, | OE1, | 24, | −1.6, | 18.3, | 43.4, | 20, B |
| GLN, | NE2, | 24, | −3.2, | 17.2, | 42.4, | 21, B |
| GLN, | C, | 24, | −0.9, | 22.4, | 40.4, | 26, B |
| GLN, | O, | 24, | −0.0, | 22.1, | 39.5, | 27, B |
| GLU, | N, | 25, | −0.8, | 23.4, | 41.2, | 27, B |
| GLU, | CA, | 25, | 0.4, | 24.3, | 41.2, | 28, B |
| GLU, | CB, | 25, | −0.1, | 25.7, | 41.1, | 34, B |
| GLU, | CG, | 25, | −1.0, | 25.9, | 39.9, | 42, B |
| GLU, | CD, | 25, | −1.3, | 27.3, | 39.6, | 47, B |
| GLU, | OE1, | 25, | −2.2, | 27.6, | 38.7, | 51, B |
| GLU, | OE2, | 25, | −0.7, | 28.2, | 40.2, | 49, B |
| GLU, | C, | 25, | 0.9, | 24.0, | 42.6, | 25, B |
| GLU, | O, | 25, | 0.3, | 24.4, | 43.6, | 26, B |
| THR, | N, | 26, | 2.1, | 23.4, | 42.7, | 22, B |
| THR, | CA, | 26, | 2.7, | 23.1, | 43.9, | 22, B |
| THR, | CB, | 26, | 3.4, | 21.7, | 43.8, | 16, B |
| THR, | OG1, | 26, | 2.4, | 20.7, | 43.7, | 21, B |
| THR, | CG2, | 26, | 4.3, | 21.5, | 45.0, | 17, B |
| THR, | C, | 26, | 3.7, | 24.1, | 44.3, | 23, B |
| THR, | O, | 26, | 4.6, | 24.4, | 43.6, | 26, B |
| LEU, | N, | 27, | 3.6, | 24.6, | 45.5, | 18, B |
| LEU, | CA, | 27, | 4.5, | 25.7, | 46.0, | 17, B |
| LEU, | CB, | 27, | 3.8, | 27.0, | 46.2, | 17, B |
| LEU, | CG, | 27, | 3.2, | 27.7, | 45.0, | 16, B |
| LEU, | CD1, | 27, | 2.7, | 29.1, | 45.4, | 16, B |
| LEU, | CD2, | 27, | 4.2, | 27.8, | 43.8, | 18, B |
| LEU, | C, | 27, | 5.0, | 25.2, | 47.4, | 19, B |
| LEU, | O, | 27, | 4.4, | 24.3, | 48.0, | 24, B |
| VAL, | N, | 28, | 6.1, | 25.9, | 47.8, | 15, B |
| VAL, | CA, | 28, | 6.6, | 25.6, | 49.1, | 15, B |
| VAL, | CB, | 28, | 7.9, | 24.7, | 49.0, | 13, B |
| VAL, | CG1, | 28, | 7.5, | 23.4, | 48.4, | 15, B |
| VAL, | CG2, | 28, | 8.9, | 25.4, | 48.2, | 13, B |
| VAL, | C, | 28, | 7.0, | 26.9, | 49.8, | 12, B |
| VAL, | O, | 28, | 7.1, | 27.9, | 49.1, | 13, B |
| ARG, | N, | 29, | 7.0, | 26.9, | 51.1, | 12, B |
| ARG, | CA, | 29, | 7.3, | 28.0, | 51.9, | 16, B |
| ARG, | CB, | 29, | 6.1, | 28.3, | 52.8, | 19, B |
| ARG, | CG, | 29, | 6.3, | 29.6, | 53.7, | 22, B |
| ARG, | CD, | 29, | 5.1, | 29.7, | 54.6, | 21, B |
| ARG, | NE, | 29, | 3.8, | 29.7, | 53.9, | 23, B |
| ARG, | CZ, | 29, | 3.4, | 30.8, | 53.2, | 27, B |
| ARG, | NH1, | 29, | 4.1, | 31.9, | 53.3, | 27, B |
| ARG, | NH2, | 29, | 2.2, | 30.8, | 52.6, | 29, B |
| ARG, | C, | 29, | 8.6, | 27.9, | 52.7, | 15, B |
| ARG, | O, | 29, | 8.6, | 27.2, | 53.7, | 23, B |
| PRO, | N, | 30, | 9.7, | 28.5, | 52.3, | 13, B |
| PRO, | CD, | 30, | 9.7, | 29.2, | 51.0, | 13, B |
| PRO, | CA, | 30, | 11.0, | 28.5, | 52.9, | 14, B |
| PRO, | CB, | 30, | 11.8, | 29.4, | 52.1, | 15, B |
| PRO, | CG, | 30, | 11.2, | 29.2, | 50.7, | 10, B |
| PRO, | C, | 30, | 10.9, | 29.0, | 54.4, | 16, B |
| PRO, | O, | 30, | 10.1, | 29.9, | 54.7, | 15, B |
| LYS, | N, | 31, | 11.6, | 28.4, | 55.3, | 11, B |
| LYS, | CA, | 31, | 11.6, | 28.9, | 56.7, | 14, B |
| LYS, | CB, | 31, | 12.2, | 27.8, | 57.6, | 15, B |
| LYS, | CG, | 31, | 11.2, | 26.7, | 57.9, | 14, B |
| LYS, | CD, | 31, | 11.7, | 25.8, | 59.0, | 22, B |
| LYS, | CE, | 31, | 10.9, | 24.5, | 59.2, | 27, B |
| LYS, | NZ, | 31, | 11.5, | 23.7, | 60.3, | 32, B |
| LYS, | C, | 31, | 12.6, | 30.1, | 56.7, | 13, B |

TABLE 1-continued

Structural coordinates of HDM2 (17-125; F55Y/Y76H) (SEQ ID NO: 2) complexed with compound 1.

LYS, O, 31, 13.3, 30.3, 55.7, 14, B
PRO, N, 32, 12.6, 30.8, 57.8, 17, B
PRO, CD, 32, 11.8, 30.5, 59.0, 16, B
PRO, CA, 32, 13.4, 32.0, 58.0, 17, B
PRO, CB, 32, 13.4, 32.2, 59.5, 14, B
PRO, CG, 32, 12.1, 31.8, 59.8, 19, B
PRO, C, 32, 14.8, 32.0, 57.3, 18, B
PRO, O, 32, 15.0, 32.9, 56.4, 20, B
LEU, N, 33, 15.7, 31.2, 57.7, 15, B
LEU, CA, 33, 17.0, 31.1, 57.2, 16, B
LEU, CB, 33, 17.9, 30.1, 57.9, 18, B
LEU, CG, 33, 18.5, 30.6, 59.2, 25, B
LEU, CD1, 33, 19.7, 29.7, 59.6, 26, B
LEU, CD2, 33, 19.0, 32.1, 59.0, 25, B
LEU, C, 33, 17.1, 30.9, 55.7, 13, B
LEU, O, 33, 17.8, 31.7, 55.0, 12, B
LEU, N, 34, 16.5, 29.9, 55.2, 11, B
LEU, CA, 34, 16.5, 29.7, 53.7, 14, B
LEU, CB, 34, 15.6, 28.4, 53.4, 14, B
LEU, CG, 34, 15.6, 28.2, 51.9, 13, B
LEU, CD1, 34, 17.0, 28.1, 51.3, 16, B
LEU, CD2, 34, 14.8, 26.9, 51.6, 13, B
LEU, C, 34, 15.9, 30.9, 53.0, 17, B
LEU, O, 34, 16.4, 31.3, 52.0, 15, B
LEU, N, 35, 14.8, 31.5, 53.5, 15, B
LEU, CA, 35, 14.2, 32.6, 52.9, 14, B
LEU, CB, 35, 13.0, 33.1, 53.7, 11, B
LEU, CG, 35, 12.2, 34.1, 52.9, 9, B
LEU, CD1, 35, 11.9, 33.7, 51.5, 11, B
LEU, CD2, 35, 10.8, 34.4, 53.6, 14, B
LEU, C, 35, 15.2, 33.8, 52.8, 14, B
LEU, O, 35, 15.3, 34.5, 51.8, 13, B
LYS, N, 36, 15.9, 34.0, 53.9, 16, B
LYS, CA, 36, 16.9, 35.0, 54.0, 19, B
LYS, CB, 36, 17.6, 34.9, 55.3, 20, B
LYS, CG, 36, 18.5, 36.1, 55.7, 24, B
LYS, CD, 36, 19.0, 36.0, 57.1, 26, B
LYS, CE, 36, 19.7, 37.3, 57.5, 25, B
LYS, NZ, 36, 19.8, 37.2, 59.0, 31, B
LYS, C, 36, 18.0, 34.8, 52.9, 20, B
LYS, O, 36, 18.4, 35.8, 52.2, 19, B
LEU, N, 37, 18.4, 33.6, 52.6, 17, B
LEU, CA, 37, 19.3, 33.3, 51.6, 22, B
LEU, CB, 37, 19.7, 31.8, 51.6, 24, B
LEU, CG, 37, 20.9, 31.3, 50.8, 26, B
LEU, CD1, 37, 21.1, 29.8, 51.2, 25, B
LEU, CD2, 37, 20.5, 31.3, 49.3, 25, B
LEU, C, 37, 18.7, 33.6, 50.2, 21, B
LEU, O, 37, 19.4, 34.2, 49.3, 21, B
LEU, N, 38, 17.5, 33.2, 49.9, 22, B
LEU, CA, 38, 16.9, 33.4, 48.7, 18, B
LEU, CB, 38, 15.5, 32.7, 48.6, 17, B
LEU, CG, 38, 15.5, 31.2, 48.8, 18, B
LEU, CD1, 38, 14.1, 30.7, 49.0, 11, B
LEU, CD2, 38, 16.2, 30.5, 47.6, 17, B
LEU, C, 38, 16.7, 34.9, 48.3, 23, B
LEU, O, 38, 17.0, 35.3, 47.2, 22, B
LYS, N, 39, 16.2, 35.6, 49.3, 23, B
LYS, CA, 39, 16.0, 37.1, 49.1, 24, B
LYS, CB, 39, 15.2, 37.6, 50.3, 24, B
LYS, CG, 39, 13.7, 37.1, 50.3, 28, B
LYS, CD, 39, 12.9, 38.1, 51.1, 26, B
LYS, CE, 39, 11.4, 37.8, 50.9, 27, B
LYS, NZ, 39, 10.5, 38.6, 51.8, 29, B
LYS, C, 39, 17.2, 37.8, 49.0, 25, B
LYS, O, 39, 17.2, 39.0, 48.6, 27, B
SER, N, 40, 18.4, 37.2, 49.3, 25, B
SER, CA, 40, 19.7, 37.8, 49.2, 23, B
SER, CB, 40, 20.7, 37.2, 50.1, 24, B
SER, OG, 40, 21.2, 36.0, 49.5, 25, B
SER, C, 40, 20.2, 37.8, 47.7, 24, B
SER, O, 40, 21.2, 38.4, 47.5, 25, B
VAL, N, 41, 19.6, 37.0, 46.9, 22, B
VAL, CA, 41, 20.0, 37.0, 45.5, 21, B
VAL, CB, 41, 20.5, 35.5, 45.1, 20, B
VAL, CG1, 41, 21.9, 35.4, 45.8, 19, B
VAL, CG2, 41, 19.6, 34.5, 45.6, 16, B
VAL, C, 41, 18.9, 37.3, 44.5, 20, B
VAL, O, 41, 18.9, 36.9, 43.3, 21, B
GLY, N, 42, 17.9, 38.0, 45.0, 20, B
GLY, CA, 42, 16.8, 38.4, 44.1, 24, B
GLY, C, 42, 15.4, 38.0, 44.5, 23, B
GLY, O, 42, 14.4, 38.7, 44.2, 21, B
ALA, N, 43, 15.2, 36.8, 45.2, 23, B
ALA, CA, 43, 13.9, 36.3, 45.6, 22, B
ALA, CB, 43, 14.1, 35.2, 46.6, 22, B
ALA, C, 43, 13.1, 37.5, 46.3, 24, B
ALA, O, 43, 13.7, 38.2, 47.1, 26, B
GLN, N, 44, 11.8, 37.5, 46.0, 21, B
GLN, CA, 44, 11.0, 38.6, 46.6, 24, B
GLN, CB, 44, 10.6, 39.5, 45.5, 28, B
GLN, CG, 44, 11.7, 40.1, 44.6, 33, B
GLN, CD, 44, 12.1, 41.5, 45.0, 36, B
GLN, OE1, 44, 11.2, 42.4, 45.0, 39, B
GLN, NE2, 44, 13.3, 41.8, 45.4, 40, B
GLN, C, 44, 9.7, 38.1, 47.3, 24, B
GLN, O, 44, 9.1, 38.9, 48.0, 25, B
LYS, N, 45, 9.4, 36.9, 47.1, 23, B
LYS, CA, 45, 8.2, 36.3, 47.7, 25, B
LYS, CB, 45, 7.4, 35.5, 46.6, 26, B
LYS, CG, 45, 8.4, 34.7, 45.7, 32, B
LYS, CD, 45, 7.9, 33.6, 44.9, 35, B
LYS, CE, 45, 6.8, 34.0, 43.9, 37, B
LYS, NZ, 45, 6.3, 32.8, 43.2, 40, B
LYS, C, 45, 8.4, 35.4, 48.9, 23, B
LYS, O, 45, 9.6, 35.2, 49.3, 22, B
ASP, N, 46, 7.3, 34.8, 49.4, 19, B
ASP, CA, 46, 7.5, 33.9, 50.5, 19, B
ASP, CB, 46, 6.5, 34.3, 51.6, 22, B
ASP, CG, 46, 6.9, 35.6, 52.3, 27, B
ASP, OD1, 46, 8.1, 35.9, 52.3, 28, B
ASP, OD2, 46, 6.0, 36.3, 52.8, 28, B
ASP, C, 46, 7.2, 32.4, 50.1, 14, B
ASP, O, 46, 7.4, 31.5, 50.9, 14, B
THR, N, 47, 6.7, 32.2, 48.9, 16, B
THR, CA, 47, 6.4, 30.9, 48.5, 14, B
THR, CB, 47, 4.9, 30.5, 48.5, 18, B
THR, OG1, 47, 4.3, 31.2, 47.4, 18, B
THR, CG2, 47, 4.3, 30.9, 49.8, 16, B
THR, C, 47, 7.0, 30.7, 47.1, 17, B
THR, O, 47, 7.0, 31.6, 46.2, 13, B
TYR, N, 48, 7.6, 29.5, 46.8, 16, B
TYR, CA, 48, 8.2, 29.2, 45.5, 14, B
TYR, CB, 48, 9.7, 29.3, 45.7, 7, B
TYR, CG, 48, 10.2, 30.6, 46.3, 13, B
TYR, CD1, 48, 10.1, 30.8, 47.6, 14, B
TYR, CE1, 48, 10.5, 32.0, 48.2, 17, B
TYR, CD2, 48, 10.6, 31.6, 45.5, 15, B
TYR, CE2, 48, 11.0, 32.8, 46.0, 16, B
TYR, CZ, 48, 10.9, 33.0, 47.3, 16, B
TYR, OH, 48, 11.3, 34.2, 47.9, 13, B
TYR, C, 48, 8.0, 27.8, 45.1, 12, B
TYR, O, 48, 7.6, 26.9, 45.9, 14, B
THR, N, 49, 8.2, 27.5, 43.8, 13, B
THR, CA, 49, 8.1, 26.2, 43.2, 15, B
THR, CB, 49, 8.0, 26.2, 41.7, 16, B
THR, OG1, 49, 9.1, 26.9, 41.1, 21, B
THR, CG2, 49, 6.7, 26.8, 41.2, 19, B
THR, C, 49, 9.5, 25.7, 43.6, 15, B
THR, O, 49, 10.4, 26.5, 43.9, 12, B
MET, N, 50, 9.7, 24.4, 43.6, 17, B
MET, CA, 50, 11.0, 23.8, 44.0, 14, B
MET, CB, 50, 11.0, 22.3, 44.0, 17, B
MET, CG, 50, 10.3, 21.7, 45.2, 20, B
MET, SD, 50, 11.2, 22.1, 46.7, 19, B
MET, CE, 50, 12.7, 21.0, 46.5, 11, B
MET, C, 50, 12.1, 24.3, 43.0, 13, B
MET, O, 50, 13.2, 24.6, 43.4, 9, B
LYS, N, 51, 11.7, 24.4, 41.7, 9, B
LYS, CA, 51, 12.7, 24.8, 40.7, 9, B
LYS, CB, 51, 12.1, 24.7, 39.3, 7, B
LYS, CG, 51, 12.2, 23.3, 38.7, 9, B

TABLE 1-continued

Structural coordinates of HDM2 (17-125; F55Y/Y76H) (SEQ ID NO: 2) complexed with compound 1.

LYS, CD, 51, 11.7, 23.4, 37.3, 14, B
LYS, CE, 51, 11.5, 22.0, 36.7, 17, B
LYS, NZ, 51, 10.4, 21.3, 37.4, 20, B
LYS, C, 51, 13.2, 26.2, 41.0, 13, B
LYS, O, 51, 14.4, 26.5, 40.8, 7, B
GLU, N, 52, 12.3, 27.1, 41.4, 10, B
GLU, CA, 52, 12.7, 28.5, 41.8, 17, B
GLU, CB, 52, 11.5, 29.3, 42.1, 17, B
GLU, CG, 52, 10.7, 29.9, 40.9, 23, B
GLU, CD, 52, 9.4, 30.6, 41.3, 28, B
GLU, OE1, 52, 8.9, 31.4, 40.6, 29, B
GLU, OE2, 52, 8.8, 30.3, 42.4, 26, B
GLU, C, 52, 13.7, 28.5, 42.9, 14, B
GLU, O, 52, 14.6, 29.3, 42.9, 13, B
VAL, N, 53, 13.4, 27.6, 43.9, 10, B
VAL, CA, 53, 14.3, 27.5, 45.0, 10, B
VAL, CB, 53, 13.8, 26.5, 46.1, 9, B
VAL, CG1, 53, 14.8, 26.3, 47.2, 8, B
VAL, CG2, 53, 12.5, 27.0, 46.7, 12, B
VAL, C, 53, 15.7, 27.1, 44.6, 7, B
VAL, O, 53, 16.7, 27.7, 45.0, 7, B
LEU, N, 54, 15.8, 26.1, 43.7, 9, B
LEU, CA, 54, 17.0, 25.7, 43.1, 7, B
LEU, CB, 54, 16.8, 24.5, 42.2, 11, B
LEU, CG, 54, 16.3, 23.2, 42.9, 6, B
LEU, CD1, 54, 16.0, 22.2, 41.8, 10, B
LEU, CD2, 54, 17.4, 22.7, 43.9, 9, B
LEU, C, 54, 17.7, 26.8, 42.3, 12, B
LEU, O, 54, 18.9, 26.9, 42.4, 12, B
TYR, N, 55, 16.9, 27.6, 41.6, 8, B
TYR, CA, 55, 17.4, 28.7, 40.8, 10, B
TYR, CB, 55, 16.3, 29.5, 40.2, 8, B
TYR, CG, 55, 16.7, 30.7, 39.5, 10, B
TYR, CD1, 55, 17.3, 30.7, 38.2, 9, B
TYR, CE1, 55, 17.6, 31.9, 37.5, 16, B
TYR, CD2, 55, 16.5, 32.0, 40.0, 11, B
TYR, CE2, 55, 16.9, 33.2, 39.4, 13, B
TYR, CZ, 55, 17.4, 33.1, 38.1, 13, B
TYR, OH, 55, 17.8, 34.2, 37.4, 17, B
TYR, C, 55, 18.2, 29.7, 41.7, 11, B
TYR, O, 55, 19.4, 30.0, 41.5, 12, B
TYR, N, 56, 17.6, 30.2, 42.8, 11, B
TYR, CA, 56, 18.2, 31.1, 43.7, 11, B
TYR, CB, 56, 17.2, 31.7, 44.6, 12, B
TYR, CG, 56, 16.2, 32.6, 43.9, 13, B
TYR, CD1, 56, 16.6, 33.8, 43.3, 16, B
TYR, CE1, 56, 15.7, 34.6, 42.6, 14, B
TYR, CD2, 56, 14.8, 32.2, 43.8, 13, B
TYR, CE2, 56, 13.9, 33.0, 43.1, 15, B
TYR, CZ, 56, 14.3, 34.2, 42.5, 17, B
TYR, OH, 56, 13.4, 34.9, 41.8, 19, B
TYR, C, 56, 19.4, 30.6, 44.4, 15, B
TYR, O, 56, 20.4, 31.3, 44.6, 12, B
LEU, N, 57, 19.4, 29.3, 44.8, 12, B
LEU, CA, 57, 20.5, 28.7, 45.5, 13, B
LEU, CB, 57, 20.3, 27.3, 45.9, 13, B
LEU, CG, 57, 19.3, 27.0, 47.1, 14, B
LEU, CD1, 57, 19.0, 25.6, 47.2, 17, B
LEU, CD2, 57, 20.0, 27.5, 48.4, 15, B
LEU, C, 57, 21.7, 28.8, 44.5, 16, B
LEU, O, 57, 22.8, 29.2, 44.8, 15, B
GLY, N, 58, 21.3, 28.4, 43.3, 14, B
GLY, CA, 58, 22.3, 28.4, 42.2, 18, B
GLY, C, 58, 22.9, 29.8, 42.1, 13, B
GLY, O, 58, 24.1, 30.0, 42.0, 19, B
GLN, N, 59, 22.0, 30.8, 42.0, 16, B
GLN, CA, 59, 22.4, 32.2, 41.9, 19, B
GLN, CB, 59, 21.1, 33.1, 42.0, 20, B
GLN, CG, 59, 20.6, 33.6, 40.6, 24, B
GLN, CD, 59, 21.1, 35.0, 40.3, 25, B
GLN, OE1, 59, 20.8, 35.5, 39.3, 33, B
GLN, NE2, 59, 21.8, 35.6, 41.2, 22, B
GLN, C, 59, 23.3, 32.6, 43.1, 22, B
GLN, O, 59, 24.4, 33.3, 42.9, 18, B
TYR, N, 60, 22.9, 32.2, 44.3, 20, B
TYR, CA, 60, 23.7, 32.5, 45.5, 17, B
TYR, CB, 60, 22.9, 31.9, 46.7, 14, B
TYR, CG, 60, 23.6, 32.1, 48.0, 11, B
TYR, CD1, 60, 23.4, 33.2, 48.8, 15, B
TYR, CE1, 60, 24.0, 33.3, 50.0, 15, B
TYR, CD2, 60, 24.4, 31.1, 48.5, 13, B
TYR, CE2, 60, 25.0, 31.2, 49.8, 13, B
TYR, CZ, 60, 24.8, 32.3, 50.5, 13, B
TYR, OH, 60, 25.3, 32.5, 51.8, 19, B
TYR, C, 60, 25.1, 31.9, 45.4, 20, B
TYR, O, 60, 26.1, 32.6, 45.6, 22, B
ILE, N, 61, 25.2, 30.6, 45.1, 17, B
ILE, CA, 61, 26.4, 29.9, 44.9, 16, B
ILE, CB, 61, 26.2, 28.4, 44.6, 16, B
ILE, CG2, 61, 27.6, 27.8, 44.2, 18, B
ILE, CG1, 61, 25.7, 27.7, 45.8, 16, B
ILE, CD1, 61, 25.3, 26.2, 45.6, 14, B
ILE, C, 61, 27.4, 30.4, 43.9, 23, B
ILE, O, 61, 28.6, 30.5, 44.1, 23, B
MET, N, 62, 26.9, 30.8, 42.7, 23, B
MET, CA, 62, 27.7, 31.3, 41.7, 26, B
MET, CB, 62, 26.9, 31.4, 40.4, 23, B
MET, CG, 62, 26.5, 30.1, 39.9, 18, B
MET, SD, 62, 27.9, 29.0, 39.7, 20, B
MET, CE, 62, 28.6, 29.7, 38.2, 24, B
MET, C, 62, 28.2, 32.7, 42.1, 29, B
MET, O, 62, 29.4, 32.9, 42.1, 32, B
THR, N, 63, 27.3, 33.6, 42.4, 32, B
THR, CA, 63, 27.6, 35.0, 42.8, 35, B
THR, CB, 63, 26.3, 35.6, 43.4, 35, B
THR, OG1, 63, 25.3, 35.7, 42.3, 35, B
THR, CG2, 63, 26.6, 37.0, 43.8, 34, B
THR, C, 63, 28.6, 35.1, 44.0, 39, B
THR, O, 63, 29.2, 36.2, 44.1, 38, B
LYS, N, 64, 28.9, 34.0, 44.7, 40, B
LYS, CA, 64, 29.8, 34.0, 45.8, 40, B
LYS, CB, 64, 29.2, 33.6, 47.1, 39, B
LYS, CG, 64, 27.8, 34.3, 47.3, 36, B
LYS, CD, 64, 27.8, 35.1, 48.6, 37, B
LYS, CE, 64, 28.1, 34.2, 49.8, 36, B
LYS, NZ, 64, 28.1, 35.0, 51.0, 35, B
LYS, C, 64, 31.0, 33.1, 45.5, 43, B
LYS, O, 64, 32.0, 33.1, 46.2, 45, B
ARG, N, 65, 30.9, 32.3, 44.5, 42, B
ARG, CA, 65, 32.0, 31.4, 44.1, 43, B
ARG, CB, 65, 33.2, 32.2, 43.7, 44, B
ARG, CG, 65, 33.0, 33.1, 42.5, 45, B
ARG, CD, 65, 34.3, 33.7, 42.1, 48, B
ARG, NE, 65, 34.2, 34.3, 40.8, 52, B
ARG, CZ, 65, 35.2, 35.0, 40.1, 55, B
ARG, NH1, 65, 36.4, 35.1, 40.7, 57, B
ARG, NH2, 65, 35.0, 35.4, 38.9, 56, B
ARG, C, 65, 32.3, 30.4, 45.1, 41, B
ARG, O, 65, 33.4, 30.0, 45.3, 42, B
LEU, N, 66, 31.2, 29.9, 45.8, 39, B
LEU, CA, 66, 31.4, 29.0, 46.9, 39, B
LEU, CB, 66, 30.1, 28.7, 47.6, 37, B
LEU, CG, 66, 29.4, 30.0, 48.1, 37, B
LEU, CD1, 66, 28.1, 29.7, 48.8, 35, B
LEU, CD2, 66, 30.3, 30.7, 49.1, 40, B
LEU, C, 66, 31.9, 27.7, 46.3, 40, B
LEU, O, 66, 32.3, 26.7, 47.1, 40, B
TYR, N, 67, 32.0, 27.6, 45.0, 41, B
TYR, CA, 67, 32.5, 26.4, 44.3, 38, B
TYR, CB, 67, 31.8, 26.1, 43.0, 40, B
TYR, CG, 67, 32.0, 27.3, 42.0, 37, B
TYR, CD1, 67, 33.1, 27.4, 41.2, 38, B
TYR, CE1, 67, 33.2, 28.5, 40.3, 36, B
TYR, CD2, 67, 31.0, 28.2, 41.9, 38, B
TYR, CE2, 67, 31.1, 29.3, 41.0, 38, B
TYR, CZ, 67, 32.2, 29.4, 40.3, 38, B
TYR, OH, 67, 32.4, 30.5, 39.4, 37, B
TYR, C, 67, 34.0, 26.4, 44.1, 44, B
TYR, O, 67, 34.6, 27.5, 43.9, 43, B
ASP, N, 68, 34.7, 25.2, 44.2, 49, B
ASP, CA, 68, 36.1, 25.1, 44.0, 55, B
ASP, CB, 68, 36.6, 23.7, 44.5, 55, B

TABLE 1-continued

Structural coordinates of HDM2 (17-125; F55Y/Y76H) (SEQ ID NO: 2) complexed with compound 1.

ASP, CG, 68, 38.0, 23.4, 44.1, 56, B
ASP, OD1, 68, 38.9, 24.3, 44.3, 56, B
ASP, OD2, 68, 38.2, 22.3, 43.6, 57, B
ASP, C, 68, 36.6, 25.3, 42.6, 58, B
ASP, O, 68, 36.3, 24.5, 41.7, 59, B
GLU, N, 69, 37.3, 26.4, 42.3, 61, B
GLU, CA, 69, 37.8, 26.8, 41.0, 64, B
GLU, CB, 69, 38.9, 27.8, 41.1, 66, B
GLU, CG, 69, 39.9, 27.6, 42.2, 67, B
GLU, CD, 69, 40.9, 28.8, 42.4, 67, B
GLU, OE1, 69, 40.4, 29.9, 42.7, 66, B
GLU, OE2, 69, 42.1, 28.6, 42.3, 66, B
GLU, C, 69, 38.3, 25.6, 40.2, 65, B
GLU, O, 69, 38.0, 25.5, 39.0, 65, B
LYS, N, 70, 38.9, 24.6, 40.8, 66, B
LYS, CA, 70, 39.4, 23.5, 40.1, 66, B
LYS, CB, 70, 40.4, 22.7, 41.1, 68, B
LYS, CG, 70, 40.9, 21.4, 40.5, 70, B
LYS, CD, 70, 41.9, 20.7, 41.4, 71, B
LYS, CE, 70, 43.1, 21.7, 41.5, 72, B
LYS, NZ, 70, 44.2, 21.1, 42.3, 72, B
LYS, C, 70, 38.2, 22.6, 39.8, 66, B
LYS, O, 70, 37.8, 22.5, 38.7, 67, B
GLN, N, 71, 37.7, 21.9, 40.8, 65, B
GLN, CA, 71, 36.5, 21.0, 40.7, 64, B
GLN, CB, 71, 36.6, 19.9, 41.7, 66, B
GLN, CG, 71, 37.9, 19.1, 41.6, 69, B
GLN, CD, 71, 37.9, 17.9, 42.5, 71, B
GLN, OE1, 71, 37.7, 18.0, 43.7, 71, B
GLN, NE2, 71, 38.2, 16.8, 41.9, 72, B
GLN, C, 71, 35.3, 21.9, 40.9, 60, B
GLN, O, 71, 34.8, 22.0, 42.0, 60, B
GLN, N, 72, 34.7, 22.4, 39.8, 56, B
GLN, CA, 72, 33.6, 23.2, 39.9, 51, B
GLN, CB, 72, 33.3, 24.0, 38.6, 51, B
GLN, CG, 72, 34.6, 24.5, 38.0, 52, B
GLN, CD, 72, 34.3, 25.7, 37.0, 54, B
GLN, OE1, 72, 33.4, 25.6, 36.2, 55, B
GLN, NE2, 72, 35.1, 26.8, 37.1, 54, B
GLN, C, 72, 32.3, 22.5, 40.4, 48, B
GLN, O, 72, 31.2, 23.2, 40.5, 49, B
HIS, N, 73, 32.3, 21.2, 40.6, 46, B
HIS, CA, 73, 31.1, 20.5, 41.0, 47, B
HIS, CB, 73, 30.9, 19.3, 40.1, 47, B
HIS, CG, 73, 31.6, 18.1, 40.6, 49, B
HIS, CD2, 73, 32.7, 17.5, 40.0, 50, B
HIS, ND1, 73, 31.3, 17.3, 41.6, 50, B
HIS, CE1, 73, 32.1, 16.3, 41.7, 49, B
HIS, NE2, 73, 33.0, 16.3, 40.8, 49, B
HIS, C, 73, 31.1, 20.2, 42.5, 47, B
HIS, O, 73, 30.4, 19.2, 42.9, 49, B
ILE, N, 74, 31.8, 20.9, 43.3, 45, B
ILE, CA, 74, 31.9, 20.7, 44.7, 42, B
ILE, CB, 74, 33.2, 20.0, 45.1, 42, B
ILE, CG2, 74, 33.3, 19.8, 46.6, 41, B
ILE, CG1, 74, 33.3, 18.7, 44.4, 43, B
ILE, CD1, 74, 34.7, 18.0, 44.6, 46, B
ILE, C, 74, 31.8, 22.1, 45.4, 41, B
ILE, O, 74, 32.6, 23.0, 45.1, 42, B
VAL, N, 75, 30.9, 22.3, 46.3, 40, B
VAL, CA, 75, 30.7, 23.6, 47.0, 41, B
VAL, CB, 75, 29.3, 24.0, 47.1, 39, B
VAL, CG1, 75, 29.1, 25.1, 48.1, 36, B
VAL, CG2, 75, 28.7, 24.4, 45.7, 38, B
VAL, C, 75, 31.3, 23.6, 48.4, 42, B
VAL, O, 75, 30.9, 22.8, 49.3, 44, B
HIS, N, 76, 32.3, 24.5, 48.6, 46, B
HIS, CA, 76, 32.9, 24.7, 49.9, 50, B
HIS, CB, 76, 34.4, 25.0, 49.8, 53, B
HIS, CG, 76, 35.2, 23.9, 49.1, 56, B
HIS, CD2, 76, 35.9, 23.9, 48.0, 55, B
HIS, ND1, 76, 35.3, 22.7, 49.7, 56, B
HIS, CE1, 76, 36.1, 21.9, 49.0, 56, B
HIS, NE2, 76, 36.5, 22.6, 47.9, 57, B
HIS, C, 76, 32.1, 25.8, 50.5, 50, B
HIS, O, 76, 32.3, 27.0, 50.1, 51, B
CYS, N, 77, 31.3, 25.5, 51.5, 49, B
CYS, CA, 77, 30.6, 26.6, 52.2, 47, B
CYS, CB, 77, 29.1, 26.4, 51.8, 48, B
CYS, SG, 77, 28.4, 24.8, 52.0, 44, B
CYS, C, 77, 30.7, 26.6, 53.7, 48, B
CYS, O, 77, 29.8, 27.1, 54.4, 46, B
SER, N, 78, 31.7, 26.1, 54.3, 49, B
SER, CA, 78, 31.9, 26.1, 55.7, 48, B
SER, CB, 78, 33.0, 25.0, 56.1, 47, B
SER, OG, 78, 32.5, 23.7, 55.9, 43, B
SER, C, 78, 32.4, 27.5, 56.1, 48, B
SER, O, 78, 33.6, 27.9, 55.9, 45, B
ASN, N, 79, 31.5, 28.2, 56.7, 49, B
ASN, CA, 79, 31.6, 29.6, 57.2, 50, B
ASN, CB, 79, 33.0, 30.1, 56.9, 53, B
ASN, CG, 79, 33.9, 30.1, 58.2, 55, B
ASN, OD1, 79, 33.5, 30.7, 59.2, 55, B
ASN, ND2, 79, 35.1, 29.6, 58.1, 55, B
ASN, C, 79, 30.6, 30.4, 56.4, 48, B
ASN, O, 79, 30.7, 31.6, 56.5, 48, B
ASP, N, 80, 29.7, 29.7, 55.7, 46, B
ASP, CA, 80, 28.7, 30.4, 55.0, 43, B
ASP, CB, 80, 28.9, 30.1, 53.5, 42, B
ASP, CG, 80, 28.0, 30.9, 52.6, 43, B
ASP, OD1, 80, 28.3, 32.1, 52.4, 44, B
ASP, OD2, 80, 26.9, 30.4, 52.1, 41, B
ASP, C, 80, 27.3, 30.0, 55.4, 38, B
ASP, O, 80, 27.1, 28.8, 55.9, 36, B
LEU, N, 81, 26.3, 30.9, 55.2, 34, B
LEU, CA, 81, 25.0, 30.6, 55.6, 30, B
LEU, CB, 81, 24.1, 31.7, 55.1, 28, B
LEU, CG, 81, 22.6, 31.7, 55.5, 30, B
LEU, CD1, 81, 22.6, 31.8, 57.1, 31, B
LEU, CD2, 81, 21.9, 33.0, 55.0, 27, B
LEU, C, 81, 24.5, 29.2, 55.0, 29, B
LEU, O, 81, 23.9, 28.4, 55.7, 30, B
LEU, N, 82, 24.8, 29.0, 53.7, 26, B
LEU, CA, 82, 24.3, 27.8, 53.1, 23, B
LEU, CB, 82, 24.9, 27.7, 51.7, 20, B
LEU, CG, 82, 24.7, 26.4, 50.9, 18, B
LEU, CD1, 82, 23.2, 26.2, 50.6, 16, B
LEU, CD2, 82, 25.4, 26.5, 49.6, 20, B
LEU, C, 82, 24.9, 26.6, 53.9, 19, B
LEU, O, 82, 24.2, 25.6, 54.0, 15, B
GLY, N, 83, 26.1, 26.7, 54.4, 22, B
GLY, CA, 83, 26.6, 25.7, 55.2, 25, B
GLY, C, 83, 25.8, 25.4, 56.4, 27, B
GLY, O, 83, 25.6, 24.2, 56.8, 30, B
ASP, N, 84, 25.4, 26.5, 57.1, 28, B
ASP, CA, 84, 24.6, 26.3, 58.3, 29, B
ASP, CB, 84, 24.3, 27.7, 58.9, 32, B
ASP, CG, 84, 25.5, 28.3, 59.5, 36, B
ASP, OD1, 84, 25.4, 29.4, 60.1, 39, B
ASP, OD2, 84, 26.6, 27.7, 59.5, 39, B
ASP, C, 84, 23.3, 25.7, 57.9, 26, B
ASP, O, 84, 22.8, 24.8, 58.6, 24, B
LEU, N, 85, 22.7, 26.0, 56.8, 24, B
LEU, CA, 85, 21.4, 25.4, 56.4, 25, B
LEU, CB, 85, 20.8, 26.2, 55.2, 29, B
LEU, CG, 85, 20.6, 27.7, 55.3, 31, B
LEU, CD1, 85, 19.6, 28.1, 54.2, 34, B
LEU, CD2, 85, 20.1, 28.0, 56.7, 32, B
LEU, C, 85, 21.5, 24.0, 56.0, 28, B
LEU, O, 85, 20.7, 23.2, 56.5, 29, B
PHE, N, 86, 22.5, 23.6, 55.2, 27, B
PHE, CA, 86, 22.7, 22.2, 54.8, 30, B
PHE, CB, 86, 23.5, 22.2, 53.5, 31, B
PHE, CG, 86, 22.7, 22.4, 52.3, 36, B
PHE, CD1, 86, 21.5, 23.2, 52.4, 37, B
PHE, CD2, 86, 23.0, 21.9, 51.1, 34, B
PHE, CE1, 86, 20.7, 23.4, 51.3, 35, B
PHE, CE2, 86, 22.2, 22.1, 50.0, 35, B
PHE, CZ, 86, 21.1, 22.9, 50.1, 34, B
PHE, C, 86, 23.3, 21.3, 55.9, 31, B
PHE, O, 86, 23.2, 20.1, 55.7, 34, B
GLY, N, 87, 23.8, 21.8, 56.9, 32, B

TABLE 1-continued

Structural coordinates of HDM2 (17-125; F55Y/Y76H) (SEQ ID NO: 2) complexed with compound 1.

| | | | | | | |
|---|---|---|---|---|---|---|
| GLY, | CA, | 87, | 24.4, | 21.0, | 58.0, 32, | B |
| GLY, | C, | 87, | 25.5, | 20.1, | 57.5, 36, | B |
| GLY, | O, | 87, | 25.7, | 19.0, | 58.0, 33, | B |
| VAL, | N, | 88, | 26.2, | 20.7, | 56.5, 36, | B |
| VAL, | CA, | 88, | 27.4, | 20.0, | 55.9, 40, | B |
| VAL, | CB, | 88, | 27.1, | 19.3, | 54.5, 42, | B |
| VAL, | CG1, | 88, | 26.5, | 17.9, | 54.8, 43, | B |
| VAL, | CG2, | 88, | 26.1, | 20.1, | 53.7, 45, | B |
| VAL, | C, | 88, | 28.5, | 21.0, | 55.6, 42, | B |
| VAL, | O, | 88, | 28.2, | 22.2, | 55.5, 43, | B |
| PRO, | N, | 89, | 29.8, | 20.6, | 55.6, 45, | B |
| PRO, | CD, | 89, | 30.1, | 19.2, | 55.8, 45, | B |
| PRO, | CA, | 89, | 30.9, | 21.4, | 55.4, 44, | B |
| PRO, | CB, | 89, | 32.1, | 20.6, | 55.9, 46, | B |
| PRO, | CG, | 89, | 31.6, | 19.2, | 55.5, 46, | B |
| PRO, | C, | 89, | 31.1, | 21.7, | 53.9, 42, | B |
| PRO, | O, | 89, | 31.5, | 22.8, | 53.5, 42, | B |
| SER, | N, | 90, | 30.7, | 20.8, | 53.1, 40, | B |
| SER, | CA, | 90, | 30.8, | 20.9, | 51.6, 39, | B |
| SER, | CB, | 90, | 32.3, | 20.9, | 51.2, 42, | B |
| SER, | OG, | 90, | 33.1, | 21.9, | 51.8, 40, | B |
| SER, | C, | 90, | 30.0, | 19.8, | 51.0, 36, | B |
| SER, | O, | 90, | 29.8, | 18.7, | 51.6, 37, | B |
| PHE, | N, | 91, | 29.6, | 20.0, | 49.8, 31, | B |
| PHE, | CA, | 91, | 28.8, | 19.0, | 49.1, 29, | B |
| PHE, | CB, | 91, | 27.3, | 19.2, | 49.4, 29, | B |
| PHE, | CG, | 91, | 26.8, | 20.5, | 48.9, 28, | B |
| PHE, | CD1, | 91, | 26.4, | 20.7, | 47.6, 29, | B |
| PHE, | CD2, | 91, | 26.7, | 21.6, | 49.8, 28, | B |
| PHE, | CE1, | 91, | 26.0, | 22.0, | 47.2, 27, | B |
| PHE, | CE2, | 91, | 26.3, | 22.8, | 49.4, 27, | B |
| PHE, | CZ, | 91, | 25.9, | 23.0, | 48.1, 27, | B |
| PHE, | C, | 91, | 29.1, | 19.0, | 47.6, 31, | B |
| PHE, | O, | 91, | 29.7, | 20.0, | 47.1, 32, | B |
| SER, | N, | 92, | 28.7, | 18.0, | 46.9, 31, | B |
| SER, | CA, | 92, | 28.8, | 17.8, | 45.5, 35, | B |
| SER, | CB, | 92, | 29.2, | 16.4, | 45.1, 37, | B |
| SER, | OG, | 92, | 29.4, | 16.2, | 43.7, 39, | B |
| SER, | C, | 92, | 27.5, | 18.2, | 44.9, 35, | B |
| SER, | O, | 92, | 26.5, | 17.5, | 45.2, 34, | B |
| VAL, | N, | 93, | 27.5, | 19.2, | 44.0, 34, | B |
| VAL, | CA, | 93, | 26.2, | 19.6, | 43.4, 35, | B |
| VAL, | CB, | 93, | 26.4, | 20.8, | 42.4, 34, | B |
| VAL, | CG1, | 93, | 27.1, | 21.9, | 43.1, 34, | B |
| VAL, | CG2, | 93, | 27.2, | 20.3, | 41.2, 33, | B |
| VAL, | C, | 93, | 25.6, | 18.4, | 42.7, 36, | B |
| VAL, | O, | 93, | 24.5, | 18.6, | 42.1, 34, | B |
| LYS, | N, | 94, | 26.2, | 17.3, | 42.7, 38, | B |
| LYS, | CA, | 94, | 25.7, | 16.1, | 42.0, 40, | B |
| LYS, | CB, | 94, | 26.8, | 15.2, | 41.5, 43, | B |
| LYS, | CG, | 94, | 27.6, | 15.8, | 40.4, 46, | B |
| LYS, | CD, | 94, | 28.8, | 14.9, | 40.0, 48, | B |
| LYS, | CE, | 94, | 29.7, | 15.6, | 38.9, 50, | B |
| LYS, | NZ, | 94, | 30.9, | 14.8, | 38.7, 48, | B |
| LYS, | C, | 94, | 24.8, | 15.3, | 43.0, 42, | B |
| LYS, | O, | 94, | 24.2, | 14.3, | 42.7, 42, | B |
| GLU, | N, | 95, | 24.9, | 15.7, | 44.3, 43, | B |
| GLU, | CA, | 95, | 24.1, | 15.0, | 45.4, 44, | B |
| GLU, | CB, | 95, | 24.7, | 15.4, | 46.7, 44, | B |
| GLU, | CG, | 95, | 26.1, | 14.8, | 46.9, 48, | B |
| GLU, | CD, | 95, | 26.6, | 14.8, | 48.3, 50, | B |
| GLU, | OE1, | 95, | 26.8, | 15.9, | 49.0, 51, | B |
| GLU, | OE2, | 95, | 26.8, | 13.7, | 48.9, 52, | B |
| GLU, | C, | 95, | 22.6, | 15.4, | 45.4, 43, | B |
| GLU, | O, | 95, | 22.1, | 15.9, | 46.4, 44, | B |
| HIS, | N, | 96, | 21.9, | 15.2, | 44.3, 42, | B |
| HIS, | CA, | 96, | 20.5, | 15.6, | 44.2, 37, | B |
| HIS, | CB, | 96, | 20.0, | 15.0, | 42.9, 35, | B |
| HIS, | CG, | 96, | 20.5, | 15.7, | 41.6, 35, | B |
| HIS, | CD2, | 96, | 21.5, | 16.5, | 41.4, 35, | B |
| HIS, | ND1, | 96, | 19.8, | 15.6, | 40.4, 35, | B |
| HIS, | CE1, | 96, | 20.5, | 16.3, | 39.5, 34, | B |
| HIS, | NE2, | 96, | 21.5, | 16.9, | 40.1, 36, | B |
| HIS, | C, | 96, | 19.6, | 15.1, | 45.3, 37, | B |
| HIS, | O, | 96, | 18.9, | 16.0, | 45.9, 35, | B |
| ARG, | N, | 97, | 19.6, | 13.9, | 45.6, 38, | B |
| ARG, | CA, | 97, | 18.8, | 13.4, | 46.7, 39, | B |
| ARG, | CB, | 97, | 18.9, | 11.9, | 46.8, 46, | B |
| ARG, | CG, | 97, | 18.2, | 11.3, | 48.0, 55, | B |
| ARG, | CD, | 97, | 18.4, | 9.8, | 48.1, 61, | B |
| ARG, | NE, | 97, | 17.8, | 9.1, | 47.0, 65, | B |
| ARG, | CZ, | 97, | 17.8, | 7.7, | 46.8, 67, | B |
| ARG, | NH1, | 97, | 18.5, | 7.0, | 47.7, 68, | B |
| ARG, | NH2, | 97, | 17.2, | 7.2, | 45.8, 69, | B |
| ARG, | C, | 97, | 19.1, | 14.0, | 48.0, 34, | B |
| ARG, | O, | 97, | 18.2, | 14.4, | 48.8, 33, | B |
| LYS, | N, | 98, | 20.4, | 14.2, | 48.3, 32, | B |
| LYS, | CA, | 98, | 20.8, | 14.8, | 49.6, 29, | B |
| LYS, | CB, | 98, | 22.3, | 14.6, | 49.8, 33, | B |
| LYS, | CG, | 98, | 22.9, | 15.0, | 51.1, 38, | B |
| LYS, | CD, | 98, | 24.3, | 14.5, | 51.4, 40, | B |
| LYS, | CE, | 98, | 24.3, | 12.9, | 51.4, 43, | B |
| LYS, | NZ, | 98, | 25.6, | 12.4, | 51.7, 44, | B |
| LYS, | C, | 98, | 20.5, | 16.3, | 49.6, 25, | B |
| LYS, | O, | 98, | 20.3, | 16.9, | 50.6, 25, | B |
| ILE, | N, | 99, | 20.4, | 16.9, | 48.4, 20, | B |
| ILE, | CA, | 99, | 20.1, | 18.3, | 48.3, 18, | B |
| ILE, | CB, | 99, | 20.5, | 18.8, | 46.9, 18, | B |
| ILE, | CG2, | 99, | 20.0, | 20.2, | 46.6, 19, | B |
| ILE, | CG1, | 99, | 22.1, | 18.8, | 46.8, 21, | B |
| ILE, | CD1, | 99, | 22.6, | 19.1, | 45.4, 22, | B |
| ILE, | C, | 99, | 18.6, | 18.5, | 48.6, 16, | B |
| ILE, | O, | 99, | 18.3, | 19.4, | 49.4, 19, | B |
| TYR, | N, | 100, | 17.8, | 17.8, | 47.9, 15, | B |
| TYR, | CA, | 100, | 16.3, | 18.0, | 48.1, 16, | B |
| TYR, | CB, | 100, | 15.5, | 16.9, | 47.3, 13, | B |
| TYR, | CG, | 100, | 15.4, | 17.3, | 45.9, 19, | B |
| TYR, | CD1, | 100, | 15.8, | 16.5, | 44.9, 18, | B |
| TYR, | CE1, | 100, | 15.7, | 16.8, | 43.5, 21, | B |
| TYR, | CD2, | 100, | 14.8, | 18.5, | 45.5, 21, | B |
| TYR, | CE2, | 100, | 14.6, | 18.9, | 44.2, 22, | B |
| TYR, | CZ, | 100, | 15.1, | 18.0, | 43.2, 23, | B |
| TYR, | OH, | 100, | 14.9, | 18.3, | 41.9, 20, | B |
| TYR, | C, | 100, | 16.0, | 17.8, | 49.6, 15, | B |
| TYR, | O, | 100, | 15.4, | 18.7, | 50.2, 17, | B |
| THR, | N, | 101, | 16.6, | 16.8, | 50.2, 16, | B |
| THR, | CA, | 101, | 16.4, | 16.6, | 51.7, 20, | B |
| THR, | CB, | 101, | 17.2, | 15.3, | 52.2, 23, | B |
| THR, | OG1, | 101, | 16.6, | 14.1, | 51.6, 23, | B |
| THR, | CG2, | 101, | 17.1, | 15.2, | 53.7, 25, | B |
| THR, | C, | 101, | 16.8, | 17.7, | 52.5, 21, | B |
| THR, | O, | 101, | 16.2, | 18.1, | 53.5, 20, | B |
| MET, | N, | 102, | 18.0, | 18.3, | 52.2, 19, | B |
| MET, | CA, | 102, | 18.4, | 19.5, | 52.9, 24, | B |
| MET, | CB, | 102, | 19.9, | 19.8, | 52.5, 29, | B |
| MET, | CG, | 102, | 20.9, | 18.7, | 52.8, 36, | B |
| MET, | SD, | 102, | 22.6, | 19.0, | 52.5, 43, | B |
| MET, | CE, | 102, | 22.8, | 18.6, | 50.8, 39, | B |
| MET, | C, | 102, | 17.4, | 20.6, | 52.7, 20, | B |
| MET, | O, | 102, | 17.2, | 21.4, | 53.6, 22, | B |
| ILE, | N, | 103, | 16.8, | 20.7, | 51.5, 16, | B |
| ILE, | CA, | 103, | 15.9, | 21.8, | 51.3, 14, | B |
| ILE, | CB, | 103, | 15.5, | 21.9, | 49.8, 14, | B |
| ILE, | CG2, | 103, | 14.5, | 23.0, | 49.6, 17, | B |
| ILE, | CG1, | 103, | 16.8, | 22.2, | 49.0, 14, | B |
| ILE, | CD1, | 103, | 16.5, | 22.3, | 47.5, 10, | B |
| ILE, | C, | 103, | 14.5, | 21.5, | 52.0, 16, | B |
| ILE, | O, | 103, | 14.0, | 22.4, | 52.7, 16, | B |
| TYR, | N, | 104, | 14.0, | 20.3, | 51.9, 14, | B |
| TYR, | CA, | 104, | 12.8, | 19.9, | 52.6, 17, | B |
| TYR, | CB, | 104, | 12.4, | 18.5, | 52.4, 16, | B |
| TYR, | CG, | 104, | 12.2, | 18.1, | 50.9, 16, | B |
| TYR, | CD1, | 104, | 12.5, | 16.8, | 50.5, 19, | B |
| TYR, | CE1, | 104, | 12.3, | 16.5, | 49.2, 17, | B |
| TYR, | CD2, | 104, | 11.7, | 19.0, | 50.0, 15, | B |
| TYR, | CE2, | 104, | 11.5, | 18.7, | 48.7, 12, | B |
| TYR, | CZ, | 104, | 11.8, | 17.4, | 48.3, 18, | B |
| TYR, | OH, | 104, | 11.7, | 17.0, | 47.0, 22, | B |
| TYR, | C, | 104, | 12.8, | 20.2, | 54.1, 21, | B |
| TYR, | O, | 104, | 11.8, | 20.4, | 54.7, 24, | B |
| ARG, | N, | 105, | 14.0, | 20.0, | 54.6, 21, | B |
| ARG, | CA, | 105, | 14.2, | 20.2, | 56.1, 22, | B |

TABLE 1-continued

Structural coordinates of HDM2 (17-125; F55Y/Y76H) (SEQ ID NO: 2) complexed with compound 1.

| | | | | | | |
|---|---|---|---|---|---|---|
| ARG | CB | 105 | 15.5 | 19.6 | 56.5 | 25, B |
| AEG | CG | 105 | 15.5 | 18.1 | 56.5 | 27, B |
| ARG | CD | 105 | 16.8 | 17.5 | 57.0 | 32, B |
| ARG | NE | 105 | 16.7 | 16.0 | 56.9 | 36, B |
| ARG | CZ | 105 | 17.8 | 15.2 | 57.0 | 38, B |
| ARG | NH1 | 105 | 19.0 | 15.6 | 57.3 | 39, B |
| ARG | NH2 | 105 | 17.6 | 13.9 | 56.9 | 39, B |
| ARG | C | 105 | 14.2 | 21.7 | 56.4 | 21, B |
| ARG | O | 105 | 14.2 | 22.1 | 57.6 | 17, B |
| ASN | N | 106 | 14.1 | 22.6 | 55.4 | 21, B |
| ASN | CA | 106 | 14.0 | 24.0 | 55.7 | 20, B |
| ASN | CB | 106 | 15.2 | 24.7 | 55.1 | 22, B |
| ASN | CG | 106 | 16.5 | 24.5 | 55.9 | 26, B |
| ASN | OD1 | 106 | 16.6 | 25.0 | 57.0 | 31, B |
| ASN | ND2 | 106 | 17.4 | 23.7 | 55.4 | 24, B |
| ASN | C | 106 | 12.7 | 24.6 | 55.1 | 21, B |
| ASN | O | 106 | 12.7 | 25.8 | 54.9 | 23, B |
| LEU | N | 107 | 11.7 | 23.8 | 54.9 | 22, B |
| LEU | CA | 107 | 10.4 | 24.3 | 54.4 | 22, B |
| LEU | CB | 107 | 10.0 | 23.5 | 53.2 | 22, B |
| LEU | CG | 107 | 10.8 | 23.6 | 51.9 | 18, B |
| LEU | CD1 | 107 | 10.2 | 22.7 | 50.9 | 18, B |
| LEU | CD2 | 107 | 10.9 | 25.0 | 51.4 | 18, B |
| LEU | C | 107 | 9.4 | 24.2 | 55.5 | 25, B |
| LEU | O | 107 | 9.4 | 23.3 | 56.3 | 25, B |
| VAL | N | 108 | 8.5 | 25.2 | 55.6 | 26, B |
| VAL | CA | 108 | 7.5 | 25.2 | 56.6 | 24, B |
| VAL | CB | 108 | 6.8 | 26.6 | 56.6 | 25, B |
| VAL | CG1 | 108 | 5.5 | 26.6 | 57.5 | 25, B |
| VAL | CG2 | 108 | 7.8 | 27.6 | 57.2 | 29, B |
| VAL | C | 108 | 6.4 | 24.2 | 56.4 | 24, B |
| VAL | O | 108 | 5.9 | 24.0 | 55.3 | 17, B |
| VAL | N | 109 | 6.0 | 23.6 | 57.5 | 27, B |
| VAL | CA | 109 | 4.9 | 22.6 | 57.4 | 30, B |
| VAL | CB | 109 | 4.9 | 21.7 | 58.7 | 29, B |
| VAL | CG1 | 109 | 3.8 | 20.7 | 58.6 | 31, B |
| VAL | CG2 | 109 | 6.3 | 21.1 | 58.9 | 30, B |
| VAL | C | 109 | 3.6 | 23.3 | 57.3 | 31, B |
| VAL | O | 109 | 3.1 | 24.0 | 58.2 | 30, B |
| VAL | N | 110 | 3.0 | 23.2 | 56.1 | 36, B |
| VAL | CA | 110 | 1.8 | 23.9 | 55.8 | 42, B |
| VAL | CB | 110 | 1.9 | 24.7 | 54.5 | 43, B |
| VAL | CG1 | 110 | 0.6 | 25.3 | 54.1 | 47, B |
| VAL | CG2 | 110 | 2.9 | 25.8 | 54.7 | 41, B |
| VAL | C | 110 | 0.6 | 22.9 | 55.6 | 45, B |
| VAL | O | 110 | −0.4 | 23.1 | 56.2 | 46, B |
| ASN | N | 111 | 0.8 | 22.0 | 54.7 | 47, B |
| ASN | CA | 111 | −0.3 | 21.0 | 54.4 | 45, B |
| ASN | CB | 111 | −0.3 | 19.9 | 55.5 | 44, B |
| ASN | CG | 111 | −0.7 | 20.5 | 56.9 | 42, B |
| ASN | OD1 | 111 | −1.8 | 21.1 | 57.0 | 41, B |
| ASN | ND2 | 111 | 0.1 | 20.2 | 57.9 | 41, B |
| ASN | C | 111 | −1.6 | 21.7 | 54.3 | 46, B |
| ASN | O | 111 | −1.7 | 22.8 | 53.9 | 46, B |
| SCH | F1 | 1 | 10.2 | 37.1 | 34.4 | 30, I |
| SCH | F2 | 1 | 8.9 | 35.8 | 35.4 | 27, I |
| SCH | F3 | 1 | 10.9 | 35.2 | 35.1 | 27, I |
| SCH | F4 | 1 | 13.0 | 28.9 | 30.6 | 24, I |
| SCH | F5 | 1 | 12.6 | 31.0 | 29.9 | 23, I |
| SCH | F6 | 1 | 10.9 | 29.6 | 30.4 | 26, I |
| SCH | C1 | 1 | 12.7 | 31.8 | 37.3 | 15, I |
| SCH | C2 | 1 | 10.8 | 34.7 | 38.0 | 21, I |
| SCH | C3 | 1 | 10.7 | 36.2 | 37.9 | 24, I |
| SCH | N1 | 1 | 12.0 | 34.0 | 38.1 | 18, I |
| SCH | C4 | 1 | 12.6 | 30.2 | 37.7 | 17, I |
| SCH | C5 | 1 | 10.1 | 36.2 | 35.3 | 28, I |
| SCH | C6 | 1 | 10.4 | 36.9 | 36.7 | 26, I |
| SCH | N2 | 1 | 11.4 | 29.5 | 37.6 | 13, I |
| SCH | C7 | 1 | 12.2 | 30.0 | 30.7 | 21, I |
| SCH | C8 | 1 | 12.0 | 32.6 | 38.4 | 19, I |
| SCH | N3 | 1 | 9.9 | 27.7 | 36.0 | 12, I |
| SCH | O1 | 1 | 12.0 | 32.1 | 36.1 | 16, I |
| SCH | C9 | 1 | 9.5 | 26.8 | 34.9 | 14, I |
| SCH | C10 | 1 | 12.2 | 30.5 | 32.1 | 19, I |
| SCH | N4 | 1 | 9.6 | 25.5 | 35.2 | 20, I |
| SCH | O2 | 1 | 9.8 | 34.0 | 37.9 | 20, I |
| SCH | O3 | 1 | 13.6 | 29.7 | 38.2 | 18, I |
| SCH | C11 | 1 | 11.5 | 28.1 | 37.9 | 14, I |
| SCH | C12 | 1 | 10.1 | 30.0 | 37.1 | 12, I |
| SCH | C13 | 1 | 9.7 | 29.2 | 35.9 | 14, I |
| SCH | C14 | 1 | 11.2 | 27.3 | 36.6 | 7, I |
| SCH | N5 | 1 | 10.9 | 38.3 | 39.2 | 25, I |
| SCH | C15 | 1 | 11.0 | 36.9 | 39.1 | 26, I |
| SCH | C16 | 1 | 11.3 | 31.5 | 32.5 | 15, I |
| SCH | C17 | 1 | 11.3 | 13.1 | 30.0 | 33.1, 15, I |
| SCH | C18 | 1 | 14.2 | 32.3 | 37.2 | 17, I |
| SCH | C19 | 1 | 12.2 | 31.5 | 34.8 | 18, I |
| SCH | C20 | 1 | 13.4 | 34.6 | 37.9 | 16, I |
| SCH | C21 | 1 | 11.3 | 32.0 | 33.8 | 17, I |
| SCH | C22 | 1 | 13.1 | 30.5 | 34.4 | 15, I |
| SCH | C23 | 1 | 10.3 | 38.3 | 36.8 | 25, I |
| SCH | C24 | 1 | 14.2 | 33.8 | 36.9 | 15, I |
| SCH | C25 | 1 | 9.1 | 27.2 | 33.7 | 16, I |
| SCH | C26 | 1 | 10.5 | 38.9 | 38.1 | 26, I |
| SCH | C27 | 1 | 9.2 | 24.5 | 34.3 | 18, I |
| SCH | C28 | 1 | 8.7 | 26.3 | 32.7 | 14, I |
| SCH | C29 | 1 | 8.7 | 24.9 | 33.0 | 13, I |
| SCH | F1 | 1 | 28.9 | 25.3 | 41.6 | 28, J |
| SCH | F2 | 1 | 28.2 | 23.6 | 40.5 | 29, J |
| SCH | F3 | 1 | 26.9 | 25.3 | 40.8 | 25, J |
| SCH | F4 | 1 | 20.6 | 23.6 | 45.1 | 22, J |
| SCH | F5 | 1 | 22.3 | 24.9 | 45.8 | 24, J |
| SCH | F6 | 1 | 22.5 | 22.7 | 45.7 | 25, J |
| SCH | C1 | 1 | 23.2 | 25.1 | 38.5 | 15, J |
| SCH | C2 | 1 | 26.7 | 24.7 | 37.9 | 21, J |
| SCH | C3 | 1 | 28.0 | 25.4 | 38.0 | 25, J |
| SCH | N1 | 1 | 25.5 | 25.5 | 37.6 | 20, J |
| SCH | C4 | 1 | 21.9 | 24.4 | 38.1 | 18, J |
| SCH | C5 | 1 | 28.1 | 24.9 | 40.6 | 26, J |
| SCH | C6 | 1 | 28.7 | 25.5 | 39.3 | 25, J |
| SCH | N2 | 1 | 21.6 | 23.0 | 38.2 | 16, J |
| SCH | C7 | 1 | 21.9 | 23.8 | 45.1 | 23, J |
| SCH | C8 | 1 | 24.3 | 24.8 | 37.4 | 17, J |
| SCH | N3 | 1 | 20.6 | 20.9 | 39.8 | 21, J |
| SCH | O1 | 1 | 23.9 | 24.5 | 39.7 | 15, J |
| SCH | C9 | 1 | 20.0 | 20.2 | 40.9 | 16, J |
| SCH | C10 | 1 | 22.4 | 24.0 | 43.7 | 21, J |
| SCH | N4 | 1 | 18.7 | 19.8 | 40.7 | 17, J |
| SCH | O2 | 1 | 26.6 | 23.5 | 38.0 | 22, J |
| SCH | O3 | 1 | 21.0 | 25.2 | 37.7 | 17, J |
| SCH | C11 | 1 | 20.3 | 22.5 | 37.9 | 19, J |
| SCH | C12 | 1 | 22.6 | 22.0 | 38.6 | 18, J |
| SCH | C13 | 1 | 22.1 | 21.3 | 39.9 | 18, J |
| SCH | C14 | 1 | 19.7 | 21.9 | 39.2 | 21, J |
| SCH | N5 | 1 | 29.8 | 26.6 | 36.9 | 30, J |
| SCH | C15 | 1 | 28.6 | 26.0 | 36.9 | 28, J |
| SCH | C16 | 1 | 23.7 | 23.5 | 43.3 | 19, J |
| SCH | C17 | 1 | 21.6 | 24.8 | 42.8 | 18, J |
| SCH | C18 | 1 | 23.1 | 26.6 | 38.6 | 14, J |
| SCH | C19 | 1 | 23.3 | 24.5 | 41.0 | 19, J |
| SCH | C20 | 1 | 25.4 | 27.0 | 37.7 | 19, J |
| SCH | C21 | 1 | 24.1 | 23.7 | 41.9 | 17, J |
| SCH | C22 | 1 | 22.1 | 25.0 | 41.5 | 16, J |
| SCH | C23 | 1 | 30.0 | 26.1 | 39.3 | 27, J |
| SCH | C24 | 1 | 24.4 | 27.4 | 38.8 | 20, J |
| SCH | C25 | 1 | 20.7 | 19.9 | 42.1 | 16, J |
| SCH | C26 | 1 | 30.5 | 26.7 | 38.1 | 29, J |
| SCH | C27 | 1 | 18.0 | 19.1 | 41.7 | 16, J |
| SCH | C28 | 1 | 20.0 | 19.2 | 43.1 | 16, J |
| SCH | C29 | 1 | 18.6 | 18.8 | 42.9 | 18, J |
| WAT | OH2 | 1 | 30.0 | 19.3 | 27.2 | 35, W |
| WAT | OH2 | 2 | 17.5 | 16.8 | 32.3 | 23, W |
| WAT | OH2 | 3 | 14.1 | 45.2 | 28.9 | 26, W |
| WAT | OH2 | 4 | 6.9 | 23.1 | 43.4 | 13, W |
| WAT | OH2 | 5 | 9.3 | 23.2 | 40.6 | 17, W |
| WAT | OH2 | 11 | 15.1 | 28.9 | 59.9 | 11, W |
| WAT | OH2 | 13 | 15.5 | 27.7 | 57.1 | 15, W |
| WAT | OH2 | 15 | 8.4 | 31.5 | 53.2 | 20, W |
| WAT | OH2 | 23 | 18.6 | 17.0 | 22.7 | 19, W |
| WAT | OH2 | 25 | 8.7 | 26.0 | 38.3 | 20, W |
| WAT | OH2 | 27 | 18.1 | 36.3 | 39.2 | 16, W |
| WAT | OH2 | 28 | 16.8 | 18.4 | 34.9 | 17, W |

TABLE 1-continued

Structural coordinates of HDM2 (17-125; F55Y/Y76H) (SEQ ID NO: 2) complexed with compound 1.

WAT, OH2, 29, 23.7, 23.7, 60.6, 29, W
WAT, OH2, 30, 14.2, 19.6, 17.6, 28, W
WAT, OH2, 32, 11.2, 20.9, 58.2, 29, W
WAT, OH2, 34, 22.9, 11.4, 47.8, 24, W
WAT, OH2, 38, 21.4, 39.5, 24.3, 11, W
WAT, OH2, 42, 17.9, 18.0, 15.4, 24, W
WAT, OH2, 45, 10.2, 36.9, 42.8, 28, W
WAT, OH2, 44, 6.5, 29.2, 37.6, 18, W
WAT, OH2, 52, 6.5, 33.1, 15.3, 24, W
WAT, OH2, 54, 18.2, 11.7, 51.7, 33, W
WAT, OH2, 57, −0.3, 32.4, 33.7, 28, W
WAT, OH2, 58, 11.1, 46.6, 35.1, 61, W
WAT, OH2, 60, 6.6, 24.9, 52.8, 24, W
WAT, OH2, 67, 6.5, 19.0, 29.3, 30, W
WAT, OH2, 69, 27.7, 26.9, 32.5, 34, W
WAT, OH2, 71, 24.9, 32.1, 36.9, 27, W
WAT, OH2, 74, 6.4, 32.3, 55.1, 39, W
WAT, OH2, 75, 15.2, 28.4, 36.4, 38, W
WAT, OH2, 82, 18.2, 38.7, 22.1, 46, W
WAT, OH2, 86, 19.3, 26.6, 16.3, 26, W
WAT, OH2, 92, 30.3, 27.3, 20.9, 27, W
WAT, OH2, 108, 22.9, 40.1, 48.9, 17, W
WAT, OH2, 109, 16.0, 25.8, 37.7, 24, W
WAT, OH2, 116, 20.6, 39.5, 60.8, 30, W
WAT, OH2, 117, 28.0, 28.5, 21.0, 32, W
WAT, OH2, 119, 18.0, 25.1, 59.3, 15, W
WAT, OH2, 122, 22.3, 40.7, 22.2, 43, W
WAT, OH2, 124, 10.9, 20.3, 40.3, 31, W
WAT, OH2, 125, 18.8, 38.3, 52.7, 26, W
WAT, OH2, 143, 11.3, 17.9, 30.8, 25, W
WAT, OH2, 149, 14.0, 18.7, 35.4, 28, W
WAT, OH2, 151, 10.5, 17.9, 44.5, 23, W
WAT, OH2, 152, 14.6, 8.1, 16.0, 29, W
WAT, OH2, 155, 6.0, 41.3, 23.9, 37, W
WAT, OH2, 157, −3.5, 14.4, 34.5, 23, W
WAT, OH2, 159, 18.4, 25.8, 39.1, 25, W
WAT, OH2, 162, 7.5, 40.8, 49.1, 45, W
WAT, OH2, 181, 0.7, 25.8, 29.3, 34, W
WAT, OH2, 184, 15.8, 39.2, 17.5, 47, W
WAT, OH2, 187, 15.9, 23.8, 13.9, 26, W
WAT, OH2, 195, 25.4, 34.4, 39.0, 31, W
WAT, OH2, 202, 8.7, 17.8, 31.2, 42, W
WAT, OH2, 205, 12.3, 15.8, 44.3, 43, W

The crystalline coordinates are set forth below in the following format (1), (2), (3) . . . (8); the legend for these data is as follows:
(1) Residue name
Three letter amino acid name
SCH = schering inhibitor
WAT = water
(2) Atom name
(3) Residue Number
(4) X-coordinate
(5) Y-coordinate
(6) Z-coordinate
(7) B-factor
(8) Chain ID
Disordered residues are not represented in the table.

TABLE 2

Structural coordinates of HDM2 (17-125; F55Y/Y76H) (SEQ ID NO: 2) complexed with compound 2.

ALA, CB, 21, 7.1, −14.9, 32.5, 66, A
ALA, C, 21, 9.1, −16.0, 31.4, 66, A
ALA, O, 21, 9.0, −17.0, 30.7, 66, A
ALA, N, 21, 9.1, −15.4, 33.8, 66, A
ALA, CA, 21, 8.2, −15.9, 32.7, 66, A
SER, N, 22, 9.8, −15.0, 31.2, 65, A
SER, CA, 22, 10.7, −14.9, 30.0, 65, A
SER, CB, 22, 9.9, −14.7, 28.7, 65, A
SER, OG, 22, 10.7, −14.5, 27.6, 65, A
SER, C, 22, 11.5, −13.6, 30.2, 64, A
SER, O, 22, 11.0, −12.7, 30.9, 64, A
GLU, N, 23, 12.8, −13.6, 29.8, 63, A
GLU, CA, 23, 13.6, −12.4, 30.0, 63, A

TABLE 2-continued

Structural coordinates of HDM2 (17-125; F55Y/Y76H) (SEQ ID NO: 2) complexed with compound 2.

GLU, CB, 23, 15.0, −12.5, 29.3, 63, A
GLU, CG, 23, 15.9, −13.4, 30.1, 63, A
GLU, CD, 23, 16.1, −12.9, 31.6, 63, A
GLU, OE1, 23, 16.6, −11.8, 31.8, 63, A
GLU, OE2, 23, 15.6, −13.6, 32.5, 63, A
GLU, C, 23, 12.9, −11.1, 29.5, 62, A
GLU, O, 23, 12.9, −10.1, 30.2, 62, A
GLN, N, 24, 12.4, −11.1, 28.3, 61, A
GLN, CA, 24, 11.7, −10.0, 27.7, 60, A
GLN, CB, 24, 11.4, −10.2, 26.2, 61, A
GLN, CG, 24, 12.6, −10.4, 25.4, 61, A
GLN, CD, 24, 13.6, −9.2, 25.6, 61, A
GLN, OE1, 24, 13.2, −8.1, 25.6, 61, A
GLN, NE2, 24, 14.9, −9.5, 25.8, 61, A
GLN, C, 24, 10.5, −9.6, 28.5, 59, A
GLN, O, 24, 10.0, −8.5, 28.4, 59, A
GLU, N, 25, 9.9, −10.6, 29.2, 58, A
GLU, CA, 25, 8.7, −10.4, 30.0, 57, A
GLU, CB, 25, 7.8, −11.6, 30.0, 57, A
GLU, CG, 25, 6.5, −11.4, 29.3, 57, A
GLU, CD, 25, 6.7, −10.7, 27.9, 58, A
GLU, OE1, 25, 5.7, −10.3, 27.3, 57, A
GLU, OE2, 25, 7.8, −10.6, 27.4, 58, A
GLU, C, 25, 9.0, −9.9, 31.4, 55, A
GLU, O, 25, 8.1, −9.8, 32.2, 55, A
THR, N, 26, 10.3, −9.7, 31.7, 54, A
THR, CA, 26, 10.6, −9.2, 33.1, 52, A
THR, CB, 26, 12.2, −8.8, 33.2, 52, A
THR, OG1, 26, 13.0, −10.0, 33.0, 52, A
THR, CG2, 26, 12.5, −8.2, 34.5, 52, A
THR, C, 26, 9.8, −7.9, 33.3, 52, A
THR, O, 26, 9.7, −7.1, 32.5, 51, A
LEU, N, 27, 9.2, −7.8, 34.5, 51, A
LEU, CA, 27, 8.5, −6.7, 34.9, 50, A
LEU, CB, 27, 7.3, −7.0, 35.8, 50, A
LEU, CG, 27, 6.2, −7.9, 35.2, 50, A
LEU, CD1, 27, 5.1, −8.1, 36.1, 50, A
LEU, CD2, 27, 5.7, −7.2, 33.9, 50, A
LEU, C, 27, 9.4, −5.6, 35.5, 50, A
LEU, O, 27, 10.2, −6.0, 36.3, 50, A
VAL, N, 28, 9.3, −4.4, 35.1, 49, A
VAL, CA, 28, 10.1, −3.3, 35.6, 49, A
VAL, CB, 28, 11.3, −3.0, 34.7, 49, A
VAL, CG1, 28, 12.0, −4.3, 34.2, 49, A
VAL, CG2, 28, 10.7, −2.3, 33.4, 49, A
VAL, C, 28, 9.4, −2.0, 35.9, 48, A
VAL, O, 28, 8.3, −1.8, 35.4, 48, A
ARG, N, 29, 10.0, −1.2, 36.8, 48, A
ARG, CA, 29, 9.4, 0.1, 37.1, 47, A
ARG, CB, 29, 9.1, 0.1, 38.6, 48, A
ARG, CG, 29, 8.5, 1.4, 39.2, 49, A
ARG, CD, 29, 7.9, 1.1, 40.6, 50, A
ARG, NE, 29, 6.8, 0.2, 40.5, 51, A
ARG, CZ, 29, 6.5, −0.7, 41.5, 52, A
ARG, NH1, 29, 7.1, −0.6, 42.7, 52, A
ARG, NH2, 29, 5.5, −1.5, 41.3, 52, A
ARG, C, 29, 10.5, 1.1, 36.8, 46, A
ARG, O, 29, 11.5, 1.2, 37.5, 46, A
PRO, N, 30, 10.4, 1.8, 35.7, 45, A
PRO, CD, 30, 9.2, 1.8, 34.8, 45, A
PRO, CA, 30, 11.4, 2.8, 35.3, 45, A
PRO, CB, 30, 10.8, 3.3, 34.0, 45, A
PRO, CG, 30, 9.3, 3.2, 34.2, 46, A
PRO, C, 30, 11.5, 3.9, 36.4, 44, A
PRO, O, 30, 10.5, 4.2, 37.0, 44, A
LYS, N, 31, 12.7, 4.4, 36.6, 44, A
LYS, CA, 31, 12.9, 5.4, 37.5, 44, A
LYS, CB, 31, 14.4, 5.6, 37.8, 44, A
LYS, CG, 31, 15.0, 4.4, 38.4, 44, A
LYS, CD, 31, 16.5, 4.4, 38.6, 44, A
LYS, CE, 31, 17.0, 3.1, 39.2, 44, A
LYS, NZ, 31, 18.5, 3.0, 39.4, 44, A
LYS, C, 31, 12.1, 6.7, 37.0, 43, A
LYS, O, 31, 11.8, 6.7, 35.9, 43, A
PRO, N, 32, 11.9, 7.6, 37.9, 43, A
PRO, CD, 32, 12.4, 7.7, 39.3, 43, A

TABLE 2-continued

Structural coordinates of HDM2 (17-125; F55Y/Y76H) (SEQ ID NO: 2) complexed with compound 2.

PRO, CA, 32, 11.2, 8.9, 37.5, 43, A
PRO, CB, 32, 11.6, 9.8, 38.7, 43, A
PRO, CG, 32, 11.7, 8.9, 39.9, 43, A
PRO, C, 32, 11.4, 9.5, 36.1, 43, A
PRO, O, 32, 10.5, 9.6, 35.4, 43, A
LEU, N, 33, 12.6, 9.9, 35.8, 43, A
LEU, CA, 33, 12.9, 10.5, 34.5, 44, A
LEU, CB, 33, 14.3, 11.0, 34.5, 44, A
LEU, CG, 33, 14.7, 12.0, 35.6, 44, A
LEU, CD1, 33, 16.0, 12.7, 35.4, 44, A
LEU, CD2, 33, 13.5, 13.0, 35.8, 44, A
LEU, C, 33, 12.6, 9.6, 33.3, 45, A
LEU, O, 33, 12.0, 10.0, 32.4, 45, A
LEU, N, 34, 13.0, 8.3, 33.4, 45, A
LEU, CA, 34, 12.7, 7.4, 32.2, 46, A
LEU, CB, 34, 13.3, 6.0, 32.4, 46, A
LEU, CG, 34, 13.0, 4.9, 31.4, 47, A
LEU, CD1, 34, 13.3, 5.4, 30.0, 47, A
LEU, CD2, 34, 13.7, 3.6, 31.7, 47, A
LEU, C, 34, 11.2, 7.3, 32.1, 47, A
LEU, O, 34, 10.6, 7.2, 31.0, 47, A
LEU, N, 35, 10.5, 7.2, 33.2, 47, A
LEU, CA, 35, 9.0, 7.1, 33.2, 48, A
LEU, CB, 35, 8.5, 7.1, 34.7, 48, A
LEU, CG, 35, 7.0, 6.8, 34.8, 48, A
LEU, CD1, 35, 6.6, 5.6, 34.0, 48, A
LEU, CD2, 35, 6.7, 6.6, 36.3, 48, A
LEU, C, 35, 8.4, 8.3, 32.5, 48, A
LEU, O, 35, 7.5, 8.2, 31.8, 48, A
LYS, N, 36, 9.0, 9.5, 32.8, 49, A
LYS, CA, 36, 8.6, 10.7, 32.2, 49, A
LYS, CB, 36, 9.4, 11.8, 32.7, 49, A
LYS, CG, 36, 9.3, 13.1, 31.9, 50, A
LYS, CD, 36, 10.2, 14.2, 32.6, 50, A
LYS, CE, 36, 10.2, 15.5, 32.0, 50, A
LYS, NZ, 36, 11.0, 16.5, 32.8, 51, A
LYS, C, 36, 8.7, 10.6, 30.7, 49, A
LYS, O, 36, 7.8, 10.9, 29.9, 49, A
LEU, N, 37, 9.9, 10.1, 30.3, 50, A
LEU, CA, 37, 10.2, 9.9, 28.9, 51, A
LEU, CB, 37, 11.6, 9.2, 28.7, 51, A
LEU, CG, 37, 12.2, 9.0, 27.4, 51, A
LEU, CD1, 37, 13.7, 8.9, 27.5, 51, A
LEU, CD2, 37, 11.6, 7.8, 26.7, 51, A
LEU, C, 37, 9.1, 9.0, 28.2, 51, A
LEU, O, 37, 8.5, 9.4, 27.2, 52, A
LEU, N, 38, 8.9, 7.8, 28.8, 52, A
LEU, CA, 38, 7.9, 6.9, 28.3, 53, A
LEU, CB, 38, 7.9, 5.6, 29.1, 53, A
LEU, CG, 38, 9.0, 4.6, 28.8, 53, A
LEU, CD1, 38, 10.3, 5.3, 28.3, 54, A
LEU, CD2, 38, 9.3, 3.7, 30.0, 53, A
LEU, C, 38, 6.5, 7.5, 28.2, 54, A
LEU, O, 38, 5.7, 7.2, 27.3, 54, A
LYS, N, 39, 6.2, 8.3, 29.3, 54, A
LYS, CA, 39, 4.9, 8.9, 29.3, 55, A
LYS, CB, 39, 4.7, 9.6, 30.7, 56, A
LYS, CG, 39, 4.5, 8.7, 31.9, 56, A
LYS, CD, 39, 3.2, 7.9, 31.9, 56, A
LYS, CE, 39, 2.9, 7.3, 33.2, 56, A
LYS, NZ, 39, 2.9, 8.3, 34.3, 56, A
LYS, C, 39, 4.7, 9.9, 28.2, 56, A
LYS, O, 39, 3.6, 10.2, 27.8, 56, A
SER, N, 40, 5.8, 10.5, 27.8, 56, A
SER, CA, 40, 5.7, 11.5, 26.7, 56, A
SER, CB, 40, 7.1, 12.3, 26.6, 56, A
SER, OG, 40, 8.1, 11.5, 26.1, 56, A
SER, C, 40, 5.4, 10.9, 25.4, 57, A
SER, O, 40, 5.2, 11.6, 24.4, 57, A
VAL, N, 41, 5.3, 9.6, 25.3, 57, A
VAL, CA, 41, 4.9, 8.9, 24.1, 58, A
VAL, CB, 41, 6.1, 8.1, 23.5, 58, A
VAL, CG1, 41, 7.1, 9.0, 22.9, 57, A
VAL, CG2, 41, 6.8, 7.2, 24.6, 58, A
VAL, C, 41, 3.7, 8.0, 24.2, 58, A
VAL, O, 41, 3.6, 6.9, 23.6, 58, A
GLY, N, 42, 2.7, 8.4, 25.1, 59, A
GLY, CA, 42, 1.6, 7.6, 25.2, 59, A
GLY, C, 42, 1.6, 6.5, 26.3, 60, A
GLY, O, 42, 0.5, 5.9, 26.5, 60, A
ALA, N, 43, 2.7, 6.2, 26.8, 60, A
ALA, CA, 43, 2.8, 5.1, 27.9, 61, A
ALA, CB, 43, 4.2, 5.0, 28.4, 60, A
ALA, C, 43, 1.8, 5.6, 29.0, 61, A
ALA, O, 43, 1.8, 6.8, 29.3, 62, A
GLN, N, 44, 1.1, 4.7, 29.6, 61, A
GLN, CA, 44, 0.1, 5.1, 30.6, 62, A
GLN, CB, 44, −1.3, 4.8, 30.1, 62, A
GLN, CG, 44, −1.5, 5.4, 28.7, 63, A
GLN, CD, 44, −2.8, 4.9, 28.1, 63, A
GLN, OE1, 44, −2.9, 3.8, 27.5, 63, A
GLN, NE2, 44, −3.8, 5.8, 28.1, 63, A
GLN, C, 44, 0.3, 4.3, 31.9, 62, A
GLN, O, 44, −0.1, 4.8, 33.0, 62, A
LYS, N, 45, 1.1, 3.2, 31.9, 61, A
LYS, CA, 45, 1.3, 2.5, 33.1, 60, A
LYS, CB, 45, 1.4, 1.0, 32.7, 61, A
LYS, CG, 45, 2.2, 0.7, 31.5, 61, A
LYS, CD, 45, 2.1, −0.7, 31.0, 61, A
LYS, CE, 45, 0.7, −1.1, 30.6, 62, A
LYS, NZ, 45, 0.5, −2.5, 30.2, 62, A
LYS, C, 45, 2.6, 2.9, 33.8, 60, A
LYS, O, 45, 3.3, 3.8, 33.3, 60, A
ASP, N, 46, 2.9, 2.2, 34.9, 59, A
ASP, CA, 46, 4.1, 2.6, 35.7, 59, A
ASP, CB, 46, 3.8, 3.0, 37.1, 59, A
ASP, CG, 46, 3.7, 4.6, 37.2, 60, A
ASP, OD1, 46, 3.1, 5.2, 36.3, 60, A
ASP, OD2, 46, 4.3, 5.1, 38.1, 60, A
ASP, C, 46, 5.0, 1.3, 35.8, 58, A
ASP, O, 46, 6.2, 1.4, 36.1, 58, A
THR, N, 47, 4.4, 0.2, 35.4, 56, A
THR, CA, 47, 5.1, −1.1, 35.4, 55, A
THR, CB, 47, 4.4, −2.1, 36.4, 55, A
THR, OG1, 47, 4.4, −1.5, 37.7, 55, A
THR, CG2, 47, 5.2, −3.4, 36.4, 55, A
THR, C, 47, 5.0, −1.6, 34.0, 54, A
THR, O, 47, 4.0, −1.6, 33.4, 54, A
TYR, N, 48, 6.2, −2.0, 33.5, 53, A
TYR, CA, 48, 6.3, −2.5, 32.1, 52, A
TYR, CB, 48, 6.9, −1.4, 31.2, 52, A
TYR, CG, 48, 6.3, −0.1, 31.2, 53, A
TYR, CD1, 48, 6.4, 0.7, 32.4, 52, A
TYR, CE1, 48, 5.9, 2.0, 32.4, 53, A
TYR, CD2, 48, 5.6, 0.4, 30.2, 53, A
TYR, CE2, 48, 5.1, 1.7, 30.2, 53, A
TYR, CZ, 48, 5.2, 2.5, 31.3, 53, A
TYR, OH, 48, 4.7, 3.8, 31.3, 53, A
TYR, C, 48, 7.2, −3.8, 32.0, 51, A
TYR, O, 48, 8.0, −4.1, 32.8, 50, A
THR, N, 49, 7.0, −4.5, 30.8, 49, A
THR, CA, 49, 7.9, −5.6, 30.6, 48, A
THR, CB, 49, 7.2, −6.6, 29.5, 48, A
THR, OG1, 49, 7.0, −5.9, 28.3, 48, A
THR, CG2, 49, 5.9, −7.2, 30.1, 48, A
THR, C, 49, 9.0, −4.9, 29.9, 48, A
THR, O, 49, 8.9, −3.8, 29.4, 47, A
MET, N, 50, 10.2, −5.6, 29.9, 47, A
MET, CA, 50, 11.4, −5.0, 29.2, 47, A
MET, CB, 50, 12.6, −5.9, 29.3, 47, A
MET, CG, 50, 13.3, −5.8, 30.7, 48, A
MET, SD, 50, 14.0, −4.2, 31.0, 49, A
MET, CE, 50, 15.3, −4.2, 29.7, 48, A
MET, C, 50, 11.1, −4.8, 27.7, 47, A
MET, O, 50, 11.6, −3.8, 27.1, 47, A
LYS, N, 51, 10.2, −5.7, 27.1, 46, A
LYS, CA, 51, 9.9, −5.5, 25.7, 46, A
LYS, CB, 51, 9.0, −6.7, 25.3, 47, A
LYS, CG, 51, 9.8, −7.7, 24.5, 48, A
LYS, CD, 51, 9.1, −9.0, 24.2, 48, A
LYS, CE, 51, 7.7, −8.8, 23.5, 49, A
LYS, NZ, 51, 6.9, −10.1, 23.6, 48, A

TABLE 2-continued

Structural coordinates of HDM2 (17-125; F55Y/Y76H)
(SEQ ID NO: 2) complexed with compound 2.

LYS, C, 51, 9.1, −4.2, 25.5, 46, A
LYS, O, 51, 9.4, −3.5, 24.6, 46, A
GLU, N, 52, 8.2, −3.9, 26.4, 46, A
GLU, CA, 52, 7.4, −2.7, 26.3, 45, A
GLU, CB, 52, 6.4, −2.6, 27.5, 46, A
GLU, CG, 52, 5.2, −3.5, 27.3, 46, A
GLU, CD, 52, 4.2, −3.4, 28.5, 46, A
GLU, OE1, 52, 4.6, −3.4, 29.7, 47, A
GLU, OE2, 52, 3.0, −3.1, 28.3, 47, A
GLU, C, 52, 8.4, −1.5, 26.4, 45, A
GLU, O, 52, 8.2, −0.5, 25.7, 45, A
VAL, N, 53, 9.4, −1.5, 27.3, 45, A
VAL, CA, 53, 10.3, −0.4, 27.4, 44, A
VAL, CB, 53, 11.3, −0.7, 28.6, 44, A
VAL, CG1, 53, 12.3, 0.5, 28.7, 44, A
VAL, CG2, 53, 10.6, −0.8, 29.9, 44, A
VAL, C, 53, 11.1, −0.2, 26.1, 45, A
VAL, O, 53, 11.3, 0.9, 25.7, 45, A
LEU, N, 54, 11.5, −1.3, 25.5, 45, A
LEU, CA, 54, 12.2, −1.2, 24.2, 45, A
LEU, CB, 54, 12.7, −2.6, 23.7, 45, A
LEU, CG, 54, 13.9, −3.2, 24.5, 45, A
LEU, CD1, 54, 14.2, −4.6, 23.9, 45, A
LEU, CD2, 54, 15.1, −2.3, 24.4, 45, A
LEU, C, 54, 11.3, −0.5, 23.2, 45, A
LEU, O, 54, 11.7, 0.3, 22.4, 45, A
TYR, N, 55, 10.0, −1.0, 23.2, 46, A
TYR, CA, 55, 9.1, −0.4, 22.3, 46, A
TYR, CB, 55, 7.7, −1.1, 22.5, 46, A
TYR, CG, 55, 6.6, −0.6, 21.5, 45, A
TYR, CD1, 55, 6.6, −0.9, 20.2, 45, A
TYR, CE1, 55, 5.6, −0.4, 19.3, 45, A
TYR, CD2, 55, 5.6, 0.2, 22.0, 45, A
TYR, CE2, 55, 4.6, 0.7, 21.2, 46, A
TYR, CZ, 55, 4.6, 0.4, 19.8, 45, A
TYR, OH, 55, 3.7, 0.9, 19.0, 46, A
TYR, C, 55, 8.8, 1.1, 22.4, 46, A
TYR, O, 55, 9.1, 1.8, 21.4, 46, A
TYR, N, 56, 8.3, 1.5, 23.5, 46, A
TYR, CA, 56, 8.1, 2.9, 23.8, 46, A
TYR, CB, 56, 7.5, 3.2, 25.1, 46, A
TYR, CG, 56, 6.0, 2.7, 25.2, 46, A
TYR, CD1, 56, 5.1, 3.3, 24.4, 46, A
TYR, CE1, 56, 3.8, 2.8, 24.3, 46, A
TYR, CD2, 56, 5.6, 1.7, 26.0, 46, A
TYR, CE2, 56, 4.3, 1.2, 26.0, 46, A
TYR, CZ, 56, 3.4, 1.8, 25.2, 46, A
TYR, OH, 56, 2.1, 1.2, 25.1, 46, A
TYR, C, 56, 9.4, 3.7, 23.6, 46, A
TYR, O, 56, 9.3, 4.9, 23.2, 47, A
LEU, N, 57, 10.5, 3.1, 23.8, 46, A
LEU, CA, 57, 11.8, 3.9, 23.6, 46, A
LEU, CB, 57, 13.0, 3.1, 24.2, 46, A
LEU, CG, 57, 13.2, 3.2, 25.7, 46, A
LEU, CD1, 57, 14.5, 2.5, 26.1, 45, A
LEU, CD2, 57, 13.2, 4.7, 26.1, 46, A
LEU, C, 57, 11.9, 4.0, 22.1, 47, A
LEU, O, 57, 12.4, 5.0, 21.7, 47, A
GLY, N, 58, 11.4, 3.0, 21.4, 47, A
GLY, CA, 58, 11.5, 3.1, 19.9, 47, A
GLY, C, 58, 10.6, 4.2, 19.4, 47, A
GLY, O, 58, 10.9, 5.0, 18.5, 47, A
GLN, N, 59, 9.4, 4.3, 20.1, 48, A
GLN, CA, 59, 8.4, 5.3, 19.7, 48, A
GLN, CB, 59, 7.2, 5.2, 20.6, 48, A
GLN, CG, 59, 6.4, 3.9, 20.4, 49, A
GLN, CD, 59, 6.0, 3.6, 19.0, 49, A
GLN, OE1, 59, 4.9, 4.0, 18.6, 49, A
GLN, NE2, 59, 6.9, 3.1, 18.2, 48, A
GLN, C, 59, 9.0, 6.7, 19.9, 49, A
GLN, O, 59, 8.9, 7.6, 19.1, 49, A
TYR, N, 60, 9.8, 6.8, 21.0, 49, A
TYR, CA, 60, 10.5, 8.1, 21.4, 49, A
TYR, CB, 60, 11.2, 7.9, 22.7, 49, A
TYR, CG, 60, 11.8, 9.2, 23.2, 49, A
TYR, CD1, 60, 11.0, 10.2, 23.8, 49, A
TYR, CE1, 60, 11.6, 11.3, 24.3, 49, A
TYR, CD2, 60, 13.2, 9.3, 23.2, 49, A
TYR, CE2, 60, 13.7, 10.5, 23.8, 49, A
TYR, CZ, 60, 12.9, 11.5, 24.3, 49, A
TYR, OH, 60, 13.5, 12.6, 24.8, 49, A
TYR, C, 60, 11.5, 8.5, 20.3, 49, A
TYR, O, 60, 11.5, 9.6, 19.8, 49, A
ILE, N, 61, 12.4, 7.6, 20.0, 49, A
ILE, CA, 61, 13.4, 7.8, 19.0, 49, A
ILE, CB, 61, 14.3, 6.6, 18.8, 49, A
ILE, CG2, 61, 15.2, 6.8, 17.6, 49, A
ILE, CG1, 61, 15.1, 6.5, 20.1, 49, A
ILE, CD1, 61, 15.9, 5.2, 20.2, 49, A
ILE, C, 61, 12.8, 8.2, 17.6, 50, A
ILE, O, 61, 13.3, 9.2, 17.0, 50, A
MET, N, 62, 11.8, 7.6, 17.2, 50, A
MET, CA, 62, 11.1, 7.9, 15.9, 51, A
MET, CB, 62, 10.2, 6.7, 15.5, 51, A
MET, CG, 62, 10.9, 5.4, 15.3, 51, A
MET, SD, 62, 12.3, 5.5, 14.2, 51, A
MET, CE, 62, 11.4, 5.3, 12.6, 51, A
MET, C, 62, 10.4, 9.2, 15.9, 52, A
MET, O, 62, 10.6, 10.0, 15.0, 53, A
THR, N, 63, 9.5, 9.4, 16.8, 54, A
THR, CA, 63, 8.7, 10.6, 16.9, 55, A
THR, CB, 63, 7.8, 10.6, 18.1, 55, A
THR, OG1, 63, 8.6, 10.6, 19.3, 55, A
THR, CG2, 63, 6.9, 9.4, 18.2, 55, A
THR, C, 63, 9.6, 11.8, 17.0, 55, A
THR, O, 63, 9.2, 12.9, 16.4, 55, A
LYS, N, 64, 10.7, 11.7, 17.7, 56, A
LYS, CA, 64, 11.6, 12.8, 17.8, 57, A
LYS, CB, 64, 12.2, 12.9, 19.2, 57, A
LYS, CG, 64, 11.2, 13.1, 20.3, 57, A
LYS, CD, 64, 11.9, 13.5, 21.6, 57, A
LYS, CE, 64, 12.7, 14.8, 21.4, 57, A
LYS, NZ, 64, 13.3, 15.3, 22.7, 58, A
LYS, C, 64, 12.7, 12.8, 16.8, 58, A
LYS, O, 64, 13.6, 13.6, 16.8, 57, A
ARG, N, 65, 12.7, 11.8, 15.9, 59, A
ARG, CA, 65, 13.7, 11.6, 14.8, 60, A
ARG, CB, 65, 13.5, 12.7, 13.8, 61, A
ARG, CG, 65, 12.1, 12.8, 13.2, 62, A
ARG, CD, 65, 11.7, 14.2, 12.7, 62, A
ARG, NE, 65, 12.2, 14.5, 11.3, 63, A
ARG, CZ, 65, 12.1, 15.7, 10.8, 64, A
ARG, NH1, 65, 11.5, 16.6, 11.4, 64, A
ARG, NH2, 65, 12.7, 15.9, 9.6, 64, A
ARG, C, 65, 15.1, 11.7, 15.4, 60, A
ARG, O, 65, 15.9, 12.4, 14.9, 61, A
LEU, N, 66, 15.4, 10.9, 16.4, 61, A
LEU, CA, 66, 16.7, 10.9, 17.1, 61, A
LEU, CB, 66, 16.5, 10.4, 18.5, 61, A
LEU, CG, 66, 15.7, 11.3, 19.4, 61, A
LEU, CD1, 66, 15.4, 10.7, 20.8, 61, A
LEU, CD2, 66, 16.4, 12.7, 19.6, 61, A
LEU, C, 66, 17.7, 10.0, 16.4, 61, A
LEU, O, 66, 18.7, 9.6, 17.0, 61, A
TYR, N, 67, 17.5, 9.6, 15.1, 61, A
TYR, CA, 67, 18.4, 8.8, 14.4, 61, A
TYR, CB, 67, 17.7, 7.5, 14.0, 61, A
TYR, CG, 67, 16.6, 7.7, 13.0, 61, A
TYR, CD1, 67, 16.8, 8.0, 11.7, 61, A
TYR, CE1, 67, 15.7, 8.3, 10.9, 61, A
TYR, CD2, 67, 15.3, 7.7, 13.5, 61, A
TYR, CE2, 67, 14.2, 8.0, 12.7, 61, A
TYR, CZ, 67, 14.4, 8.3, 11.4, 61, A
TYR, OH, 67, 13.3, 8.5, 10.6, 61, A
TYR, C, 67, 19.0, 9.5, 13.2, 62, A
TYR, O, 67, 18.4, 10.5, 12.7, 61, A
ASP, N, 68, 20.1, 9.1, 12.7, 62, A
ASP, CA, 68, 20.7, 9.7, 11.5, 62, A
ASP, CB, 68, 22.2, 9.4, 11.5, 63, A
ASP, CG, 68, 22.9, 9.8, 10.2, 63, A
ASP, OD1, 68, 22.8, 11.0, 9.9, 63, A
ASP, OD2, 68, 23.5, 8.9, 9.5, 63, A

TABLE 2-continued

Structural coordinates of HDM2 (17-125; F55Y/Y76H) (SEQ ID NO: 2) complexed with compound 2.

ASP, C, 68, 20.0, 9.1, 10.2, 62, A
ASP, O, 68, 19.8, 7.9, 10.1, 62, A
GLU, N, 69, 19.7, 10.0, 9.3, 62, A
GLU, CA, 69, 19.1, 9.6, 8.1, 62, A
GLU, CB, 69, 18.6, 10.8, 7.3, 63, A
GLU, CG, 69, 17.4, 11.5, 7.8, 64, A
GLU, CD, 69, 16.2, 10.6, 8.0, 64, A
GLU, OE1, 69, 16.0, 9.7, 7.2, 64, A
GLU, OE2, 69, 15.5, 10.7, 9.0, 64, A
GLU, C, 69, 20.0, 8.7, 7.2, 62, A
GLU, O, 69, 19.5, 7.9, 6.5, 62, A
LYS, N, 70, 21.3, 8.9, 7.3, 62, A
LYS, CA, 70, 22.2, 8.1, 6.5, 61, A
LYS, CB, 70, 23.5, 8.9, 6.3, 62, A
LYS, CG, 70, 24.5, 8.2, 5.4, 62, A
LYS, CD, 70, 25.7, 9.2, 5.1, 62, A
LYS, CE, 70, 26.6, 8.6, 3.9, 63, A
LYS, NZ, 70, 27.4, 9.7, 3.3, 63, A
LYS, C, 70, 22.5, 6.8, 7.2, 61, A
LYS, O, 70, 22.6, 5.8, 6.5, 60, A
GLN, N, 71, 22.7, 6.9, 8.5, 59, A
GLN, CA, 71, 23.0, 5.7, 9.3, 58, A
GLN, CB, 71, 24.3, 5.8, 10.0, 59, A
GLN, CG, 71, 25.1, 4.5, 10.1, 59, A
GLN, CD, 71, 26.5, 4.7, 10.4, 60, A
GLN, OE1, 71, 27.3, 5.5, 9.8, 60, A
GLN, NE2, 71, 27.0, 4.0, 11.5, 60, A
GLN, C, 71, 21.9, 5.5, 10.3, 57, A
GLN, O, 71, 22.1, 5.7, 11.5, 57, A
GLN, N, 72, 20.7, 5.1, 9.8, 56, A
GLN, CA, 72, 19.5, 4.9, 10.7, 55, A
GLN, CB, 72, 18.4, 4.2, 9.8, 55, A
GLN, CG, 72, 18.1, 5.0, 8.6, 54, A
GLN, CD, 72, 16.8, 4.5, 8.0, 54, A
GLN, OE1, 72, 16.4, 3.3, 8.0, 54, A
GLN, NE2, 72, 16.0, 5.5, 7.4, 54, A
GLN, C, 72, 19.7, 4.1, 11.9, 55, A
GLN, O, 72, 18.9, 4.2, 12.9, 55, A
HIS, N, 73, 20.7, 3.2, 11.9, 54, A
HIS, CA, 73, 21.0, 2.4, 13.1, 54, A
HIS, CB, 73, 21.8, 1.1, 12.7, 54, A
HIS, CG, 73, 23.2, 1.4, 12.3, 54, A
HIS, CD2, 73, 23.7, 1.6, 11.1, 54, A
HIS, ND1, 73, 24.2, 1.3, 13.2, 55, A
HIS, CE1, 73, 25.3, 1.6, 12.6, 55, A
HIS, NE2, 73, 25.1, 1.8, 11.3, 55, A
HIS, C, 73, 21.8, 3.2, 14.2, 53, A
HIS, O, 73, 22.1, 2.6, 15.3, 53, A
ILE, N, 74, 22.2, 4.4, 13.9, 52, A
ILE, CA, 74, 22.9, 5.2, 14.9, 51, A
ILE, CB, 74, 24.0, 6.0, 14.3, 52, A
ILE, CG2, 74, 24.7, 6.8, 15.4, 52, A
ILE, CG1, 74, 25.1, 5.1, 13.7, 52, A
ILE, CD1, 74, 25.9, 4.3, 14.7, 52, A
ILE, C, 74, 21.9, 6.2, 15.5, 51, A
ILE, O, 74, 21.2, 7.0, 14.9, 51, A
VAL, N, 75, 21.8, 6.2, 16.9, 50, A
VAL, CA, 75, 20.9, 7.1, 17.6, 49, A
VAL, CB, 75, 20.2, 6.5, 18.7, 49, A
VAL, CG1, 75, 19.5, 7.5, 19.6, 49, A
VAL, CG2, 75, 19.2, 5.5, 18.2, 49, A
VAL, C, 75, 21.8, 8.3, 18.1, 48, A
VAL, O, 75, 22.8, 8.1, 18.6, 48, A
HIS, N, 76, 21.3, 9.5, 17.9, 47, A
HIS, CA, 76, 22.0, 10.7, 18.3, 47, A
HIS, CB, 76, 22.2, 11.7, 17.2, 47, A
HIS, CG, 76, 23.3, 11.3, 16.3, 47, A
HIS, CD2, 76, 23.3, 10.7, 15.1, 47, A
HIS, ND1, 76, 24.6, 11.5, 16.6, 47, A
HIS, CE1, 76, 25.4, 10.9, 15.7, 47, A
HIS, NE2, 76, 24.6, 10.5, 14.7, 47, A
HIS, C, 76, 21.1, 11.3, 19.4, 46, A
HIS, O, 76, 19.9, 11.6, 19.2, 46, A
CYS, N, 77, 21.6, 11.6, 20.6, 45, A
CYS, CA, 77, 20.9, 12.1, 21.7, 45, A
CYS, CB, 77, 20.3, 10.9, 22.5, 44, A
CYS, SG, 77, 21.5, 9.6, 22.9, 42, A
CYS, C, 77, 21.7, 12.9, 22.7, 45, A
CYS, O, 77, 21.4, 12.9, 23.9, 45, A
SER, N, 78, 22.8, 13.5, 22.2, 45, A
SER, CA, 78, 23.6, 14.3, 23.1, 46, A
SER, CB, 78, 24.8, 14.9, 22.3, 46, A
SER, OG, 78, 24.3, 16.0, 21.5, 46, A
SER, C, 78, 22.9, 15.5, 23.8, 46, A
SER, O, 78, 23.3, 15.8, 25.0, 45, A
ASN, N, 79, 22.0, 16.1, 23.2, 46, A
ASN, CA, 79, 21.2, 17.2, 23.8, 47, A
ASN, CB, 79, 21.3, 18.4, 22.8, 47, A
ASN, CG, 79, 20.8, 19.7, 23.5, 48, A
ASN, OD1, 79, 21.1, 19.9, 24.7, 47, A
ASN, ND2, 79, 20.0, 20.5, 22.7, 48, A
ASN, C, 79, 19.8, 16.8, 24.0, 47, A
ASN, O, 79, 18.9, 17.6, 24.0, 47, A
ASP, N, 80, 19.6, 15.5, 24.3, 46, A
ASP, CA, 80, 18.2, 15.0, 24.6, 46, A
ASP, CB, 80, 17.8, 14.0, 23.5, 47, A
ASP, CG, 80, 16.4, 13.6, 23.6, 48, A
ASP, OD1, 80, 15.6, 14.3, 23.0, 48, A
ASP, OD2, 80, 16.1, 12.6, 24.3, 48, A
ASP, C, 80, 18.2, 14.3, 25.9, 46, A
ASP, O, 80, 19.2, 13.9, 26.5, 46, A
LEU, N, 81, 17.0, 14.1, 26.5, 45, A
LEU, CA, 81, 16.8, 13.5, 27.8, 44, A
LEU, CB, 81, 15.4, 13.5, 28.2, 44, A
LEU, CG, 81, 15.1, 12.7, 29.5, 45, A
LEU, CD1, 81, 16.0, 13.3, 30.6, 45, A
LEU, CD2, 81, 13.7, 12.8, 29.9, 45, A
LEU, C, 81, 17.3, 12.0, 27.7, 43, A
LEU, O, 81, 17.8, 11.5, 28.7, 43, A
LEU, N, 82, 17.2, 11.4, 26.5, 42, A
LEU, CA, 82, 17.6, 10.0, 26.3, 42, A
LEU, CB, 82, 17.3, 9.6, 24.8, 41, A
LEU, CG, 82, 17.8, 8.2, 24.4, 42, A
LEU, CD1, 82, 17.1, 7.2, 25.4, 41, A
LEU, CD2, 82, 17.4, 7.9, 23.0, 41, A
LEU, C, 82, 19.1, 9.9, 26.6, 41, A
LEU, O, 82, 19.6, 9.0, 27.3, 41, A
GLY, N, 83, 19.9, 10.8, 26.0, 41, A
GLY, CA, 83, 21.3, 10.8, 26.2, 40, A
GLY, C, 83, 21.7, 11.1, 27.6, 39, A
GLY, O, 83, 22.7, 10.6, 28.1, 38, A
ASP, N, 84, 20.9, 11.9, 28.4, 38, A
ASP, CA, 84, 21.3, 12.2, 29.8, 38, A
ASP, CB, 84, 20.4, 13.3, 30.3, 37, A
ASP, CG, 84, 20.5, 14.6, 29.5, 37, A
ASP, OD1, 84, 21.6, 15.1, 29.3, 37, A
ASP, OD2, 84, 19.4, 15.1, 29.1, 37, A
ASP, C, 84, 21.1, 10.9, 30.6, 38, A
ASP, O, 84, 21.9, 10.5, 31.4, 38, A
LEU, N, 85, 20.0, 10.2, 30.3, 38, A
LEU, CA, 85, 19.6, 9.0, 31.0, 39, A
LEU, CB, 85, 18.2, 8.6, 30.8, 39, A
LEU, CG, 85, 17.1, 9.6, 31.2, 40, A
LEU, CD1, 85, 15.8, 9.0, 31.3, 40, A
LEU, CD2, 85, 17.4, 10.2, 32.6, 40, A
LEU, C, 85, 20.6, 7.8, 30.7, 39, A
LEU, O, 85, 20.9, 7.0, 31.5, 39, A
PHE, N, 86, 20.9, 7.7, 29.4, 39, A
PHE, CA, 86, 21.8, 6.6, 28.9, 39, A
PHE, CB, 86, 21.6, 6.3, 27.4, 39, A
PHE, CG, 86, 20.4, 5.4, 27.1, 39, A
PHE, CD1, 86, 19.5, 5.0, 28.1, 39, A
PHE, CD2, 86, 20.2, 4.9, 25.8, 39, A
PHE, CE1, 86, 18.5, 4.2, 27.8, 39, A
PHE, CE2, 86, 19.2, 4.1, 25.5, 39, A
PHE, CZ, 86, 18.3, 3.7, 26.5, 39, A
PHE, C, 86, 23.2, 6.9, 29.3, 39, A
PHE, O, 86, 24.0, 5.9, 29.4, 38, A
GLY, N, 87, 23.5, 8.2, 29.4, 39, A
GLY, CA, 87, 24.9, 8.6, 29.7, 39, A
GLY, C, 87, 25.8, 8.6, 28.5, 39, A
GLY, O, 87, 27.0, 8.6, 28.7, 39, A

TABLE 2-continued

Structural coordinates of HDM2 (17-125; F55Y/Y76H) (SEQ ID NO: 2) complexed with compound 2.

| | | | | | | |
|---|---|---|---|---|---|---|
| VAL, N, | 88, | 25.3, | 8.6, | 27.3, | 40, | A |
| VAL, CA, | 88, | 26.1, | 8.7, | 26.1, | 41, | A |
| VAL, CB, | 88, | 26.1, | 7.2, | 25.4, | 41, | A |
| VAL, CG1, | 88, | 27.0, | 6.3, | 26.2, | 41, | A |
| VAL, CG2, | 88, | 24.7, | 6.6, | 25.3, | 41, | A |
| VAL, C, | 88, | 25.5, | 9.6, | 25.1, | 41, | A |
| VAL, O, | 88, | 24.3, | 9.9, | 25.0, | 42, | A |
| PRO, N, | 89, | 26.3, | 10.2, | 24.2, | 41, | A |
| PRO, CD, | 89, | 27.8, | 10.2, | 24.2, | 41, | A |
| PRO, CA, | 89, | 25.8, | 11.2, | 23.2, | 41, | A |
| PRO, CB, | 89, | 27.0, | 12.0, | 22.8, | 41, | A |
| PRO, CG, | 89, | 28.1, | 10.9, | 22.9, | 41, | A |
| PRO, C, | 89, | 25.2, | 10.5, | 22.0, | 41, | A |
| PRO, O, | 89, | 24.4, | 11.1, | 21.3, | 41, | A |
| SER, N, | 90, | 25.6, | 9.2, | 21.8, | 42, | A |
| SER, CA, | 90, | 25.1, | 8.4, | 20.6, | 42, | A |
| SER, CB, | 90, | 25.9, | 8.8, | 19.4, | 41, | A |
| SER, OG, | 90, | 27.3, | 8.6, | 19.4, | 41, | A |
| SER, C, | 90, | 25.4, | 7.0, | 20.9, | 42, | A |
| SER, O, | 90, | 26.2, | 6.6, | 21.7, | 42, | A |
| PHE, N, | 91, | 24.6, | 6.1, | 20.2, | 42, | A |
| PHE, CA, | 91, | 24.8, | 4.7, | 20.4, | 42, | A |
| PHE, CB, | 91, | 24.1, | 4.2, | 21.7, | 42, | A |
| PHE, CG, | 91, | 22.6, | 4.3, | 21.6, | 42, | A |
| PHE, CD1, | 91, | 21.8, | 3.4, | 21.0, | 42, | A |
| PHE, CD2, | 91, | 21.9, | 5.4, | 22.3, | 42, | A |
| PHE, CE1, | 91, | 20.4, | 3.4, | 21.0, | 41, | A |
| PHE, CE2, | 91, | 20.5, | 5.4, | 22.3, | 41, | A |
| PHE, CZ, | 91, | 19.8, | 4.5, | 21.7, | 41, | A |
| PHE, C, | 91, | 24.2, | 3.9, | 19.2, | 43, | A |
| PHE, O, | 91, | 23.4, | 4.4, | 18.5, | 43, | A |
| SER, N, | 92, | 24.8, | 2.7, | 19.0, | 43, | A |
| SER, CA, | 92, | 24.4, | 1.8, | 17.9, | 44, | A |
| SER, CB, | 92, | 25.6, | 1.0, | 17.4, | 44, | A |
| SER, OG, | 92, | 25.1, | −0.0, | 16.6, | 45, | A |
| SER, C, | 92, | 23.2, | 0.9, | 18.4, | 44, | A |
| SER, O, | 92, | 23.3, | 0.3, | 19.4, | 44, | A |
| VAL, N, | 93, | 22.2, | 0.8, | 17.6, | 45, | A |
| VAL, CA, | 93, | 21.0, | 0.0, | 17.8, | 46, | A |
| VAL, CB, | 93, | 19.9, | 0.2, | 16.8, | 46, | A |
| VAL, CG1, | 93, | 18.7, | −0.5, | 17.1, | 46, | A |
| VAL, CG2, | 93, | 19.7, | 1.7, | 16.6, | 47, | A |
| VAL, C, | 93, | 21.3, | −1.5, | 17.9, | 46, | A |
| VAL, O, | 93, | 20.6, | −2.3, | 18.5, | 47, | A |
| LYS, N, | 94, | 22.5, | −1.9, | 17.3, | 47, | A |
| LYS, CA, | 94, | 22.9, | −3.3, | 17.3, | 47, | A |
| LYS, CB, | 94, | 23.8, | −3.5, | 16.1, | 47, | A |
| LYS, CG, | 94, | 23.2, | −3.3, | 14.7, | 48, | A |
| LYS, CD, | 94, | 24.3, | −3.4, | 13.7, | 48, | A |
| LYS, CE, | 94, | 23.8, | −3.3, | 12.3, | 48, | A |
| LYS, NZ, | 94, | 24.8, | −3.1, | 11.3, | 49, | A |
| LYS, C, | 94, | 23.6, | −3.7, | 18.6, | 47, | A |
| LYS, O, | 94, | 23.6, | −4.9, | 18.9, | 48, | A |
| GLU, N, | 95, | 24.2, | −2.7, | 19.3, | 47, | A |
| GLU, CA, | 95, | 24.9, | −2.9, | 20.5, | 47, | A |
| GLU, CB, | 95, | 25.7, | −1.7, | 20.8, | 48, | A |
| GLU, CG, | 95, | 26.7, | −1.3, | 19.7, | 49, | A |
| GLU, CD, | 95, | 27.4, | 0.1, | 20.0, | 51, | A |
| GLU, OE1, | 95, | 26.6, | 1.0, | 20.3, | 51, | A |
| GLU, OE2, | 95, | 28.6, | 0.2, | 19.9, | 51, | A |
| GLU, C, | 95, | 23.9, | −3.2, | 21.6, | 47, | A |
| GLU, O, | 95, | 23.7, | −2.4, | 22.5, | 47, | A |
| HIS, N, | 96, | 23.2, | −4.4, | 21.5, | 46, | A |
| HIS, CA, | 96, | 22.2, | −4.8, | 22.5, | 46, | A |
| HIS, CB, | 96, | 21.6, | −6.1, | 22.2, | 46, | A |
| HIS, CG, | 96, | 20.7, | −6.1, | 21.0, | 47, | A |
| HIS, CD2, | 96, | 20.4, | −5.1, | 20.1, | 47, | A |
| HIS, ND1, | 96, | 20.0, | −7.2, | 20.6, | 47, | A |
| HIS, CE1, | 96, | 19.3, | −6.9, | 19.5, | 47, | A |
| HIS, NE2, | 96, | 19.5, | −5.6, | 19.2, | 47, | A |
| HIS, C, | 96, | 22.8, | −4.8, | 24.0, | 46, | A |
| HIS, O, | 96, | 22.1, | −4.3, | 24.9, | 46, | A |
| ARG, N, | 97, | 23.9, | −5.4, | 24.2, | 46, | A |
| ARG, CA, | 97, | 24.6, | −5.5, | 25.5, | 47, | A |
| ARG, CB, | 97, | 26.0, | −6.0, | 25.3, | 47, | A |
| ARG, CG, | 97, | 27.0, | −5.7, | 26.4, | 49, | A |
| ARG, CD, | 97, | 28.4, | −6.3, | 26.2, | 49, | A |
| ARG, NE, | 97, | 29.2, | −5.5, | 25.3, | 50, | A |
| ARG, CZ, | 97, | 30.0, | −4.5, | 25.6, | 51, | A |
| ARG, NH1, | 97, | 30.0, | −4.1, | 26.9, | 51, | A |
| ARG, NH2, | 97, | 30.7, | −3.8, | 24.7, | 51, | A |
| ARG, C, | 97, | 24.7, | −4.1, | 26.1, | 46, | A |
| ARG, O, | 97, | 24.3, | −3.9, | 27.3, | 46, | A |
| LYS, N, | 98, | 25.2, | −3.1, | 25.4, | 45, | A |
| LYS, CA, | 98, | 25.4, | −1.8, | 25.9, | 45, | A |
| LYS, CB, | 98, | 26.2, | −1.0, | 24.8, | 46, | A |
| LYS, CG, | 98, | 27.7, | −1.1, | 24.9, | 46, | A |
| LYS, CD, | 98, | 28.3, | −0.7, | 23.6, | 47, | A |
| LYS, CE, | 98, | 27.6, | 0.5, | 23.0, | 48, | A |
| LYS, NZ, | 98, | 27.6, | 1.7, | 23.9, | 48, | A |
| LYS, C, | 98, | 24.1, | −1.1, | 26.2, | 44, | A |
| LYS, O, | 98, | 23.9, | −0.5, | 27.2, | 44, | A |
| ILE, N, | 99, | 23.1, | −1.3, | 25.3, | 43, | A |
| ILE, CA, | 99, | 21.8, | −0.7, | 25.5, | 42, | A |
| ILE, CB, | 99, | 20.9, | −0.9, | 24.2, | 41, | A |
| ILE, CG2, | 99, | 19.5, | −0.4, | 24.5, | 40, | A |
| ILE, CG1, | 99, | 21.5, | −0.1, | 23.0, | 41, | A |
| ILE, CD1, | 99, | 20.8, | −0.4, | 21.7, | 40, | A |
| ILE, C, | 99, | 21.1, | −1.3, | 26.7, | 42, | A |
| ILE, O, | 99, | 20.3, | −0.6, | 27.4, | 41, | A |
| TYR, N, | 100, | 21.3, | −2.6, | 27.0, | 41, | A |
| TYR, CA, | 100, | 20.7, | −3.2, | 28.1, | 41, | A |
| TYR, CB, | 100, | 20.9, | −4.7, | 28.2, | 41, | A |
| TYR, CG, | 100, | 19.9, | −5.4, | 27.4, | 42, | A |
| TYR, CD1, | 100, | 20.2, | −6.3, | 26.4, | 42, | A |
| TYR, CE1, | 100, | 19.2, | −7.0, | 25.7, | 42, | A |
| TYR, CD2, | 100, | 18.5, | −5.3, | 27.7, | 41, | A |
| TYR, CE2, | 100, | 17.5, | −5.9, | 27.0, | 42, | A |
| TYR, CZ, | 100, | 17.9, | −6.8, | 26.0, | 42, | A |
| TYR, OH, | 100, | 16.9, | −7.4, | 25.3, | 43, | A |
| TYR, C, | 100, | 21.3, | −2.6, | 29.4, | 40, | A |
| TYR, O, | 100, | 20.5, | −2.2, | 30.3, | 40, | A |
| THR, N, | 101, | 22.6, | −2.4, | 29.4, | 40, | A |
| THR, CA, | 101, | 23.2, | −1.8, | 30.6, | 40, | A |
| THR, CB, | 101, | 24.8, | −1.7, | 30.3, | 40, | A |
| THR, OG1, | 101, | 25.3, | −3.1, | 30.2, | 40, | A |
| THR, CG2, | 101, | 25.5, | −1.0, | 31.5, | 40, | A |
| THR, C, | 101, | 22.6, | −0.4, | 30.9, | 40, | A |
| THR, O, | 101, | 22.3, | −0.1, | 32.0, | 41, | A |
| MET, N, | 102, | 22.5, | 0.4, | 29.8, | 40, | A |
| MET, CA, | 102, | 22.0, | 1.7, | 30.0, | 40, | A |
| MET, CB, | 102, | 22.2, | 2.5, | 28.7, | 40, | A |
| MET, CG, | 102, | 23.6, | 2.7, | 28.5, | 40, | A |
| MET, SD, | 102, | 24.0, | 3.6, | 27.0, | 41, | A |
| MET, CE, | 102, | 23.4, | 2.5, | 25.7, | 41, | A |
| MET, C, | 102, | 20.5, | 1.8, | 30.5, | 39, | A |
| MET, O, | 102, | 20.2, | 2.6, | 31.3, | 39, | A |
| ILE, N, | 103, | 19.7, | 0.9, | 30.0, | 39, | A |
| ILE, CA, | 103, | 18.3, | 0.8, | 30.4, | 39, | A |
| ILE, CB, | 103, | 17.4, | −0.1, | 29.5, | 38, | A |
| ILE, CG2, | 103, | 16.1, | −0.4, | 30.1, | 38, | A |
| ILE, CG1, | 103, | 17.2, | 0.6, | 28.1, | 38, | A |
| ILE, CD1, | 103, | 16.4, | −0.2, | 27.1, | 38, | A |
| ILE, C, | 103, | 18.1, | 0.3, | 31.8, | 39, | A |
| ILE, O, | 103, | 17.3, | 0.9, | 32.6, | 39, | A |
| TYR, N, | 104, | 18.9, | −0.7, | 32.2, | 39, | A |
| TYR, CA, | 104, | 18.8, | −1.3, | 33.5, | 40, | A |
| TYR, CB, | 104, | 19.8, | −2.4, | 33.7, | 40, | A |
| TYR, CG, | 104, | 19.5, | −3.7, | 32.9, | 40, | A |
| TYR, CD1, | 104, | 20.5, | −4.5, | 32.5, | 40, | A |
| TYR, CE1, | 104, | 20.2, | −5.7, | 31.8, | 40, | A |
| TYR, CD2, | 104, | 18.2, | −4.0, | 32.5, | 40, | A |
| TYR, CE2, | 104, | 17.9, | −5.2, | 31.9, | 40, | A |
| TYR, CZ, | 104, | 18.9, | −6.0, | 31.5, | 41, | A |
| TYR, OH, | 104, | 18.6, | −7.2, | 30.9, | 40, | A |
| TYR, C, | 104, | 19.0, | −0.2, | 34.6, | 41, | A |
| TYR, O, | 104, | 18.3, | −0.1, | 35.6, | 41, | A |
| ARG, N, | 105, | 20.1, | 0.6, | 34.4, | 41, | A |
| ARG, CA, | 105, | 20.4, | 1.6, | 35.3, | 42, | A |
| ARG, CB, | 105, | 21.6, | 2.4, | 34.8, | 42, | A |
| ARG, CG, | 105, | 23.0, | 1.6, | 34.8, | 43, | A |
| ARG, CD, | 105, | 24.0, | 2.4, | 34.1, | 44, | A |

TABLE 2-continued

Structural coordinates of HDM2 (17-125; F55Y/Y76H)
(SEQ ID NO: 2) complexed with compound 2.

```
ARG, NE, 105, 25.3, 1.7, 34.1, 44, A
ARG, CZ, 105, 26.4, 2.1, 33.5, 44, A
ARG, NH1, 105, 26.4, 3.2, 32.8, 45, A
ARG, NH2, 105, 27.5, 1.4, 33.6, 44, A
ARG, C, 105, 19.3, 2.5, 35.5, 42, A
ARG, O, 105, 19.2, 3.2, 36.6, 42, A
ASN, N, 106, 18.3, 2.6, 34.6, 42, A
ASN, CA, 106, 17.2, 3.5, 34.7, 42, A
ASN, CB, 106, 17.0, 4.2, 33.4, 41, A
ASN, CG, 106, 18.0, 5.2, 33.1, 41, A
ASN, OD1, 106, 17.9, 6.3, 33.6, 41, A
ASN, ND2, 106, 19.1, 4.8, 32.4, 41, A
ASN, C, 106, 15.9, 2.8, 35.2, 42, A
ASN, O, 106, 14.8, 3.4, 34.9, 41, A
LEU, N, 107, 15.9, 1.7, 35.8, 42, A
LEU, CA, 107, 14.7, 1.1, 36.3, 42, A
LEU, CB, 107, 14.1, 0.2, 35.2, 42, A
LEU, CG, 107, 15.1, −0.9, 34.6, 42, A
LEU, CD1, 107, 15.1, −2.1, 35.6, 41, A
LEU, CD2, 107, 14.6, −1.3, 33.2, 41, A
LEU, C, 107, 15.0, 0.2, 37.5, 42, A
LEU, O, 107, 16.1, −0.0, 37.9, 42, A
VAL, N, 108, 13.9, −0.3, 38.1, 43, A
VAL, CA, 108, 13.8, −1.2, 39.2, 44, A
VAL, CB, 108, 13.1, −0.5, 40.4, 44, A
VAL, CG1, 108, 12.9, −1.4, 41.6, 45, A
VAL, CG2, 108, 14.0, 0.7, 40.9, 44, A
VAL, C, 108, 13.1, −2.4, 38.8, 44, A
VAL, O, 108, 12.1, −2.3, 38.1, 44, A
VAL, N, 109, 13.5, −3.6, 39.2, 44, A
VAL, CA, 109, 12.8, −4.8, 38.8, 44, A
VAL, CB, 109, 13.7, −6.0, 38.8, 44, A
VAL, CG1, 109, 13.0, −7.2, 38.2, 44, A
VAL, CG2, 109, 15.0, −5.7, 37.9, 44, A
VAL, C, 109, 11.7, −5.0, 39.8, 44, A
VAL, O, 109, 11.9, −4.7, 41.0, 44, A
VAL, N, 110, 10.6, −5.5, 39.4, 44, A
VAL, CA, 110, 9.4, −5.8, 40.3, 45, A
VAL, CB, 110, 8.4, −4.7, 40.2, 45, A
VAL, CG1, 110, 8.9, −3.3, 40.6, 44, A
VAL, CG2, 110, 7.8, −4.7, 38.7, 44, A
VAL, C, 110, 8.8, −7.1, 40.0, 45, A
VAL, O, 110, 9.1, −7.8, 39.0, 45, A
ASN, N, 111, 7.9, −7.5, 40.9, 46, A
ASN, CA, 111, 7.1, −8.8, 40.8, 47, A
ASN, CB, 111, 6.3, −9.1, 42.1, 48, A
ASN, CG, 111, 7.2, −9.6, 43.2, 48, A
ASN, OD1, 111, 8.0, −10.5, 42.9, 49, A
ASN, ND2, 111, 7.2, −9.0, 44.3, 49, A
ASN, C, 111, 6.1, −8.6, 39.7, 47, A
ASN, O, 111, 5.2, −7.7, 39.7, 46, A
ALA, N, 21, 24.5, −0.7, 1.4, 69, B
ALA, CA, 21, 25.1, −0.2, 2.6, 69, B
ALA, CB, 21, 24.4, 1.2, 2.9, 69, B
ALA, C, 21, 24.7, −1.2, 3.8, 69, B
ALA, O, 21, 25.6, −1.6, 4.5, 69, B
SER, N, 22, 23.5, −1.5, 3.9, 69, B
SER, CA, 22, 23.0, −2.5, 4.9, 69, B
SER, CB, 22, 22.6, −1.8, 6.1, 69, B
SER, OG, 22, 23.6, −0.9, 6.6, 69, B
SER, C, 22, 21.7, −3.2, 4.3, 69, B
SER, O, 22, 21.0, −2.5, 3.5, 69, B
GLU, N, 23, 21.5, −4.4, 4.6, 68, B
GLU, CA, 23, 20.4, −5.1, 4.0, 68, B
GLU, CB, 23, 20.2, −6.5, 4.6, 68, B
GLU, CG, 23, 19.1, −7.4, 4.0, 69, B
GLU, CD, 23, 19.0, −8.8, 4.6, 69, B
GLU, OE1, 23, 20.1, −9.5, 4.7, 69, B
GLU, OE2, 23, 17.9, −9.2, 5.0, 69, B
GLU, C, 23, 19.1, −4.3, 4.4, 67, B
GLU, O, 23, 18.1, −4.3, 3.7, 67, B
GLN, N, 24, 19.2, −3.6, 5.6, 66, B
GLN, CA, 24, 18.1, −2.8, 6.1, 65, B
GLN, CB, 24, 18.2, −2.7, 7.6, 66, B
GLN, CG, 24, 18.1, −4.0, 8.3, 66, B
GLN, CD, 24, 19.5, −4.6, 8.6, 66, B
GLN, OE1, 24, 20.3, −4.8, 7.7, 66, B
GLN, NE2, 24, 19.8, −4.7, 9.9, 66, B
GLN, C, 24, 18.1, −1.4, 5.5, 64, B
GLN, N, 24, 17.1, −0.7, 5.5, 64, B
GLU, N, 25, 19.3, −0.9, 5.0, 63, B
GLU, CA, 25, 19.4, 0.4, 4.4, 62, B
GLU, CB, 25, 20.8, 1.0, 4.5, 62, B
GLU, CG, 25, 20.8, 2.3, 5.4, 62, B
GLU, CD, 25, 20.5, 2.0, 6.9, 62, B
GLU, OE1, 25, 20.5, 3.0, 7.6, 62, B
GLU, OE2, 25, 20.2, 0.9, 7.2, 62, B
GLU, C, 25, 19.0, 0.4, 2.9, 61, B
GLU, O, 25, 19.1, 1.4, 2.2, 61, B
THR, N, 26, 18.6, −0.8, 2.4, 59, B
THR, CA, 26, 18.2, −0.9, 1.0, 58, B
THR, CB, 26, 17.9, −2.4, 0.7, 58, B
THR, OG1, 26, 19.0, −3.2, 0.8, 58, B
THR, CG2, 26, 17.3, −2.5, −0.8, 58, B
THR, C, 26, 16.9, −0.1, 0.8, 57, B
THR, O, 26, 15.9, −0.3, 1.5, 57, B
LEU, N, 27, 16.9, 0.7, −0.2, 56, B
LEU, CA, 27, 15.7, 1.5, −0.5, 55, B
LEU, CB, 27, 16.1, 2.8, −1.4, 55, B
LEU, CG, 27, 17.1, 3.8, −0.7, 55, B
LEU, CD1, 27, 17.3, 4.9, −1.7, 55, B
LEU, CD2, 27, 16.5, 4.3, 0.6, 55, B
LEU, C, 27, 14.7, 0.7, −1.3, 54, B
LEU, O, 27, 15.0, 0.0, −2.2, 54, B
VAL, N, 28, 13.5, 0.8, −0.8, 54, B
VAL, CA, 28, 12.4, 0.0, −1.4, 54, B
VAL, CB, 28, 12.0, −1.2, −0.5, 53, B
VAL, CG1, 28, 13.2, −2.1, −0.3, 54, B
VAL, CG2, 28, 11.5, −0.7, 0.8, 53, B
VAL, C, 28, 11.1, 0.8, −1.6, 53, B
VAL, O, 28, 10.9, 1.9, −1.0, 53, B
ARG, N, 29, 10.3, 0.4, −2.6, 53, B
ARG, CA, 29, 9.1, 1.0, −2.9, 53, B
ARG, CB, 29, 9.2, 1.5, −4.4, 54, B
ARG, CG, 29, 8.1, 2.6, −4.8, 54, B
ARG, CD, 29, 8.5, 3.2, −6.2, 55, B
ARG, NE, 29, 9.7, 4.0, −6.1, 56, B
ARG, CZ, 29, 10.4, 4.4, −7.2, 56, B
ARG, NH1, 29, 9.9, 4.0, −8.4, 56, B
ARG, NH2, 29, 11.5, 5.1, −7.1, 56, B
ARG, C, 29, 8.0, −0.1, −2.8, 53, B
ARG, O, 29, 7.9, −1.0, −3.6, 52, B
PRO, N, 30, 7.1, 0.1, −1.8, 52, B
PRO, CD, 30, 7.1, 1.1, −0.8, 52, B
PRO, CA, 30, 6.1, −0.9, −1.5, 52, B
PRO, CB, 30, 5.4, −0.3, −0.3, 52, B
PRO, CG, 30, 6.5, 0.5, 0.4, 52, B
PRO, C, 30, 5.1, −1.0, −2.7, 52, B
PRO, O, 30, 4.9, −0.0, −3.4, 52, B
LYS, N, 31, 4.5, −2.2, −2.8, 51, B
LYS, CA, 31, 3.5, −2.4, −3.9, 51, B
LYS, CB, 31, 3.4, −3.8, −4.3, 51, B
LYS, CG, 31, 4.6, −4.3, −5.0, 50, B
LYS, CD, 31, 4.6, −5.8, −5.4, 50, B
LYS, CE, 31, 5.8, −6.3, −6.2, 50, B
LYS, NZ, 31, 6.0, −7.7, −6.3, 49, B
LYS, C, 31, 2.3, −1.7, −3.4, 52, B
LYS, O, 31, 2.1, −1.5, −2.1, 52, B
PRO, N, 32, 1.3, −1.4, −4.2, 52, B
PRO, CD, 32, 1.3, −1.8, −5.7, 52, B
PRO, CA, 32, 0.0, −0.8, −3.8, 52, B
PRO, CB, 32, −0.9, −1.2, −5.0, 52, B
PRO, CG, 32, 0.1, −1.1, −6.2, 52, B
PRO, C, 32, −0.6, −1.2, −2.5, 52, B
PRO, O, 32, −0.8, −0.4, −1.6, 52, B
LEU, N, 33, −0.9, −2.5, −2.3, 53, B
LEU, CA, 33, −1.5, −2.9, −1.0, 54, B
LEU, CB, 33, −1.9, −4.4, −1.1, 54, B
LEU, CG, 33, −2.8, −4.8, −2.3, 54, B
LEU, CD1, 33, −3.3, −6.2, −2.1, 54, B
LEU, CD2, 33, −4.0, −3.8, −2.3, 54, B
LEU, C, 33, −0.6, −2.6, 0.2, 54, B
```

TABLE 2-continued

Structural coordinates of HDM2 (17-125; F55Y/Y76H) (SEQ ID NO: 2) complexed with compound 2.

| | | | | | | |
|---|---|---|---|---|---|---|
| LEU, | O, | 33, | −1.1, | −2.0, | 1.2, | 55, B |
| LEU, | N, | 34, | 0.6, | −3.1, | 0.2, | 54, B |
| LEU, | CA, | 34, | 1.5, | −2.8, | 1.3, | 55, B |
| LEU, | CB, | 34, | 2.9, | −3.3, | 1.0, | 55, B |
| LEU, | CG, | 34, | 4.0, | −2.9, | 2.0, | 55, B |
| LEU, | CD1, | 34, | 3.5, | −3.3, | 3.4, | 55, B |
| LEU, | CD2, | 34, | 5.3, | −3.6, | 1.7, | 54, B |
| LEU, | C, | 34, | 1.6, | −1.4, | 1.6, | 55, B |
| LEU, | O, | 34, | 1.5, | −1.0, | 2.8, | 55, B |
| LEU, | N, | 35, | 1.7, | −0.5, | 0.6, | 55, B |
| LEU, | CA, | 35, | 1.7, | 0.9, | 0.7, | 55, B |
| LEU, | CB, | 35, | 1.7, | 1.6, | −0.6, | 55, B |
| LEU, | CG, | 35, | 1.8, | 3.1, | −0.6, | 55, B |
| LEU, | CD1, | 35, | 3.2, | 3.5, | −0.1, | 55, B |
| LEU, | CD2, | 35, | 1.6, | 3.7, | −2.0, | 55, B |
| LEU, | C, | 35, | 0.4, | 1.3, | 1.5, | 55, B |
| LEU, | O, | 35, | 0.5, | 2.2, | 2.4, | 55, B |
| LYS, | N, | 36, | −0.7, | 0.7, | 1.1, | 56, B |
| LYS, | CA, | 36, | −2.0, | 1.0, | 1.8, | 56, B |
| LYS, | CB, | 36, | −3.0, | 0.1, | 1.1, | 57, B |
| LYS, | CG, | 36, | −4.5, | 0.2, | 1.6, | 57, B |
| LYS, | CD, | 36, | −5.4, | −0.9, | 1.1, | 58, B |
| LYS, | CE, | 36, | −6.8, | −0.8, | 1.6, | 58, B |
| LYS, | NZ, | 36, | −7.6, | −2.0, | 1.4, | 58, B |
| LYS, | C, | 36, | −1.8, | 0.7, | 3.2, | 56, B |
| LYS, | O, | 36, | −2.1, | 1.6, | 4.1, | 56, B |
| LEU, | N, | 37, | −1.4, | −0.5, | 3.5, | 57, B |
| LEU, | CA, | 37, | −1.2, | −0.9, | 4.9, | 57, B |
| LEU, | CB, | 37, | −0.6, | −2.3, | 4.9, | 56, B |
| LEU, | CG, | 37, | −0.5, | −3.1, | 6.3, | 56, B |
| LEU, | CD1, | 37, | −0.3, | −4.6, | 6.0, | 56, B |
| LEU, | CD2, | 37, | 0.6, | −2.5, | 7.1, | 56, B |
| LEU, | C, | 37, | −0.3, | 0.1, | 5.7, | 57, B |
| LEU, | O, | 37, | −0.7, | 0.5, | 6.8, | 56, B |
| LEU, | N, | 38, | 0.8, | 0.4, | 5.1, | 57, B |
| LEU, | CA, | 38, | 1.8, | 1.3, | 5.8, | 57, B |
| LEU, | CB, | 38, | 3.0, | 1.5, | 4.9, | 57, B |
| LEU, | CG, | 38, | 4.3, | 0.7, | 5.3, | 57, B |
| LEU, | CD1, | 38, | 3.9, | −0.7, | 5.6, | 57, B |
| LEU, | CD2, | 38, | 5.3, | 0.8, | 4.2, | 57, B |
| LEU, | C, | 38, | 1.2, | 2.7, | 6.1, | 57, B |
| LEU, | O, | 38, | 1.3, | 3.2, | 7.2, | 57, B |
| LYS, | N, | 39, | 0.6, | 3.3, | 5.1, | 58, B |
| LYS, | CA, | 39, | 0.0, | 4.7, | 5.3, | 58, B |
| LYS, | CB, | 39, | −0.5, | 5.2, | 3.9, | 59, B |
| LYS, | CG, | 39, | 0.6, | 5.5, | 2.9, | 59, B |
| LYS, | CD, | 39, | 0.0, | 6.3, | 1.7, | 59, B |
| LYS, | CE, | 39, | 1.1, | 6.7, | 0.8, | 59, B |
| LYS, | NZ, | 39, | 0.6, | 7.5, | −0.4, | 60, B |
| LYS, | C, | 39, | −1.1, | 4.6, | 6.3, | 58, B |
| LYS, | O, | 39, | −1.4, | 5.6, | 6.9, | 58, B |
| SER, | N, | 40, | −1.7, | 3.5, | 6.4, | 59, B |
| SER, | CA, | 40, | −2.8, | 3.4, | 7.4, | 60, B |
| SER, | CB, | 40, | −3.5, | 2.0, | 7.2, | 60, B |
| SER, | OG, | 40, | −3.0, | 1.1, | 8.1, | 59, B |
| SER, | C, | 40, | −2.3, | 3.5, | 8.8, | 60, B |
| SER, | O, | 40, | −3.1, | 3.4, | 9.8, | 60, B |
| VAL, | N, | 41, | −1.0, | 3.6, | 9.0, | 61, B |
| VAL, | CA, | 41, | −0.4, | 3.8, | 10.3, | 61, B |
| VAL, | CB, | 41, | 0.2, | 2.5, | 10.8, | 61, B |
| VAL, | CG1, | 41, | −0.8, | 1.3, | 10.8, | 61, B |
| VAL, | CG2, | 41, | 1.4, | 2.1, | 10.0, | 61, B |
| VAL, | C, | 41, | 0.6, | 4.9, | 10.5, | 61, B |
| VAL, | O, | 41, | 1.5, | 4.8, | 11.3, | 61, B |
| GLY, | N, | 42, | 0.4, | 5.9, | 9.7, | 62, B |
| GLY, | CA, | 42, | 1.3, | 7.1, | 9.8, | 62, B |
| GLY, | C, | 42, | 2.5, | 7.2, | 8.9, | 63, B |
| GLY, | O, | 42, | 3.4, | 7.9, | 9.2, | 63, B |
| ALA, | N, | 43, | 2.5, | 6.5, | 7.7, | 63, B |
| ALA, | CA, | 43, | 3.6, | 6.5, | 6.8, | 63, B |
| ALA, | CB, | 43, | 4.1, | 5.1, | 6.6, | 63, B |
| ALA, | C, | 43, | 3.2, | 7.1, | 5.5, | 63, B |
| ALA, | O, | 43, | 2.7, | 6.4, | 4.6, | 64, B |
| GLN, | N, | 44, | 3.4, | 8.4, | 5.3, | 63, B |
| GLN, | CA, | 44, | 3.0, | 9.1, | 4.1, | 63, B |
| GLN, | CB, | 44, | 2.5, | 10.5, | 4.4, | 63, B |

TABLE 2-continued

Structural coordinates of HDM2 (17-125; F55Y/Y76H) (SEQ ID NO: 2) complexed with compound 2.

| | | | | | | |
|---|---|---|---|---|---|---|
| GLN, | CG, | 44, | 2.1, | 11.4, | 3.1, | 64, B |
| GLN, | CD, | 44, | 1.3, | 12.6, | 3.5, | 64, B |
| GLN, | OE1, | 44, | 1.2, | 13.5, | 2.7, | 64, B |
| GLN, | NE2, | 44, | 0.8, | 12.7, | 4.7, | 64, B |
| GLN, | C, | 44, | 4.0, | 9.1, | 2.9, | 62, B |
| GLN, | O, | 44, | 3.8, | 9.6, | 1.9, | 63, B |
| LYS, | N, | 45, | 5.1, | 8.4, | 3.2, | 61, B |
| LYS, | CA, | 45, | 6.2, | 8.4, | 2.2, | 60, B |
| LYS, | CB, | 45, | 7.6, | 8.1, | 2.9, | 60, B |
| LYS, | CG, | 45, | 8.4, | 9.3, | 3.1, | 60, B |
| LYS, | CD, | 45, | 9.5, | 9.1, | 4.1, | 61, B |
| LYS, | CE, | 45, | 10.2, | 7.7, | 4.0, | 61, B |
| LYS, | NZ, | 45, | 11.4, | 7.6, | 4.8, | 61, B |
| LYS, | C, | 45, | 6.0, | 7.3, | 1.2, | 59, B |
| LYS, | O, | 45, | 5.2, | 6.4, | 1.3, | 59, B |
| ASP, | N, | 46, | 6.7, | 7.5, | 0.1, | 58, B |
| ASP, | CA, | 46, | 6.6, | 6.6, | −1.1, | 57, B |
| ASP, | CB, | 46, | 6.5, | 7.3, | −2.4, | 57, B |
| ASP, | CG, | 46, | 5.1, | 8.0, | −2.5, | 58, B |
| ASP, | OD1, | 46, | 4.6, | 8.6, | −1.5, | 58, B |
| ASP, | OD2, | 46, | 4.5, | 8.0, | −3.6, | 58, B |
| ASP, | C, | 46, | 7.8, | 5.7, | −1.1, | 56, B |
| ASP, | O, | 46, | 7.8, | 4.5, | −1.6, | 56, B |
| THR, | N, | 47, | 8.9, | 6.1, | −0.5, | 55, B |
| THR, | CA, | 47, | 10.2, | 5.4, | −0.5, | 54, B |
| THR, | CB, | 47, | 11.3, | 6.1, | −1.3, | 54, B |
| THR, | OG1, | 47, | 10.9, | 6.4, | −2.6, | 54, B |
| THR, | CG2, | 47, | 12.6, | 5.3, | −1.3, | 54, B |
| THR, | C, | 47, | 10.7, | 5.2, | 0.9, | 53, B |
| THR, | O, | 47, | 10.7, | 6.1, | 1.7, | 53, B |
| TYR, | N, | 48, | 11.1, | 3.9, | 1.2, | 52, B |
| TYR, | CA, | 48, | 11.5, | 3.6, | 2.5, | 50, B |
| TYR, | CB, | 48, | 10.4, | 2.8, | 3.3, | 51, B |
| TYR, | CG, | 48, | 9.1, | 3.5, | 3.3, | 51, B |
| TYR, | CD1, | 48, | 8.3, | 3.5, | 2.2, | 51, B |
| TYR, | CE1, | 48, | 7.0, | 4.1, | 2.3, | 51, B |
| TYR, | CD2, | 48, | 8.6, | 4.1, | 4.5, | 51, B |
| TYR, | CE2, | 48, | 7.4, | 4.6, | 4.6, | 51, B |
| TYR, | CZ, | 48, | 6.6, | 4.7, | 3.4, | 51, B |
| TYR, | OH, | 48, | 5.3, | 5.2, | 3.5, | 51, B |
| TYR, | C, | 48, | 12.7, | 2.7, | 2.5, | 49, B |
| TYR, | O, | 48, | 13.1, | 2.1, | 1.5, | 49, B |
| THR, | N, | 49, | 13.4, | 2.6, | 3.7, | 48, B |
| THR, | CA, | 49, | 14.5, | 1.7, | 3.8, | 47, B |
| THR, | CB, | 49, | 15.5, | 2.2, | 4.9, | 46, B |
| THR, | OG1, | 49, | 14.8, | 2.4, | 6.1, | 45, B |
| THR, | CG2, | 49, | 16.2, | 3.5, | 4.5, | 46, B |
| THR, | C, | 49, | 13.8, | 0.5, | 4.4, | 47, B |
| THR, | O, | 49, | 12.7, | 0.6, | 4.9, | 47, B |
| MET, | N, | 50, | 14.4, | −0.7, | 4.3, | 47, B |
| MET, | CA, | 50, | 13.8, | −1.9, | 4.8, | 46, B |
| MET, | CB, | 50, | 14.7, | −3.2, | 4.6, | 47, B |
| MET, | CG, | 50, | 14.6, | −3.8, | 3.2, | 48, B |
| MET, | SD, | 50, | 13.1, | −4.8, | 2.9, | 49, B |
| MET, | CE, | 50, | 13.0, | −5.8, | 4.3, | 49, B |
| MET, | C, | 50, | 13.5, | −1.8, | 6.3, | 46, B |
| MET, | O, | 50, | 12.6, | −2.3, | 6.8, | 45, B |
| LYS, | N, | 51, | 14.4, | −1.0, | 7.0, | 45, B |
| LYS, | CA, | 51, | 14.3, | −0.7, | 8.4, | 45, B |
| LYS, | CB, | 51, | 15.3, | 0.3, | 8.9, | 45, B |
| LYS, | CG, | 51, | 16.7, | −0.3, | 9.3, | 46, B |
| LYS, | CD, | 51, | 17.5, | 0.7, | 10.1, | 46, B |
| LYS, | CE, | 51, | 18.9, | 0.2, | 10.4, | 46, B |
| LYS, | NZ, | 51, | 18.9, | −1.0, | 11.2, | 47, B |
| LYS, | C, | 51, | 12.9, | −0.1, | 8.7, | 44, B |
| LYS, | O, | 51, | 12.1, | −0.6, | 9.5, | 44, B |
| GLU, | N, | 52, | 12.6, | 1.0, | 7.9, | 44, B |
| GLU, | CA, | 52, | 11.4, | 1.7, | 8.1, | 44, B |
| GLU, | CB, | 52, | 11.4, | 2.9, | 7.2, | 44, B |
| GLU, | CG, | 52, | 12.5, | 3.9, | 7.5, | 44, B |
| GLU, | CD, | 52, | 12.6, | 5.1, | 6.6, | 45, B |
| GLU, | OE1, | 52, | 12.3, | 4.9, | 5.4, | 45, B |
| GLU, | OE2, | 52, | 12.9, | 6.2, | 7.2, | 45, B |
| GLU, | C, | 52, | 10.2, | 0.8, | 7.9, | 43, B |
| GLU, | O, | 52, | 9.2, | 0.9, | 8.6, | 43, B |
| VAL, | N, | 53, | 10.3, | −0.0, | 6.8, | 42, B |

TABLE 2-continued

Structural coordinates of HDM2 (17-125; F55Y/Y76H) (SEQ ID NO: 2) complexed with compound 2.

| | | | | | | |
|---|---|---|---|---|---|---|
| VAL, | CA, | 53, | 9.2, | −1.0, | 6.5, | 42, B |
| VAL, | CB, | 53, | 9.5, | −1.8, | 5.3, | 42, B |
| VAL, | CG1, | 53, | 8.6, | −3.0, | 5.2, | 42, B |
| VAL, | CG2, | 53, | 9.4, | −0.9, | 4.0, | 42, B |
| VAL, | C, | 53, | 8.9, | −1.9, | 7.7, | 42, B |
| VAL, | O, | 53, | 7.8, | −2.1, | 8.1, | 42, B |
| LEU, | N, | 54, | 10.0, | −2.4, | 8.3, | 42, B |
| LEU, | CA, | 54, | 9.8, | −3.3, | 9.5, | 42, B |
| LEU, | CB, | 54, | 11.2, | −3.8, | 10.0, | 42, B |
| LEU, | CG, | 54, | 11.8, | −4.8, | 9.0, | 42, B |
| LEU, | CD1, | 54, | 13.2, | −5.2, | 9.6, | 42, B |
| LEU, | CD2, | 54, | 10.9, | −6.0, | 8.9, | 42, B |
| LEU, | C, | 54, | 9.1, | −2.6, | 10.6, | 43, B |
| LEU, | O, | 54, | 8.1, | −3.1, | 11.1, | 43, B |
| TYR, | N, | 55, | 9.5, | −1.4, | 10.9, | 43, B |
| TYR, | CA, | 55, | 8.9, | −0.5, | 12.0, | 44, B |
| TYR, | CB, | 55, | 9.6, | 0.8, | 12.0, | 43, B |
| TYR, | CG, | 55, | 9.0, | 1.8, | 13.0, | 43, B |
| TYR, | CD1, | 55, | 8.9, | 1.5, | 14.4, | 43, B |
| TYR, | CE1, | 55, | 8.2, | 2.4, | 15.2, | 43, B |
| TYR, | CD2, | 55, | 8.4, | 3.0, | 12.5, | 43, B |
| TYR, | CE2, | 55, | 7.8, | 3.9, | 13.4, | 43, B |
| TYR, | CZ, | 55, | 7.7, | 3.6, | 14.7, | 43, B |
| TYR, | OH, | 55, | 7.2, | 4.5, | 15.6, | 43, B |
| TYR, | C, | 55, | 7.4, | −0.3, | 11.7, | 44, B |
| TYR, | O, | 55, | 6.6, | −0.6, | 12.6, | 44, B |
| TYR, | N, | 56, | 7.1, | 0.3, | 10.6, | 45, B |
| TYR, | CA, | 56, | 5.7, | 0.6, | 10.3, | 45, B |
| TYR, | CB, | 56, | 5.6, | 1.4, | 9.0, | 45, B |
| TYR, | CG, | 56, | 6.1, | 2.8, | 9.2, | 46, B |
| TYR, | CD1, | 56, | 5.5, | 3.7, | 10.2, | 46, B |
| TYR, | CE1, | 56, | 6.0, | 4.9, | 10.4, | 46, B |
| TYR, | CD2, | 56, | 7.2, | 3.3, | 8.5, | 46, B |
| TYR, | CE2, | 56, | 7.6, | 4.6, | 8.7, | 46, B |
| TYR, | CZ, | 56, | 7.1, | 5.4, | 9.7, | 46, B |
| TYR, | OH, | 56, | 7.6, | 6.7, | 9.9, | 46, B |
| TYR, | C, | 56, | 4.8, | −0.7, | 10.3, | 46, B |
| TYR, | O, | 56, | 3.7, | −0.6, | 10.8, | 47, B |
| LEU, | N, | 57, | 5.4, | −1.7, | 9.7, | 46, B |
| LEU, | CA, | 57, | 4.6, | −3.0, | 9.7, | 47, B |
| LEU, | CB, | 57, | 5.4, | −4.1, | 9.0, | 46, B |
| LEU, | CG, | 57, | 5.5, | −4.1, | 7.5, | 46, B |
| LEU, | CD1, | 57, | 6.4, | −5.2, | 7.0, | 47, B |
| LEU, | CD2, | 57, | 4.1, | −4.3, | 6.9, | 46, B |
| LEU, | C, | 57, | 4.4, | −3.4, | 11.2, | 47, B |
| LEU, | O, | 57, | 3.3, | −3.9, | 11.5, | 47, B |
| GLY, | N, | 58, | 5.4, | −3.1, | 12.0, | 48, B |
| GLY, | CA, | 58, | 5.3, | −3.4, | 13.4, | 48, B |
| GLY, | C, | 58, | 4.2, | −2.6, | 14.1, | 48, B |
| GLY, | O, | 58, | 3.6, | −3.0, | 15.1, | 48, B |
| GLN, | N, | 59, | 4.1, | −1.3, | 13.6, | 48, B |
| GLN, | CA, | 59, | 3.1, | −0.4, | 14.2, | 49, B |
| GLN, | CB, | 59, | 3.2, | 1.0, | 13.6, | 49, B |
| GLN, | CG, | 59, | 4.4, | 1.8, | 14.0, | 49, B |
| GLN, | CD, | 59, | 4.4, | 2.0, | 15.5, | 49, B |
| GLN, | OE1, | 59, | 4.7, | 1.1, | 16.4, | 49, B |
| GLN, | NE2, | 59, | 4.0, | 3.2, | 15.9, | 49, B |
| GLN, | C, | 59, | 1.7, | −0.9, | 13.9, | 49, B |
| GLN, | O, | 59, | 0.8, | −0.9, | 14.7, | 49, B |
| TYR, | N, | 60, | 1.6, | −1.5, | 12.7, | 50, B |
| TYR, | CA, | 60, | 0.3, | −2.0, | 12.2, | 50, B |
| TYR, | CB, | 60, | 0.4, | −2.6, | 10.8, | 50, B |
| TYR, | CG, | 60, | −0.8, | −3.1, | 10.2, | 50, B |
| TYR, | CD1, | 60, | −1.8, | −2.2, | 9.7, | 50, B |
| TYR, | CE1, | 60, | −3.0, | −2.7, | 9.1, | 50, B |
| TYR, | CD2, | 60, | −1.0, | −4.5, | 10.0, | 50, B |
| TYR, | CE2, | 60, | −2.2, | −5.0, | 9.4, | 50, B |
| TYR, | CZ, | 60, | −3.1, | −4.1, | 8.9, | 50, B |
| TYR, | OH, | 60, | −4.3, | −4.6, | 8.3, | 50, B |
| TYR, | C, | 60, | −0.2, | −3.1, | 13.2, | 50, B |
| TYR, | O, | 60, | −1.3, | −3.1, | 13.6, | 50, B |
| ILE, | N, | 61, | 0.7, | −4.1, | 13.4, | 50, B |
| ILE, | CA, | 61, | 0.4, | −5.2, | 14.3, | 51, B |
| ILE, | CB, | 61, | 1.7, | −6.2, | 14.4, | 51, B |
| ILE, | CG2, | 61, | 1.4, | −7.2, | 15.4, | 51, B |
| ILE, | CG1, | 61, | 1.9, | −6.8, | 13.0, | 51, B |
| ILE, | CD1, | 61, | 3.1, | −7.7, | 13.0, | 50, B |
| ILE, | C, | 61, | 0.1, | −4.8, | 15.7, | 52, B |
| ILE, | O, | 61, | −0.8, | −5.4, | 16.3, | 51, B |
| MET, | N, | 62, | 0.7, | −3.8, | 16.2, | 53, B |
| MET, | CA, | 62, | 0.5, | −3.3, | 17.5, | 54, B |
| MET, | CB, | 62, | 1.6, | −2.3, | 18.0, | 54, B |
| MET, | CG, | 62, | 3.0, | −3.0, | 18.1, | 54, B |
| MET, | SD, | 62, | 2.9, | −4.3, | 19.3, | 54, B |
| MET, | CE, | 62, | 3.5, | −3.4, | 20.8, | 54, B |
| MET, | C, | 62, | −0.9, | −2.5, | 17.6, | 55, B |
| MET, | O, | 62, | −1.7, | −2.8, | 18.5, | 55, B |
| THR, | N, | 63, | −1.1, | −1.6, | 16.7, | 56, B |
| THR, | CA, | 63, | −2.3, | −0.9, | 16.6, | 58, B |
| THR, | CB, | 63, | −2.3, | 0.1, | 15.4, | 58, B |
| THR, | OG1, | 63, | −1.9, | −0.7, | 14.2, | 58, B |
| THR, | CG2, | 63, | −1.3, | 1.2, | 15.6, | 58, B |
| THR, | C, | 63, | −3.5, | −1.7, | 16.5, | 59, B |
| THR, | O, | 63, | −4.6, | −1.4, | 16.9, | 59, B |
| LYS, | N, | 64, | −3.4, | −2.9, | 15.8, | 60, B |
| LYS, | CA, | 64, | −4.5, | −3.8, | 15.6, | 61, B |
| LYS, | CB, | 64, | −4.6, | −4.2, | 14.1, | 61, B |
| LYS, | CG, | 64, | −4.8, | −3.0, | 13.2, | 61, B |
| LYS, | CD, | 64, | −5.1, | −3.4, | 11.8, | 62, B |
| LYS, | CE, | 64, | −6.4, | −4.2, | 11.7, | 62, B |
| LYS, | NZ, | 64, | −6.9, | −4.4, | 10.4, | 62, B |
| LYS, | C, | 64, | −4.4, | −5.0, | 16.5, | 62, B |
| LYS, | O, | 64, | −5.1, | −6.0, | 16.3, | 62, B |
| ARG, | N, | 65, | −3.4, | −5.0, | 17.4, | 63, B |
| ARG, | CA, | 65, | −3.1, | −6.1, | 18.3, | 64, B |
| ARG, | CB, | 65, | −4.1, | −6.1, | 19.4, | 64, B |
| ARG, | CG, | 65, | −3.9, | −5.0, | 20.5, | 65, B |
| ARG, | CD, | 65, | −4.8, | −5.1, | 21.7, | 65, B |
| ARG, | NE, | 65, | −4.9, | −6.5, | 22.1, | 65, B |
| ARG, | CZ, | 65, | −6.0, | −7.2, | 22.1, | 65, B |
| ARG, | NH1, | 65, | −7.1, | −6.7, | 21.6, | 65, B |
| ARG, | NH2, | 65, | −6.0, | −8.4, | 22.5, | 66, B |
| ARG, | C, | 65, | −3.1, | −7.5, | 17.6, | 65, B |
| ARG, | O, | 65, | −3.8, | −8.4, | 18.1, | 65, B |
| LEU, | N, | 66, | −2.5, | −7.6, | 16.5, | 66, B |
| LEU, | CA, | 66, | −2.4, | −8.9, | 15.8, | 66, B |
| LEU, | CB, | 66, | −2.0, | −8.6, | 14.3, | 66, B |
| LEU, | CG, | 66, | −2.9, | −7.7, | 13.5, | 66, B |
| LEU, | CD1, | 66, | −2.4, | −7.6, | 12.1, | 66, B |
| LEU, | CD2, | 66, | −4.4, | −8.1, | 13.5, | 66, B |
| LEU, | C, | 66, | −1.4, | −9.9, | 16.4, | 67, B |
| LEU, | O, | 66, | −0.6, | −10.4, | 15.7, | 67, B |
| TYR, | N, | 67, | −1.5, | −10.0, | 17.7, | 68, B |
| TYR, | CA, | 67, | −0.6, | −10.9, | 18.4, | 69, B |
| TYR, | CB, | 67, | 0.6, | −10.2, | 18.9, | 69, B |
| TYR, | CG, | 67, | 0.3, | −9.0, | 19.8, | 69, B |
| TYR, | CD1, | 67, | 0.2, | −9.1, | 21.1, | 69, B |
| TYR, | CE1, | 67, | 0.0, | −7.9, | 21.9, | 69, B |
| TYR, | CD2, | 67, | 0.2, | −7.7, | 19.2, | 69, B |
| TYR, | CE2, | 67, | −0.0, | −6.6, | 19.9, | 69, B |
| TYR, | CZ, | 67, | −0.1, | −6.7, | 21.3, | 69, B |
| TYR, | OH, | 67, | −0.3, | −5.6, | 22.1, | 69, B |
| TYR, | C, | 67, | −1.4, | −11.6, | 19.6, | 70, B |
| TYR, | O, | 67, | −2.2, | −10.9, | 20.3, | 70, B |
| ASP, | N, | 68, | −1.1, | −12.9, | 19.8, | 71, B |
| ASP, | CA, | 68, | −1.7, | −13.6, | 20.9, | 72, B |
| ASP, | CB, | 68, | −1.3, | −15.1, | 20.8, | 72, B |
| ASP, | CG, | 68, | −1.9, | −15.9, | 22.0, | 72, B |
| ASP, | OD1, | 68, | −3.0, | −15.6, | 22.5, | 73, B |
| ASP, | OD2, | 68, | −1.2, | −16.8, | 22.5, | 72, B |
| ASP, | C, | 68, | −1.3, | −13.0, | 22.3, | 72, B |
| ASP, | O, | 68, | −0.2, | −12.8, | 22.6, | 72, B |
| GLU, | N, | 69, | −2.4, | −12.8, | 23.1, | 73, B |
| GLU, | CA, | 69, | −2.2, | −12.2, | 24.4, | 73, B |
| GLU, | CB, | 69, | −3.4, | −12.4, | 25.3, | 74, B |
| GLU, | CG, | 69, | −4.6, | −11.7, | 24.7, | 74, B |
| GLU, | CD, | 69, | −4.2, | −10.3, | 24.2, | 74, B |
| GLU, | OE1, | 69, | −3.9, | −9.4, | 25.1, | 74, B |
| GLU, | OE2, | 69, | −4.2, | −10.0, | 23.0, | 74, B |
| GLU, | C, | 69, | −1.0, | −12.8, | 25.2, | 73, B |
| GLU, | O, | 69, | −0.1, | −12.1, | 25.7, | 73, B |
| LYS, | N, | 70, | −0.9, | −14.1, | 25.3, | 73, B |

TABLE 2-continued

Structural coordinates of HDM2 (17-125; F55Y/Y76H)
(SEQ ID NO: 2) complexed with compound 2.

| | | | | | | |
|---|---|---|---|---|---|---|
| LYS, | CA, | 70, | 0.2, | −14.8, | 26.0, | 73, B |
| LYS, | CB, | 70, | −0.3, | −16.0, | 26.7, | 74, B |
| LYS, | CG, | 70, | 0.5, | −16.6, | 27.8, | 74, B |
| LYS, | CD, | 70, | −0.2, | −17.7, | 28.5, | 74, B |
| LYS, | CE, | 70, | 0.7, | −18.4, | 29.6, | 74, B |
| LYS, | NZ, | 70, | −0.0, | −19.6, | 30.1, | 75, B |
| LYS, | C, | 70, | 1.4, | −15.1, | 25.1, | 73, B |
| LYS, | O, | 70, | 2.6, | −14.8, | 25.5, | 73, B |
| GLN, | N, | 71, | 1.2, | −15.7, | 24.0, | 72, B |
| GLN, | CA, | 71, | 2.3, | −16.0, | 23.1, | 72, B |
| GLN, | CB, | 71, | 2.0, | −17.2, | 22.2, | 72, B |
| GLN, | CG, | 71, | 3.2, | −18.0, | 21.7, | 72, B |
| GLN, | CD, | 71, | 2.8, | −19.3, | 21.1, | 73, B |
| GLN, | OE1, | 71, | 3.6, | −20.1, | 20.6, | 73, B |
| GLN, | NE2, | 71, | 1.5, | −19.7, | 21.2, | 73, B |
| GLN, | C, | 71, | 2.7, | −14.8, | 22.2, | 71, B |
| GLN, | O, | 71, | 2.4, | −14.7, | 21.0, | 71, B |
| GLN, | N, | 72, | 3.3, | −13.8, | 22.9, | 70, B |
| GLN, | CA, | 72, | 3.7, | −12.5, | 22.2, | 69, B |
| GLN, | CB, | 72, | 4.3, | −11.6, | 23.3, | 69, B |
| GLN, | CG, | 72, | 3.3, | −10.7, | 23.9, | 69, B |
| GLN, | CD, | 72, | 4.0, | −9.6, | 24.7, | 70, B |
| GLN, | OE1, | 72, | 4.9, | −8.9, | 24.1, | 70, B |
| GLN, | NE2, | 72, | 3.7, | −9.4, | 25.9, | 70, B |
| GLN, | C, | 72, | 4.6, | −12.5, | 21.0, | 68, B |
| GLN, | O, | 72, | 4.8, | −11.4, | 20.4, | 68, B |
| HIS, | N, | 73, | 5.2, | −13.6, | 20.6, | 67, B |
| HIS, | CA, | 73, | 6.1, | −13.5, | 19.4, | 66, B |
| HIS, | CB, | 73, | 7.4, | −14.2, | 19.7, | 66, B |
| HIS, | CG, | 73, | 7.4, | −15.6, | 20.2, | 67, B |
| HIS, | CD2, | 73, | 7.9, | −16.7, | 19.8, | 67, B |
| HIS, | ND1, | 73, | 6.7, | −15.9, | 21.4, | 67, B |
| HIS, | CE1, | 73, | 6.8, | −17.1, | 21.7, | 68, B |
| HIS, | NE2, | 73, | 7.5, | −17.7, | 20.7, | 67, B |
| HIS, | C, | 73, | 5.4, | −14.2, | 18.2, | 64, B |
| HIS, | O, | 73, | 6.1, | −14.3, | 17.1, | 64, B |
| ILE, | N, | 74, | 4.2, | −14.5, | 18.3, | 63, B |
| ILE, | CA, | 74, | 3.4, | −15.1, | 17.2, | 61, B |
| ILE, | CB, | 74, | 2.7, | −16.3, | 17.6, | 61, B |
| ILE, | CG2, | 74, | 2.0, | −17.0, | 16.4, | 61, B |
| ILE, | CG1, | 74, | 3.6, | −17.3, | 18.3, | 61, B |
| ILE, | CD1, | 74, | 4.8, | −17.8, | 17.4, | 60, B |
| ILE, | C, | 74, | 2.4, | −14.1, | 16.7, | 59, B |
| ILE, | O, | 74, | 1.6, | −13.5, | 17.4, | 59, B |
| VAL, | N, | 75, | 2.4, | −13.8, | 15.4, | 57, B |
| VAL, | CA, | 75, | 1.5, | −12.8, | 14.8, | 55, B |
| VAL, | CB, | 75, | 2.1, | −12.0, | 13.6, | 55, B |
| VAL, | CG1, | 75, | 1.1, | −11.2, | 12.9, | 55, B |
| VAL, | CG2, | 75, | 3.2, | −11.1, | 14.2, | 55, B |
| VAL, | C, | 75, | 0.3, | −13.6, | 14.2, | 54, B |
| VAL, | O, | 75, | 0.4, | −14.7, | 13.6, | 54, B |
| HIS, | N, | 76, | −0.9, | −13.1, | 14.4, | 52, B |
| HIS, | CA, | 76, | −2.2, | −13.7, | 14.0, | 50, B |
| HIS, | CB, | 76, | −3.1, | −14.0, | 15.1, | 51, B |
| HIS, | CG, | 76, | −2.6, | −15.2, | 15.9, | 50, B |
| HIS, | CD2, | 76, | −2.1, | −15.3, | 17.1, | 51, B |
| HIS, | ND1, | 76, | −2.7, | −16.5, | 15.4, | 50, B |
| HIS, | CE1, | 76, | −2.1, | −17.3, | 16.3, | 51, B |
| HIS, | NE2, | 76, | −1.8, | −16.6, | 17.3, | 50, B |
| HIS, | C, | 76, | −2.8, | −12.7, | 13.0, | 49, B |
| HIS, | O, | 76, | −3.4, | −11.7, | 13.4, | 49, B |
| CYS, | N, | 77, | −2.8, | −13.1, | 11.7, | 48, B |
| CYS, | CA, | 77, | −3.3, | −12.2, | 10.7, | 48, B |
| CYS, | CB, | 77, | −2.2, | −11.5, | 10.1, | 47, B |
| CYS, | SG, | 77, | −0.8, | −12.5, | 9.6, | 47, B |
| CYS, | C, | 77, | −4.1, | −13.0, | 9.6, | 47, B |
| CYS, | O, | 77, | −4.1, | −12.5, | 8.4, | 47, B |
| SER, | N, | 78, | −4.7, | −14.1, | 9.9, | 47, B |
| SER, | CA, | 78, | −5.4, | −14.9, | 9.0, | 46, B |
| SER, | CB, | 78, | −5.9, | −16.2, | 9.6, | 46, B |
| SER, | OG, | 78, | −7.0, | −15.9, | 10.4, | 46, B |
| SER, | C, | 78, | −6.6, | −14.2, | 8.3, | 47, B |
| SER, | O, | 78, | −7.0, | −14.6, | 7.2, | 46, B |
| ASN, | N, | 79, | −7.2, | −13.3, | 9.0, | 46, B |
| ASN, | CA, | 79, | −8.4, | −12.6, | 8.5, | 47, B |
| ASN, | CB, | 79, | −9.6, | −12.8, | 9.5, | 46, B |

TABLE 2-continued

Structural coordinates of HDM2 (17-125; F55Y/Y76H)
(SEQ ID NO: 2) complexed with compound 2.

| | | | | | | |
|---|---|---|---|---|---|---|
| ASN, | CG, | 79, | −10.9, | −12.1, | 9.1, | 46, B |
| ASN, | OD1, | 79, | −11.2, | −12.0, | 7.9, | 46, B |
| ASN, | ND2, | 79, | −11.6, | −11.5, | 10.0, | 46, B |
| ASN, | C, | 79, | −8.1, | −11.1, | 8.4, | 47, B |
| ASN, | O, | 79, | −8.9, | −10.2, | 8.4, | 47, B |
| ASP, | N, | 80, | −6.8, | −10.8, | 8.2, | 46, B |
| ASP, | CA, | 80, | −6.4, | −9.4, | 8.0, | 46, B |
| ASP, | CB, | 80, | −5.5, | −8.9, | 9.2, | 47, B |
| ASP, | CG, | 80, | −5.4, | −7.4, | 9.3, | 47, B |
| ASP, | OD1, | 80, | −6.4, | −6.8, | 9.7, | 48, B |
| ASP, | OD2, | 80, | −4.4, | −6.8, | 8.8, | 47, B |
| ASP, | C, | 80, | −5.6, | −9.1, | 6.7, | 46, B |
| ASP, | O, | 80, | −5.0, | −10.0, | 6.1, | 45, B |
| LEU, | N, | 81, | −5.6, | −7.9, | 6.3, | 46, B |
| LEU, | CA, | 81, | −4.8, | −7.5, | 5.1, | 46, B |
| LEU, | CB, | 81, | −4.9, | −6.0, | 4.9, | 46, B |
| LEU, | CG, | 81, | −4.1, | −5.5, | 3.7, | 46, B |
| LEU, | CD1, | 81, | −4.3, | −6.4, | 2.5, | 46, B |
| LEU, | CD2, | 81, | −4.4, | −4.0, | 3.3, | 47, B |
| LEU, | C, | 81, | −3.4, | −8.0, | 5.2, | 45, B |
| LEU, | O, | 81, | −2.8, | −8.3, | 4.2, | 45, B |
| LEU, | N, | 82, | −2.8, | −8.0, | 6.4, | 44, B |
| LEU, | CA, | 82, | −1.4, | −8.4, | 6.5, | 44, B |
| LEU, | CB, | 82, | −0.9, | −8.2, | 7.9, | 43, B |
| LEU, | CG, | 82, | 0.5, | −8.8, | 8.2, | 43, B |
| LEU, | CD1, | 82, | 1.5, | −8.2, | 7.2, | 43, B |
| LEU, | CD2, | 82, | 0.9, | −8.4, | 9.7, | 43, B |
| LEU, | C, | 82, | −1.3, | −9.9, | 6.2, | 43, B |
| LEU, | O, | 82, | −0.3, | −10.3, | 5.5, | 43, B |
| GLY, | N, | 83, | −2.2, | −10.7, | 6.6, | 42, B |
| GLY, | CA, | 83, | −2.2, | −12.1, | 6.3, | 42, B |
| GLY, | C, | 83, | −2.3, | −12.3, | 4.8, | 42, B |
| GLY, | O, | 83, | −1.8, | −13.3, | 4.3, | 41, B |
| ASP, | N, | 84, | −3.1, | −11.5, | 4.2, | 41, B |
| ASP, | CA, | 84, | −3.3, | −11.6, | 2.7, | 42, B |
| ASP, | CB, | 84, | −4.4, | −10.7, | 2.2, | 41, B |
| ASP, | CG, | 84, | −5.7, | −10.8, | 3.0, | 41, B |
| ASP, | OD1, | 84, | −6.1, | −12.0, | 3.1, | 42, B |
| ASP, | OD2, | 84, | −6.2, | −9.8, | 3.4, | 41, B |
| ASP, | C, | 84, | −2.0, | −11.3, | 2.0, | 41, B |
| ASP, | O, | 84, | −1.6, | −12.0, | 1.0, | 42, B |
| LEU, | N, | 85, | −1.3, | −10.3, | 2.4, | 41, B |
| LEU, | CA, | 85, | −0.0, | −9.9, | 1.7, | 41, B |
| LEU, | CB, | 85, | 0.4, | −8.5, | 2.1, | 42, B |
| LEU, | CG, | 85, | −0.8, | −7.5, | 1.8, | 42, B |
| LEU, | CD1, | 85, | −0.3, | −6.1, | 2.0, | 42, B |
| LEU, | CD2, | 85, | −1.2, | −7.8, | 0.3, | 42, B |
| LEU, | C, | 85, | 1.1, | −10.9, | 2.0, | 41, B |
| LEU, | O, | 85, | 1.9, | −11.2, | 1.1, | 41, B |
| PHE, | N, | 86, | 1.2, | −11.4, | 3.2, | 40, B |
| PHE, | CA, | 86, | 2.3, | −12.3, | 3.6, | 41, B |
| PHE, | CB, | 86, | 2.5, | −12.3, | 5.1, | 41, B |
| PHE, | CG, | 86, | 3.4, | −11.2, | 5.6, | 41, B |
| PHE, | CD1, | 86, | 3.7, | −10.2, | 4.8, | 41, B |
| PHE, | CD2, | 86, | 3.9, | −11.3, | 6.9, | 41, B |
| PHE, | CE1, | 86, | 4.5, | −9.2, | 5.3, | 41, B |
| PHE, | CE2, | 86, | 4.7, | −10.3, | 7.4, | 41, B |
| PHE, | CZ, | 86, | 5.0, | −9.2, | 6.6, | 41, B |
| PHE, | C, | 86, | 2.0, | −13.7, | 3.1, | 41, B |
| PHE, | O, | 86, | 2.9, | −14.5, | 2.9, | 40, B |
| GLY, | N, | 87, | 0.7, | −14.0, | 3.0, | 41, B |
| GLY, | CA, | 87, | 0.3, | −15.3, | 2.5, | 41, B |
| GLY, | C, | 87, | 0.3, | −16.4, | 3.6, | 41, B |
| GLY, | O, | 87, | 0.2, | −17.6, | 3.4, | 41, B |
| VAL, | N, | 88, | 0.3, | −15.9, | 4.9, | 42, B |
| VAL, | CA, | 88, | 0.2, | −16.9, | 6.0, | 43, B |
| VAL, | CB, | 88, | 1.6, | −17.0, | 6.7, | 42, B |
| VAL, | CG1, | 88, | 2.7, | −17.5, | 5.8, | 43, B |
| VAL, | CG2, | 88, | 2.0, | −15.7, | 7.3, | 42, B |
| VAL, | C, | 88, | −0.8, | −16.4, | 7.1, | 43, B |
| VAL, | O, | 88, | −1.1, | −15.2, | 7.2, | 43, B |
| PRO, | N, | 89, | −1.4, | −17.4, | 7.8, | 43, B |
| PRO, | CD, | 89, | −1.3, | −18.8, | 7.5, | 43, B |
| PRO, | CA, | 89, | −2.3, | −17.1, | 8.8, | 43, B |
| PRO, | CB, | 89, | −3.0, | −18.4, | 9.1, | 43, B |
| PRO, | CG, | 89, | −2.0, | −19.4, | 8.8, | 43, B |

TABLE 2-continued

Structural coordinates of HDM2 (17-125; F55Y/Y76H) (SEQ ID NO: 2) complexed with compound 2.

| | | | | | | |
|---|---|---|---|---|---|---|
| PRO, | C, | 89, | −1.6, | −16.5, | 10.1, | 44, B |
| PRO, | O, | 89, | −2.2, | −15.7, | 10.8, | 44, B |
| SER, | N, | 90, | −0.4, | −17.0, | 10.2, | 43, B |
| SER, | CA, | 90, | 0.4, | −16.5, | 11.4, | 44, B |
| SER, | CB, | 90, | −0.1, | −17.3, | 12.6, | 43, B |
| SER, | OG, | 90, | 0.3, | −18.7, | 12.5, | 43, B |
| SER, | C, | 90, | 1.9, | −16.8, | 11.1, | 44, B |
| SER, | O, | 90, | 2.2, | −17.6, | 10.3, | 44, B |
| PHE, | N, | 91, | 2.7, | −16.1, | 11.9, | 44, B |
| PHE, | CA, | 91, | 4.1, | −16.3, | 11.8, | 44, B |
| PHE, | CB, | 91, | 4.7, | −15.5, | 10.6, | 43, B |
| PHE, | CG, | 91, | 4.6, | −14.0, | 10.7, | 43, B |
| PHE, | CD1, | 91, | 5.6, | −13.3, | 11.4, | 43, B |
| PHE, | CD2, | 91, | 3.5, | −13.3, | 10.2, | 43, B |
| PHE, | CE1, | 91, | 5.5, | −12.0, | 11.5, | 43, B |
| PHE, | CE2, | 91, | 3.4, | −12.0, | 10.4, | 43, B |
| PHE, | CZ, | 91, | 4.4, | −11.3, | 11.0, | 43, B |
| PHE, | C, | 91, | 4.8, | −15.8, | 13.1, | 45, B |
| PHE, | O, | 91, | 4.2, | −15.1, | 13.8, | 45, B |
| SER, | N, | 92, | 6.0, | −16.3, | 13.3, | 46, B |
| SER, | CA, | 92, | 6.7, | −15.8, | 14.5, | 47, B |
| SER, | CB, | 92, | 7.5, | −17.0, | 15.1, | 47, B |
| SER, | OG, | 92, | 8.4, | −16.5, | 16.1, | 47, B |
| SER, | C, | 92, | 7.7, | −14.7, | 14.2, | 48, B |
| SER, | O, | 92, | 8.3, | −14.6, | 13.1, | 48, B |
| VAL, | N, | 93, | 7.8, | −13.8, | 15.2, | 48, B |
| VAL, | CA, | 93, | 8.7, | −12.7, | 15.1, | 49, B |
| VAL, | CB, | 93, | 8.4, | −11.7, | 16.3, | 49, B |
| VAL, | CG1, | 93, | 9.1, | −10.4, | 16.2, | 50, B |
| VAL, | CG2, | 93, | 6.9, | −11.5, | 16.4, | 50, B |
| VAL, | C, | 93, | 10.2, | −13.0, | 15.1, | 49, B |
| VAL, | O, | 93, | 11.0, | −12.2, | 14.8, | 50, B |
| LYS, | N, | 94, | 10.5, | −14.3, | 15.3, | 50, B |
| LYS, | CA, | 94, | 11.9, | −14.7, | 15.3, | 51, B |
| LYS, | CB, | 94, | 12.1, | −15.8, | 16.4, | 51, B |
| LYS, | CG, | 94, | 12.1, | −15.3, | 17.8, | 52, B |
| LYS, | CD, | 94, | 12.3, | −16.4, | 18.8, | 52, B |
| LYS, | CE, | 94, | 12.4, | −15.8, | 20.3, | 53, B |
| LYS, | NZ, | 94, | 12.5, | −16.9, | 21.3, | 53, B |
| LYS, | C, | 94, | 12.2, | −15.3, | 13.9, | 51, B |
| LYS, | O, | 94, | 13.4, | −15.6, | 13.7, | 51, B |
| GLU, | N, | 95, | 11.2, | −15.5, | 13.1, | 51, B |
| GLU, | CA, | 95, | 11.5, | −16.0, | 11.7, | 51, B |
| GLU, | CB, | 95, | 10.2, | −16.8, | 11.2, | 52, B |
| GLU, | CG, | 95, | 9.8, | −17.9, | 12.1, | 52, B |
| GLU, | CD, | 95, | 8.6, | −18.7, | 11.5, | 53, B |
| GLU, | OE1, | 95, | 7.4, | −18.1, | 11.7, | 52, B |
| GLU, | OE2, | 95, | 8.8, | −19.7, | 11.0, | 54, B |
| GLU, | C, | 95, | 11.8, | −14.9, | 10.8, | 51, B |
| GLU, | O, | 95, | 11.1, | −14.6, | 9.8, | 51, B |
| HIS, | N, | 96, | 13.0, | −14.3, | 11.0, | 51, B |
| HIS, | CA, | 96, | 13.5, | −13.2, | 10.2, | 51, B |
| HIS, | CB, | 96, | 14.9, | −12.8, | 10.8, | 51, B |
| HIS, | CG, | 96, | 14.8, | −12.3, | 12.2, | 51, B |
| HIS, | CD2, | 96, | 13.8, | −12.2, | 13.1, | 51, B |
| HIS, | ND1, | 96, | 15.9, | −11.8, | 12.9, | 51, B |
| HIS, | CE1, | 96, | 15.6, | −11.5, | 14.1, | 51, B |
| HIS, | NE2, | 96, | 14.3, | −11.7, | 14.3, | 51, B |
| HIS, | C, | 96, | 13.6, | −13.5, | 8.7, | 50, B |
| HIS, | O, | 96, | 13.1, | −12.7, | 7.9, | 50, B |
| ARG, | N, | 97, | 14.2, | −14.6, | 8.4, | 51, B |
| ARG, | CA, | 97, | 14.4, | −14.9, | 7.0, | 51, B |
| ARG, | CB, | 97, | 14.9, | −16.4, | 6.8, | 51, B |
| ARG, | CG, | 97, | 14.9, | −16.9, | 5.4, | 53, B |
| ARG, | CD, | 97, | 15.4, | −18.3, | 5.3, | 54, B |
| ARG, | NE, | 97, | 14.4, | −19.3, | 5.7, | 55, B |
| ARG, | CZ, | 97, | 13.3, | −19.5, | 5.1, | 55, B |
| ARG, | NH1, | 97, | 12.9, | −18.9, | 4.0, | 56, B |
| ARG, | NH2, | 97, | 12.4, | −20.5, | 5.6, | 56, B |
| ARG, | C, | 97, | 13.0, | −14.9, | 6.3, | 50, B |
| ARG, | O, | 97, | 12.8, | −14.2, | 5.3, | 50, B |
| LYS, | N, | 98, | 12.1, | −15.8, | 6.8, | 49, B |
| LYS, | CA, | 98, | 10.8, | −15.9, | 6.3, | 48, B |
| LYS, | CB, | 98, | 10.0, | −16.9, | 7.1, | 49, B |
| LYS, | CG, | 98, | 9.9, | −18.3, | 6.5, | 50, B |
| LYS, | CD, | 98, | 9.8, | −19.4, | 7.6, | 51, B |
| LYS, | CE, | 98, | 11.2, | −19.7, | 8.3, | 51, B |
| LYS, | NZ, | 98, | 11.1, | −21.0, | 9.0, | 51, B |
| LYS, | C, | 98, | 10.0, | −14.5, | 6.2, | 48, B |
| LYS, | O, | 98, | 9.4, | −14.3, | 5.2, | 47, B |
| ILE, | N, | 99, | 10.2, | −13.7, | 7.2, | 47, B |
| ILE, | CA, | 99, | 9.5, | −12.4, | 7.2, | 46, B |
| ILE, | CB, | 99, | 9.7, | −11.7, | 8.5, | 46, B |
| ILE, | CG2, | 99, | 9.3, | −10.2, | 8.4, | 45, B |
| ILE, | CG1, | 99, | 9.0, | −12.4, | 9.6, | 46, B |
| ILE, | CD1, | 99, | 9.1, | −11.8, | 11.0, | 46, B |
| ILE, | C, | 99, | 10.1, | −11.6, | 6.0, | 46, B |
| ILE, | O, | 99, | 9.3, | −10.9, | 5.3, | 45, B |
| TYR, | N, | 100, | 11.4, | −11.6, | 5.9, | 46, B |
| TYR, | CA, | 100, | 12.0, | −10.8, | 4.8, | 46, B |
| TYR, | CB, | 100, | 13.5, | −11.0, | 4.8, | 46, B |
| TYR, | CG, | 100, | 14.2, | −10.0, | 5.7, | 47, B |
| TYR, | CD1, | 100, | 15.3, | −10.4, | 6.5, | 47, B |
| TYR, | CE1, | 100, | 16.0, | −9.5, | 7.4, | 47, B |
| TYR, | CD2, | 100, | 13.8, | −8.7, | 5.8, | 47, B |
| TYR, | CE2, | 100, | 14.5, | −7.8, | 6.6, | 47, B |
| TYR, | CZ, | 100, | 15.5, | −8.2, | 7.4, | 47, B |
| TYR, | OH, | 100, | 16.2, | −7.3, | 8.2, | 47, B |
| TYR, | C, | 100, | 11.5, | −11.3, | 3.5, | 45, B |
| TYR, | O, | 100, | 11.1, | −10.6, | 2.6, | 45, B |
| THR, | N, | 101, | 11.3, | −12.7, | 3.4, | 45, B |
| THR, | CA, | 101, | 10.8, | −13.2, | 2.1, | 45, B |
| THR, | CB, | 101, | 10.7, | −14.7, | 2.2, | 45, B |
| THR, | OG1, | 101, | 12.0, | −15.3, | 2.5, | 45, B |
| THR, | CG2, | 101, | 10.2, | −15.3, | 0.9, | 45, B |
| THR, | C, | 101, | 9.4, | −12.7, | 1.9, | 44, B |
| THR, | O, | 101, | 9.1, | −12.1, | 0.8, | 44, B |
| MET, | N, | 102, | 8.5, | −12.8, | 2.8, | 44, B |
| MET, | CA, | 102, | 7.1, | −12.3, | 2.7, | 43, B |
| MET, | CB, | 102, | 6.3, | −12.7, | 3.9, | 43, B |
| MET, | CG, | 102, | 6.1, | −14.1, | 4.2, | 43, B |
| MET, | SD, | 102, | 5.1, | −14.5, | 5.6, | 44, B |
| MET, | CE, | 102, | 6.1, | −13.9, | 6.9, | 43, B |
| MET, | C, | 102, | 7.0, | −10.9, | 2.4, | 42, B |
| MET, | O, | 102, | 6.1, | −10.4, | 1.6, | 42, B |
| ILE, | N, | 103, | 8.0, | −10.1, | 2.9, | 42, B |
| ILE, | CA, | 103, | 8.0, | −8.7, | 2.7, | 42, B |
| ILE, | CB, | 103, | 8.9, | −8.0, | 3.7, | 41, B |
| ILE, | CG2, | 103, | 9.2, | −6.5, | 3.3, | 41, B |
| ILE, | CG1, | 103, | 8.3, | −8.0, | 5.1, | 41, B |
| ILE, | CD1, | 103, | 9.1, | −7.2, | 6.1, | 40, B |
| ILE, | C, | 103, | 8.5, | −8.3, | 1.3, | 42, B |
| ILE, | O, | 103, | 7.9, | −7.5, | 0.6, | 42, B |
| TYR, | N, | 104, | 9.6, | −9.0, | 0.8, | 42, B |
| TYR, | CA, | 104, | 10.2, | −8.7, | −0.5, | 44, B |
| TYR, | CB, | 104, | 11.3, | −9.8, | −0.7, | 44, B |
| TYR, | CG, | 104, | 12.5, | −9.5, | 0.1, | 44, B |
| TYR, | CD1, | 104, | 13.4, | −10.4, | 0.4, | 44, B |
| TYR, | CE1, | 104, | 14.6, | −10.1, | 1.1, | 45, B |
| TYR, | CD2, | 104, | 12.8, | −8.2, | 0.4, | 44, B |
| TYR, | CE2, | 104, | 13.9, | −7.8, | 1.2, | 45, B |
| TYR, | CZ, | 104, | 14.8, | −8.8, | 1.5, | 45, B |
| TYR, | OH, | 104, | 15.9, | −8.5, | 2.2, | 45, B |
| TYR, | C, | 104, | 9.1, | −8.8, | −1.6, | 44, B |
| TYR, | O, | 104, | 9.1, | −7.9, | −2.4, | 44, B |
| ARG, | N, | 105, | 8.3, | −9.8, | −1.6, | 45, B |
| ARG, | CA, | 105, | 7.2, | −10.0, | −2.6, | 45, B |
| ARG, | CB, | 105, | 6.4, | −11.2, | −2.3, | 46, B |
| ARG, | CG, | 105, | 7.2, | −12.5, | −2.1, | 47, B |
| ARG, | CD, | 105, | 6.3, | −13.7, | −1.8, | 49, B |
| ARG, | NE, | 105, | 7.0, | −15.0, | −1.8, | 49, B |
| ARG, | CZ, | 105, | 7.8, | −15.4, | −2.8, | 50, B |
| ARG, | NH1, | 105, | 8.1, | −14.6, | −3.8, | 51, B |
| ARG, | NH2, | 105, | 8.4, | −16.6, | −2.7, | 50, B |
| ARG, | C, | 105, | 6.3, | −8.8, | −2.7, | 45, B |
| ARG, | O, | 105, | 5.7, | −8.5, | −3.7, | 45, B |
| ASN, | N, | 106, | 6.2, | −8.0, | −1.6, | 44, B |
| ASN, | CA, | 106, | 5.4, | −6.8, | −1.7, | 43, B |

TABLE 2-continued

Structural coordinates of HDM2 (17-125; F55Y/Y76H) (SEQ ID NO: 2) complexed with compound 2.

```
ASN, CB, 106, 4.5, -6.7, -0.4, 43, B
ASN, CG, 106, 3.6, -8.0, -0.3, 42, B
ASN, OD1, 106, 4.1, -9.0, 0.2, 42, B
ASN, ND2, 106, 2.4, -7.9, -0.8, 42, B
ASN, C, 106, 6.1, -5.5, -1.9, 43, B
ASN, O, 106, 5.6, -4.4, -1.6, 43, B
LEU, N, 107, 7.4, -5.6, -2.3, 44, B
LEU, CA, 107, 8.2, -4.4, -2.5, 43, B
LEU, CB, 107, 9.3, -4.3, -1.5, 44, B
LEU, CG, 107, 8.9, -4.2, -0.0, 44, B
LEU, CD1, 107, 10.2, -4.2, 0.8, 44, B
LEU, CD2, 107, 8.2, -2.9, 0.2, 44, B
LEU, C, 107, 8.9, -4.5, -3.9, 43, B
LEU, O, 107, 8.8, -5.5, -4.5, 43, B
VAL, N, 108, 9.5, -3.4, -4.3, 43, B
VAL, CA, 108, 10.3, -3.3, -5.5, 44, B
VAL, CB, 108, 9.5, -2.5, -6.6, 44, B
VAL, CG1, 108, 10.5, -1.9, -7.5, 44, B
VAL, CG2, 108, 8.6, -3.4, -7.3, 44, B
VAL, C, 108, 11.5, -2.5, -5.0, 44, B
VAL, O, 108, 11.4, -1.4, -4.4, 44, B
VAL, N, 109, 12.7, -2.9, -5.3, 45, B
VAL, CA, 109, 13.9, -2.2, -4.9, 46, B
VAL, CB, 109, 15.2, -3.1, -4.9, 45, B
VAL, CG1, 109, 16.3, -2.5, -4.2, 45, B
VAL, CG2, 109, 14.9, -4.5, -4.3, 45, B
VAL, C, 109, 14.2, -1.1, -5.9, 46, B
VAL, O, 109, 14.0, -1.2, -7.1, 47, B
VAL, N, 110, 14.6, 0.1, -5.4, 47, B
VAL, CA, 110, 14.8, 1.3, -6.2, 49, B
VAL, CB, 110, 13.7, 2.3, -6.1, 48, B
VAL, CG1, 110, 12.4, 1.7, -6.7, 48, B
VAL, CG2, 110, 13.4, 2.6, -4.6, 48, B
VAL, C, 110, 16.1, 2.0, -5.8, 50, B
VAL, O, 110, 16.8, 1.5, -4.9, 50, B
ASN, N, 111, 16.4, 3.1, -6.5, 51, B
ASN, CA, 111, 17.6, 3.8, -6.2, 52, B
ASN, CB, 111, 18.1, 4.7, -7.4, 53, B
ASN, CG, 111, 18.5, 3.8, -8.5, 53, B
ASN, OD1, 111, 18.9, 2.7, -8.4, 53, B
ASN, ND2, 111, 18.3, 4.3, -9.7, 53, B
ASN, C, 111, 17.4, 4.8, -5.0, 53, B
ASN, O, 111, 17.9, 5.9, -5.0, 53, B
SCH, F1, 1, 16.3, 3.0, 22.7, 44, I
SCH, F2, 1, 17.8, 1.5, 22.6, 44, I
SCH, F3, 1, 15.9, 1.0, 23.5, 44, I
SCH, F4, 1, 17.3, 2.6, 14.6, 45, I
SCH, F5, 1, 15.5, 3.1, 15.8, 44, I
SCH, F6, 1, 16.6, 4.7, 14.8, 44, I
SCH, C1, 1, 11.8, 0.7, 17.3, 44, I
SCH, C2, 1, 11.9, 2.0, 16.5, 45, I
SCH, C3, 1, 12.2, 1.8, 15.0, 44, I
SCH, N1, 1, 13.3, 0.8, 14.8, 44, I
SCH, C4, 1, 13.2, -0.6, 15.5, 45, I
SCH, C5, 1, 13.0, -0.3, 17.0, 44, I
SCH, C6, 1, 12.8, -1.7, 17.8, 45, I
SCH, N2, 1, 13.8, -2.6, 18.0, 45, I
SCH, O1, 1, 11.7, -1.9, 18.2, 45, I
SCH, O2, 1, 14.3, 0.4, 17.4, 44, I
SCH, C7, 1, 14.7, 0.7, 18.7, 44, I
SCH, C8, 1, 16.0, 1.2, 18.7, 44, I
SCH, C9, 1, 16.6, 1.6, 20.0, 44, I
SCH, C10, 1, 15.9, 1.4, 21.2, 44, I
SCH, C11, 1, 14.6, 0.8, 21.1, 44, I
SCH, C12, 1, 14.0, 0.4, 19.9, 44, I
SCH, C13, 1, 14.5, 1.0, 14.0, 44, I
SCH, O3, 1, 15.4, 0.2, 14.0, 43, I
SCH, C14, 1, 14.6, 2.2, 13.1, 44, I
SCH, C15, 1, 13.8, 2.2, 11.9, 44, I
SCH, N3, 1, 13.8, 3.2, 11.1, 44, I
SCH, C16, 1, 14.6, 4.3, 11.3, 44, I
SCH, C17, 1, 15.4, 4.4, 12.5, 44, I
SCH, C18, 1, 15.4, 3.3, 13.4, 44, I
SCH, C19, 1, 13.5, -3.8, 18.8, 46, I
SCH, C20, 1, 14.4, -3.8, 20.1, 46, I
SCH, N4, 1, 15.8, -3.8, 19.7, 47, I
SCH, C21, 1, 16.2, -2.7, 18.7, 46, I
SCH, C22, 1, 15.2, -2.6, 17.5, 46, I
SCH, C23, 1, 16.7, -4.0, 20.8, 47, I
SCH, C24, 1, 17.4, -3.0, 21.4, 47, I
SCH, C25, 1, 18.3, -3.2, 22.5, 48, I
SCH, C26, 1, 18.4, -4.5, 23.1, 48, I
SCH, C27, 1, 17.6, -5.6, 22.5, 48, I
SCH, C28, 1, 16.8, -5.4, 21.3, 48, I
SCH, O4, 1, 16.1, -6.4, 20.7, 48, I
SCH, C32, 1, 15.3, -7.3, 21.4, 49, I
SCH, C33, 1, 13.9, -7.6, 20.8, 49, I
SCH, O5, 1, 12.9, -7.3, 21.7, 50, I
SCH, C34, 1, 12.5, -8.4, 22.5, 49, I
SCH, C35, 1, 16.5, 1.8, 22.6, 44, I
SCH, C36, 1, 16.2, 3.4, 14.7, 44, I
SCH, C37, 1, 11.9, -1.3, 14.8, 45, I
SCH, C38, 1, 12.0, -1.7, 13.4, 45, I
SCH, C39, 1, 13.1, -2.4, 12.8, 45, I
SCH, F1, 1, 5.5, -7.6, 10.2, 44, J
SCH, F2, 1, 6.9, -9.2, 10.2, 43, J
SCH, F3, 1, 7.4, -7.3, 9.5, 44, J
SCH, F4, 1, 5.6, -9.5, 18.0, 46, J
SCH, F5, 1, 5.0, -7.6, 17.0, 46, J
SCH, F6, 1, 3.5, -8.9, 17.8, 46, J
SCH, C1, 1, 7.9, -4.0, 16.2, 45, J
SCH, C2, 1, 6.5, -4.2, 16.9, 45, J
SCH, C3, 1, 6.6, -4.6, 18.3, 45, J
SCH, N1, 1, 7.6, -5.8, 18.5, 45, J
SCH, C4, 1, 8.9, -5.7, 17.9, 45, J
SCH, C5, 1, 8.8, -5.3, 16.3, 45, J
SCH, C6, 1, 10.2, -5.0, 15.7, 45, J
SCH, N2, 1, 11.1, -6.1, 15.5, 45, J
SCH, O1, 1, 10.4, -3.9, 15.4, 44, J
SCH, O2, 1, 8.1, -6.4, 15.8, 44, J
SCH, C7, 1, 7.8, -6.7, 14.4, 44, J
SCH, C8, 1, 7.3, -8.0, 14.2, 44, J
SCH, C9, 1, 6.9, -8.4, 12.9, 44, J
SCH, C10, 1, 7.1, -7.5, 11.8, 44, J
SCH, C11, 1, 7.6, -6.2, 12.0, 43, J
SCH, C12, 1, 7.9, -5.8, 13.3, 44, J
SCH, C13, 1, 7.2, -7.0, 19.1, 45, J
SCH, O3, 1, 8.0, -7.9, 19.1, 45, J
SCH, C14, 1, 6.0, -7.1, 19.9, 46, J
SCH, C15, 1, 5.9, -6.5, 21.2, 46, J
SCH, N3, 1, 4.8, -6.6, 22.0, 46, J
SCH, C16, 1, 3.7, -7.2, 21.5, 46, J
SCH, C17, 1, 3.7, -7.8, 20.2, 46, J
SCH, C18, 1, 4.8, -7.8, 19.4, 46, J
SCH, C19, 1, 12.5, -5.7, 15.0, 45, J
SCH, C20, 1, 12.6, -6.3, 13.6, 46, J
SCH, N4, 1, 12.5, -7.8, 13.7, 46, J
SCH, C21, 1, 11.3, -8.3, 14.5, 46, J
SCH, C22, 1, 11.0, -7.5, 15.8, 45, J
SCH, C23, 1, 12.9, -8.4, 12.4, 46, J
SCH, C24, 1, 11.9, -9.0, 11.6, 46, J
SCH, C25, 1, 12.3, -9.7, 10.4, 46, J
SCH, C26, 1, 13.7, -9.7, 10.0, 46, J
SCH, C27, 1, 14.6, -9.1, 10.8, 47, J
SCH, C28, 1, 14.3, -8.5, 12.0, 47, J
SCH, O4, 1, 15.2, -7.9, 12.9, 48, J
SCH, C32, 1, 16.4, -7.2, 12.4, 49, J
SCH, C33, 1, 16.2, -5.6, 12.5, 49, J
SCH, O5, 1, 16.2, -5.3, 13.9, 49, J
SCH, C34, 1, 16.1, -4.0, 14.2, 49, J
SCH, C35, 1, 6.7, -7.9, 10.4, 43, J
SCH, C36, 1, 4.8, -8.5, 18.0, 46, J
SCH, C37, 1, 9.8, -4.6, 18.7, 45, J
SCH, C38, 1, 10.1, -5.1, 20.0, 45, J
SCH, C39, 1, 9.6, -4.5, 21.2, 46, J
WAT, OH2, 1, 15.2, 9.1, 37.4, 35, W
WAT, OH2, 2, 14.6, 16.2, 26.0, 46, W
WAT, OH2, 3, 25.5, 12.6, 18.7, 43, W
```

TABLE 2-continued

Structural coordinates of HDM2 (17-125; F55Y/Y76H) (SEQ ID NO: 2) complexed with compound 2.

| | | | | | | | |
|---|---|---|---|---|---|---|---|
| WAT, | OH2, | 4, | 26.9, | −0.8, | 36.1, | 55, | W |
| WAT, | OH2, | 5, | 13.1, | −17.7, | 9.6, | 55, | W |
| WAT, | OH2, | 6, | 15.5, | −16.8, | 10.3, | 51, | W |
| WAT, | OH2, | 7, | 18.2, | −10.5, | 11.8, | 59, | W |

The crystalline coordinates are set forth below in the following format (1), (2), (3) . . . (8); the legend for these data is as follows:
(1) Residue name
Three letter amino acid name
SCH = schering inhibitor
WAT = water
(2) Atom name
(3) Residue Number
(4) X-coordinate
(5) Y-coordinate
(6) Z-coordinate
(7) B-factor
(8) Chain ID
Disordered residues are not represented in the table.

TABLE 3

Structural coordinates of HDM2 (17-125; F55Y/Y76H) (SEQ ID NO: 2) complexed with compound 3.

ALA, CB, 21, 7.9, −16.4, 33.3, 66, A
ALA, C, 21, 9.4, −17.6, 31.8, 66, A
ALA, O, 21, 9.2, −18.4, 30.9, 66, A
ALA, N, 21, 9.6, −17.9, 34.2, 66, A
ALA, CA, 21, 8.7, −17.7, 33.1, 66, A
SER, N, 22, 10.4, −16.7, 31.7, 65, A
SER, CA, 22, 11.2, −16.5, 30.5, 65, A
SER, CB, 22, 10.4, −16.4, 29.2, 65, A
SER, OG, 22, 11.2, −16.2, 28.1, 65, A
SER, C, 22, 11.9, −15.1, 30.7, 64, A
SER, O, 22, 11.3, −14.2, 31.3, 64, A
GLU, N, 23, 13.1, −15.0, 30.2, 64, A
GLU, CA, 23, 13.9, −13.8, 30.4, 63, A
GLU, CB, 23, 15.3, −13.9, 29.7, 64, A
GLU, CG, 23, 16.3, −14.8, 30.4, 64, A
GLU, CD, 23, 16.5, −14.5, 31.9, 65, A
GLU, OE1, 23, 16.8, −13.3, 32.2, 65, A
GLU, OE2, 23, 16.3, −15.4, 32.7, 65, A
GLU, C, 23, 13.1, −12.5, 29.9, 62, A
GLU, O, 23, 12.9, −11.6, 30.7, 62, A
GLN, N, 24, 12.8, −12.5, 28.6, 61, A
GLN, CA, 24, 12.1, −11.3, 28.1, 60, A
GLN, CB, 24, 11.8, −11.5, 26.6, 61, A
GLN, CG, 24, 13.0, −11.5, 25.8, 61, A
GLN, CD, 24, 13.9, −10.3, 26.1, 61, A
GLN, OE1, 24, 13.6, −9.1, 25.8, 61, A
GLN, NE2, 24, 15.0, −10.6, 26.8, 61, A
GLN, C, 24, 10.8, −11.1, 28.9, 59, A
GLN, O, 24, 10.2, −10.0, 28.9, 59, A
GLU, N, 25, 10.3, −12.1, 29.6, 58, A
GLU, CA, 25, 9.1, −12.0, 30.4, 58, A
GLU, CB, 25, 8.3, −13.3, 30.4, 58, A
GLU, CG, 25, 7.0, −13.2, 29.6, 59, A
GLU, CD, 25, 7.2, −13.0, 28.1, 60, A
GLU, OE1, 25, 6.2, −12.9, 27.4, 60, A
GLU, OE2, 25, 8.3, −13.1, 27.7, 60, A
GLU, C, 25, 9.4, −11.7, 31.9, 56, A
GLU, O, 25, 8.6, −12.0, 32.8, 56, A
THR, N, 26, 10.6, −11.1, 32.2, 54, A
THR, CA, 26, 10.9, −10.8, 33.6, 52, A
THR, CB, 26, 12.4, −10.4, 33.7, 52, A
THR, OG1, 26, 13.2, −11.6, 33.5, 52, A
THR, CG2, 26, 12.7, −9.9, 35.1, 52, A
THR, C, 26, 10.1, −9.5, 34.0, 51, A
THR, O, 26, 9.9, −8.6, 33.2, 50, A
LEU, N, 27, 9.6, −9.5, 35.2, 50, A
LEU, CA, 27, 8.8, −8.4, 35.7, 49, A
LEU, CB, 27, 7.8, −8.9, 36.7, 49, A
LEU, CG, 27, 6.8, −10.0, 36.1, 49, A
LEU, CD1, 27, 6.0, −10.6, 37.2, 49, A
LEU, CD2, 27, 6.0, −9.3, 35.1, 49, A
LEU, C, 27, 9.7, −7.4, 36.3, 48, A

TABLE 3-continued

Structural coordinates of HDM2 (17-125; F55Y/Y76H) (SEQ ID NO: 2) complexed with compound 3.

LEU, O, 27, 10.4, −7.6, 37.3, 48, A
VAL, N, 28, 9.7, −6.2, 35.7, 46, A
VAL, CA, 28, 10.6, −5.1, 36.1, 45, A
VAL, CB, 28, 11.6, −4.8, 35.0, 45, A
VAL, CG1, 28, 12.4, −6.0, 34.7, 45, A
VAL, CG2, 28, 11.0, −4.2, 33.8, 45, A
VAL, C, 28, 9.8, −3.8, 36.4, 45, A
VAL, O, 28, 8.7, −3.6, 35.9, 45, A
ARG, N, 29, 10.4, −3.0, 37.3, 45, A
ARG, CA, 29, 9.7, −1.8, 37.7, 44, A
ARG, CB, 29, 9.4, −1.9, 39.2, 45, A
ARG, CG, 29, 8.5, −0.8, 39.8, 46, A
ARG, CD, 29, 7.7, −1.3, 41.0, 47, A
ARG, NE, 29, 6.7, −2.2, 40.7, 48, A
ARG, CZ, 29, 5.9, −2.8, 41.7, 48, A
ARG, NH1, 29, 6.1, −2.6, 43.0, 48, A
ARG, NH2, 29, 4.9, −3.6, 41.3, 48, A
ARG, C, 29, 10.7, −0.7, 37.5, 43, A
ARG, O, 29, 11.7, −0.5, 38.2, 44, A
PRO, N, 30, 10.5, 0.1, 36.4, 42, A
PRO, CD, 30, 9.4, 0.1, 35.4, 42, A
PRO, CA, 30, 11.4, 1.2, 36.1, 42, A
PRO, CB, 30, 10.9, 1.7, 34.8, 42, A
PRO, CG, 30, 9.5, 1.4, 34.8, 42, A
PRO, C, 30, 11.5, 2.3, 37.1, 41, A
PRO, O, 30, 10.5, 2.7, 37.7, 41, A
LYS, N, 31, 12.7, 2.8, 37.3, 40, A
LYS, CA, 31, 12.9, 3.9, 38.3, 40, A
LYS, CB, 31, 14.4, 4.0, 38.6, 40, A
LYS, CG, 31, 15.0, 2.7, 39.3, 39, A
LYS, CD, 31, 16.4, 2.8, 39.7, 40, A
LYS, CE, 31, 16.8, 1.5, 40.5, 40, A
LYS, NZ, 31, 18.2, 1.4, 40.7, 40, A
LYS, C, 31, 12.3, 5.1, 37.7, 40, A
LYS, O, 31, 12.2, 5.2, 36.4, 39, A
PRO, N, 32, 12.0, 6.1, 38.5, 40, A
PRO, CD, 32, 12.4, 6.1, 39.9, 40, A
PRO, CA, 32, 11.4, 7.4, 38.1, 40, A
PRO, CB, 32, 11.8, 8.3, 39.3, 40, A
PRO, CG, 32, 11.7, 7.4, 40.4, 40, A
PRO, C, 32, 11.7, 8.0, 36.7, 39, A
PRO, O, 32, 10.8, 8.0, 35.9, 39, A
LEU, N, 33, 12.9, 8.5, 36.5, 39, A
LEU, CA, 33, 13.2, 9.1, 35.3, 39, A
LEU, CB, 33, 14.7, 9.5, 35.3, 40, A
LEU, CG, 33, 14.9, 10.5, 36.4, 40, A
LEU, CD1, 33, 16.3, 11.1, 36.3, 40, A
LEU, CD2, 33, 13.9, 11.7, 36.2, 41, A
LEU, C, 33, 12.9, 8.2, 34.1, 39, A
LEU, O, 33, 12.3, 8.6, 33.1, 39, A
LEU, N, 34, 13.4, 6.9, 34.1, 39, A
LEU, CA, 34, 13.1, 6.0, 33.0, 39, A
LEU, CB, 34, 13.8, 4.6, 33.2, 39, A
LEU, CG, 34, 13.4, 3.5, 32.3, 39, A
LEU, CD1, 34, 13.5, 3.9, 30.9, 39, A
LEU, CD2, 34, 14.2, 2.2, 32.6, 39, A
LEU, C, 34, 11.6, 5.8, 32.9, 39, A
LEU, O, 34, 11.0, 5.6, 31.9, 39, A
LEU, N, 35, 10.9, 5.8, 34.1, 39, A
LEU, CA, 35, 9.5, 5.7, 34.1, 40, A
LEU, CB, 35, 8.9, 5.6, 35.5, 40, A
LEU, CG, 35, 7.4, 5.4, 35.5, 41, A
LEU, CD1, 35, 7.1, 4.0, 34.8, 40, A
LEU, CD2, 35, 6.8, 5.4, 36.9, 41, A
LEU, C, 35, 8.9, 6.9, 33.4, 40, A
LEU, O, 35, 8.0, 6.7, 32.6, 40, A
LYS, N, 36, 9.4, 8.0, 33.7, 41, A
LYS, CA, 36, 9.0, 9.3, 33.1, 41, A
LYS, CB, 36, 9.8, 10.4, 33.7, 42, A
LYS, CG, 36, 9.7, 11.7, 32.8, 43, A
LYS, CD, 36, 10.7, 12.7, 33.4, 43, A
LYS, CE, 36, 10.6, 14.1, 32.9, 44, A
LYS, NZ, 36, 11.4, 15.1, 33.6, 44, A
LYS, C, 36, 9.1, 9.3, 31.6, 42, A
LYS, O, 36, 8.3, 9.7, 30.8, 42, A
LEU, N, 37, 10.3, 8.7, 31.1, 41, A

TABLE 3-continued

Structural coordinates of HDM2 (17-125; F55Y/Y76H)
(SEQ ID NO: 2) complexed with compound 3.

LEU, CA, 37, 10.5, 8.6, 29.7, 42, A
LEU, CB, 37, 12.0, 8.1, 29.5, 41, A
LEU, CG, 37, 12.6, 8.1, 28.1, 41, A
LEU, CD1, 37, 14.1, 7.9, 28.3, 41, A
LEU, CD2, 37, 12.0, 7.0, 27.3, 41, A
LEU, C, 37, 9.6, 7.7, 29.0, 42, A
LEU, O, 37, 9.0, 8.0, 27.9, 42, A
LEU, N, 38, 9.3, 6.5, 29.6, 43, A
LEU, CA, 38, 8.4, 5.5, 29.1, 44, A
LEU, CB, 38, 8.3, 4.3, 30.0, 44, A
LEU, CG, 38, 9.2, 3.1, 29.6, 44, A
LEU, CD1, 38, 10.4, 3.5, 28.8, 44, A
LEU, CD2, 38, 9.6, 2.3, 30.8, 44, A
LEU, C, 38, 7.0, 6.2, 29.0, 45, A
LEU, O, 38, 6.2, 6.0, 28.0, 45, A
LYS, N, 39, 6.6, 6.9, 30.1, 47, A
LYS, CA, 39, 5.3, 7.5, 30.2, 48, A
LYS, CB, 39, 5.1, 8.2, 31.5, 49, A
LYS, CG, 39, 5.1, 7.2, 32.7, 49, A
LYS, CD, 39, 3.9, 6.3, 32.7, 50, A
LYS, CE, 39, 3.8, 5.5, 34.0, 50, A
LYS, NZ, 39, 3.5, 6.5, 35.2, 50, A
LYS, C, 39, 5.1, 8.5, 29.1, 48, A
LYS, O, 39, 3.9, 8.7, 28.7, 48, A
SER, N, 40, 6.1, 9.2, 28.6, 48, A
SER, CA, 40, 6.0, 10.2, 27.5, 48, A
SER, CB, 40, 7.3, 11.0, 27.4, 48, A
SER, OG, 40, 8.3, 10.3, 26.8, 48, A
SER, C, 40, 5.7, 9.7, 26.1, 49, A
SER, O, 40, 5.5, 10.4, 25.2, 49, A
VAL, N, 41, 5.7, 8.3, 26.0, 50, A
VAL, CA, 41, 5.3, 7.8, 24.7, 51, A
VAL, CB, 41, 6.5, 7.0, 24.1, 51, A
VAL, CG1, 41, 7.6, 8.0, 23.5, 51, A
VAL, CG2, 41, 7.2, 6.2, 25.2, 51, A
VAL, C, 41, 4.1, 6.9, 24.7, 51, A
VAL, O, 41, 3.9, 6.1, 23.7, 52, A
GLY, N, 42, 3.4, 6.9, 25.7, 52, A
GLY, CA, 42, 2.2, 6.0, 25.8, 53, A
GLY, C, 42, 2.1, 5.1, 27.0, 53, A
GLY, O, 42, 1.0, 4.8, 27.5, 53, A
ALA, N, 43, 3.2, 4.6, 27.4, 53, A
ALA, CA, 43, 3.2, 3.7, 28.6, 54, A
ALA, CB, 43, 4.7, 3.4, 29.0, 54, A
ALA, C, 43, 2.5, 4.2, 29.7, 55, A
ALA, O, 43, 2.6, 5.3, 30.2, 55, A
GLN, N, 44, 1.6, 3.4, 30.3, 55, A
GLN, CA, 44, 0.7, 3.8, 31.4, 55, A
GLN, CB, 44, −0.7, 3.7, 31.0, 56, A
GLN, CG, 44, −1.2, 4.8, 30.0, 57, A
GLN, CD, 44, −2.6, 4.6, 29.6, 58, A
GLN, OE1, 44, −2.9, 3.7, 28.8, 58, A
GLN, NE2, 44, −3.5, 5.4, 30.1, 58, A
GLN, C, 44, 1.0, 3.0, 32.6, 55, A
GLN, O, 44, 0.7, 3.5, 33.8, 55, A
LYS, N, 45, 1.4, 1.7, 32.5, 54, A
LYS, CA, 45, 1.6, 0.9, 33.6, 53, A
LYS, CB, 45, 1.7, −0.6, 33.2, 53, A
LYS, CG, 45, 2.8, −0.8, 32.2, 53, A
LYS, CD, 45, 2.9, −2.3, 31.7, 54, A
LYS, CE, 45, 1.6, −2.7, 30.9, 53, A
LYS, NZ, 45, 1.8, −4.0, 30.3, 53, A
LYS, C, 45, 2.9, 1.3, 34.3, 52, A
LYS, O, 45, 3.7, 2.0, 33.8, 52, A
ASP, N, 46, 3.1, 0.8, 35.5, 51, A
ASP, CA, 46, 4.3, 1.1, 36.3, 50, A
ASP, CB, 46, 3.9, 1.5, 37.7, 51, A
ASP, CG, 46, 3.8, 3.0, 37.8, 51, A
ASP, OD1, 46, 3.1, 3.7, 37.0, 52, A
ASP, OD2, 46, 4.4, 3.6, 38.8, 52, A
ASP, C, 46, 5.2, −0.2, 36.3, 49, A
ASP, O, 46, 6.4, −0.1, 36.6, 49, A
THR, N, 47, 4.6, −1.3, 36.1, 48, A
THR, CA, 47, 5.3, −2.6, 36.0, 47, A
THR, CB, 47, 4.6, −3.6, 36.9, 47, A
THR, OG1, 47, 4.5, −3.2, 38.3, 46, A
THR, CG2, 47, 5.4, −5.0, 36.9, 47, A
THR, C, 47, 5.4, −3.1, 34.6, 46, A
THR, O, 47, 4.3, −3.0, 33.9, 46, A
TYR, N, 48, 6.5, −3.5, 34.1, 45, A
TYR, CA, 48, 6.7, −4.0, 32.8, 45, A
TYR, CB, 48, 7.4, −2.9, 31.9, 45, A
TYR, CG, 48, 6.7, −1.5, 31.9, 46, A
TYR, CD1, 48, 6.8, −0.7, 33.1, 46, A
TYR, CE1, 48, 6.3, 0.6, 33.1, 46, A
TYR, CD2, 48, 6.1, −1.0, 30.8, 46, A
TYR, CE2, 48, 5.5, 0.3, 30.8, 47, A
TYR, CZ, 48, 5.6, 1.0, 32.0, 46, A
TYR, OH, 48, 5.1, 2.3, 31.9, 46, A
TYR, C, 48, 7.6, −5.2, 32.6, 44, A
TYR, O, 48, 8.3, −5.6, 33.5, 44, A
THR, N, 49, 7.5, −5.8, 31.4, 43, A
THR, CA, 49, 8.3, −7.0, 31.1, 42, A
THR, CB, 49, 7.7, −7.9, 30.0, 42, A
THR, OG1, 49, 7.4, −7.2, 28.8, 42, A
THR, CG2, 49, 6.4, −8.5, 30.5, 42, A
THR, C, 49, 9.5, −6.4, 30.4, 42, A
THR, O, 49, 9.4, −5.2, 29.9, 41, A
MET, N, 50, 10.6, −7.1, 30.2, 43, A
MET, CA, 50, 11.8, −6.6, 29.6, 43, A
MET, CB, 50, 12.9, −7.5, 29.7, 44, A
MET, CG, 50, 13.6, −7.5, 31.0, 45, A
MET, SD, 50, 14.3, −5.9, 31.4, 46, A
MET, CE, 50, 15.8, −6.0, 30.4, 45, A
MET, C, 50, 11.4, −6.2, 28.1, 43, A
MET, O, 50, 12.0, −5.3, 27.5, 43, A
LYS, N, 51, 10.5, −7.0, 27.5, 43, A
LYS, CA, 51, 10.2, −6.8, 26.1, 43, A
LYS, CB, 51, 9.2, −7.9, 25.6, 44, A
LYS, CG, 51, 9.9, −9.3, 25.5, 45, A
LYS, CD, 51, 8.8, −10.3, 25.2, 46, A
LYS, CE, 51, 8.1, −10.1, 23.9, 46, A
LYS, NZ, 51, 7.1, −11.2, 23.7, 47, A
LYS, C, 51, 9.5, −5.4, 25.9, 41, A
LYS, O, 51, 9.8, −4.7, 25.0, 41, A
GLU, N, 52, 8.5, −5.1, 26.8, 40, A
GLU, CA, 52, 7.8, −3.9, 26.7, 39, A
GLU, CB, 52, 6.7, −3.9, 27.7, 39, A
GLU, CG, 52, 5.6, −5.0, 27.5, 39, A
GLU, CD, 52, 4.6, −5.1, 28.7, 40, A
GLU, OE1, 52, 5.0, −5.0, 29.9, 39, A
GLU, OE2, 52, 3.4, −5.3, 28.4, 40, A
GLU, C, 52, 8.7, −2.7, 26.9, 37, A
GLU, O, 52, 8.7, −1.7, 26.2, 37, A
VAL, N, 53, 9.6, −2.8, 27.9, 36, A
VAL, CA, 53, 10.6, −1.7, 28.1, 34, A
VAL, CB, 53, 11.6, −2.1, 29.2, 34, A
VAL, CG1, 53, 12.6, −0.9, 29.4, 34, A
VAL, CG2, 53, 10.9, −2.4, 30.5, 34, A
VAL, C, 53, 11.3, −1.4, 26.8, 34, A
VAL, O, 53, 11.4, −0.2, 26.4, 34, A
LEU, N, 54, 11.8, −2.4, 26.2, 33, A
LEU, CA, 54, 12.4, −2.3, 24.9, 33, A
LEU, CB, 54, 12.9, −3.7, 24.4, 33, A
LEU, CG, 54, 14.0, −4.4, 25.2, 34, A
LEU, CD1, 54, 14.1, −5.8, 24.6, 34, A
LEU, CD2, 54, 15.3, −3.7, 25.1, 33, A
LEU, C, 54, 11.6, −1.7, 23.8, 32, A
LEU, O, 54, 12.0, −0.9, 23.0, 33, A
TYR, N, 55, 10.3, −2.0, 23.8, 33, A
TYR, CA, 55, 9.4, −1.5, 22.8, 33, A
TYR, CB, 55, 8.0, −2.2, 23.0, 33, A
TYR, CG, 55, 6.9, −1.7, 22.1, 33, A
TYR, CD1, 55, 7.0, −1.9, 20.7, 33, A
TYR, CE1, 55, 6.0, −1.5, 19.8, 32, A
TYR, CD2, 55, 5.8, −1.1, 22.5, 32, A
TYR, CE2, 55, 4.8, −0.7, 21.7, 33, A
TYR, CZ, 55, 4.9, −0.9, 20.3, 32, A
TYR, OH, 55, 3.9, −0.5, 19.5, 31, A
TYR, C, 55, 9.2, 0.0, 23.0, 33, A
TYR, O, 55, 9.3, 0.8, 22.0, 33, A
TYR, N, 56, 8.9, 0.5, 24.2, 33, A

TABLE 3-continued

Structural coordinates of HDM2 (17-125; F55Y/Y76H) (SEQ ID NO: 2) complexed with compound 3.

TYR, CA, 56, 8.7, 1.9, 24.4, 33, A
TYR, CB, 56, 8.0, 2.1, 25.8, 33, A
TYR, CG, 56, 6.6, 1.6, 25.8, 33, A
TYR, CD1, 56, 5.6, 2.1, 25.0, 34, A
TYR, CE1, 56, 4.3, 1.6, 25.0, 34, A
TYR, CD2, 56, 6.2, 0.5, 26.7, 34, A
TYR, CE2, 56, 4.9, 0.1, 26.7, 34, A
TYR, CZ, 56, 4.0, 0.6, 25.8, 34, A
TYR, OH, 56, 2.7, 0.2, 25.8, 34, A
TYR, C, 56, 10.0, 2.6, 24.3, 33, A
TYR, O, 56, 10.0, 3.8, 23.8, 34, A
LEU, N, 57, 11.1, 2.0, 24.6, 32, A
LEU, CA, 57, 12.3, 2.7, 24.4, 32, A
LEU, CB, 57, 13.6, 1.9, 24.8, 32, A
LEU, CG, 57, 13.9, 2.0, 26.4, 32, A
LEU, CD1, 57, 15.0, 1.0, 26.7, 31, A
LEU, CD2, 57, 14.3, 3.4, 26.7, 32, A
LEU, C, 57, 12.4, 2.9, 22.8, 32, A
LEU, O, 57, 12.8, 4.0, 22.3, 32, A
GLY, N, 58, 12.0, 1.9, 22.1, 31, A
GLY, CA, 58, 12.0, 2.0, 20.6, 31, A
GLY, C, 58, 11.0, 3.1, 20.2, 30, A
GLY, O, 58, 11.3, 3.9, 19.2, 29, A
GLN, N, 59, 9.8, 3.1, 20.8, 31, A
GLN, CA, 59, 8.8, 4.1, 20.5, 32, A
GLN, CB, 59, 7.6, 3.8, 21.4, 32, A
GLN, CG, 59, 6.8, 2.6, 21.0, 33, A
GLN, CD, 59, 6.3, 2.7, 19.5, 33, A
GLN, OE1, 59, 5.2, 3.1, 19.3, 34, A
GLN, NE2, 59, 7.2, 2.3, 18.6, 32, A
GLN, C, 59, 9.4, 5.5, 20.7, 32, A
GLN, O, 59, 9.1, 6.4, 20.0, 33, A
TYR, N, 60, 10.2, 5.6, 21.8, 33, A
TYR, CA, 60, 10.8, 6.9, 22.1, 33, A
TYR, CB, 60, 11.4, 6.8, 23.5, 32, A
TYR, CG, 60, 12.1, 8.0, 24.0, 32, A
TYR, CD1, 60, 11.3, 9.0, 24.6, 32, A
TYR, CE1, 60, 11.9, 10.2, 25.1, 32, A
TYR, CD2, 60, 13.5, 8.2, 23.9, 32, A
TYR, CE2, 60, 14.1, 9.3, 24.4, 31, A
TYR, CZ, 60, 13.3, 10.3, 25.0, 31, A
TYR, OH, 60, 13.9, 11.4, 25.6, 31, A
TYR, C, 60, 11.8, 7.3, 21.1, 34, A
TYR, O, 60, 11.9, 8.5, 20.7, 34, A
ILE, N, 61, 12.7, 6.4, 20.7, 35, A
ILE, CA, 61, 13.7, 6.7, 19.8, 36, A
ILE, CB, 61, 14.7, 5.5, 19.6, 36, A
ILE, CG2, 61, 15.9, 5.9, 18.8, 36, A
ILE, CG1, 61, 15.2, 5.1, 21.0, 36, A
ILE, CD1, 61, 16.3, 4.0, 21.0, 35, A
ILE, C, 61, 13.2, 7.2, 18.4, 37, A
ILE, O, 61, 13.8, 8.1, 17.8, 37, A
MET, N, 62, 12.1, 6.6, 18.0, 37, A
MET, CA, 62, 11.5, 6.9, 16.7, 38, A
MET, CB, 62, 10.6, 5.7, 16.3, 37, A
MET, CG, 62, 11.3, 4.4, 16.0, 36, A
MET, SD, 62, 12.6, 4.6, 14.7, 36, A
MET, CE, 62, 11.5, 4.7, 13.2, 36, A
MET, C, 62, 10.8, 8.2, 16.7, 39, A
MET, O, 62, 10.9, 9.0, 15.8, 38, A
THR, N, 63, 9.9, 8.4, 17.7, 40, A
THR, CA, 63, 9.2, 9.7, 17.7, 41, A
THR, CB, 63, 8.1, 9.8, 18.9, 42, A
THR, OG1, 63, 8.8, 10.0, 20.1, 43, A
THR, CG2, 63, 7.3, 8.5, 19.0, 42, A
THR, C, 63, 10.1, 10.9, 17.9, 42, A
THR, O, 63, 9.7, 12.0, 17.7, 42, A
LYS, N, 64, 11.4, 10.6, 18.3, 43, A
LYS, CA, 64, 12.3, 11.7, 18.5, 45, A
LYS, CB, 64, 12.9, 11.7, 19.8, 45, A
LYS, CG, 64, 11.9, 11.7, 21.0, 45, A
LYS, CD, 64, 12.5, 12.1, 22.3, 45, A
LYS, CE, 64, 12.8, 13.6, 22.3, 45, A
LYS, NZ, 64, 13.2, 14.1, 23.7, 45, A
LYS, C, 64, 13.4, 11.8, 17.4, 46, A
LYS, O, 64, 14.2, 12.7, 17.3, 45, A
ARG, N, 65, 13.5, 10.7, 16.6, 47, A
ARG, CA, 65, 14.5, 10.7, 15.5, 48, A
ARG, CB, 65, 14.2, 11.9, 14.6, 49, A
ARG, CG, 65, 12.8, 12.0, 14.0, 51, A
ARG, CD, 65, 12.5, 13.4, 13.5, 52, A
ARG, NE, 65, 13.3, 13.9, 12.4, 53, A
ARG, CZ, 65, 13.2, 15.0, 11.7, 53, A
ARG, NH1, 65, 12.2, 15.9, 12.1, 54, A
ARG, NH2, 65, 14.0, 15.3, 10.7, 54, A
ARG, C, 65, 15.9, 10.8, 16.1, 48, A
ARG, O, 65, 16.8, 11.4, 15.6, 48, A
LEU, N, 66, 16.1, 10.1, 17.2, 49, A
LEU, CA, 66, 17.3, 10.0, 17.9, 49, A
LEU, CB, 66, 17.1, 9.6, 19.3, 48, A
LEU, CG, 66, 16.1, 10.4, 20.1, 48, A
LEU, CD1, 66, 16.0, 9.9, 21.5, 48, A
LEU, CD2, 66, 16.5, 11.9, 20.1, 48, A
LEU, C, 66, 18.4, 9.1, 17.3, 49, A
LEU, O, 66, 19.4, 8.8, 17.9, 49, A
TYR, N, 67, 18.2, 8.8, 16.0, 49, A
TYR, CA, 67, 19.1, 7.9, 15.3, 50, A
TYR, CB, 67, 18.4, 6.6, 14.9, 50, A
TYR, CG, 67, 17.2, 6.9, 14.0, 49, A
TYR, CD1, 67, 17.4, 7.0, 12.6, 49, A
TYR, CE1, 67, 16.4, 7.3, 11.8, 49, A
TYR, CD2, 67, 16.0, 7.0, 14.5, 49, A
TYR, CE2, 67, 14.9, 7.3, 13.7, 49, A
TYR, CZ, 67, 15.1, 7.5, 12.3, 49, A
TYR, OH, 67, 14.0, 7.8, 11.5, 49, A
TYR, C, 67, 19.6, 8.6, 14.1, 51, A
TYR, O, 67, 18.9, 9.4, 13.5, 51, A
ASP, N, 68, 20.8, 8.2, 13.7, 53, A
ASP, CA, 68, 21.4, 8.8, 12.5, 55, A
ASP, CB, 68, 22.8, 8.4, 12.3, 55, A
ASP, CG, 68, 23.4, 8.8, 11.0, 56, A
ASP, OD1, 68, 23.3, 10.0, 10.7, 56, A
ASP, OD2, 68, 24.1, 8.0, 10.4, 57, A
ASP, C, 68, 20.6, 8.4, 11.2, 55, A
ASP, O, 68, 20.3, 7.2, 11.1, 55, A
GLU, N, 69, 20.3, 9.4, 10.4, 56, A
GLU, CA, 69, 19.5, 9.1, 9.2, 57, A
GLU, CB, 69, 19.2, 10.5, 8.4, 58, A
GLU, CG, 69, 18.0, 11.2, 8.9, 59, A
GLU, CD, 69, 16.8, 10.4, 8.8, 60, A
GLU, OE1, 69, 16.6, 9.7, 7.8, 60, A
GLU, OE2, 69, 15.9, 10.6, 9.7, 60, A
GLU, C, 69, 20.3, 8.2, 8.2, 57, A
GLU, O, 69, 19.7, 7.3, 7.6, 57, A
LYS, N, 70, 21.6, 8.4, 8.2, 57, A
LYS, CA, 70, 22.4, 7.6, 7.3, 56, A
LYS, CB, 70, 23.7, 8.4, 6.9, 57, A
LYS, CG, 70, 24.4, 8.0, 5.6, 57, A
LYS, CD, 70, 25.6, 8.8, 5.3, 58, A
LYS, CE, 70, 26.3, 8.4, 4.1, 58, A
LYS, NZ, 70, 27.6, 9.1, 3.9, 58, A
LYS, C, 70, 22.9, 6.3, 7.9, 56, A
LYS, O, 70, 23.1, 5.3, 7.2, 56, A
GLN, N, 71, 22.9, 6.2, 9.2, 55, A
GLN, CA, 71, 23.3, 4.9, 9.9, 54, A
GLN, CB, 71, 24.7, 5.1, 10.5, 55, A
GLN, CG, 71, 25.4, 3.7, 10.7, 56, A
GLN, CD, 71, 26.8, 3.9, 11.2, 56, A
GLN, OE1, 71, 27.5, 4.9, 10.9, 56, A
GLN, NE2, 71, 27.3, 3.0, 12.1, 56, A
GLN, C, 71, 22.3, 4.7, 11.0, 53, A
GLN, O, 71, 22.6, 4.8, 12.2, 52, A
GLN, N, 72, 21.1, 4.2, 10.6, 51, A
GLN, CA, 72, 20.0, 3.9, 11.5, 50, A
GLN, CB, 72, 18.8, 3.5, 10.6, 49, A
GLN, CG, 72, 18.6, 4.4, 9.5, 49, A
GLN, CD, 72, 17.3, 4.0, 8.7, 49, A
GLN, OE1, 72, 17.1, 2.9, 8.3, 49, A
GLN, NE2, 72, 16.5, 5.0, 8.5, 49, A
GLN, C, 72, 20.2, 3.0, 12.7, 49, A
GLN, O, 72, 19.3, 2.9, 13.5, 48, A
HIS, N, 73, 21.3, 2.3, 12.7, 48, A

TABLE 3-continued

Structural coordinates of HDM2 (17-125; F55Y/Y76H) (SEQ ID NO: 2) complexed with compound 3.

HIS, CA, 73, 21.6, 1.4, 13.8, 47, A
HIS, CB, 73, 22.4, 0.2, 13.4, 47, A
HIS, CG, 73, 23.9, 0.4, 13.2, 47, A
HIS, CD2, 73, 24.6, 0.9, 12.2, 47, A
HIS, ND1, 73, 24.8, 0.2, 14.2, 47, A
HIS, CE1, 73, 26.0, 0.5, 13.8, 47, A
HIS, NE2, 73, 25.9, 0.9, 12.5, 47, A
HIS, C, 73, 22.3, 2.1, 15.0, 46, A
HIS, O, 73, 22.5, 1.6, 16.1, 46, A
ILE, N, 74, 22.6, 3.4, 14.8, 45, A
ILE, CA, 74, 23.3, 4.2, 15.8, 44, A
ILE, CB, 74, 24.5, 5.0, 15.2, 44, A
ILE, CG2, 74, 25.1, 5.9, 16.3, 44, A
ILE, CG1, 74, 25.5, 4.0, 14.6, 44, A
ILE, CD1, 74, 26.2, 3.1, 15.7, 44, A
ILE, C, 74, 22.4, 5.3, 16.4, 43, A
ILE, O, 74, 21.9, 6.2, 15.8, 43, A
VAL, N, 75, 22.1, 5.1, 17.7, 43, A
VAL, CA, 75, 21.3, 6.1, 18.5, 42, A
VAL, CB, 75, 20.6, 5.4, 19.7, 42, A
VAL, CG1, 75, 19.7, 6.4, 20.4, 42, A
VAL, CG2, 75, 19.8, 4.2, 19.2, 42, A
VAL, C, 75, 22.1, 7.2, 19.0, 42, A
VAL, O, 75, 23.1, 7.0, 19.7, 42, A
HIS, N, 76, 21.7, 8.4, 18.7, 41, A
HIS, CA, 76, 22.5, 9.6, 19.2, 41, A
HIS, CB, 76, 22.7, 10.6, 18.1, 41, A
HIS, CG, 76, 23.8, 10.1, 17.2, 41, A
HIS, CD2, 76, 23.8, 9.8, 15.9, 41, A
HIS, ND1, 76, 25.1, 10.0, 17.6, 42, A
HIS, CE1, 76, 25.9, 9.5, 16.6, 41, A
HIS, NE2, 76, 25.1, 9.4, 15.6, 42, A
HIS, C, 76, 21.6, 10.3, 20.3, 40, A
HIS, O, 76, 20.5, 10.7, 20.0, 40, A
CYS, N, 77, 22.1, 10.3, 21.5, 39, A
CYS, CA, 77, 21.3, 10.8, 22.7, 38, A
CYS, CB, 77, 20.7, 9.6, 23.4, 37, A
CYS, SG, 77, 21.8, 8.3, 23.8, 36, A
CYS, C, 77, 22.1, 11.7, 23.7, 38, A
CYS, O, 77, 21.7, 11.9, 24.8, 38, A
SER, N, 78, 23.3, 12.1, 23.3, 38, A
SER, CA, 78, 24.1, 12.9, 24.1, 38, A
SER, CB, 78, 25.2, 13.6, 23.3, 38, A
SER, OG, 78, 24.7, 14.7, 22.6, 38, A
SER, C, 78, 23.4, 14.0, 24.9, 38, A
SER, O, 78, 23.7, 14.3, 26.0, 38, A
ASN, N, 79, 22.5, 14.6, 24.2, 37, A
ASN, CA, 79, 21.7, 15.7, 24.7, 37, A
ASN, CB, 79, 21.7, 16.9, 23.8, 38, A
ASN, CG, 79, 21.2, 18.2, 24.4, 38, A
ASN, OD1, 79, 21.5, 18.6, 25.5, 38, A
ASN, ND2, 79, 20.3, 18.9, 23.7, 38, A
ASN, C, 79, 20.2, 15.4, 25.0, 37, A
ASN, O, 79, 19.4, 16.2, 25.0, 37, A
ASP, N, 80, 20.0, 14.1, 25.4, 36, A
ASP, CA, 80, 18.6, 13.7, 25.7, 36, A
ASP, CB, 80, 18.0, 12.9, 24.6, 36, A
ASP, CG, 80, 16.6, 12.7, 24.7, 37, A
ASP, OD1, 80, 15.8, 13.5, 24.2, 37, A
ASP, OD2, 80, 16.2, 11.7, 25.3, 37, A
ASP, C, 80, 18.6, 12.9, 27.0, 35, A
ASP, O, 80, 19.6, 12.4, 27.4, 35, A
LEU, N, 81, 17.4, 12.9, 27.6, 34, A
LEU, CA, 81, 17.2, 12.1, 28.9, 34, A
LEU, CB, 81, 15.8, 12.1, 29.3, 34, A
LEU, CG, 81, 15.5, 11.4, 30.6, 35, A
LEU, CD1, 81, 16.5, 11.9, 31.7, 34, A
LEU, CD2, 81, 14.1, 11.7, 31.0, 34, A
LEU, C, 81, 17.7, 10.7, 28.7, 33, A
LEU, O, 81, 18.4, 10.1, 29.6, 33, A
LEU, N, 82, 17.4, 10.0, 27.6, 34, A
LEU, CA, 82, 17.9, 8.7, 27.4, 34, A
LEU, CB, 82, 17.5, 8.2, 26.0, 34, A
LEU, CG, 82, 18.0, 6.7, 25.7, 35, A
LEU, CD1, 82, 17.2, 5.8, 26.6, 34, A
LEU, CD2, 82, 17.7, 6.4, 24.2, 34, A
LEU, C, 82, 19.4, 8.6, 27.6, 34, A
LEU, O, 82, 19.9, 7.6, 28.1, 33, A
GLY, N, 83, 20.1, 9.6, 27.1, 34, A
GLY, CA, 83, 21.5, 9.6, 27.2, 34, A
GLY, C, 83, 22.0, 9.7, 28.7, 34, A
GLY, O, 83, 22.9, 9.1, 29.1, 34, A
ASP, N, 84, 21.2, 10.5, 29.5, 34, A
ASP, CA, 84, 21.6, 10.7, 30.9, 34, A
ASP, CB, 84, 20.8, 11.8, 31.5, 34, A
ASP, CG, 84, 20.9, 13.1, 30.7, 34, A
ASP, OD1, 84, 22.0, 13.5, 30.5, 34, A
ASP, OD2, 84, 19.9, 13.6, 30.3, 34, A
ASP, C, 84, 21.3, 9.4, 31.7, 35, A
ASP, O, 84, 22.0, 9.1, 32.6, 35, A
LEU, N, 85, 20.2, 8.7, 31.3, 35, A
LEU, CA, 85, 19.8, 7.5, 32.0, 36, A
LEU, CB, 85, 18.4, 7.1, 31.7, 36, A
LEU, CG, 85, 17.3, 8.2, 32.0, 36, A
LEU, CD1, 85, 16.0, 7.6, 31.7, 36, A
LEU, CD2, 85, 17.5, 8.5, 33.5, 36, A
LEU, C, 85, 20.8, 6.4, 31.6, 36, A
LEU, O, 85, 21.2, 5.6, 32.5, 36, A
PHE, N, 86, 21.1, 6.3, 30.3, 35, A
PHE, CA, 86, 22.0, 5.3, 29.9, 35, A
PHE, CB, 86, 21.8, 5.1, 28.3, 34, A
PHE, CG, 86, 20.7, 4.1, 28.0, 34, A
PHE, CD1, 86, 19.7, 3.8, 28.9, 34, A
PHE, CD2, 86, 20.6, 3.5, 26.8, 34, A
PHE, CE1, 86, 18.6, 2.9, 28.6, 34, A
PHE, CE2, 86, 19.6, 2.6, 26.4, 34, A
PHE, CZ, 86, 18.6, 2.3, 27.3, 34, A
PHE, C, 86, 23.5, 5.6, 30.2, 35, A
PHE, O, 86, 24.3, 4.7, 30.3, 35, A
GLY, N, 87, 23.8, 6.9, 30.3, 35, A
GLY, CA, 87, 25.2, 7.2, 30.6, 35, A
GLY, C, 87, 26.1, 7.3, 29.3, 35, A
GLY, O, 87, 27.3, 7.3, 29.5, 35, A
VAL, N, 88, 25.5, 7.3, 28.2, 34, A
VAL, CA, 88, 26.3, 7.4, 26.9, 35, A
VAL, CB, 88, 26.3, 6.0, 26.2, 34, A
VAL, CG1, 88, 27.3, 5.1, 26.8, 33, A
VAL, CG2, 88, 24.9, 5.4, 26.2, 33, A
VAL, C, 88, 25.7, 8.4, 25.9, 35, A
VAL, O, 88, 24.6, 8.8, 25.9, 36, A
PRO, N, 89, 26.7, 9.0, 25.1, 36, A
PRO, CD, 89, 28.1, 8.9, 25.3, 37, A
PRO, CA, 89, 26.3, 10.0, 24.1, 37, A
PRO, CB, 89, 27.7, 10.6, 23.8, 37, A
PRO, CG, 89, 28.6, 9.5, 24.0, 37, A
PRO, C, 89, 25.7, 9.4, 22.9, 37, A
PRO, O, 89, 24.9, 10.0, 22.2, 37, A
SER, N, 90, 26.0, 8.1, 22.8, 38, A
SER, CA, 90, 25.4, 7.3, 21.7, 38, A
SER, CB, 90, 26.0, 7.7, 20.3, 38, A
SER, OG, 90, 27.4, 7.5, 20.4, 39, A
SER, C, 90, 25.7, 5.8, 21.9, 38, A
SER, O, 90, 26.5, 5.4, 22.8, 38, A
PHE, N, 91, 25.1, 4.9, 21.1, 38, A
PHE, CA, 91, 25.2, 3.5, 21.2, 37, A
PHE, CB, 91, 24.6, 3.0, 22.4, 37, A
PHE, CG, 91, 23.1, 3.1, 22.5, 36, A
PHE, CD1, 91, 22.3, 2.1, 22.0, 36, A
PHE, CD2, 91, 22.5, 4.2, 23.1, 36, A
PHE, CE1, 91, 20.9, 2.2, 22.0, 36, A
PHE, CE2, 91, 21.1, 4.3, 23.1, 35, A
PHE, CZ, 91, 20.3, 3.3, 22.6, 35, A
PHE, C, 91, 24.6, 2.8, 20.0, 37, A
PHE, O, 91, 23.8, 3.3, 19.3, 37, A
SER, N, 92, 25.1, 1.6, 19.7, 38, A
SER, CA, 92, 24.6, 0.7, 18.6, 38, A
SER, CB, 92, 25.8, −0.2, 18.2, 38, A
SER, OG, 92, 25.4, −1.1, 17.2, 38, A
SER, C, 92, 23.4, −0.1, 19.1, 38, A
SER, O, 92, 23.4, −0.7, 20.2, 38, A
VAL, N, 93, 22.4, −0.2, 18.2, 39, A
VAL, CA, 93, 21.2, −1.0, 18.5, 39, A

TABLE 3-continued

Structural coordinates of HDM2 (17-125; F55Y/Y76H) (SEQ ID NO: 2) complexed with compound 3.

VAL, CB, 93, 20.1, −0.6, 17.5, 40, A
VAL, CG1, 93, 18.9, −1.6, 17.8, 39, A
VAL, CG2, 93, 19.7, 0.8, 17.7, 39, A
VAL, C, 93, 21.6, −2.5, 18.5, 40, A
VAL, O, 93, 20.8, −3.3, 19.0, 40, A
LYS, N, 94, 22.7, −2.8, 17.8, 41, A
LYS, CA, 94, 23.1, −4.2, 17.7, 42, A
LYS, CB, 94, 24.1, −4.4, 16.6, 42, A
LYS, CG, 94, 23.5, −4.1, 15.2, 43, A
LYS, CD, 94, 24.7, −4.3, 14.2, 44, A
LYS, CE, 94, 24.2, −4.0, 12.7, 45, A
LYS, NZ, 94, 25.3, −4.3, 11.7, 45, A
LYS, C, 94, 23.8, −4.7, 19.0, 42, A
LYS, O, 94, 24.0, −5.9, 19.2, 42, A
GLU, N, 95, 24.2, −3.8, 19.9, 42, A
GLU, CA, 95, 24.9, −4.1, 21.1, 43, A
GLU, CB, 95, 25.8, −2.9, 21.5, 44, A
GLU, CG, 95, 26.8, −2.6, 20.4, 45, A
GLU, CD, 95, 27.7, −1.4, 20.8, 46, A
GLU, OE1, 95, 27.2, −0.3, 21.0, 47, A
GLU, OE2, 95, 28.9, −1.7, 20.9, 47, A
GLU, C, 95, 23.9, −4.4, 22.2, 43, A
GLU, O, 95, 23.8, −3.7, 23.2, 42, A
HIS, N, 96, 23.2, −5.5, 22.1, 43, A
HIS, CA, 96, 22.2, −6.0, 23.0, 43, A
HIS, CB, 96, 21.6, −7.3, 22.6, 44, A
HIS, CG, 96, 20.8, −7.2, 21.3, 44, A
HIS, CD2, 96, 20.6, −6.2, 20.4, 44, A
HIS, ND1, 96, 20.1, −8.3, 20.7, 44, A
HIS, CE1, 96, 19.6, −7.9, 19.6, 44, A
HIS, NE2, 96, 19.9, −6.6, 19.4, 44, A
HIS, C, 96, 22.7, −6.1, 24.4, 43, A
HIS, O, 96, 22.0, −5.8, 25.4, 43, A
ARG, N, 97, 23.9, −6.6, 24.6, 44, A
ARG, CA, 97, 24.6, −6.8, 25.9, 44, A
ARG, CB, 97, 26.0, −7.4, 25.7, 45, A
ARG, CG, 97, 26.9, −7.5, 26.9, 47, A
ARG, CD, 97, 28.2, −8.2, 26.6, 48, A
ARG, NE, 97, 28.9, −7.6, 25.4, 49, A
ARG, CZ, 97, 29.5, −6.4, 25.5, 49, A
ARG, NH1, 97, 29.6, −5.7, 26.6, 49, A
ARG, NH2, 97, 30.1, −6.0, 24.4, 49, A
ARG, C, 97, 24.7, −5.5, 26.7, 43, A
ARG, O, 97, 24.3, −5.4, 27.8, 43, A
LYS, N, 98, 25.3, −4.5, 26.0, 43, A
LYS, CA, 98, 25.4, −3.2, 26.6, 42, A
LYS, CB, 98, 26.2, −2.3, 25.6, 43, A
LYS, CG, 98, 27.7, −2.5, 25.7, 44, A
LYS, CD, 98, 28.4, −1.9, 24.4, 45, A
LYS, CE, 98, 27.6, −0.6, 23.9, 46, A
LYS, NZ, 98, 27.7, 0.5, 24.9, 47, A
LYS, C, 98, 24.1, −2.5, 26.9, 41, A
LYS, O, 98, 23.9, −1.9, 28.0, 40, A
ILE, N, 99, 23.2, −2.6, 25.9, 39, A
ILE, CA, 99, 21.9, −2.0, 26.1, 38, A
ILE, CB, 99, 21.0, −2.3, 24.9, 38, A
ILE, CG2, 99, 19.5, −1.9, 25.2, 37, A
ILE, CG1, 99, 21.5, −1.6, 23.7, 38, A
ILE, CD1, 99, 20.9, −2.0, 22.4, 38, A
ILE, C, 99, 21.2, −2.6, 27.3, 37, A
ILE, O, 99, 20.6, −1.9, 28.1, 37, A
TYR, N, 100, 21.3, −3.9, 27.5, 37, A
TYR, CA, 100, 20.7, −4.6, 28.7, 37, A
TYR, CB, 100, 20.9, −6.1, 28.7, 37, A
TYR, CG, 100, 19.8, −6.8, 27.9, 37, A
TYR, CD1, 100, 20.2, −7.7, 26.9, 37, A
TYR, CE1, 100, 19.2, −8.3, 26.1, 37, A
TYR, CD2, 100, 18.5, −6.6, 28.2, 37, A
TYR, CE2, 100, 17.5, −7.3, 27.4, 37, A
TYR, CZ, 100, 17.9, −8.1, 26.4, 37, A
TYR, OH, 100, 16.9, −8.7, 25.6, 37, A
TYR, C, 100, 21.3, −4.0, 30.0, 37, A
TYR, O, 100, 20.6, −3.8, 30.9, 37, A
THR, N, 101, 22.6, −3.9, 29.9, 37, A
THR, CA, 101, 23.3, −3.3, 31.1, 37, A
THR, CB, 101, 24.8, −3.2, 30.7, 38, A

TABLE 3-continued

Structural coordinates of HDM2 (17-125; F55Y/Y76H) (SEQ ID NO: 2) complexed with compound 3.

THR, OG1, 101, 25.4, −4.4, 30.3, 38, A
THR, CG2, 101, 25.6, −2.7, 32.0, 38, A
THR, C, 101, 22.8, −2.0, 31.5, 38, A
THR, O, 101, 22.5, −1.8, 32.6, 37, A
MET, N, 102, 22.7, −1.1, 30.5, 37, A
MET, CA, 102, 22.2, 0.3, 30.8, 37
MET, CB, 102, 22.4, −1.1, 29.5, 37, A
MET, CG, 102, 23.8, 1.2, 29.0, 37, A
MET, SD, 102, 24.0, 2.3, 27.6, 38, A
MET, CE, 102, 23.3, 1.3, 26.3, 38, A
MET, C, 102, 20.8, 0.3, 31.2, 36, A
MET, O, 102, 20.4, 1.2, 32.0, 36, A
ILE, N, 103, 20.0, −0.6, 30.7, 35, A
ILE, CA, 103, 18.6, −0.7, 31.1, 35, A
ILE, CB, 103, 17.8, −1.6, 30.2, 35, A
ILE, CG2, 103, 16.4, −1.9, 30.8, 34, A
ILE, CG1, 103, 17.6, −0.9, 28.8, 34, A
ILE, CD1, 103, 16.9, −1.7, 27.8, 35, A
ILE, C, 103, 18.4, −1.2, 32.6, 36, A
ILE, O, 103, 17.6, −0.7, 33.4, 36, A
TYR, N, 104, 19.2, −2.2, 32.9, 37, A
TYR, CA, 104, 19.1, −2.9, 34.2, 38, A
TYR, CB, 104, 20.1, −4.0, 34.3, 38, A
TYR, CG, 104, 19.7, −5.3, 33.5, 38, A
TYR, CD1, 104, 20.7, −6.1, 33.0, 38, A
TYR, CE1, 104, 20.3, −7.3, 32.3, 38, A
TYR, CD2, 104, 18.4, −5.6, 33.3, 38, A
TYR, CE2, 104, 18.0, −6.7, 32.7, 38, A
TYR, CZ, 104, 18.9, −7.6, 32.2, 38, A
TYR, OH, 104, 18.6, −8.7, 31.5, 38, A
TYR, C, 104, 19.4, −1.9, 35.3, 38, A
TYR, O, 104, 18.7, −1.9, 36.3, 39, A
ARG, N, 105, 20.4, −1.0, 35.1, 40, A
ARG, CA, 105, 20.7, 0.0, 36.1, 41, A
ARG, CB, 105, 21.8, 0.9, 35.6, 42, A
ARG, CG, 105, 23.2, 0.2, 35.5, 43, A
ARG, CD, 105, 24.3, 1.2, 35.1, 44, A
ARG, NE, 105, 25.5, 0.4, 34.8, 46, A
ARG, CZ, 105, 26.7, 0.9, 34.4, 47, A
ARG, NH1, 105, 26.9, 2.2, 34.2, 47, A
ARG, NH2, 105, 27.7, 0.1, 34.2, 47, A
ARG, C, 105, 19.5, 0.9, 36.4, 41, A
ARG, O, 105, 19.3, 1.3, 37.6, 42, A
ASN, N, 106, 18.7, 1.1, 35.4, 40, A
ASN, CA, 106, 17.5, 2.0, 35.5, 40, A
ASN, CB, 106, 17.3, 2.7, 34.2, 39, A
ASN, CG, 106, 18.3, 3.8, 34.0, 39, A
ASN, OD1, 106, 18.2, 4.9, 34.6, 39, A
ASN, ND2, 106, 19.4, 3.5, 33.3, 38, A
ASN, C, 106, 16.2, 1.3, 36.0, 40, A
ASN, O, 106, 15.2, 1.9, 36.0, 39, A
LEU, N, 107, 16.3, 0.1, 36.5, 39, A
LEU, CA, 107, 15.1, −0.5, 37.0, 39, A
LEU, CB, 107, 14.4, −1.3, 35.9, 39, A
LEU, CG, 107, 15.3, −2.1, 35.0, 39, A
LEU, CD1, 107, 15.9, −3.2, 35.8, 39, A
LEU, CD2, 107, 14.4, −2.7, 33.9, 38, A
LEU, C, 107, 15.4, −1.5, 38.1, 39, A
LEU, O, 107, 16.6, −1.7, 38.5, 39, A
VAL, N, 108, 14.4, −2.1, 38.7, 39, A
VAL, CA, 108, 14.4, −3.1, 39.7, 39, A
VAL, CB, 108, 14.1, −2.4, 41.1, 40, A
VAL, CG1, 108, 13.5, −3.4, 42.0, 40, A
VAL, CG2, 108, 15.3, −1.8, 41.7, 39, A
VAL, C, 108, 13.5, −4.2, 39.4, 39, A
VAL, O, 108, 12.3, −3.9, 39.1, 40, A
VAL, N, 109, 14.0, −5.4, 39.5, 40, A
VAL, CA, 109, 13.1, −6.6, 39.3, 40, A
VAL, CB, 109, 14.0, −7.9, 39.2, 40, A
VAL, CG1, 109, 13.1, −9.1, 38.8, 39, A
VAL, CG2, 109, 15.1, −7.7, 38.2, 39, A
VAL, C, 109, 12.1, −6.8, 40.3, 40, A
VAL, O, 109, 12.4, −6.6, 41.5, 41, A
VAL, N, 110, 10.9, −7.2, 40.0, 41, A
VAL, CA, 110, 9.8, −7.4, 40.9, 42, A
VAL, CB, 110, 8.7, −6.3, 40.9, 42, A

TABLE 3-continued

Structural coordinates of HDM2 (17-125; F55Y/Y76H) (SEQ ID NO: 2) complexed with compound 3.

VAL, CG1, 110, 9.3, −5.0, 41.3, 41, A
VAL, CG2, 110, 8.1, −6.3, 39.5, 42, A
VAL, C, 110, 9.1, −8.8, 40.7, 43, A
VAL, O, 110, 9.3, −9.4, 39.7, 43, A
ASN, N, 111, 8.3, −9.2, 41.7, 45, A
ASN, CA, 111, 7.5, −10.4, 41.6, 46, A
ASN, CB, 111, 6.7, −10.6, 42.9, 47, A
ASN, CG, 111, 7.5, −11.4, 43.9, 48, A
ASN, OD1, 111, 7.9, −12.5, 43.7, 49, A
ASN, ND2, 111, 7.6, −10.8, 45.2, 48, A
ASN, C, 111, 6.6, −10.5, 40.4, 46, A
ASN, O, 111, 5.9, −11.5, 40.2, 46, A
ALA, N, 21, 24.9, −0.9, 1.9, 69, B
ALA, CA, 21, 25.3, −0.7, 3.3, 69, B
ALA, CB, 21, 24.5, 0.5, 3.8, 69, B
ALA, C, 21, 25.0, −1.9, 4.1, 69, B
ALA, O, 21, 25.8, −2.8, 4.2, 69, B
SER, N, 22, 23.8, −2.0, 4.7, 68, B
SER, CA, 22, 23.4, −3.1, 5.5, 68, B
SER, CB, 22, 23.1, −2.7, 6.9, 68, B
SER, OG, 22, 24.2, −2.1, 7.6, 69, B
SER, C, 22, 22.2, −3.7, 4.8, 68, B
SER, O, 22, 21.6, −3.0, 3.9, 68, B
GLU, N, 23, 21.8, −4.9, 5.2, 67, B
GLU, CA, 23, 20.6, −5.5, 4.6, 67, B
GLU, CB, 23, 20.4, −6.9, 5.0, 67, B
GLU, CG, 23, 19.4, −7.7, 4.1, 67, B
GLU, CD, 23, 19.0, −9.1, 4.7, 68, B
GLU, OE1, 23, 19.9, −9.9, 5.0, 68, B
GLU, OE2, 23, 17.8, −9.4, 4.7, 68, B
GLU, C, 23, 19.4, −4.7, 5.1, 66, B
GLU, O, 23, 18.4, −4.5, 4.4, 66, B
GLN, N, 24, 19.6, −4.1, 6.3, 64, B
GLN, CA, 24, 18.5, −3.3, 6.9, 63, B
GLN, CB, 24, 18.7, −3.3, 8.5, 63, B
GLN, CG, 24, 18.8, −4.6, 9.1, 63, B
GLN, CD, 24, 20.2, −5.0, 9.5, 63, B
GLN, OE1, 24, 21.1, −5.4, 8.7, 63, B
GLN, NE2, 24, 20.5, −4.9, 10.8, 64, B
GLN, C, 24, 18.6, −1.8, 6.4, 62, B
GLN, O, 24, 17.7, −1.0, 6.8, 61, B
GLU, N, 25, 19.6, −1.5, 5.6, 60, B
GLU, CA, 25, 19.7, −0.1, 5.1, 58, B
GLU, CB, 25, 21.2, 0.3, 5.3, 59, B
GLU, CG, 25, 21.3, 1.7, 5.9, 60, B
GLU, CD, 25, 21.3, 1.7, 7.4, 60, B
GLU, OE1, 25, 21.0, 2.7, 8.1, 61, B
GLU, OE2, 25, 21.6, 0.6, 8.0, 61, B
GLU, C, 25, 19.3, 0.0, 3.7, 57, B
GLU, O, 25, 19.1, 1.1, 3.2, 57, B
THR, N, 26, 19.2, −1.1, 3.0, 54, B
THR, CA, 26, 18.8, −1.1, 1.6, 52, B
THR, CB, 26, 18.4, −2.5, 1.1, 52, B
THR, OG1, 26, 19.5, −3.4, 1.2, 52, B
THR, CG2, 26, 17.9, −2.5, −0.3, 52, B
THR, C, 26, 17.6, −0.2, 1.4, 51, B
THR, O, 26, 16.7, −0.2, 2.2, 50, B
LEU, N, 27, 17.5, 0.5, 0.2, 49, B
LEU, CA, 27, 16.4, 1.3, −0.1, 47, B
LEU, CB, 27, 16.8, 2.5, −0.9, 47, B
LEU, CG, 27, 17.7, 3.6, −0.3, 47, B
LEU, CD1, 27, 18.1, 4.6, −1.3, 48, B
LEU, CD2, 27, 17.0, 4.1, 0.9, 47, B
LEU, C, 27, 15.3, 0.5, −0.8, 46, B
LEU, O, 27, 15.6, −0.1, −1.8, 45, B
VAL, N, 28, 14.1, 0.6, −0.3, 44, B
VAL, CA, 28, 13.0, −0.1, −0.8, 43, B
VAL, CB, 28, 12.6, −1.4, 0.0, 43, B
VAL, CG1, 28, 13.8, −2.3, 0.2, 43, B
VAL, CG2, 28, 12.1, −0.9, 1.4, 43, B
VAL, C, 28, 11.7, 0.7, −1.0, 43, B
VAL, O, 28, 11.5, 1.7, −0.3, 42, B
ARG, N, 29, 10.9, 0.3, −2.0, 42, B
ARG, CA, 29, 9.7, 1.0, −2.4, 41, B
ARG, CB, 29, 9.8, 1.6, −3.8, 42, B
ARG, CG, 29, 8.5, 2.4, −4.3, 43, B
ARG, CD, 29, 8.7, 2.7, −5.8, 44, B
ARG, NE, 29, 9.8, 3.6, −6.0, 45, B
ARG, CZ, 29, 10.4, 3.7, −7.2, 46, B
ARG, NH1, 29, 9.9, 3.0, −8.3, 46, B
ARG, NH2, 29, 11.4, 4.6, −7.4, 46, B
ARG, C, 29, 8.6, −0.1, −2.3, 41, B
ARG, O, 29, 8.5, −1.0, −3.2, 40, B
PRO, N, 30, 7.8, −0.1, −1.3, 40, B
PRO, CD, 30, 8.0, 0.8, −0.2, 39, B
PRO, CA, 30, 6.7, −1.0, −1.0, 39, B
PRO, CB, 30, 6.1, −0.5, 0.3, 39, B
PRO, CG, 30, 7.3, 0.1, 1.0, 39, B
PRO, C, 30, 5.6, −1.1, −2.1, 38, B
PRO, O, 30, 5.1, −0.1, −2.6, 38, B
LYS, N, 31, 5.3, −2.3, −2.5, 38, B
LYS, CA, 31, 4.2, −2.4, −3.6, 37, B
LYS, CB, 31, 4.1, −3.8, −4.1, 37, B
LYS, CG, 31, 5.3, −4.2, −4.9, 37, B
LYS, CD, 31, 5.2, −5.7, −5.4, 37, B
LYS, CE, 31, 6.5, −6.2, −6.2, 37, B
LYS, NZ, 31, 6.6, −7.7, −6.2, 36, B
LYS, C, 31, 2.9, −1.9, −2.9, 37, B
LYS, O, 31, 2.8, −2.0, −1.7, 37, B
PRO, N, 32, 2.0, −1.4, −3.7, 37, B
PRO, CD, 32, 2.0, −1.5, −5.2, 38, B
PRO, CA, 32, 0.7, −0.8, −3.3, 37, B
PRO, CB, 32, −0.2, −1.1, −4.5, 37, B
PRO, CG, 32, 0.8, −0.8, −5.6, 38, B
PRO, C, 32, 0.0, −1.3, −2.0, 37, B
PRO, O, 32, −0.1, −0.5, −1.0, 37, B
LEU, N, 33, −0.4, −2.5, −1.9, 37, B
LEU, CA, 33, −1.1, −3.0, −0.7, 37, B
LEU, CB, 33, −1.5, −4.5, −0.9, 38, B
LEU, CG, 33, −2.5, −4.7, −2.1, 38, B
LEU, CD1, 33, −2.9, −6.2, −2.2, 38, B
LEU, CD2, 33, −3.7, −3.8, −2.0, 38, B
LEU, C, 33, −0.2, −2.9, 0.6, 37, B
LEU, O, 33, −0.7, −2.5, 1.7, 37, B
LEU, N, 34, 1.1, −3.2, 0.5, 38, B
LEU, CA, 34, 1.9, −3.1, 1.7, 38, B
LEU, CB, 34, 3.3, −3.7, 1.4, 38, B
LEU, CG, 34, 4.4, −3.3, 2.3, 38, B
LEU, CD1, 34, 4.0, −3.6, 3.8, 38, B
LEU, CD2, 34, 5.7, −4.1, 2.0, 37, B
LEU, C, 34, 2.1, −1.6, 2.0, 38, B
LEU, O, 34, 2.2, −1.2, 3.1, 37, B
LEU, N, 35, 2.1, −0.8, 0.9, 39, B
LEU, CA, 35, 2.3, 0.6, 1.1, 40, B
LEU, CB, 35, 2.3, 1.4, −0.2, 40, B
LEU, CG, 35, 2.5, 2.9, −0.1, 39, B
LEU, CD1, 35, 3.7, 3.1, 0.8, 40, B
LEU, CD2, 35, 2.8, 3.5, −1.4, 39, B
LEU, C, 35, 1.1, 1.1, 1.9, 42, B
LEU, O, 35, 1.2, 1.9, 2.9, 42, B
LYS, N, 36, −0.1, 0.7, 1.5, 43, B
LYS, CA, 36, −1.4, 1.1, 2.1, 44, B
LYS, CB, 36, −2.6, 0.6, 1.3, 45, B
LYS, CG, 36, −3.7, 0.0, 2.1, 45, B
LYS, CD, 36, −4.9, −0.3, 1.1, 46, B
LYS, CE, 36, −6.0, −1.2, 1.7, 46, B
LYS, NZ, 36, −7.2, −1.2, 0.9, 45, B
LYS, C, 36, −1.4, 0.5, 3.6, 45, B
LYS, O, 36, −1.9, 1.2, 4.5, 45, B
LEU, N, 37, −0.8, −0.6, 3.7, 45, B
LEU, CA, 37, −0.8, −1.2, 5.1, 46, B
LEU, CB, 37, −0.2, −2.7, 5.0, 46, B
LEU, CG, 37, −0.1, −3.5, 6.3, 46, B
LEU, CD1, 37, 0.1, −5.0, 5.9, 46, B
LEU, CD2, 37, 0.9, −3.0, 7.2, 46, B
LEU, C, 37, 0.1, −0.4, 6.0, 46, B
LEU, O, 37, −0.3, −0.1, 7.1, 46, B
LEU, N, 38, 1.2, 0.1, 5.5, 46, B
LEU, CA, 38, 2.1, 0.9, 6.3, 46, B
LEU, CB, 38, 3.5, 1.0, 5.6, 46, B
LEU, CG, 38, 4.5, 0.0, 6.0, 46, B
LEU, CD1, 38, 3.9, −1.3, 6.5, 46, B

TABLE 3-continued

Structural coordinates of HDM2 (17-125; F55Y/Y76H) (SEQ ID NO: 2) complexed with compound 3.

LEU, CD2, 38, 5.5, −0.3, 4.8, 46, B
LEU, C, 38, 1.6, 2.3, 6.6, 47, B
LEU, O, 38, 1.8, 2.8, 7.7, 46, B
LYS, N, 39, 1.0, 3.0, 5.7, 47, B
LYS, CA, 39, 0.4, 4.3, 5.9, 48, B
LYS, CB, 39, −0.0, 4.9, 4.6, 48, B
LYS, CG, 39, 1.1, 5.2, 3.6, 48, B
LYS, CD, 39, 0.7, 6.0, 2.4, 49, B
LYS, CE, 39, 2.0, 6.2, 1.6, 49, B
LYS, NZ, 39, 1.7, 6.9, 0.3, 49, B
LYS, C, 39, −0.7, 4.3, 6.9, 48, B
LYS, O, 39, −0.8, 5.3, 7.7, 48, B
SER, N, 40, −1.4, 3.2, 7.0, 48, B
SER, CA, 40, −2.5, 3.1, 7.9, 48, B
SER, CB, 40, −3.2, 1.8, 7.8, 48, B
SER, OG, 40, −2.6, 0.7, 8.5, 48, B
SER, C, 40, −2.0, 3.2, 9.4, 49, B
SER, O, 40, −2.8, 3.4, 10.3, 49, B
VAL, N, 41, −0.7, 3.2, 9.6, 49, B
VAL, CA, 41, −0.2, 3.3, 10.9, 49, B
VAL, CB, 41, 0.6, 2.1, 11.4, 49, B
VAL, CG1, 41, −0.3, 0.9, 11.6, 49, B
VAL, CG2, 41, 1.7, 1.7, 10.4, 49, B
VAL, C, 41, 0.7, 4.5, 11.1, 50, B
VAL, O, 41, 1.6, 4.6, 11.9, 50, B
GLY, N, 42, 0.5, 5.5, 10.2, 51, B
GLY, CA, 42, 1.2, 6.8, 10.3, 52, B
GLY, C, 42, 2.6, 6.8, 9.7, 53, B
GLY, O, 42, 3.6, 7.1, 10.3, 54, B
ALA, N, 43, 2.6, 6.4, 8.4, 54, B
ALA, CA, 43, 3.8, 6.4, 7.6, 54, B
ALA, CB, 43, 4.4, 5.0, 7.6, 54, B
ALA, C, 43, 3.5, 6.9, 6.2, 54, B
ALA, O, 43, 3.2, 6.1, 5.3, 55, B
GLN, N, 44, 3.4, 8.2, 6.0, 55, B
GLN, CA, 44, 3.1, 8.8, 4.7, 55, B
GLN, CB, 44, 2.3, 10.1, 4.9, 56, B
GLN, CG, 44, 1.8, 10.7, 3.6, 57, B
GLN, CD, 44, 1.2, 12.1, 3.8, 58, B
GLN, OE1, 44, 0.7, 12.7, 2.8, 58, B
GLN, NE2, 44, 1.1, 12.5, 5.0, 58, B
GLN, C, 44, 4.3, 9.0, 3.9, 55, B
GLN, O, 44, 4.6, 10.1, 3.4, 55, B
LYS, N, 45, 5.1, 7.9, 3.8, 54, B
LYS, CA, 45, 6.4, 8.0, 3.0, 52, B
LYS, CB, 45, 7.5, 7.8, 4.0, 53, B
LYS, CG, 45, 8.9, 8.1, 3.4, 53, B
LYS, CD, 45, 9.9, 8.1, 4.4, 53, B
LYS, CE, 45, 9.9, 6.7, 5.1, 52, B
LYS, NZ, 45, 11.1, 6.7, 6.1, 52, B
LYS, C, 45, 6.3, 6.9, 1.9, 51, B
LYS, O, 45, 5.5, 6.0, 2.0, 51, B
ASP, N, 46, 7.1, 7.1, 0.9, 50, B
ASP, CA, 46, 7.1, 6.1, −0.2, 49, B
ASP, CB, 46, 7.0, 6.9, −1.5, 50, B
ASP, CG, 46, 5.6, 7.3, −1.8, 50, B
ASP, OD1, 46, 5.0, 8.1, −1.0, 51, B
ASP, OD2, 46, 5.0, 6.8, −2.7, 50, B
ASP, C, 46, 8.3, 5.2, −0.3, 47, B
ASP, O, 46, 8.2, 4.0, −0.7, 47, B
THR, N, 47, 9.5, 5.6, 0.2, 45, B
THR, CA, 47, 10.7, 4.9, 0.1, 43, B
THR, CB, 47, 11.8, 5.6, −0.6, 44, B
THR, OG1, 47, 11.4, 5.9, −2.0, 43, B
THR, CG2, 47, 13.1, 4.8, −0.7, 44, B
THR, C, 47, 11.2, 4.6, 1.5, 42, B
THR, O, 47, 11.2, 5.5, 2.4, 42, B
TYR, N, 48, 11.5, 3.3, 1.8, 41, B
TYR, CA, 48, 12.0, 3.0, 3.2, 40, B
TYR, CB, 48, 10.9, 2.2, 3.9, 40, B
TYR, CG, 48, 9.6, 2.8, 4.0, 41, B
TYR, CD1, 48, 8.7, 2.9, 2.9, 41, B
TYR, CE1, 48, 7.5, 3.5, 3.1, 42, B
TYR, CD2, 48, 9.2, 3.4, 5.2, 42, B
TYR, CE2, 48, 8.0, 4.0, 5.4, 42, B
TYR, CZ, 48, 7.1, 4.0, 4.3, 42, B
TYR, OH, 48, 5.9, 4.7, 4.5, 43, B
TYR, C, 48, 13.2, 2.1, 3.2, 39, B
TYR, O, 48, 13.7, 1.6, 2.2, 40, B
THR, N, 49, 13.8, 2.0, 4.4, 38, B
THR, CA, 49, 15.0, 1.2, 4.6, 37, B
THR, CB, 49, 16.0, 1.7, 5.7, 37, B
THR, OG1, 49, 15.4, 1.6, 7.0, 36, B
THR, CG2, 49, 16.3, 3.2, 5.4, 36, B
THR, C, 49, 14.3, −0.1, 5.1, 36, B
THR, O, 49, 13.1, 0.1, 5.6, 35, B
MET, N, 50, 14.9, −1.2, 5.0, 35, B
MET, CA, 50, 14.2, −2.4, 5.6, 36, B
MET, CB, 50, 15.1, −3.7, 5.3, 36, B
MET, CG, 50, 15.0, −4.3, 3.9, 38, B
MET, SD, 50, 13.3, −4.9, 3.5, 38, B
MET, CE, 50, 13.4, −6.6, 4.2, 38, B
MET, C, 50, 13.9, −2.3, 7.1, 35, B
MET, O, 50, 13.0, −2.9, 7.6, 35, B
LYS, N, 51, 14.8, −1.5, 7.8, 35, B
LYS, CA, 51, 14.6, −1.3, 9.2, 36, B
LYS, CB, 51, 15.6, −0.4, 9.8, 36, B
LYS, CG, 51, 17.0, −1.0, 10.0, 38, B
LYS, CD, 51, 17.8, −0.2, 11.0, 38, B
LYS, CE, 51, 19.2, −0.8, 11.1, 38, B
LYS, NZ, 51, 19.1, −2.2, 11.5, 39, B
LYS, C, 51, 13.2, −0.7, 9.4, 35, B
LYS, O, 51, 12.4, −1.3, 10.1, 34, B
GLU, N, 52, 13.0, 0.5, 8.8, 34, B
GLU, CA, 52, 11.7, 1.2, 9.0, 35, B
GLU, CB, 52, 11.7, 2.4, 8.0, 35, B
GLU, CG, 52, 13.0, 3.2, 8.2, 36, B
GLU, CD, 52, 13.0, 4.5, 7.4, 37, B
GLU, OE1, 52, 12.5, 4.4, 6.2, 38, B
GLU, OE2, 52, 13.4, 5.5, 7.9, 37, B
GLU, C, 52, 10.6, 0.3, 8.6, 34, B
GLU, O, 52, 9.6, 0.2, 9.3, 33, B
VAL, N, 53, 10.7, −0.4, 7.4, 33, B
VAL, CA, 53, 9.6, −1.3, 7.0, 32, B
VAL, CB, 53, 10.0, −2.1, 5.7, 32, B
VAL, CG1, 53, 9.2, −3.4, 5.6, 32, B
VAL, CG2, 53, 9.8, −1.2, 4.5, 32, B
VAL, C, 53, 9.3, −2.3, 8.1, 33, B
VAL, O, 53, 8.1, −2.6, 8.4, 33, B
LEU, N, 54, 10.3, −2.8, 8.7, 32, B
LEU, CA, 54, 10.1, −3.8, 9.8, 32, B
LEU, CB, 54, 11.5, −4.4, 10.2, 32, B
LEU, CG, 54, 12.0, −5.5, 9.4, 32, B
LEU, CD1, 54, 13.4, −5.9, 9.9, 31, B
LEU, CD2, 54, 11.1, −6.8, 9.5, 31, B
LEU, C, 54, 9.4, −3.1, 11.0, 33, B
LEU, O, 54, 8.6, −3.8, 11.7, 34, B
TYR, N, 55, 9.8, −1.9, 11.3, 34, B
TYR, CA, 55, 9.2, −1.2, 12.4, 34, B
TYR, CB, 55, 10.0, 0.1, 12.6, 35, B
TYR, CG, 55, 9.3, 1.1, 13.6, 35, B
TYR, CD1, 55, 9.3, 0.8, 15.0, 35, B
TYR, CE1, 55, 8.6, 1.6, 15.9, 36, B
TYR, CD2, 55, 8.6, 2.2, 13.2, 36, B
TYR, CE2, 55, 7.9, 3.0, 14.1, 36, B
TYR, CZ, 55, 7.9, 2.7, 15.4, 36, B
TYR, OH, 55, 7.2, 3.5, 16.3, 36, B
TYR, C, 55, 7.8, −0.8, 12.2, 35, B
TYR, O, 55, 7.0, −1.1, 13.1, 34, B
TYR, N, 56, 7.4, −0.3, 11.1, 35, B
TYR, CA, 56, 6.0, 0.0, 10.8, 36, B
TYR, CB, 56, 5.9, 0.9, 9.6, 37, B
TYR, CG, 56, 6.5, 2.2, 9.8, 38, B
TYR, CD1, 56, 6.0, 3.1, 10.7, 38, B
TYR, CE1, 56, 6.6, 4.4, 10.9, 38, B
TYR, CD2, 56, 7.6, 2.6, 9.0, 38, B
TYR, CE2, 56, 8.3, 3.9, 9.3, 38, B
TYR, CZ, 56, 7.8, 4.7, 10.2, 39, B
TYR, OH, 56, 8.4, 5.9, 10.5, 39, B
TYR, C, 56, 5.1, −1.2, 10.7, 36, B
TYR, O, 56, 3.9, −1.2, 11.0, 36, B
LEU, N, 57, 5.7, −2.3, 10.3, 36, B

TABLE 3-continued

Structural coordinates of HDM2 (17-125; F55Y/Y76H) (SEQ ID NO: 2) complexed with compound 3.

| | | | | | | |
|---|---|---|---|---|---|---|
| LEU, | CA, | 57, | 5.0, | −3.6, | 10.2, | 36, B |
| LEU, | CB, | 57, | 5.8, | −4.7, | 9.6, | 36, B |
| LEU, | CG, | 57, | 5.7, | −4.7, | 8.0, | 36, B |
| LEU, | CD1, | 57, | 6.8, | −5.6, | 7.5, | 36, B |
| LEU, | CD2, | 57, | 4.3, | −5.1, | 7.6, | 36, B |
| LEU, | C, | 57, | 4.7, | −4.0, | 11.7, | 36, B |
| LEU, | O, | 57, | 3.6, | −4.5, | 12.0, | 36, B |
| GLY, | N, | 58, | 5.6, | −3.7, | 12.6, | 36, B |
| GLY, | CA, | 58, | 5.4, | −4.0, | 14.0, | 35, B |
| GLY, | C, | 58, | 4.3, | −3.2, | 14.6, | 35, B |
| GLY, | O, | 58, | 3.5, | −3.6, | 15.3, | 35, B |
| GLN, | N, | 59, | 4.2, | −1.9, | 14.2, | 35, B |
| GLN, | CA, | 59, | 3.2, | −1.0, | 14.7, | 35, B |
| GLN, | CB, | 59, | 3.4, | 0.4, | 14.1, | 35, B |
| GLN, | CG, | 59, | 4.6, | 1.1, | 14.7, | 34, B |
| GLN, | CD, | 59, | 4.6, | 1.1, | 16.2, | 35, B |
| GLN, | OE1, | 59, | 5.0, | 0.1, | 16.8, | 35, B |
| GLN, | NE2, | 59, | 4.2, | 2.2, | 16.8, | 35, B |
| GLN, | C, | 59, | 1.9, | −1.5, | 14.3, | 35, B |
| GLN, | O, | 59, | 0.9, | −1.6, | 15.1, | 35, B |
| TYR, | N, | 60, | 1.7, | −1.9, | 13.0, | 34, B |
| TYR, | CA, | 60, | 0.5, | −2.5, | 12.5, | 34, B |
| TYR, | CB, | 60, | 0.8, | −2.9, | 11.0, | 34, B |
| TYR, | CG, | 60, | −0.5, | −3.4, | 10.3, | 33, B |
| TYR, | CD1, | 60, | −1.4, | −2.6, | 9.7, | 33, B |
| TYR, | CE1, | 60, | −2.5, | −3.0, | 9.0, | 33, B |
| TYR, | CD2, | 60, | −0.7, | −4.8, | 10.3, | 33, B |
| TYR, | CE2, | 60, | −1.8, | −5.3, | 9.6, | 33, B |
| TYR, | CZ, | 60, | −2.7, | −4.4, | 9.0, | 33, B |
| TYR, | OH, | 60, | −3.8, | −4.9, | 8.3, | 33, B |
| TYR, | C, | 60, | 0.1, | −3.7, | 13.3, | 35, B |
| TYR, | O, | 60, | −1.1, | −3.8, | 13.7, | 34, B |
| ILE, | N, | 61, | 1.0, | −4.6, | 13.5, | 35, B |
| ILE, | CA, | 61, | 0.8, | −5.8, | 14.3, | 36, B |
| ILE, | CB, | 61, | 2.0, | −6.7, | 14.3, | 36, B |
| ILE, | CG2, | 61, | 1.8, | −7.8, | 15.3, | 36, B |
| ILE, | CG1, | 61, | 2.2, | −7.3, | 12.9, | 36, B |
| ILE, | CD1, | 61, | 3.4, | −8.3, | 12.8, | 35, B |
| ILE, | C, | 61, | 0.4, | −5.5, | 15.7, | 37, B |
| ILE, | O, | 61, | −0.5, | −6.1, | 16.3, | 37, B |
| MET, | N, | 62, | 1.0, | −4.5, | 16.3, | 38, B |
| MET, | CA, | 62, | 0.7, | −4.1, | 17.7, | 40, B |
| MET, | CB, | 62, | 1.8, | −3.1, | 18.2, | 40, B |
| MET, | CG, | 62, | 3.1, | −3.8, | 18.5, | 40, B |
| MET, | SD, | 62, | 3.0, | −5.2, | 19.5, | 41, B |
| MET, | CE, | 62, | 2.8, | −4.3, | 21.2, | 41, B |
| MET, | C, | 62, | −0.7, | −3.4, | 17.9, | 41, B |
| MET, | O, | 62, | −1.5, | −3.8, | 18.6, | 41, B |
| THR, | N, | 63, | −0.9, | −2.3, | 17.1, | 42, B |
| THR, | CA, | 63, | −2.1, | −1.6, | 17.2, | 44, B |
| THR, | CB, | 63, | −2.1, | −0.4, | 16.2, | 45, B |
| THR, | OG1, | 63, | −2.0, | −0.8, | 14.9, | 45, B |
| THR, | CG2, | 63, | −1.0, | 0.6, | 16.6, | 45, B |
| THR, | C, | 63, | −3.3, | −2.5, | 16.9, | 46, B |
| THR, | O, | 63, | −4.4, | −2.3, | 17.5, | 46, B |
| LYS, | N, | 64, | −3.2, | −3.4, | 16.0, | 47, B |
| LYS, | CA, | 64, | −4.3, | −4.3, | 15.6, | 49, B |
| LYS, | CB, | 64, | −4.2, | −4.6, | 14.1, | 49, B |
| LYS, | CG, | 64, | −4.4, | −3.4, | 13.2, | 49, B |
| LYS, | CD, | 64, | −4.7, | −3.8, | 11.8, | 49, B |
| LYS, | CE, | 64, | −6.1, | −4.5, | 11.7, | 49, B |
| LYS, | NZ, | 64, | −6.5, | −4.7, | 10.3, | 48, B |
| LYS, | C, | 64, | −4.3, | −5.6, | 16.4, | 50, B |
| LYS, | O, | 64, | −5.2, | −6.4, | 16.2, | 50, B |
| ARG, | N, | 65, | −3.3, | −5.8, | 17.3, | 51, B |
| ARG, | CA, | 65, | −3.3, | −7.0, | 18.2, | 52, B |
| ARG, | CB, | 65, | −4.5, | −7.0, | 19.1, | 53, B |
| ARG, | CG, | 65, | −4.5, | −5.9, | 20.2, | 55, B |
| ARG, | CD, | 65, | −5.8, | −6.0, | 21.1, | 55, B |
| ARG, | NE, | 65, | −5.8, | −7.3, | 21.8, | 56, B |
| ARG, | CZ, | 65, | −6.8, | −7.6, | 22.6, | 57, B |
| ARG, | NH1, | 65, | −7.8, | −6.7, | 22.8, | 57, B |
| ARG, | NH2, | 65, | −6.8, | −8.8, | 23.2, | 57, B |
| ARG, | C, | 65, | −3.3, | −8.3, | 17.4, | 53, B |
| ARG, | O, | 65, | −4.0, | −9.2, | 17.7, | 53, B |
| LEU, | N, | 66, | −2.4, | −8.4, | 16.4, | 53, B |
| LEU, | CA, | 66, | −2.4, | −9.6, | 15.6, | 53, B |
| LEU, | CB, | 66, | −1.9, | −9.3, | 14.2, | 53, B |
| LEU, | CG, | 66, | −2.7, | −8.3, | 13.4, | 52, B |
| LEU, | CD1, | 66, | −2.2, | −8.2, | 12.0, | 52, B |
| LEU, | CD2, | 66, | −4.2, | −8.7, | 13.4, | 52, B |
| LEU, | C, | 66, | −1.5, | −10.7, | 16.2, | 54, B |
| LEU, | O, | 66, | −0.7, | −11.2, | 15.6, | 54, B |
| TYR, | N, | 67, | −1.8, | −10.9, | 17.5, | 55, B |
| TYR, | CA, | 67, | −1.1, | −12.0, | 18.2, | 56, B |
| TYR, | CB, | 67, | 0.3, | −11.4, | 18.6, | 55, B |
| TYR, | CG, | 67, | 0.2, | −10.2, | 19.6, | 55, B |
| TYR, | CD1, | 67, | 0.2, | −10.5, | 21.0, | 55, B |
| TYR, | CE1, | 67, | 0.1, | −9.4, | 21.9, | 54, B |
| TYR, | CD2, | 67, | 0.1, | −8.9, | 19.2, | 55, B |
| TYR, | CE2, | 67, | 0.1, | −7.9, | 20.1, | 55, B |
| TYR, | CZ, | 67, | 0.1, | −8.1, | 21.4, | 54, B |
| TYR, | OH, | 67, | −0.0, | −7.1, | 22.3, | 54, B |
| TYR, | C, | 67, | −1.8, | −12.5, | 19.4, | 57, B |
| TYR, | O, | 67, | −2.6, | −11.8, | 20.1, | 57, B |
| ASP, | N, | 68, | −1.5, | −13.8, | 19.8, | 59, B |
| ASP, | CA, | 68, | −2.2, | −14.4, | 20.9, | 60, B |
| ASP, | CB, | 68, | −1.9, | −15.9, | 20.8, | 61, B |
| ASP, | CG, | 68, | −2.2, | −16.6, | 22.1, | 62, B |
| ASP, | OD1, | 68, | −3.3, | −16.3, | 22.7, | 62, B |
| ASP, | OD2, | 68, | −1.4, | −17.4, | 22.6, | 62, B |
| ASP, | C, | 68, | −1.7, | −13.8, | 22.2, | 61, B |
| ASP, | O, | 68, | −0.6, | −13.3, | 22.3, | 61, B |
| GLU, | N, | 69, | −2.5, | −13.9, | 23.2, | 62, B |
| GLU, | CA, | 69, | −2.2, | −13.4, | 24.5, | 62, B |
| GLU, | CB, | 69, | −3.4, | −13.5, | 25.5, | 63, B |
| GLU, | CG, | 69, | −4.7, | −12.9, | 25.0, | 64, B |
| GLU, | CD, | 69, | −4.4, | −11.5, | 24.3, | 64, B |
| GLU, | OE1, | 69, | −3.6, | −10.7, | 24.8, | 65, B |
| GLU, | OE2, | 69, | −5.0, | −11.3, | 23.2, | 64, B |
| GLU, | C, | 69, | −1.0, | −13.9, | 25.2, | 62, B |
| GLU, | O, | 69, | −0.1, | −13.2, | 25.6, | 62, B |
| LYS, | N, | 70, | −0.9, | −15.3, | 25.3, | 62, B |
| LYS, | CA, | 70, | 0.3, | −15.9, | 25.9, | 63, B |
| LYS, | CB, | 70, | −0.1, | −17.2, | 26.6, | 63, B |
| LYS, | CG, | 70, | 0.7, | −17.5, | 27.8, | 64, B |
| LYS, | CD, | 70, | 0.1, | −18.6, | 28.7, | 64, B |
| LYS, | CE, | 70, | 0.9, | −18.8, | 30.0, | 64, B |
| LYS, | NZ, | 70, | 0.2, | −19.8, | 30.9, | 64, B |
| LYS, | C, | 70, | 1.5, | −16.1, | 25.0, | 63, B |
| LYS, | O, | 70, | 2.7, | −16.0, | 25.5, | 63, B |
| GLN, | N, | 71, | 1.3, | −16.4, | 23.7, | 62, B |
| GLN, | CA, | 71, | 2.4, | −16.7, | 22.8, | 61, B |
| GLN, | CB, | 71, | 2.2, | −17.9, | 22.0, | 62, B |
| GLN, | CG, | 71, | 3.4, | −18.3, | 21.2, | 62, B |
| GLN, | CD, | 71, | 3.7, | −19.8, | 21.1, | 63, B |
| GLN, | OE1, | 71, | 4.7, | −20.2, | 20.5, | 63, B |
| GLN, | NE2, | 71, | 2.8, | −20.6, | 21.7, | 63, B |
| GLN, | C, | 71, | 2.6, | −15.4, | 22.0, | 60, B |
| GLN, | O, | 71, | 2.2, | −15.3, | 20.8, | 60, B |
| GLN, | N, | 72, | 3.3, | −14.5, | 22.5, | 59, B |
| GLN, | CA, | 72, | 3.6, | −13.2, | 21.9, | 58, B |
| GLN, | CB, | 72, | 4.3, | −12.2, | 22.9, | 58, B |
| GLN, | CG, | 72, | 3.4, | −11.9, | 24.1, | 58, B |
| GLN, | CD, | 72, | 4.2, | −11.1, | 25.1, | 58, B |
| GLN, | OE1, | 72, | 4.8, | −10.0, | 24.8, | 58, B |
| GLN, | NE2, | 72, | 4.2, | −11.6, | 26.3, | 58, B |
| GLN, | C, | 72, | 4.5, | −13.2, | 20.7, | 57, B |
| GLN, | O, | 72, | 4.5, | −12.2, | 19.9, | 57, B |
| HIS, | N, | 73, | 5.3, | −14.3, | 20.5, | 55, B |
| HIS, | CA, | 73, | 6.2, | −14.3, | 19.3, | 54, B |
| HIS, | CB, | 73, | 7.6, | −14.8, | 19.7, | 55, B |
| HIS, | CG, | 73, | 7.7, | −16.3, | 20.0, | 55, B |
| HIS, | CD2, | 73, | 7.3, | −17.4, | 19.2, | 56, B |
| HIS, | ND1, | 73, | 8.2, | −16.8, | 21.1, | 56, B |
| HIS, | CE1, | 73, | 8.2, | −18.1, | 21.1, | 56, B |
| HIS, | NE2, | 73, | 7.7, | −18.5, | 19.9, | 56, B |
| HIS, | C, | 73, | 5.6, | −15.0, | 18.1, | 53, B |
| HIS, | O, | 73, | 6.3, | −15.4, | 17.2, | 53, B |
| ILE, | N, | 74, | 4.2, | −15.1, | 18.1, | 51, B |
| ILE, | CA, | 74, | 3.5, | −15.8, | 17.1, | 49, B |
| ILE, | CB, | 74, | 2.9, | −17.1, | 17.5, | 49, B |

TABLE 3-continued

Structural coordinates of HDM2 (17-125; F55Y/Y76H)
(SEQ ID NO: 2) complexed with compound 3.

| | |
|---|---|
| ILE, CG2, 74, 1.9, −17.6, 16.5, 49, B | |
| ILE, CG1, 74, 3.9, −18.1, 17.8, 49, B | |
| ILE, CD1, 74, 4.8, −18.5, 16.6, 49, B | |
| ILE, C, 74, 2.4, −14.8, 16.6, 48, B | |
| ILE, O, 74, 1.5, −14.5, 17.3, 47, B | |
| VAL, N, 75, 2.6, −14.4, 15.3, 46, B | |
| VAL, CA, 75, 1.6, −13.5, 14.8, 44, B | |
| VAL, CB, 75, 2.2, −12.5, 13.8, 44, B | |
| VAL, CG1, 75, 1.2, −11.7, 13.1, 44, B | |
| VAL, CG2, 75, 3.2, −11.6, 14.5, 44, B | |
| VAL, C, 75, 0.5, −14.3, 14.0, 43, B | |
| VAL, O, 75, 0.8, −15.1, 13.2, 44, B | |
| HIS, N, 76, −0.8, −14.0, 14.3, 42, B | |
| HIS, CA, 76, −1.9, −14.6, 13.7, 41, B | |
| HIS, CB, 76, −3.0, −15.1, 14.7, 41, B | |
| HIS, CG, 76, −2.5, −16.2, 15.6, 41, B | |
| HIS, CD2, 76, −2.1, −16.2, 16.9, 40, B | |
| HIS, ND1, 76, −2.4, −17.5, 15.1, 41, B | |
| HIS, CE1, 76, −1.9, −18.2, 16.1, 40, B | |
| HIS, NE2, 76, −1.7, −17.4, 17.2, 40, B | |
| HIS, C, 76, −2.5, −13.6, 12.7, 40, B | |
| HIS, O, 76, −2.8, −12.5, 13.1, 39, B | |
| CYS, N, 77, −2.6, −13.9, 11.4, 39, B | |
| CYS, CA, 77, −3.0, −12.9, 10.4, 38, B | |
| CYS, CB, 77, −1.9, −12.1, 9.9, 37, B | |
| CYS, SG, 77, −0.5, −13.2, 9.4, 37, B | |
| CYS, C, 77, −3.8, −13.5, 9.3, 37, B | |
| CYS, O, 77, −3.9, −12.9, 8.2, 37, B | |
| SER, N, 78, −4.4, −14.7, 9.4, 36, B | |
| SER, CA, 78, −5.1, −15.3, 8.4, 36, B | |
| SER, CB, 78, −5.7, −16.7, 8.9, 37, B | |
| SER, OG, 78, −6.6, −16.5, 9.9, 37, B | |
| SER, C, 78, −6.3, −14.5, 7.8, 36, B | |
| SER, O, 78, −6.7, −14.7, 6.7, 36, B | |
| ASN, N, 79, −6.9, −13.7, 8.7, 36, B | |
| ASN, CA, 79, −8.1, −12.9, 8.4, 36, B | |
| ASN, CB, 79, −9.2, −13.2, 9.4, 36, B | |
| ASN, CG, 79, −10.5, −12.7, 8.9, 37, B | |
| ASN, OD1, 79, −10.9, −12.8, 7.8, 37, B | |
| ASN, ND2, 79, −11.3, −12.1, 9.9, 37, B | |
| ASN, C, 79, −7.8, −11.5, 8.3, 35, B | |
| ASN, O, 79, −8.6, −10.6, 8.3, 35, B | |
| ASP, N, 80, −6.5, −11.2, 8.1, 35, B | |
| ASP, CA, 80, −6.0, −9.8, 8.0, 34, B | |
| ASP, CB, 80, −5.1, −9.4, 9.2, 35, B | |
| ASP, CG, 80, −4.8, −8.0, 9.3, 35, B | |
| ASP, OD1, 80, −5.5, −7.3, 10.1, 36, B | |
| ASP, OD2, 80, −3.9, −7.5, 8.6, 34, B | |
| ASP, C, 80, −5.3, −9.6, 6.7, 34, B | |
| ASP, O, 80, −4.8, −10.6, 6.1, 33, B | |
| LEU, N, 81, −5.2, −8.4, 6.2, 33, B | |
| LEU, CA, 81, −4.5, −8.1, 5.0, 33, B | |
| LEU, CB, 81, −4.6, −6.6, 4.7, 33, B | |
| LEU, CG, 81, −3.8, −6.0, 3.6, 34, B | |
| LEU, CD1, 81, −4.1, −6.7, 2.3, 34, B | |
| LEU, CD2, 81, −4.2, −4.5, 3.4, 34, B | |
| LEU, C, 81, −3.0, −8.5, 5.1, 33, B | |
| LEU, O, 81, −2.4, −9.0, 4.1, 32, B | |
| LEU, N, 82, −2.4, −8.4, 6.2, 33, B | |
| LEU, CA, 82, −1.0, −8.9, 6.4, 33, B | |
| LEU, CB, 82, −0.6, −8.7, 7.9, 33, B | |
| LEU, CG, 82, 0.8, −9.3, 8.2, 34, B | |
| LEU, CD1, 82, 1.9, −8.8, 7.3, 33, B | |
| LEU, CD2, 82, 1.2, −9.0, 9.7, 33, B | |
| LEU, C, 82, −0.9, −10.3, 6.0, 33, B | |
| LEU, O, 82, 0.0, −10.7, 5.2, 34, B | |
| GLY, N, 83, −1.8, −11.2, 6.4, 34, B | |
| GLY, CA, 83, −1.8, −12.5, 6.0, 34, B | |
| GLY, C, 83, −1.9, −12.7, 4.5, 34, B | |
| GLY, O, 83, −1.3, −13.6, 3.9, 33, B | |
| ASP, N, 84, −2.6, −11.8, 3.8, 35, B | |
| ASP, CA, 84, −2.8, −11.9, 2.4, 35, B | |
| ASP, CB, 84, −3.9, −11.0, 1.9, 35, B | |
| ASP, CG, 84, −5.2, −11.3, 2.5, 35, B | |
| ASP, OD1, 84, −5.7, −12.5, 2.6, 35, B | |
| ASP, OD2, 84, −5.9, −10.3, 3.0, 34, B | |
| ASP, C, 84, −1.5, −11.6, 1.6, 35, B | |
| ASP, O, 84, −1.1, −12.3, 0.7, 36, B | |
| LEU, N, 85, −0.8, −10.5, 2.1, 35, B | |
| LEU, CA, 85, 0.4, −10.1, 1.5, 36, B | |
| LEU, CB, 85, 0.9, −8.7, 2.0, 36, B | |
| LEU, CG, 85, −0.1, −7.5, 1.8, 37, B | |
| LEU, CD1, 85, 0.6, −6.3, 2.4, 37, B | |
| LEU, CD2, 85, −0.4, −7.4, 0.4, 37, B | |
| LEU, C, 85, 1.5, −11.0, 1.8, 35, B | |
| LEU, O, 85, 2.4, −11.3, 0.9, 36, B | |
| PHE, N, 86, 1.5, −11.6, 3.0, 34, B | |
| PHE, CA, 86, 2.6, −12.5, 3.4, 34, B | |
| PHE, CB, 86, 2.6, −12.6, 5.0, 33, B | |
| PHE, CG, 86, 3.7, −11.7, 5.5, 32, B | |
| PHE, CD1, 86, 4.0, −10.5, 4.9, 31, B | |
| PHE, CD2, 86, 4.3, −12.0, 6.7, 31, B | |
| PHE, CE1, 86, 4.9, −9.6, 5.5, 31, B | |
| PHE, CE2, 86, 5.2, −11.2, 7.3, 31, B | |
| PHE, CZ, 86, 5.5, −10.0, 6.7, 31, B | |
| PHE, C, 86, 2.3, −13.9, 2.9, 34, B | |
| PHE, O, 86, 3.2, −14.7, 2.6, 34, B | |
| GLY, N, 87, 1.0, −14.2, 2.7, 34, B | |
| GLY, CA, 87, 0.6, −15.5, 2.2, 33, B | |
| GLY, C, 87, 0.6, −16.6, 3.2, 34, B | |
| GLY, O, 87, 0.6, −17.8, 2.8, 33, B | |
| VAL, N, 88, 0.6, −16.3, 4.5, 33, B | |
| VAL, CA, 88, 0.5, −17.4, 5.5, 34, B | |
| VAL, CB, 88, 1.9, −17.5, 6.2, 34, B | |
| VAL, CG1, 88, 2.9, −18.0, 5.2, 33, B | |
| VAL, CG2, 88, 2.3, −16.3, 6.9, 33, B | |
| VAL, C, 88, −0.5, −17.0, 6.5, 34, B | |
| VAL, O, 88, −0.8, −15.8, 6.7, 34, B | |
| PRO, N, 89, −1.1, −17.9, 7.2, 34, B | |
| PRO, CD, 89, −0.9, −19.4, 7.1, 34, B | |
| PRO, CA, 89, −2.1, −17.7, 8.3, 34, B | |
| PRO, CB, 89, −2.8, −19.0, 8.5, 34, B | |
| PRO, CG, 89, −1.7, −20.0, 8.3, 34, B | |
| PRO, C, 89, −1.5, −17.2, 9.6, 34, B | |
| PRO, O, 89, −2.1, −16.5, 10.3, 34, B | |
| SER, N, 90, −0.2, −17.5, 9.8, 35, B | |
| SER, CA, 90, 0.5, −17.1, 11.0, 35, B | |
| SER, CB, 90, −0.0, −17.9, 12.2, 35, B | |
| SER, OG, 90, 0.4, −19.3, 12.1, 34, B | |
| SER, C, 90, 2.0, −17.4, 10.8, 35, B | |
| SER, O, 90, 2.4, −18.2, 9.9, 35, B | |
| PHE, N, 91, 2.8, −16.9, 11.8, 36, B | |
| PHE, CA, 91, 4.2, −17.1, 11.7, 36, B | |
| PHE, CB, 91, 4.9, −16.4, 10.6, 36, B | |
| PHE, CG, 91, 4.8, −14.9, 10.6, 35, B | |
| PHE, CD1, 91, 5.8, −14.1, 11.2, 35, B | |
| PHE, CD2, 91, 3.6, −14.2, 10.2, 35, B | |
| PHE, CE1, 91, 5.7, −12.8, 11.3, 35, B | |
| PHE, CE2, 91, 3.5, −12.8, 10.3, 35, B | |
| PHE, CZ, 91, 4.5, −12.1, 10.9, 35, B | |
| PHE, C, 91, 4.9, −16.7, 13.0, 37, B | |
| PHE, O, 91, 4.4, −15.9, 13.8, 37, B | |
| SER, N, 92, 6.1, −17.2, 13.2, 38, B | |
| SER, CA, 92, 6.9, −16.8, 14.4, 38, B | |
| SER, CB, 92, 7.8, −17.9, 14.8, 39, B | |
| SER, OG, 92, 8.8, −17.5, 15.8, 39, B | |
| SER, C, 92, 7.8, −15.6, 14.1, 39, B | |
| SER, O, 92, 8.4, −15.5, 13.1, 38, B | |
| VAL, N, 93, 7.8, −14.7, 15.1, 39, B | |
| VAL, CA, 93, 8.6, −13.5, 15.1, 40, B | |
| VAL, CB, 93, 8.3, −12.6, 16.3, 40, B | |
| VAL, CG1, 93, 9.4, −11.6, 16.5, 41, B | |
| VAL, CG2, 93, 7.0, −11.9, 16.0, 40, B | |
| VAL, C, 93, 10.1, −13.8, 15.0, 39, B | |
| VAL, O, 93, 10.9, −13.0, 14.7, 38, B | |
| LYS, N, 94, 10.4, −15.1, 15.4, 40, B | |
| LYS, CA, 94, 11.8, −15.5, 15.4, 41, B | |
| LYS, CB, 94, 12.0, −16.7, 16.3, 43, B | |
| LYS, CG, 94, 11.8, −16.3, 17.8, 44, B | |
| LYS, CD, 94, 11.9, −17.5, 18.7, 45, B | |
| LYS, CE, 94, 12.0, −17.1, 20.2, 46, B | |
| LYS, NZ, 94, 12.2, −18.3, 21.2, 46, B |

TABLE 3-continued

Structural coordinates of HDM2 (17-125; F55Y/Y76H) (SEQ ID NO: 2) complexed with compound 3.

LYS, C, 94, 12.3, −16.0, 14.0, 42, B
LYS, O, 94, 13.5, −15.8, 13.7, 42, B
GLU, N, 95, 11.4, −16.5, 13.2, 42, B
GLU, CA, 95, 11.7, −16.9, 11.8, 42, B
GLU, CB, 95, 10.5, −17.7, 11.2, 43, B
GLU, CG, 95, 10.0, −18.9, 12.0, 43, B
GLU, CD, 95, 8.7, −19.5, 11.5, 43, B
GLU, OE1, 95, 7.7, −18.9, 11.5, 43, B
GLU, OE2, 95, 8.8, −20.7, 11.1, 44, B
GLU, C, 95, 12.1, −15.8, 10.9, 42, B
GLU, O, 95, 11.3, −15.3, 10.1, 42, B
HIS, N, 96, 13.3, −15.3, 11.2, 42, B
HIS, CA, 96, 13.8, −14.1, 10.4, 42, B
HIS, CB, 96, 15.1, −13.7, 11.1, 43, B
HIS, CG, 96, 15.0, −13.2, 12.5, 43, B
HIS, CD2, 96, 13.8, −13.0, 13.2, 43, B
HIS, ND1, 96, 16.0, −12.9, 13.3, 43, B
HIS, CE1, 96, 15.6, −12.5, 14.5, 43, B
HIS, NE2, 96, 14.2, −12.5, 14.5, 43, B
HIS, C, 96, 14.0, −14.2, 8.9, 42, B
HIS, O, 96, 13.6, −13.3, 8.2, 42, B
ARG, N, 97, 14.6, −15.3, 8.5, 42, B
ARG, CA, 97, 14.8, −15.5, 7.0, 42, B
ARG, CB, 97, 15.6, −16.9, 6.8, 43, B
ARG, CG, 97, 15.4, −17.4, 5.4, 44, B
ARG, CD, 97, 15.9, −18.9, 5.3, 45, B
ARG, NE, 97, 15.3, −19.8, 6.2, 46, B
ARG, CZ, 97, 14.0, −20.0, 6.3, 47, B
ARG, NH1, 97, 13.2, −19.3, 5.6, 47, B
ARG, NH2, 97, 13.6, −21.0, 7.2, 47, B
ARG, C, 97, 13.5, −15.6, 6.3, 41, B
ARG, O, 97, 13.3, −14.9, 5.3, 40, B
LYS, N, 98, 12.6, −16.3, 6.9, 41, B
LYS, CA, 98, 11.2, −16.5, 6.4, 40, B
LYS, CB, 98, 10.5, −17.4, 7.3, 41, B
LYS, CG, 98, 9.4, −18.3, 6.7, 42, B
LYS, CD, 98, 9.3, −19.7, 7.4, 43, B
LYS, CE, 98, 10.7, −20.4, 7.2, 44, B
LYS, NZ, 98, 10.7, −21.8, 7.8, 44, B
LYS, C, 98, 10.5, −15.2, 6.2, 39, B
LYS, O, 98, 9.9, −14.9, 5.2, 39, B
ILE, N, 99, 10.5, −14.3, 7.2, 38, B
ILE, CA, 99, 9.9, −13.1, 7.2, 37, B
ILE, CB, 99, 9.9, −12.4, 8.6, 37, B
ILE, CG2, 99, 9.4, −11.0, 8.6, 37, B
ILE, CG1, 99, 9.1, −13.2, 9.6, 37, B
ILE, CD1, 99, 9.2, −12.8, 11.0, 37, B
ILE, C, 99, 10.4, −12.1, 6.1, 36, B
ILE, O, 99, 9.7, −11.4, 5.5, 35, B
TYR, N, 100, 11.7, −12.2, 5.9, 36, B
TYR, CA, 100, 12.4, −11.3, 4.9, 35, B
TYR, CB, 100, 13.9, −11.5, 4.9, 36, B
TYR, CG, 100, 14.6, −10.7, 6.0, 37, B
TYR, CD1, 100, 15.4, −11.2, 6.9, 37, B
TYR, CE1, 100, 16.1, −10.4, 7.8, 37, B
TYR, CD2, 100, 14.6, −9.3, 5.9, 37, B
TYR, CE2, 100, 15.2, −8.5, 6.8, 37, B
TYR, CZ, 100, 16.0, −9.0, 7.8, 37, B
TYR, OH, 100, 16.7, −8.2, 8.6, 37, B
TYR, C, 100, 11.8, −11.7, 3.6, 35, B
TYR, O, 100, 11.6, −10.8, 2.7, 34, B
THR, N, 101, 11.7, −13.0, 3.3, 34, B
THR, CA, 101, 11.2, −13.5, 2.1, 34, B
THR, CB, 101, 11.2, −15.1, 2.1, 35, B
THR, OG1, 101, 12.6, −15.5, 2.0, 36, B
THR, CG2, 101, 10.5, −15.6, 0.9, 35, B
THR, C, 101, 9.8, −13.0, 1.8, 34, B
THR, O, 101, 9.5, −12.6, 0.7, 34, B
MET, N, 102, 8.9, −13.0, 2.8, 33, B
MET, CA, 102, 7.6, −12.5, 2.7, 33, B
MET, CB, 102, 6.7, −12.9, 3.9, 33, B
MET, CG, 102, 6.8, −14.4, 4.2, 33, B
MET, SD, 102, 5.6, −15.0, 5.4, 33, B
MET, CE, 102, 6.4, −14.5, 7.0, 33, B
MET, C, 102, 7.6, −11.0, 2.4, 33, B
MET, O, 102, 6.8, −10.6, 1.6, 34, B

TABLE 3-continued

Structural coordinates of HDM2 (17-125; F55Y/Y76H) (SEQ ID NO: 2) complexed with compound 3.

ILE, N, 103, 8.4, −10.3, 3.0, 33, B
ILE, CA, 103, 8.5, −8.8, 2.8, 32, B
ILE, CB, 103, 9.4, −8.2, 3.9, 32, B
ILE, CG2, 103, 9.5, −6.7, 3.6, 32, B
ILE, CG1, 103, 8.8, −8.3, 5.3, 32, B
ILE, CD1, 103, 9.6, −7.7, 6.4, 31, B
ILE, C, 103, 9.0, −8.4, 1.5, 33, B
ILE, O, 103, 8.5, −7.5, 0.9, 33, B
TYR, N, 104, 10.0, −9.1, 1.0, 34, B
TYR, CA, 104, 10.6, −8.9, −0.3, 35, B
TYR, CB, 104, 11.8, −9.9, −0.6, 34, B
TYR, CG, 104, 13.0, −9.7, 0.2, 35, B
TYR, CD1, 104, 13.8, −10.8, 0.6, 35, B
TYR, CE1, 104, 14.9, −10.6, 1.4, 35, B
TYR, CD2, 104, 13.4, −8.4, 0.5, 35, B
TYR, CE2, 104, 14.6, −8.2, 1.3, 35, B
TYR, CZ, 104, 15.3, −9.3, 1.7, 35, B
TYR, OH, 104, 16.5, −9.1, 2.4, 35, B
TYR, C, 104, 9.6, −9.0, −1.4, 35, B
TYR, O, 104, 9.5, −8.1, −2.3, 35, B
ARG, N, 105, 8.8, −10.0, −1.4, 36, B
ARG, CA, 105, 7.7, −10.2, −2.4, 36, B
ARG, CB, 105, 6.8, −11.3, −2.0, 37, B
ARG, CG, 105, 7.4, −12.7, −2.0, 39, B
ARG, CD, 105, 6.2, −13.8, −2.2, 41, B
ARG, NE, 105, 6.6, −15.1, −1.9, 42, B
ARG, CZ, 105, 7.7, −15.8, −2.4, 43, B
ARG, NH1, 105, 8.5, −15.1, −3.3, 43, B
ARG, NH2, 105, 8.0, −17.0, −2.0, 43, B
ARG, C, 105, 6.9, −9.0, −2.6, 36, B
ARG, O, 105, 6.5, −8.7, −3.7, 35, B
ASN, N, 106, 6.7, −8.2, −1.5, 36, B
ASN, CA, 106, 5.9, −7.0, −1.6, 36, B
ASN, CB, 106, 5.0, −6.9, −0.3, 36, B
ASN, CG, 106, 4.1, −8.1, −0.2, 36, B
ASN, OD1, 106, 4.4, −9.1, 0.4, 36, B
ASN, ND2, 106, 2.9, −8.0, −0.7, 37, B
ASN, C, 106, 6.7, −5.7, −1.7, 37, B
ASN, O, 106, 6.2, −4.6, −1.4, 36, B
LEU, N, 107, 7.9, −5.9, −2.1, 37, B
LEU, CA, 107, 8.8, −4.7, −2.3, 37, B
LEU, CB, 107, 9.9, −4.8, −1.1, 37, B
LEU, CG, 107, 9.6, −4.1, 0.2, 38, B
LEU, CD1, 107, 10.6, −4.4, 1.2, 38, B
LEU, CD2, 107, 9.5, −2.6, −0.1, 38, B
LEU, C, 107, 9.6, −4.7, −3.6, 36, B
LEU, O, 107, 9.7, −5.7, −4.2, 36, B
VAL, N, 108, 10.1, −3.5, −3.9, 37, B
VAL, CA, 108, 10.9, −3.2, −5.0, 37, B
VAL, CB, 108, 10.1, −2.4, −6.1, 37, B
VAL, CG1, 108, 11.1, −1.7, −7.1, 37, B
VAL, CG2, 108, 9.1, −3.3, −6.9, 37, B
VAL, C, 108, 12.1, −2.5, −4.5, 37, B
VAL, O, 108, 11.9, −1.5, −3.8, 38, B
VAL, N, 109, 13.3, −2.9, −4.9, 38, B
VAL, CA, 109, 14.5, −2.2, −4.4, 39, B
VAL, CB, 109, 15.7, −3.2, −4.5, 38, B
VAL, CG1, 109, 17.0, −2.5, −4.1, 38, B
VAL, CG2, 109, 15.5, −4.4, −3.6, 38, B
VAL, C, 109, 14.8, −1.0, −5.3, 39, B
VAL, O, 109, 14.7, −1.1, −6.5, 40, B
VAL, N, 110, 15.2, 0.1, −4.7, 40, B
VAL, CA, 110, 15.5, 1.3, −5.5, 41, B
VAL, CB, 110, 14.4, 2.4, −5.2, 41, B
VAL, CG1, 110, 13.1, 1.9, −5.8, 41, B
VAL, CG2, 110, 14.3, 2.7, −3.8, 41, B
VAL, C, 110, 16.8, 1.9, −5.1, 42, B
VAL, O, 110, 17.5, 1.5, −4.2, 42, B
ASN, N, 111, 17.2, 2.9, −5.9, 43, B
ASN, CA, 111, 18.5, 3.6, −5.7, 45, B
ASN, CB, 111, 18.8, 4.7, −6.8, 45, B
ASN, CG, 111, 19.1, 4.0, −8.1, 45, B
ASN, OD1, 111, 19.5, 2.9, −8.2, 45, B
ASN, ND2, 111, 18.9, 4.8, −9.2, 45, B
ASN, C, 111, 18.5, 4.4, −4.4, 45, B
ASN, O, 111, 18.6, 5.6, −4.4, 46, B

TABLE 3-continued

Structural coordinates of HDM2 (17-125; F55Y/Y76H) (SEQ ID NO: 2) complexed with compound 3.

SCH, F1, 1, 16.7, 1.8, 23.4, 34, I
SCH, F2, 1, 18.1, 0.2, 23.1, 34, I
SCH, F3, 1, 16.2, −0.2, 24.1, 35, I
SCH, F4, 1, 17.7, 1.5, 15.3, 34, I
SCH, F5, 1, 16.0, 2.1, 16.4, 35, I
SCH, F6, 1, 17.3, 3.6, 15.6, 34, I
SCH, C1, 1, 12.2, −0.2, 17.7, 33, I
SCH, C2, 1, 12.4, 1.2, 17.1, 33, I
SCH, C3, 1, 12.7, 1.0, 15.6, 33, I
SCH, N1, 1, 13.7, −0.0, 15.3, 32, I
SCH, C4, 1, 13.5, −1.4, 15.9, 33, I
SCH, C5, 1, 13.4, −1.2, 17.5, 33, I
SCH, C6, 1, 13.0, −2.7, 18.1, 33, I
SCH, N2, 1, 14.0, −3.6, 18.3, 34, I
SCH, O1, 1, 11.8, −2.9, 18.4, 34, I
SCH, O2, 1, 14.6, −0.6, 17.9, 33, I
SCH, C7, 1, 15.0, −0.4, 19.2, 34, I
SCH, C8, 1, 16.3, 0.2, 19.3, 34, I
SCH, C9, 1, 16.9, 0.5, 20.6, 34, I
SCH, C10, 1, 16.2, 0.2, 21.8, 34, I
SCH, C11, 1, 14.9, −0.4, 21.7, 34, I
SCH, C12, 1, 14.3, −0.7, 20.5, 34, I
SCH, C13, 1, 14.9, 0.2, 14.5, 32, I
SCH, O3, 1, 15.8, −0.7, 14.5, 32, I
SCH, C14, 1, 15.1, 1.4, 13.7, 32, I
SCH, C15, 1, 14.3, 1.5, 12.5, 33, I
SCH, N3, 1, 14.4, 2.6, 11.7, 33, I
SCH, C16, 1, 15.3, 3.6, 12.0, 33, I
SCH, C17, 1, 16.1, 3.6, 13.2, 33, I
SCH, C18, 1, 16.0, 2.5, 14.1, 33, I
SCH, C19, 1, 13.6, −4.9, 19.0, 34, I
SCH, C20, 1, 14.5, −5.0, 20.3, 34, I
SCH, N4, 1, 15.9, −5.0, 20.0, 35, I
SCH, C21, 1, 16.4, −3.9, 19.0, 34, I
SCH, C22, 1, 15.4, −3.6, 17.8, 34, I
SCH, C23, 1, 16.8, −5.3, 21.1, 35, I
SCH, C24, 1, 17.5, −4.3, 21.8, 35, I
SCH, C25, 1, 18.3, −4.7, 22.9, 35, I
SCH, C26, 1, 18.4, −6.0, 23.4, 35, I
SCH, C27, 1, 17.6, −7.0, 22.7, 36, I
SCH, C28, 1, 16.8, −6.7, 21.5, 36, I
SCH, O4, 1, 16.1, −7.6, 20.8, 37, I
SCH, C32, 1, 15.5, −8.8, 21.4, 38, I
SCH, C33, 1, 14.0, −8.9, 21.1, 39, I
SCH, O5, 1, 13.3, −8.6, 22.3, 40, I
SCH, C34, 1, 12.3, −9.6, 22.7, 40, I
SCH, C35, 1, 16.8, 0.5, 23.2, 34, I
SCH, C36, 1, 16.8, 2.4, 15.4, 34, I
SCH, C37, 1, 12.4, −2.2, 15.2, 32, I
SCH, C38, 1, 12.7, −2.4, 13.6, 32, I
SCH, C39, 1, 13.9, −3.3, 13.4, 31, I
SCH, F1, 1, 5.6, −8.3, 10.6, 33, J
SCH, F2, 1, 7.1, −9.8, 10.7, 33, J
SCH, F3, 1, 7.6, −7.9, 9.9, 33, J
SCH, F4, 1, 5.4, −10.2, 17.9, 37, J
SCH, F5, 1, 4.9, −8.2, 17.3, 37, J
SCH, F6, 1, 3.3, −9.6, 17.9, 38, J
SCH, C1, 1, 8.1, −4.7, 16.7, 34, J
SCH, C2, 1, 6.6, −4.9, 17.3, 34, J
SCH, C3, 1, 6.6, −5.6, 18.7, 34, J
SCH, N1, 1, 7.5, −6.7, 18.8, 34, J
SCH, C4, 1, 9.0, −6.4, 18.4, 34, J
SCH, C5, 1, 8.9, −6.0, 16.9, 34, J
SCH, C6, 1, 10.4, −5.7, 16.3, 34, J
SCH, N2, 1, 11.3, −6.7, 16.1, 35, J
SCH, O1, 1, 10.7, −4.5, 16.1, 34, J
SCH, O2, 1, 8.3, −7.1, 16.2, 34, J
SCH, C7, 1, 8.0, −7.3, 14.9, 33, J
SCH, C8, 1, 7.2, −8.5, 14.6, 33, J
SCH, C9, 1, 6.9, −8.9, 13.3, 33, J
SCH, C10, 1, 7.3, −8.1, 12.2, 33, J
SCH, C11, 1, 8.1, −7.0, 12.4, 33, J
SCH, C12, 1, 8.5, −6.6, 13.7, 33, J
SCH, C13, 1, 7.2, −8.0, 19.3, 35, J
SCH, O3, 1, 8.0, −8.9, 19.1, 35, J
SCH, C14, 1, 6.0, −8.2, 20.1, 36, J
SCH, C15, 1, 6.0, −7.9, 21.5, 37, J
SCH, N3, 1, 5.0, −8.0, 22.3, 37, J
SCH, C16, 1, 3.8, −8.6, 21.8, 37, J
SCH, C17, 1, 3.7, −8.9, 20.5, 37, J
SCH, C18, 1, 4.8, −8.8, 19.6, 37, J
SCH, C19, 1, 12.7, −6.4, 15.5, 35, J
SCH, C20, 1, 12.8, −7.0, 14.2, 35, J
SCH, N4, 1, 12.6, −8.5, 14.2, 36, J
SCH, C21, 1, 11.5, −9.0, 15.0, 36, J
SCH, C22, 1, 11.2, −8.2, 16.3, 35, J
SCH, C23, 1, 13.0, −9.1, 12.9, 37, J
SCH, C24, 1, 12.0, −9.6, 12.1, 36, J
SCH, C25, 1, 12.3, −10.2, 10.8, 37, J
SCH, C26, 1, 13.6, −10.4, 10.5, 37, J
SCH, C27, 1, 14.6, −9.9, 11.3, 37, J
SCH, C28, 1, 14.4, −9.3, 12.6, 37, J
SCH, O4, 1, 15.4, −8.8, 13.5, 38, J
SCH, C32, 1, 16.6, −8.3, 12.9, 39, J
SCH, C33, 1, 16.6, −6.8, 12.7, 39, J
SCH, O5, 1, 16.8, −6.2, 14.0, 40, J
SCH, C34, 1, 17.3, −4.8, 13.9, 40, J
SCH, C35, 1, 6.9, −8.5, 10.8, 33, J
SCH, C36, 1, 4.6, −9.2, 18.1, 37, J
SCH, C37, 1, 9.7, −5.5, 19.3, 34, J
SCH, C38, 1, 9.8, −6.0, 20.8, 34, J
SCH, C39, 1, 10.9, −5.3, 21.6, 35, J
WAT, OH2, 1, 9.1, 0.6, 19.1, 28, W
WAT, OH2, 101, 15.6, 7.6, 38.1, 32, W
WAT, OH2, 102, 1.5, −1.9, 36.6, 58, W
WAT, OH2, 103, 24.8, −8.9, 22.3, 43, W
WAT, OH2, 104, 19.7, −10.8, 22.1, 38, W
WAT, OH2, 105, 19.4, 3.3, 42.4, 35, W
WAT, OH2, 106, 0.6, −4.8, −4.3, 34, W
WAT, OH2, 107, 1.2, −5.1, −7.2, 39, W
WAT, OH2, 108, 9.4, 9.2, −0.7, 58, W
WAT, OH2, 109, 7.4, −1.5, 15.7, 36, W
WAT, OH2, 110, 13.0, −18.3, 9.2, 36, W
WAT, OH2, 111, 15.8, −17.0, 10.7, 45, W
WAT, OH2, 201, 7.3, −11.3, 21.0, 41, W
WAT, OH2, 202, 14.4, −9.0, 16.4, 34, W
WAT, OH2, 203, 13.1, −11.4, 17.5, 41, W
WAT, OH2, 204, 4.5, −19.9, 8.4, 55, W
WAT, OH2, 205, 3.4, −20.3, 12.6, 35, W
WAT, OH2, 206, 1.9, 0.7, 21.0, 39, W
WAT, OH2, 207, 11.5, 14.1, 26.0, 40, W
WAT, OH2, 208, 29.1, 10.0, 19.6, 42, W
WAT, OH2, 209, 27.6, 12.1, 20.2, 51, W
WAT, OH2, 210, 23.6, −10.1, 24.8, 41, W
WAT, OH2, 211, −5.2, −15.4, 12.6, 31, W
WAT, OH2, 212, 8.8, −19.8, 17.9, 45, W
WAT, OH2, 301, 17.6, −10.4, 17.3, 36, W

The crystalline coordinates are set forth below in the following format (1), (2), (3) . . . (8); the legend for these data is as follows:
(1) Residue name
Three letter amino acid name
SCH = schering inhibitor
WAT = water
(2) Atom name
(3) Residue Number
(4) X - coordinate
(5) Y - coordinate
(6) Z - coordinate
(7) B-factor
(8) Chain ID
Disordered residues are not represented in the table.

TABLE 4

Structural coordinates of HDM2 (17-125; F55Y/Y76H) (SEQ ID NO: 2) complexed with compound 4.

GLN, N, 18, −33.6, 23.0, 22.8, 57, A
GLN, CA, 18, −32.2, 22.8, 22.6, 56, A
GLN, C, 18, −31.8, 21.4, 22.1, 56, A

TABLE 4-continued

Structural coordinates of HDM2 (17-125; F55Y/Y76H) (SEQ ID NO: 2) complexed with compound 4.

GLN, O, 18, −31.0, 20.8, 22.6, 57, A
GLN, CB, 18, −31.4, 23.2, 23.8, 58, A
GLN, CG, 18, −30.7, 24.6, 23.6, 81, A
GLN, CD, 18, −30.0, 25.1, 24.9, 0, A
GLN, OE1, 18, −29.2, 24.4, 25.5, 0, A
GLN, NE2, 18, −30.3, 26.3, 25.3, 0, A
ILE, N, 19, −32.5, 21.0, 21.0, 46, A
ILE, CA, 19, −32.3, 19.7, 20.3, 42, A
ILE, C, 19, −31.9, 20.2, 18.9, 39, A
ILE, O, 19, −32.4, 21.3, 18.5, 36, A
ILE, CB, 19, −33.6, 18.9, 20.3, 45, A
ILE, CG1, 19, −33.3, 17.4, 20.6, 46, A
ILE, CG2, 19, −34.3, 19.0, 19.0, 45, A
ILE, CD1, 19, −34.2, 16.8, 21.6, 48, A
PRO, N, 20, −31.0, 19.5, 18.2, 33, A
PRO, CA, 20, −30.7, 20.1, 16.9, 31, A
PRO, C, 20, −31.9, 20.1, 16.0, 36, A
PRO, O, 20, −32.8, 19.4, 16.1, 34, A
PRO, CB, 20, −29.5, 19.3, 16.4, 32, A
PRO, CG, 20, −29.5, 18.0, 17.3, 37, A
PRO, CD, 20, −30.1, 18.4, 18.6, 33, A
ALA, N, 21, −31.9, 21.1, 15.0, 33, A
ALA, CA, 21, −33.0, 21.2, 14.0, 34, A
ALA, C, 21, −33.0, 20.1, 13.1, 35, A
ALA, O, 21, −34.0, 19.9, 12.4, 33, A
ALA, CB, 21, −32.9, 22.6, 13.3, 35, A
SER, N, 22, −31.9, 19.3, 13.0, 31, A
SER, CA, 22, −31.8, 18.1, 12.2, 29, A
SER, C, 22, −30.6, 17.3, 12.6, 29, A
SER, O, 22, −29.7, 17.8, 13.3, 31, A
SER, CB, 22, −31.6, 18.5, 10.7, 28, A
SER, OG, 22, −30.4, 19.0, 10.5, 31, A
GLU, N, 23, −30.5, 16.1, 12.2, 25, A
GLU, CA, 23, −29.4, 15.2, 12.5, 25, A
GLU, C, 23, −28.0, 15.8, 12.3, 29, A
GLU, O, 23, −27.1, 15.9, 13.1, 28, A
GLU, CB, 23, −29.6, 13.8, 11.9, 26, A
GLU, CG, 23, −28.6, 12.7, 12.4, 30, A
GLU, CD, 23, −28.8, 12.3, 13.8, 46, A
GLU, OE1, 23, −28.0, 11.6, 14.4, 35, A
GLU, OE2, 23, −29.9, 12.7, 14.4, 29, A
GLN, N, 24, −27.8, 16.4, 11.1, 24, A
GLN, CA, 24, −26.6, 17.0, 10.7, 24, A
GLN, C, 24, −26.3, 18.4, 11.4, 29, A
GLN, O, 24, −25.2, 18.9, 11.3, 27, A
GLN, CB, 24, −26.4, 17.1, 9.2, 25, A
GLN, CG, 24, −26.2, 15.8, 8.5, 46, A
GLN, CD, 24, −27.6, 15.2, 8.1, 93, A
GLN, OE1, 24, −28.7, 15.6, 8.6, 92, A
GLN, NE2, 24, −27.5, 14.2, 7.2, 92, A
GLU, N, 25, −27.3, 18.9, 12.1, 26, A
GLU, CA, 25, −27.1, 20.2, 12.8, 24, A
GLU, C, 25, −26.6, 19.9, 14.2, 28, A
GLU, O, 25, −26.5, 20.8, 15.0, 28, A
GLU, CB, 25, −28.4, 21.0, 12.8, 25, A
GLU, CG, 25, −28.6, 21.6, 11.4, 33, A
GLU, CD, 25, −27.6, 22.6, 10.9, 42, A
GLU, OE1, 25, −27.5, 23.7, 11.5, 29, A
GLU, OE2, 25, −26.7, 22.2, 10.1, 31, A
THR, N, 26, −26.3, 18.7, 14.5, 25, A
THR, CA, 26, −25.8, 18.3, 15.8, 22, A
THR, C, 26, −24.6, 19.1, 16.1, 24, A
THR, O, 26, −23.8, 19.3, 15.2, 22, A
THR, CB, 26, −25.5, 16.8, 15.8, 23, A
THR, OG1, 26, −26.6, 16.0, 15.8, 23, A
THR, CG2, 26, −24.6, 16.3, 17.1, 19, A
LEU, N, 27, −24.5, 19.7, 17.3, 23, A
LEU, CA, 27, −23.3, 20.5, 17.6, 25, A
LEU, C, 27, −22.2, 19.6, 18.2, 28, A
LEU, O, 27, −22.5, 18.8, 19.1, 26, A
LEU, CB, 27, −23.6, 21.7, 18.5, 25, A
LEU, CG, 27, −24.5, 22.7, 17.8, 30, A
LEU, CD1, 27, −25.0, 23.7, 18.8, 30, A
LEU, CD2, 27, −23.8, 23.4, 16.6, 30, A
VAL, N, 28, −21.0, 19.7, 17.7, 22, A
VAL, CA, 28, −19.9, 18.9, 18.2, 21, A
VAL, C, 28, −18.7, 19.7, 18.5, 28, A
VAL, O, 28, −18.4, 20.7, 17.8, 27, A
VAL, CB, 28, −19.6, 17.7, 17.3, 23, A
VAL, CG1, 28, −20.9, 16.9, 17.0, 22, A
VAL, CG2, 28, −19.1, 18.3, 15.9, 22, A
ARG, N, 29, −17.9, 19.2, 19.4, 25, A
ARG, CA, 29, −16.6, 19.8, 19.7, 27, A
ARG, C, 29, −15.5, 18.8, 19.4, 28, A
ARG, O, 29, −15.3, 17.7, 20.0, 28, A
ARG, CB, 29, −16.5, 20.2, 21.2, 29, A
ARG, CG, 29, −16.9, 21.7, 21.3, 40, A
ARG, CD, 29, −16.9, 22.3, 22.7, 42, A
ARG, NE, 29, −18.0, 23.3, 22.9, 49, A
ARG, CZ, 29, −18.4, 23.7, 24.1, 57, A
ARG, NH1, 29, −17.9, 23.1, 25.2, 35, A
ARG, NH2, 29, −19.4, 24.6, 24.2, 44, A
PRO, N, 30, −14.7, 19.0, 18.3, 26, A
PRO, CA, 30, −13.7, 18.1, 17.9, 25, A
PRO, C, 30, −12.6, 17.9, 19.0, 31, A
PRO, O, 30, −12.3, 18.9, 19.7, 30, A
PRO, CB, 30, −13.1, 18.7, 16.6, 27, A
PRO, CG, 30, −14.3, 19.6, 16.0, 31, A
PRO, CD, 30, −14.9, 20.2, 17.3, 26, A
LYS, N, 31, −12.1, 16.7, 19.1, 28, A
LYS, CA, 31, −11.0, 16.5, 20.0, 27, A
LYS, C, 31, −9.7, 17.1, 19.4, 29, A
LYS, O, 31, −9.7, 17.4, 18.2, 25, A
LYS, CB, 31, −10.8, 15.0, 20.3, 28, A
LYS, CG, 31, −12.1, 14.4, 20.9, 37, A
LYS, CD, 31, −12.0, 12.9, 20.8, 44, A
LYS, CE, 31, −12.7, 12.3, 22.0, 59, A
LYS, NZ, 31, −13.2, 10.9, 21.8, 67, A
PRO, N, 32, −8.7, 17.4, 20.2, 30, A
PRO, CA, 32, −7.6, 18.2, 19.7, 30, A
PRO, C, 32, −7.0, 17.9, 18.4, 33, A
PRO, O, 32, −6.8, 18.8, 17.6, 34, A
PRO, CB, 32, −6.5, 18.0, 20.9, 32, A
PRO, CG, 32, −7.3, 17.8, 22.1, 35, A
PRO, CD, 32, −8.7, 17.2, 21.7, 31, A
LEU, N, 33, −6.8, 16.6, 18.1, 28, A
LEU, CA, 33, −6.2, 16.2, 16.8, 29, A
LEU, C, 33, −7.1, 16.5, 15.6, 32, A
LEU, O, 33, −6.7, 17.1, 14.6, 33, A
LEU, CB, 33, −5.7, 14.8, 16.7, 31, A
LEU, CG, 33, −4.3, 14.5, 17.3, 39, A
LEU, CD1, 33, −4.2, 15.2, 18.6, 40, A
LEU, CD2, 33, −4.0, 13.0, 17.4, 42, A
LEU, N, 34, −8.4, 16.2, 15.7, 26, A
LEU, CA, 34, −9.4, 16.6, 14.7, 26, A
LEU, C, 34, −9.4, 18.1, 14.5, 28, A
LEU, O, 34, −9.4, 18.6, 13.4, 25, A
LEU, CB, 34, −10.8, 15.9, 15.0, 24, A
LEU, CG, 34, −11.9, 16.4, 14.0, 26, A
LEU, CD1, 34, −11.5, 16.2, 12.6, 24, A
LEU, CD2, 34, −13.3, 15.8, 14.3, 26, A
LEU, N, 35, −9.5, 18.8, 15.6, 28, A
LEU, CA, 35, −9.5, 20.3, 15.6, 28, A
LEU, C, 35, −8.2, 20.8, 14.8, 30, A
LEU, O, 35, −8.3, 21.7, 14.0, 28, A
LEU, CB, 35, −9.4, 20.9, 17.0, 29, A
LEU, CG, 35, −9.5, 22.4, 17.2, 33, A
LEU, CD1, 35, −10.7, 22.9, 16.4, 34, A
LEU, CD2, 35, −9.6, 22.7, 18.7, 35, A
LYS, N, 36, −7.1, 20.2, 15.1, 27, A
LYS, CA, 36, −5.9, 20.5, 14.4, 26, A
LYS, C, 36, −6.0, 20.3, 12.9, 29, A
LYS, O, 36, −5.6, 21.1, 12.1, 30, A
LYS, CB, 36, −4.7, 19.6, 14.9, 28, A
LYS, CG, 36, −3.4, 19.9, 14.1, 35, A
LYS, CD, 36, −2.3, 18.9, 14.6, 48, A
LYS, CE, 36, −1.0, 19.1, 13.9, 53, A
LYS, NZ, 36, 0.0, 18.1, 14.2, 68, A
LEU, N, 37, −6.6, 19.2, 12.5, 27, A
LEU, CA, 37, −6.9, 18.9, 11.1, 27, A
LEU, C, 37, −7.8, 20.0, 10.5, 32, A
LEU, O, 37, −7.5, 20.6, 9.4, 31, A

TABLE 4-continued

Structural coordinates of HDM2 (17-125; F55Y/Y76H) (SEQ ID NO: 2) complexed with compound 4.

| | |
|---|---|
| LEU, CB, 37, −7.5, 17.5, 10.9, 28, A | TYR, N, 48, −18.9, 23.1, 16.0, 26, A |
| LEU, CG, 37, −7.4, 17.0, 9.4, 33, A | TYR, CA, 48, −19.4, 23.0, 14.6, 26, A |
| LEU, CD1, 37, −7.5, 15.5, 9.4, 34, A | TYR, C, 48, −20.7, 22.2, 14.6, 29, A |
| LEU, CD2, 37, −8.5, 17.8, 8.6, 36, A | TYR, O, 48, −20.9, 21.3, 15.4, 28, A |
| LEU, N, 38, −8.9, 20.3, 11.2, 28, A | TYR, CB, 48, −18.3, 22.2, 13.8, 28, A |
| LEU, CA, 38, −9.8, 21.4, 10.7, 28, A | TYR, CG, 48, −17.0, 22.8, 13.8, 29, A |
| LEU, C, 38, −9.1, 22.7, 10.5, 32, A | TYR, CD1, 48, −16.1, 22.6, 14.9, 31, A |
| LEU, O, 38, −9.4, 23.5, 9.5, 29, A | TYR, CD2, 48, −16.6, 23.6, 12.8, 31, A |
| LEU, CB, 38, −11.0, 21.5, 11.6, 28, A | TYR, CE1, 48, −14.8, 23.3, 14.9, 33, A |
| LEU, CG, 38, −12.2, 20.6, 11.4, 32, A | TYR, CE2, 48, −15.3, 24.2, 12.7, 32, A |
| LEU, CD1, 38, −11.9, 19.4, 10.5, 32, A | TYR, CZ, 48, −14.5, 24.0, 13.8, 41, A |
| LEU, CD2, 38, −12.8, 20.2, 12.8, 34, A | TYR, OH, 48, −13.2, 24.6, 13.7, 43, A |
| LYS, N, 39, −8.3, 23.1, 11.5, 29, A | THR, N, 49, −21.4, 22.3, 13.5, 26, A |
| LYS, CA, 39, −7.6, 24.4, 11.5, 29, A | THR, CA, 49, −22.5, 21.4, 13.2, 26, A |
| LYS, C, 39, −6.6, 24.5, 10.3, 32, A | THR, C, 49, −21.8, 20.2, 12.5, 30, A |
| LYS, O, 39, −6.4, 25.6, 9.8, 31, A | THR, O, 49, −20.7, 20.3, 12.0, 28, A |
| LYS, CB, 39, −6.8, 24.6, 12.8, 32, A | THR, CB, 49, −23.6, 22.0, 12.2, 27, A |
| LYS, CG, 39, −7.7, 25.0, 14.0, 49, A | THR, OG1, 49, −22.9, 22.4, 11.0, 25, A |
| LYS, CD, 39, −7.0, 24.9, 15.3, 49, A | THR, CG2, 49, −24.3, 23.2, 12.9, 26, A |
| LYS, CE, 39, −5.6, 25.5, 15.2, 55, A | MET, N, 50, −22.4, 19.0, 12.5, 26, A |
| LYS, NZ, 39, −4.8, 25.2, 16.4, 62, A | MET, CA, 50, −21.8, 17.8, 11.9, 25, A |
| SER, N, 40, −6.1, 23.4, 9.8, 30, A | MET, C, 50, −21.5, 18.2, 10.4, 27, A |
| SER, CA, 40, −5.2, 23.4, 8.7, 30, A | MET, O, 50, −20.6, 17.7, 9.8, 26, A |
| SER, C, 40, −5.9, 23.8, 7.4, 35, A | MET, CB, 50, −22.6, 16.6, 12.0, 26, A |
| SER, O, 40, −5.3, 24.1, 6.4, 37, A | MET, CG, 50, −22.4, 15.8, 13.4, 29, A |
| SER, CB, 40, −4.5, 22.0, 8.6, 34, A | MET, SD, 50, −20.8, 15.1, 13.5, 32, A |
| SER, OG, 40, −5.3, 21.1, 7.8, 40, A | MET, CE, 50, −20.8, 14.0, 12.0, 27, A |
| VAL, N, 41, −7.2, 23.7, 7.5, 30, A | LYS, N, 51, −22.5, 18.9, 9.7, 23, A |
| VAL, CA, 41, −8.0, 24.0, 6.3, 31, A | LYS, CA, 51, −22.4, 19.3, 8.3, 23, A |
| VAL, C, 41, −8.8, 25.3, 6.4, 36, A | LYS, C, 51, −21.1, 20.0, 8.1, 26, A |
| VAL, O, 41, −9.8, 25.5, 5.7, 37, A | LYS, O, 51, −20.4, 19.7, 7.1, 25, A |
| VAL, CB, 41, −8.8, 22.8, 5.7, 34, A | LYS, CB, 51, −23.5, 20.3, 8.0, 24, A |
| VAL, CG1, 41, −7.9, 21.9, 4.9, 34, A | LYS, CG, 51, −24.7, 19.8, 7.3, 42, A |
| VAL, CG2, 41, −9.6, 22.1, 6.8, 34, A | LYS, CD, 51, −25.7, 20.9, 7.2, 35, A |
| GLY, N, 42, −8.5, 26.1, 7.4, 34, A | LYS, CE, 51, −27.1, 20.3, 7.2, 29, A |
| GLY, CA, 42, −9.2, 27.4, 7.6, 34, A | LYS, NZ, 51, −28.2, 21.3, 6.7, 49, A |
| GLY, C, 42, −10.2, 27.5, 8.7, 37, A | GLU, N, 52, −20.8, 21.0, 9.0, 21, A |
| GLY, O, 42, −10.5, 28.6, 9.1, 37, A | GLU, CA, 52, −19.5, 21.7, 8.9, 21, A |
| ALA, N, 43, −10.6, 26.4, 9.3, 33, A | GLU, C, 52, −18.3, 20.8, 9.0, 25, A |
| ALA, CA, 43, −11.6, 26.4, 10.4, 33, A | GLU, O, 52, −17.3, 21.1, 8.4, 25, A |
| ALA, C, 43, −11.0, 27.1, 11.6, 42, A | GLU, CB, 52, −19.4, 22.8, 10.0, 23, A |
| ALA, O, 43, −9.8, 26.8, 11.9, 44, A | GLU, CG, 52, −20.3, 24.0, 9.6, 28, A |
| ALA, CB, 43, −12.1, 25.0, 10.7, 32, A | GLU, CD, 52, −20.6, 24.9, 10.9, 35, A |
| GLN, N, 44, −11.7, 27.9, 12.3, 39, A | GLU, OE1, 52, −20.1, 24.5, 12.0, 26, A |
| GLN, CA, 44, −11.2, 28.7, 13.4, 40, A | GLU, OE2, 52, −21.3, 25.9, 10.7, 32, A |
| GLN, C, 44, −12.1, 28.7, 14.7, 41, A | VAL, N, 53, −18.4, 19.8, 9.9, 23, A |
| GLN, O, 44, −11.9, 29.5, 15.6, 44, A | VAL, CA, 53, −17.2, 18.9, 10.1, 22, A |
| GLN, CB, 44, −11.0, 30.1, 13.0, 41, A | VAL, C, 53, −17.0, 18.2, 8.7, 26, A |
| GLN, CG, 44, −10.3, 30.2, 11.6, 66, A | VAL, O, 53, −15.9, 18.1, 8.2, 26, A |
| GLN, CD, 44, −10.7, 31.6, 10.8, 80, A | VAL, CB, 53, −17.4, 18.0, 11.3, 23, A |
| GLN, OE1, 44, −11.4, 31.6, 9.9, 72, A | VAL, CG1, 53, −16.3, 16.9, 11.2, 22, A |
| GLN, NE2, 44, −10.1, 32.6, 11.3, 66, A | VAL, CG2, 53, −17.4, 18.8, 12.6, 22, A |
| LYS, N, 45, −13.0, 27.8, 14.7, 34, A | LEU, N, 54, −18.1, 17.7, 8.2, 24, A |
| LYS, CA, 45, −14.0, 27.6, 15.8, 30, A | LEU, CA, 54, −18.0, 16.9, 6.9, 23, A |
| LYS, C, 45, −13.6, 26.4, 16.6, 32, A | LEU, C, 54, −17.5, 17.9, 5.8, 27, A |
| LYS, O, 45, −12.8, 25.6, 16.2, 31, A | LEU, O, 54, −16.7, 17.4, 5.0, 28, A |
| LYS, CB, 45, −15.4, 27.4, 15.2, 30, A | LEU, CB, 54, −19.4, 16.4, 6.5, 24, A |
| LYS, CG, 45, −16.0, 28.5, 14.5, 36, A | LEU, CG, 54, −19.9, 15.2, 7.3, 29, A |
| LYS, CD, 45, −17.4, 28.3, 14.3, 36, A | LEU, CD1, 54, −21.4, 15.1, 7.1, 29, A |
| LYS, CE, 45, −17.7, 27.5, 13.0, 39, A | LEU, CD2, 54, −19.1, 13.9, 6.9, 26, A |
| LYS, NZ, 45, −19.1, 27.0, 13.2, 39, A | TYR, N, 55, −17.9, 19.1, 5.8, 23, A |
| ASP, N, 46, −14.4, 26.3, 17.7, 28, A | TYR, CA, 55, −17.4, 20.1, 4.9, 25, A |
| ASP, CA, 46, −14.3, 25.1, 18.6, 28, A | TYR, C, 55, −15.9, 20.4, 5.0, 30, A |
| ASP, C, 46, −15.5, 24.2, 18.4, 30, A | TYR, O, 55, −15.2, 20.3, 4.0, 29, A |
| ASP, O, 46, −15.4, 23.0, 18.5, 29, A | TYR, CB, 55, −18.2, 21.4, 4.9, 26, A |
| ASP, CB, 46, −14.2, 25.5, 20.1, 30, A | TYR, CG, 55, −17.6, 22.6, 4.2, 27, A |
| ASP, CG, 46, −13.0, 26.4, 20.4, 37, A | TYR, CD1, 55, −17.8, 22.7, 2.8, 28, A |
| ASP, OD1, 46, −13.2, 27.6, 20.4, 33, A | TYR, CD2, 55, −16.8, 23.5, 4.8, 28, A |
| ASP, OD2, 46, −11.9, 25.8, 20.6, 40, A | TYR, CE1, 55, −17.1, 23.7, 2.1, 29, A |
| THR, N, 47, −16.6, 24.9, 18.1, 28, A | TYR, CE2, 55, −16.2, 24.5, 4.2, 28, A |
| THR, CA, 47, −17.9, 24.1, 17.9, 28, A | TYR, CZ, 55, −16.3, 24.6, 2.8, 35, A |
| THR, C, 47, −18.4, 24.2, 16.5, 31, A | TYR, OH, 55, −15.7, 25.7, 2.2, 36, A |
| THR, O, 47, −18.5, 25.3, 15.9, 31, A | TYR, N, 56, −15.4, 20.6, 6.2, 27, A |
| THR, CB, 47, −19.0, 24.7, 18.9, 32, A | TYR, CA, 56, −14.0, 20.9, 6.4, 27, A |
| THR, OG1, 47, −18.4, 24.7, 20.2, 33, A | TYR, C, 56, −13.1, 19.6, 6.1, 30, A |
| THR, CG2, 47, −20.2, 23.8, 18.8, 28, A | TYR, O, 56, −12.0, 19.7, 5.5, 28, A |

TABLE 4-continued

Structural coordinates of HDM2 (17-125; F55Y/Y76H) (SEQ ID NO: 2) complexed with compound 4.

TYR, CB, 56, −13.7, 21.4, 7.8, 28, A
TYR, CG, 56, −14.1, 22.8, 7.9, 32, A
TYR, CD1, 56, −13.4, 23.8, 7.1, 32, A
TYR, CD2, 56, −15.1, 23.3, 8.8, 33, A
TYR, CE1, 56, −13.8, 25.1, 7.1, 29, A
TYR, CE2, 56, −15.4, 24.6, 8.9, 35, A
TYR, CZ, 56, −14.8, 25.5, 8.0, 42, A
TYR, OH, 56, −15.1, 26.9, 8.0, 44, A
LEU, N, 57, −13.7, 18.4, 6.4, 26, A
LEU, CA, 57, −13.0, 17.2, 6.0, 25, A
LEU, C, 57, −12.9, 17.1, 4.5, 28, A
LEU, O, 57, −11.8, 16.7, 3.9, 27, A
LEU, CB, 57, −13.5, 16.0, 6.7, 25, A
LEU, CG, 57, −13.3, 15.8, 8.2, 28, A
LEU, CD1, 57, −14.3, 14.8, 8.7, 27, A
LEU, CD2, 57, −11.8, 15.4, 8.5, 31, A
GLY, N, 58, −13.9, 17.5, 3.8, 25, A
GLY, CA, 58, −13.9, 17.6, 2.3, 25, A
GLY, C, 58, −12.8, 18.5, 1.8, 29, A
GLY, O, 58, −12.1, 18.2, 0.9, 29, A
GLN, N, 59, −12.7, 19.7, 2.5, 25, A
GLN, CA, 59, −11.6, 20.7, 2.1, 26, A
GLN, C, 59, −10.2, 20.1, 2.2, 30, A
GLN, O, 59, −9.4, 20.4, 1.3, 30, A
GLN, CB, 59, −11.7, 21.9, 3.0, 27, A
GLN, CG, 59, −12.9, 22.9, 2.8, 33, A
GLN, CD, 59, −12.9, 23.4, 1.4, 40, A
GLN, OE1, 59, −12.4, 24.4, 1.1, 43, A
GLN, NE2, 59, −13.6, 22.7, 0.5, 37, A
TYR, N, 60, −10.0, 19.4, 3.3, 25, A
TYR, CA, 60, −8.7, 18.8, 3.5, 25, A
TYR, C, 60, −8.4, 17.8, 2.3, 29, A
TYR, O, 60, −7.4, 17.8, 1.7, 28, A
TYR, CB, 60, −8.8, 18.0, 4.8, 27, A
TYR, CG, 60, −7.5, 17.4, 5.2, 29, A
TYR, CD1, 60, −6.5, 18.1, 5.8, 33, A
TYR, CD2, 60, −7.2, 16.0, 4.9, 28, A
TYR, CE1, 60, −5.3, 17.5, 6.2, 33, A
TYR, CE2, 60, −6.1, 15.4, 5.3, 29, A
TYR, CZ, 60, −5.1, 16.2, 5.9, 37, A
TYR, OH, 60, −3.9, 15.5, 6.3, 33, A
ILE, N, 61, −9.4, 16.9, 2.0, 26, A
ILE, CA, 61, −9.3, 15.9, 0.9, 25, A
ILE, C, 61, −9.1, 16.5, −0.5, 29, A
ILE, O, 61, −8.3, 16.0, −1.3, 31, A
ILE, CB, 61, −10.6, 15.0, 0.9, 27, A
ILE, CG1, 61, −10.6, 14.1, 2.2, 27, A
ILE, CG2, 61, −10.8, 14.2, −0.4, 25, A
ILE, CD1, 61, −12.0, 13.6, 2.5, 25, A
MET, N, 62, −9.7, 17.7, −0.7, 25, A
MET, CA, 62, −9.6, 18.4, −2.0, 25, A
MET, C, 62, −8.3, 19.1, −2.1, 32, A
MET, O, 62, −7.7, 19.1, −3.1, 34, A
MET, CB, 62, −10.8, 19.4, −2.1, 26, A
MET, CG, 62, −12.2, 18.8, −2.2, 27, A
MET, SD, 62, −12.4, 17.7, −3.7, 28, A
MET, CE, 62, −12.4, 19.0, −5.0, 24, A
THR, N, 63, −7.9, 19.8, −1.1, 28, A
THR, CA, 63, −6.6, 20.6, −1.1, 29, A
THR, C, 63, −5.4, 19.6, −1.2, 34, A
THR, O, 63, −4.5, 19.9, −1.9, 34, A
THR, CB, 63, −6.5, 21.5, 0.1, 41, A
THR, OG1, 63, −6.5, 20.7, 1.3, 44, A
THR, CG2, 63, −7.6, 22.5, 0.2, 41, A
LYS, N, 64, −5.5, 18.4, −0.6, 28, A
LYS, CA, 64, −4.4, 17.5, −0.6, 28, A
LYS, C, 64, −4.6, 16.5, −1.8, 32, A
LYS, O, 64, −3.7, 15.7, −2.0, 31, A
LYS, CB, 64, −4.3, 16.8, 0.7, 30, A
LYS, CG, 64, −3.9, 17.7, 1.9, 41, A
LYS, CD, 64, −3.6, 16.8, 3.1, 48, A
LYS, CE, 64, −2.2, 17.1, 3.5, 53, A
LYS, NZ, 64, −1.4, 15.8, 3.8, 64, A
ARG, N, 65, −5.7, 16.6, −2.5, 31, A
ARG, CA, 65, −6.0, 15.7, −3.6, 30, A
ARG, C, 65, −5.8, 14.2, −3.1, 32, A

ARG, O, 65, −5.0, 13.5, −3.6, 30, A
ARG, CB, 65, −5.0, 15.9, −4.7, 32, A
ARG, CG, 65, −5.1, 17.3, −5.3, 46, A
ARG, CD, 65, −4.2, 17.4, −6.6, 66, A
ARG, NE, 65, −5.0, 16.9, −7.7, 80, A
ARG, CZ, 65, −4.9, 17.4, −8.9, 97, A
ARG, NH1, 65, −4.0, 18.4, −9.2, 88, A
ARG, NH2, 65, −5.6, 16.9, −9.9, 82, A
LEU, N, 66, −6.6, 13.9, −2.1, 29, A
LEU, CA, 66, −6.4, 12.5, −1.5, 27, A
LEU, C, 66, −7.2, 11.4, −2.3, 30, A
LEU, O, 66, −7.1, 10.3, −1.9, 32, A
LEU, CB, 66, −6.7, 12.5, −0.0, 26, A
LEU, CG, 66, −5.9, 13.4, 0.8, 30, A
LEU, CD1, 66, −6.3, 13.4, 2.3, 28, A
LEU, CD2, 66, −4.4, 13.0, 0.7, 31, A
TYR, N, 67, −8.0, 11.9, −3.3, 26, A
TYR, CA, 67, −8.9, 11.0, −4.0, 25, A
TYR, C, 67, −8.4, 10.5, −5.3, 27, A
TYR, O, 67, −7.6, 11.1, −5.9, 26, A
TYR, CB, 67, −10.3, 11.7, −4.2, 25, A
TYR, CG, 67, −10.1, 13.0, −4.9, 24, A
TYR, CD1, 67, −10.1, 13.1, −6.3, 27, A
TYR, CD2, 67, −9.8, 14.2, −4.2, 24, A
TYR, CE1, 67, −9.9, 14.3, −7.0, 31, A
TYR, CE2, 67, −9.6, 15.4, −4.9, 27, A
TYR, CZ, 67, −9.7, 15.4, −6.3, 38, A
TYR, OH, 67, −9.4, 16.6, −6.9, 40, A
ASP, N, 68, −9.1, 9.4, −5.7, 27, A
ASP, CA, 68, −8.7, 8.8, −7.0, 28, A
ASP, C, 68, −9.2, 9.6, −8.2, 31, A
ASP, O, 68, −10.2, 10.3, −8.2, 28, A
ASP, CB, 68, −9.3, 7.3, −7.0, 29, A
ASP, CG, 68, −10.8, 7.3, −7.1, 35, A
ASP, OD1, 68, −11.3, 6.7, −8.1, 34, A
ASP, OD2, 68, −11.5, 7.7, −6.2, 34, A
GLU, N, 69, −8.5, 9.3, −9.4, 29, A
GLU, CA, 69, −8.9, 10.0-10.6, 30, A
GLU, C, 69, −10.1, 9.3-11.3, 37, A
GLU, O, 69, −11.0, 10.0-11.7, 35, A
GLU, CB, 69, −7.6, 9.9-11.6, 33, A,
GLU, CG, 69, −8.0, 9.7-13.0, 45, A,
GLU, CD, 69, −8.7, 10.9-13.6, 80, A,
GLU, OE1, 69, −9.5, 10.7-14.6, 61, A,
GLU, OE2, 69, −8.5, 12.0-13.0, 85, A,
LYS, N, 70, −10.2, 8.0-11.2, 36, A,
LYS, CA, 70, −11.2, 7.2-11.9, 36, A,
LYS, C, 70, −12.7, 7.6-11.5, 41, A,
LYS, O, 70, −13.5, 7.9-12.3, 40, A,
LYS, CB, 70, −11.0, 5.7-11.8, 37, A,
LYS, CG, 70, −11.8, 4.9-12.8, 47, A,
LYS, CD, 70, −12.8, 4.0-12.2, 58, A,
LYS, CE, 70, −12.3, 2.5-12.1, 64, A,
LYS, NZ, 70, −12.1, 1.9-13.4, 70, A,
GLN, N, 71, −12.9, 7.5-10.2, 35, A,
GLN, CA, 71, −14.3, 7.8, −9.7, 33, A
GLN, C, 71, −14.5, 9.0, −8.8, 32, A
GLN, O, 71, −15.6, 9.3, −8.5, 30, A
GLN, CB, 71, −14.8, 6.5, −9.0, 35, A
GLN, CG, 71, −16.2, 6.0, −9.5, 61, A
GLN, CD, 71, −16.3, 4.5, −9.4, 73, A
GLN, OE1, 71, −17.1, 3.9-10.1, 73, A,
GLN, NE2, 71, −15.6, 3.9, −8.4, 54, A
GLN, N, 72, −13.3, 9.5, −8.3, 27, A
GLN, CA, 72, −13.4, 10.6, −7.3, 27, A
GLN, C, 72, −14.1, 10.2, −6.1, 34, A
GLN, O, 72, −14.9, 11.0, −5.6, 34, A
GLN, CB, 72, −13.9, 11.9, −7.9, 27, A
GLN, CG, 72, −13.0, 12.5, −9.1, 28, A
GLN, CD, 72, −13.4, 13.8, −9.7, 33, A
GLN, OE1, 72, −14.6, 14.1, −9.7, 28, A
GLN, NE2, 72, −12.5, 14.7-10.0, 27, A,
HIS, N, 73, −13.9, 9.0, −5.7, 33, A
HIS, CA, 73, −14.6, 8.5, −4.5, 34, A
HIS, C, 73, −13.8, 7.6, −3.5, 34, A
HIS, O, 73, −14.3, 7.4, −2.4, 32, A

TABLE 4-continued

Structural coordinates of HDM2 (17-125; F55Y/Y76H) (SEQ ID NO: 2) complexed with compound 4.

HIS, CB, 73, −16.1, 8.1, −4.8, 36, A
HIS, CG, 73, −16.3, 6.7, −5.1, 40, A
HIS, ND1, 73, −17.5, 6.2, −5.5, 42, A
HIS, CD2, 73, −15.4, 5.6, −5.0, 43, A
HIS, CE1, 73, −17.4, 4.9, −5.6, 43, A
HIS, NE2, 73, −16.2, 4.5, −5.4, 44, A
ILE, N, 74, −12.6, 7.2, −3.9, 29, A
ILE, CA, 74, −11.8, 6.5, −3.0, 29, A
ILE, C, 74, −10.8, 7.5, −2.4, 33, A
ILE, O, 74, −10.0, 8.2, −3.1, 32, A
ILE, CB, 74, −11.0, 5.3, −3.7, 30, A
ILE, CG1, 74, −12.0, 4.3, −4.4, 30, A
ILE, CG2, 74, −10.1, 4.6, −2.7, 29, A
ILE, CD1, 74, −13.0, 3.6, −3.4, 29, A
VAL, N, 75, −10.7, 7.6, −1.1, 28, A
VAL, CA, 75, −9.8, 8.4, −0.4, 27, A
VAL, C, 75, −8.5, 7.6, 0.1, 31, A
VAL, O, 75, −8.7, 6.5, 0.7, 28, A
VAL, CB, 75, −10.4, 9.2, 0.8, 28, A
VAL, CG1, 75, −9.4, 10.0, 1.6, 26, A
VAL, CG2, 75, −11.6, 10.1, 0.3, 28, A
HIS, N, 76, −7.3, 8.0, −0.2, 31, A
HIS, CA, 76, −6.1, 7.4, 0.3, 33, A
HIS, C, 76, −5.5, 8.3, 1.3, 32, A
HIS, O, 76, −5.1, 9.5, 1.0, 30, A
HIS, CB, 76, −5.1, 7.0, −0.8, 35, A
HIS, CG, 76, −5.4, 5.7, −1.4, 40, A
HIS, ND1, 76, −6.4, 5.4, −2.3, 43, A
HIS, CD2, 76, −4.7, 4.5, −1.3, 44, A
HIS, CE1, 76, −6.4, 4.2, −2.7, 43, A
HIS, NE2, 76, −5.3, 3.6, −2.1, 43, A
CYS, N, 77, −5.3, 7.8, 2.6, 28, A
CYS, CA, 77, −4.7, 8.6, 3.7, 25, A
CYS, C, 77, −3.9, 7.8, 4.6, 29, A
CYS, O, 77, −3.8, 8.2, 5.8, 27, A
CYS, CB, 77, −5.9, 9.2, 4.5, 24, A
CYS, SG, 77, −7.3, 7.9, 4.8, 26, A
SER, N, 78, −3.2, 6.8, 4.2, 27, A
SER, CA, 78, −2.4, 6.0, 5.1, 27, A
SER, C, 78, −1.3, 6.7, 5.9, 28, A
SER, O, 78, −0.9, 6.3, 7.0, 25, A
SER, CB, 78, −1.8, 4.7, 4.4, 29, A
SER, OG, 78, −1.0, 5.1, 3.4, 34, A
ASN, N, 79, −0.7, 7.8, 5.3, 25, A
ASN, CA, 79, 0.4, 8.5, 5.9, 25, A
ASN, C, 79, 0.1, 9.9, 6.3, 32, A
ASN, O, 79, 1.0, 10.7, 6.4, 33, A
ASN, CB, 79, 1.6, 8.5, 4.9, 30, A
ASN, CG, 79, 2.9, 9.0, 5.5, 50, A
ASN, OD1, 79, 3.3, 8.6, 6.6, 37, A
ASN, ND2, 79, 3.6, 9.8, 4.7, 53, A
ASP, N, 80, −1.2, 10.2, 6.6, 29, A
ASP, CA, 80, −1.5, 11.5, 6.9, 28, A
ASP, C, 80, −2.4, 11.6, 8.1, 32, A
ASP, O, 80, −3.0, 10.6, 8.5, 31, A
ASP, CB, 80, −1.9, 12.3, 5.7, 31, A
ASP, CG, 80, −3.4, 12.4, 5.5, 46, A
ASP, OD1, 80, −3.9, 13.5, 5.3, 54, A
ASP, OD2, 80, −4.1, 11.4, 5.6, 48, A
LEU, N, 81, −2.5, 12.8, 8.7, 29, A
LEU, CA, 81, −3.4, 13.0, 9.9, 28, A
LEU, C, 81, −4.8, 12.4, 9.7, 31, A
LEU, O, 81, −5.3, 11.8, 10.6, 31, A
LEU, CB, 81, −3.5, 14.5, 10.2, 28, A
LEU, CG, 81, −4.1, 14.8, 11.6, 32, A
LEU, CD1, 81, −3.5, 13.9, 12.7, 32, A
LEU, CD2, 81, −4.0, 16.3, 11.9, 37, A
LEU, N, 82, −5.4, 12.6, 8.5, 25, A
LEU, CA, 82, −6.7, 12.1, 8.3, 24, A
LEU, C, 82, −6.8, 10.5, 8.5, 27, A
LEU, O, 82, −7.7, 10.0, 9.2, 25, A
LEU, CB, 82, −7.2, 12.5, 6.9, 23, A
LEU, CG, 82, −8.6, 11.8, 6.5, 28, A
LEU, CD1, 82, −9.7, 12.3, 7.4, 25, A
LEU, CD2, 82, −8.9, 12.0, 5.0, 28, A
GLY, N, 83, −5.7, 9.8, 8.0, 25, A
GLY, CA, 83, −5.7, 8.4, 8.2, 25, A
GLY, C, 83, −5.5, 8.0, 9.7, 26, A
GLY, O, 83, −6.0, 7.0, 10.2, 24, A
ASP, N, 84, −4.7, 8.8, 10.4, 23, A
ASP, CA, 84, −4.5, 8.6, 11.8, 25, A
ASP, C, 84, −5.8, 8.7, 12.6, 27, A
ASP, O, 84, −6.0, 7.8, 13.5, 25, A
ASP, CB, 84, −3.4, 9.6, 12.3, 27, A
ASP, CG, 84, −2.1, 9.4, 11.6, 31, A
ASP, OD1, 84, −1.8, 8.3, 11.3, 32, A
ASP, OD2, 84, −1.4, 10.4, 11.4, 29, A
LEU, N, 85, −6.5, 9.7, 12.3, 23, A
LEU, CA, 85, −7.8, 10.0, 13.0, 25, A
LEU, C, 85, −8.9, 9.0, 12.7, 27, A
LEU, O, 85, −9.7, 8.5, 13.5, 28, A
LEU, CB, 85, −8.2, 11.4, 12.8, 26, A
LEU, CG, 85, −7.2, 12.5, 13.1, 33, A
LEU, CD1, 85, −7.9, 13.8, 12.9, 32, A
LEU, CD2, 85, −6.7, 12.3, 14.6, 36, A
PHE, N, 86, −9.0, 8.7, 11.4, 23, A
PHE, CA, 86, −10.1, 7.7, 10.9, 23, A
PHE, C, 86, −9.7, 6.3, 11.2, 28, A
PHE, O, 86, −10.7, 5.4, 11.5, 25, A
PHE, CB, 86, −10.4, 7.9, 9.4, 23, A
PHE, CG, 86, −11.4, 9.0, 9.1, 23, A
PHE, CD1, 86, −11.8, 9.9, 10.0, 26, A
PHE, CD2, 86, −11.9, 9.0, 7.8, 24, A
PHE, CE1, 86, −12.7, 10.9, 9.7, 26, A
PHE, CE2, 86, −12.8, 10.0, 7.5, 27, A
PHE, CZ, 86, −13.2, 10.9, 8.5, 25, A
GLY, N, 87, −8.5, 6.0, 11.3, 25, A
GLY, CA, 87, −8.0, 4.6, 11.6, 26, A
GLY, C, 87, −8.0, 3.7, 10.4, 27, A
GLY, O, 87, −7.9, 2.5, 10.6, 26, A
VAL, N, 88, −8.0, 4.2, 9.2, 23, A
VAL, CA, 88, −8.0, 3.4, 7.9, 22, A
VAL, C, 88, −7.0, 4.1, 6.9, 26, A
VAL, O, 88, −6.7, 5.3, 7.0, 25, A
VAL, CB, 88, −9.4, 3.3, 7.3, 25, A
VAL, CG1, 88, −10.2, 2.4, 8.2, 25, A
VAL, CG2, 88, −10.0, 4.7, 7.0, 24, A
PRO, N, 89, −6.5, 3.3, 6.0, 24, A
PRO, CA, 89, −5.5, 3.8, 5.1, 22, A
PRO, C, 89, −6.3, 4.3, 3.9, 29, A
PRO, O, 89, −5.7, 5.1, 3.1, 27, A
PRO, CB, 89, −4.7, 2.5, 4.6, 24, A
PRO, CG, 89, −5.6, 1.4, 4.9, 28, A
PRO, CD, 89, −6.4, 1.8, 6.2, 24, A
SER, N, 90, −7.5, 3.9, 3.8, 26, A
SER, CA, 90, −8.4, 4.4, 2.7, 27, A
SER, C, 90, −9.8, 4.1, 2.9, 28, A
SER, O, 90, −10.1, 3.3, 3.8, 25, A
SER, CB, 90, −7.9, 3.8, 1.4, 31, A
SER, OG, 90, −8.1, 2.4, 1.3, 36, A
PHE, N, 91, −10.7, 4.8, 2.2, 25, A
PHE, CA, 91, −12.1, 4.5, 2.3, 25, A
PHE, C, 91, −12.9, 5.0, 1.1, 28, A
PHE, O, 91, −12.3, 5.9, 0.4, 28, A
PHE, CB, 91, −12.7, 5.0, 3.6, 25, A
PHE, CG, 91, −12.6, 6.5, 3.7, 25, A
PHE, CD1, 91, −13.6, 7.4, 3.4, 27, A
PHE, CD2, 91, −11.3, 7.1, 4.1, 24, A
PHE, CE1, 91, −13.5, 8.8, 3.5, 27, A
PHE, CE2, 91, −11.2, 8.5, 4.2, 26, A
PHE, CZ, 91, −12.3, 9.3, 3.9, 24, A
SER, N, 92, −14.1, 4.6, 0.9, 24, A
SER, CA, 92, −14.9, 5.1, −0.1, 25, A
SER, C, 92, −15.8, 6.2, 0.5, 28, A
SER, O, 92, −16.4, 6.0, 1.5, 27, A
SER, CB, 92, −15.9, 4.1, −0.8, 30, A
SER, OG, 92, −16.8, 4.8, −1.7, 33, A
VAL, N, 93, −15.9, 7.3, −0.2, 27, A
VAL, CA, 93, −16.8, 8.5, 0.2, 28, A
VAL, C, 93, −18.3, 8.1, 0.3, 31, A
VAL, O, 93, −19.1, 8.8, 0.9, 31, A
VAL, CB, 93, −16.6, 9.7, −0.8, 33, A

TABLE 4-continued

Structural coordinates of HDM2 (17-125; F55Y/Y76H) (SEQ ID NO: 2) complexed with compound 4.

| Atom | Res | # | X | Y | Z | B | Chain |
|---|---|---|---|---|---|---|---|
| VAL | CG1 | 93 | −17.7 | 10.8 | −0.4 | 33 | A |
| VAL | CG2 | 93 | −15.2 | 10.2 | −0.7 | 32 | A |
| LYS | N | 94 | −18.7 | 6.9 | −0.3 | 27 | A |
| LYS | CA | 94 | −20.0 | 6.5 | −0.3 | 27 | A |
| LYS | C | 94 | −20.3 | 5.6 | 1.0 | 32 | A |
| LYS | O | 94 | −21.5 | 5.2 | 1.2 | 32 | A |
| LYS | CB | 94 | −20.4 | 5.7 | −1.6 | 27 | A |
| LYS | CG | 94 | −20.2 | 6.5 | −2.8 | 41 | A |
| LYS | CD | 94 | −21.1 | 6.0 | −4.0 | 55 | A |
| LYS | CE | 94 | −20.3 | 5.0 | −4.9 | 68 | A |
| LYS | NZ | 94 | −21.1 | 3.9 | −5.4 | 71 | A |
| GLU | N | 95 | −19.3 | 5.3 | 1.8 | 26 | A |
| GLU | CA | 95 | −19.6 | 4.4 | 2.9 | 26 | A |
| GLU | C | 95 | −19.9 | 5.4 | 4.1 | 28 | A |
| GLU | O | 95 | −19.1 | 5.5 | 5.0 | 27 | A |
| GLU | CB | 95 | −18.4 | 3.5 | 3.3 | 27 | A |
| GLU | CG | 95 | −18.0 | 2.5 | 2.2 | 34 | A |
| GLU | CD | 95 | −16.8 | 1.8 | 2.6 | 57 | A |
| GLU | OE1 | 95 | −15.7 | 2.4 | 2.7 | 45 | A |
| GLU | OE2 | 95 | −16.9 | 0.5 | 2.7 | 52 | A |
| HIS | N | 96 | −21.1 | 6.1 | 4.0 | 26 | A |
| HIS | CA | 96 | −21.5 | 7.0 | 5.0 | 25 | A |
| HIS | C | 96 | −21.5 | 6.5 | 6.4 | 29 | A |
| HIS | O | 96 | −21.1 | 7.1 | 7.4 | 29 | A |
| HIS | CB | 96 | −22.8 | 7.7 | 4.6 | 27 | A |
| HIS | CG | 96 | −22.8 | 8.5 | 3.3 | 32 | A |
| HIS | ND1 | 96 | −23.9 | 9.0 | 2.7 | 34 | A |
| HIS | CD2 | 96 | −21.8 | 8.8 | 2.5 | 35 | A |
| HIS | CE1 | 96 | −23.6 | 9.6 | 1.6 | 34 | A |
| HIS | NE2 | 96 | −22.3 | 9.5 | 1.4 | 35 | A |
| ARG | N | 97 | −22.1 | 5.3 | 6.6 | 25 | A |
| ARG | CA | 97 | −22.1 | 4.8 | 8.0 | 28 | A |
| ARG | C | 97 | −20.7 | 4.6 | 8.6 | 35 | A |
| ARG | O | 97 | −20.5 | 5.0 | 9.8 | 35 | A |
| ARG | CB | 97 | −22.9 | 3.5 | 8.1 | 30 | A |
| ARG | CG | 97 | −22.6 | 2.6 | 9.3 | 50 | A |
| ARG | CD | 97 | −21.8 | 1.4 | 8.9 | 69 | A |
| ARG | NE | 97 | −21.3 | 0.6 | 10.1 | 84 | A |
| ARG | CZ | 97 | −21.6 | −0.7 | 10.3 | 0 | A |
| ARG | NH1 | 97 | −22.3 | −1.3 | 9.4 | 92 | A |
| ARG | NH2 | 97 | −21.2 | −1.3 | 11.4 | 98 | A |
| LYS | N | 98 | −19.7 | 4.1 | 7.8 | 31 | A |
| LYS | CA | 98 | −18.4 | 4.0 | 8.3 | 30 | A |
| LYS | C | 98 | −17.7 | 5.3 | 8.7 | 29 | A |
| LYS | O | 98 | −17.0 | 5.4 | 9.7 | 27 | A |
| LYS | CB | 98 | −17.5 | 3.2 | 7.3 | 29 | A |
| LYS | CG | 98 | −17.8 | 1.8 | 7.2 | 30 | A |
| LYS | CD | 98 | −17.0 | 1.1 | 6.0 | 41 | A |
| LYS | CE | 98 | −17.5 | −0.3 | 5.8 | 42 | A |
| LYS | NZ | 98 | −16.8 | −0.9 | 4.6 | 54 | A |
| ILE | N | 99 | −17.9 | 6.3 | 7.8 | 24 | A |
| ILE | CA | 99 | −17.3 | 7.6 | 8.0 | 24 | A |
| ILE | C | 99 | −17.9 | 8.2 | 9.2 | 29 | A |
| ILE | O | 99 | −17.2 | 8.9 | 10.0 | 29 | A |
| ILE | CB | 99 | −17.5 | 8.5 | 6.7 | 27 | A |
| ILE | CG1 | 99 | −16.8 | 7.9 | 5.5 | 26 | A |
| ILE | CG2 | 99 | −17.2 | 9.9 | 7.0 | 26 | A |
| ILE | CD1 | 99 | −17.3 | 8.4 | 4.2 | 26 | A |
| TYR | N | 100 | −19.2 | 8.1 | 9.4 | 26 | A |
| TYR | CA | 100 | −19.8 | 8.8 | 10.5 | 26 | A |
| TYR | C | 100 | −19.2 | 8.2 | 11.8 | 28 | A |
| TYR | O | 100 | −18.8 | 8.9 | 12.7 | 28 | A |
| TYR | CB | 100 | −21.3 | 8.6 | 10.6 | 27 | A |
| TYR | CG | 100 | −22.1 | 9.6 | 9.8 | 26 | A |
| TYR | CD1 | 100 | −23.1 | 9.2 | 8.9 | 29 | A |
| TYR | CD2 | 100 | −21.9 | 11.0 | 10.0 | 25 | A |
| TYR | CE1 | 100 | −23.9 | 10.2 | 8.3 | 29 | A |
| TYR | CE2 | 100 | −22.7 | 11.9 | 9.4 | 26 | A |
| TYR | CZ | 100 | −23.7 | 11.5 | 8.5 | 29 | A |
| TYR | OH | 100 | −24.5 | 12.4 | 7.8 | 29 | A |
| THR | N | 101 | −19.0 | 6.8 | 11.8 | 26 | A |
| THR | CA | 101 | −18.4 | 6.1 | 12.9 | 26 | A |
| THR | C | 101 | −17.0 | 6.6 | 13.2 | 28 | A |
| THR | O | 101 | −16.7 | 6.9 | 14.4 | 28 | A |
| THR | CB | 101 | −18.4 | 4.6 | 12.7 | 31 | A |
| THR | OG1 | 101 | −19.7 | 4.1 | 12.6 | 33 | A |
| THR | CG2 | 101 | −17.6 | 3.8 | 13.9 | 23 | A |
| MET | N | 102 | −16.2 | 6.8 | 12.2 | 24 | A |
| MET | CA | 102 | −14.8 | 7.3 | 12.3 | 23 | A |
| MET | C | 102 | −14.8 | 8.8 | 12.8 | 26 | A |
| MET | O | 102 | −13.9 | 9.1 | 13.6 | 24 | A |
| MET | CB | 102 | −14.1 | 7.2 | 11.0 | 24 | A |
| MET | CG | 102 | −13.9 | 5.7 | 10.7 | 27 | A |
| NET | SD | 102 | −12.9 | 5.3 | 9.2 | 28 | A |
| MET | CE | 102 | −14.0 | 5.8 | 7.8 | 24 | A |
| ILE | N | 103 | −15.7 | 9.6 | 12.4 | 23 | A |
| ILE | CA | 103 | −15.8 | 11.0 | 12.8 | 23 | A |
| ILE | C | 103 | −16.2 | 11.1 | 14.3 | 27 | A |
| ILE | O | 103 | −15.6 | 11.9 | 15.0 | 27 | A |
| ILE | CB | 103 | −16.7 | 11.8 | 11.9 | 27 | A |
| ILE | CG1 | 103 | −16.2 | 11.9 | 10.4 | 25 | A |
| ILE | CG2 | 103 | −17.0 | 13.2 | 12.5 | 25 | A |
| ILE | CD1 | 103 | −17.2 | 12.4 | 9.4 | 27 | A |
| TYR | N | 104 | −17.2 | 10.3 | 14.7 | 24 | A |
| TYR | CA | 104 | −17.8 | 10.4 | 16.0 | 24 | A |
| TYR | C | 104 | −16.7 | 10.1 | 17.1 | 28 | A |
| TYR | O | 104 | −16.7 | 10.7 | 18.1 | 26 | A |
| TYR | CB | 104 | −19.0 | 9.4 | 16.2 | 26 | A |
| TYR | CG | 104 | −20.2 | 9.8 | 15.5 | 31 | A |
| TYR | CD1 | 104 | −21.1 | 8.9 | 14.9 | 34 | A |
| TYR | CD2 | 104 | −20.6 | 11.1 | 15.4 | 32 | A |
| TYR | CE1 | 104 | −22.2 | 9.2 | 14.2 | 35 | A |
| TYR | CE2 | 104 | −21.8 | 11.5 | 14.7 | 34 | A |
| TYR | CZ | 104 | −22.6 | 10.5 | 14.1 | 39 | A |
| TYR | OH | 104 | −23.8 | 10.8 | 13.5 | 40 | A |
| ARG | N | 105 | −15.8 | 9.1 | 16.8 | 27 | A |
| ARG | CA | 105 | −14.7 | 8.8 | 17.8 | 28 | A |
| ARG | C | 105 | −13.8 | 10.0 | 18.0 | 31 | A |
| ARG | O | 105 | −13.1 | 10.1 | 19.0 | 29 | A |
| ARG | CB | 105 | −13.9 | 7.6 | 17.2 | 30 | A |
| ARG | CG | 105 | −14.7 | 6.3 | 17.2 | 33 | A |
| ARG | CD | 105 | −14.0 | 5.3 | 16.3 | 25 | A |
| ARG | NE | 105 | −14.8 | 4.0 | 16.3 | 29 | A |
| ARG | CZ | 105 | −14.5 | 3.0 | 15.6 | 35 | A |
| ARG | NH1 | 105 | −13.5 | 3.0 | 14.7 | 24 | A |
| ARG | NH2 | 105 | −15.2 | 1.9 | 15.7 | 26 | A |
| ASN | N | 106 | −13.8 | 11.0 | 17.0 | 25 | A |
| ASN | CA | 106 | −12.9 | 12.1 | 17.1 | 25 | A |
| ASN | C | 106 | −13.6 | 13.4 | 17.6 | 28 | A |
| ASN | O | 106 | −13.0 | 14.5 | 17.4 | 24 | A |
| ASN | CB | 106 | −12.3 | 12.4 | 15.7 | 21 | A |
| ASN | CG | 106 | −11.3 | 11.2 | 15.4 | 38 | A |
| ASN | OD1 | 106 | −10.2 | 11.1 | 15.9 | 32 | A |
| ASN | ND2 | 106 | −11.8 | 10.2 | 14.6 | 26 | A |
| LEU | N | 107 | −14.7 | 13.3 | 18.2 | 26 | A |
| LEU | CA | 107 | −15.4 | 14.5 | 18.8 | 24 | A |
| LEU | C | 107 | −16.2 | 14.2 | 20.0 | 28 | A |
| LEU | O | 107 | −16.4 | 13.1 | 20.4 | 26 | A |
| LEU | CB | 107 | −16.3 | 15.2 | 17.7 | 24 | A |
| LEU | CG | 107 | −17.2 | 14.2 | 17.0 | 28 | A |
| LEU | CD1 | 107 | −18.4 | 13.8 | 17.9 | 28 | A |
| LEU | CD2 | 107 | −17.7 | 14.8 | 15.7 | 29 | A |
| VAL | N | 108 | −16.8 | 15.3 | 20.6 | 25 | A |
| VAL | CA | 108 | −17.7 | 15.1 | 21.7 | 26 | A |
| VAL | C | 108 | −18.9 | 15.9 | 21.3 | 27 | A |
| VAL | O | 108 | −18.8 | 16.9 | 20.6 | 24 | A |
| VAL | CB | 108 | −17.1 | 15.7 | 23.0 | 30 | A |
| VAL | CG1 | 108 | −18.1 | 15.9 | 24.1 | 32 | A |
| VAL | CG2 | 108 | −16.1 | 14.6 | 23.6 | 29 | A |
| VAL | N | 109 | −20.1 | 15.4 | 21.7 | 24 | A |
| VAL | CA | 109 | −21.3 | 16.1 | 21.3 | 24 | A |
| VAL | C | 109 | −21.5 | 17.2 | 22.4 | 28 | A |
| VAL | O | 109 | −21.3 | 16.9 | 23.6 | 28 | A |
| VAL | CB | 109 | −22.6 | 15.2 | 21.2 | 27 | A |
| VAL | CG1 | 109 | −23.8 | 16.0 | 21.0 | 25 | A |
| VAL | CG2 | 109 | −22.3 | 14.1 | 20.1 | 27 | A |
| VAL | N | 110 | −21.9 | 18.4 | 22.0 | 25 | A |
| VAL | CA | 110 | −22.2 | 19.5 | 23.0 | 25 | A |
| VAL | C | 110 | −23.6 | 20.1 | 22.6 | 31 | A |
| VAL | O | 110 | −24.1 | 19.9 | 21.5 | 31 | A |
| VAL | CB | 110 | −21.1 | 20.6 | 23.0 | 28 | A |
| VAL | CG1 | 110 | −19.7 | 19.9 | 23.4 | 27 | A |

TABLE 4-continued

Structural coordinates of HDM2 (17-125; F55Y/Y76H) (SEQ ID NO: 2) complexed with compound 4.

| | | | | | | |
|---|---|---|---|---|---|---|
| VAL, | CG2, | 110, | −20.9, | 21.3, | 21.6, 28, | A |
| ASN, | N, | 111, | −24.1, | 21.0, | 23.5, 32, | A |
| ASN, | CA, | 111, | −25.4, | 21.6, | 23.2, 33, | A |
| ASN, | C, | 111, | −25.3, | 23.1, | 22.9, 38, | A |
| ASN, | O, | 111, | −26.3, | 23.8, | 22.6, 40, | A |
| ASN, | CB, | 111, | −26.5, | 21.4, | 24.3, 38, | A |
| ASN, | CG, | 111, | −26.1, | 21.9, | 25.7, 62, | A |
| ASN, | OD1, | 111, | −25.3, | 22.8, | 25.8, 58, | A |
| ASN, | ND2, | 111, | −26.5, | 21.2, | 26.7, 58, | A |
| GLN, | N, | 112, | −24.0, | 23.6, | 22.9, 35, | A |
| GLN, | CA, | 112, | −23.8, | 25.0, | 22.5, 35, | A |
| GLN, | C, | 112, | −22.3, | 25.4, | 22.3, 36, | A |
| GLN, | O, | 112, | −21.4, | 24.7, | 22.7, 38, | A |
| GLN, | CB, | 112, | −24.4, | 26.0, | 23.6, 37, | A |
| GLN, | CG, | 112, | −24.9, | 25.3, | 24.9, 63, | A |
| GLN, | CD, | 112, | −24.3, | 26.0, | 26.1, 80, | A |
| GLN, | OE1, | 112, | −23.8, | 27.1, | 26.0, 77, | A |
| GLN, | NE2, | 112, | −24.5, | 25.4, | 27.3, 62, | A |
| GLN, | N, | 113, | −22.2, | 26.5, | 21.6, 30, | A |
| GLN, | CA, | 113, | −20.9, | 27.0, | 21.3, 46, | A |
| GLN, | C, | 113, | −20.5, | 27.9, | 22.5, 65, | A |
| GLN, | O, | 113, | −21.3, | 27.8, | 23.5, 42, | A |
| GLN, | CB, | 113, | −20.9, | 27.9, | 20.0, 47, | A |
| GLN, | CG, | 113, | −22.2, | 28.6, | 19.8, 71, | A |
| GLN, | CD, | 113, | −21.9, | 29.9, | 18.9, 85, | A |
| GLN, | OE1, | 113, | −20.9, | 30.5, | 19.0, 76, | A |
| GLN, | NE2, | 113, | −22.9, | 30.1, | 18.0, 79, | A |
| SCH, | F1, | 1, | −13.7, | 12.9, | 5.1, 27, | I |
| SCH, | F2, | 1, | −15.2, | 11.5, | 4.8, 25, | I |
| SCH, | F3, | 1, | −15.8, | 13.2, | 5.9, 31, | I |
| SCH, | F4, | 1, | −15.1, | 12.7, | −3.1, 45, | I |
| SCH, | F5, | 1, | −14.2, | 14.3, | −2.1, 31, | I |
| SCH, | F6, | 1, | −12.9, | 13.2, | −3.2, 33, | I |
| SCH, | C1, | 1, | −16.7, | 17.5, | −0.2, 19, | I |
| SCH, | C2, | 1, | −15.5, | 17.6, | −1.1, 16, | I |
| SCH, | C3, | 1, | −16.0, | 17.3, | −2.5, 18, | I |
| SCH, | N1, | 1, | −16.9, | 16.1, | −2.6, 22, | I |
| SCH, | C4, | 1, | −18.0, | 16.0, | −1.8, 22, | I |
| SCH, | C5, | 1, | −17.6, | 16.2, | −0.3, 26, | I |
| SCH, | C6, | 1, | −18.9, | 16.4, | 0.5, 36, | I |
| SCH, | N2, | 1, | −19.8, | 15.4, | 0.5, 28, | I |
| SCH, | O1, | 1, | −19.2, | 17.5, | 1.0, 29, | I |
| SCH, | O2, | 1, | −16.8, | 15.0, | −0.0, 28, | I |
| SCH, | C7, | 1, | −16.5, | 14.6, | 1.2, 22, | I |
| SCH, | C8, | 1, | −15.8, | 13.4, | 1.1, 24, | I |
| SCH, | C9, | 1, | −15.4, | 12.9, | 2.3, 19, | I |
| SCH, | C10, | 1, | −15.6, | 13.5, | 3.6, 30, | I |
| SCH, | C11, | 1, | −16.3, | 14.7, | 3.6, 23, | I |
| SCH, | C12, | 1, | −16.8, | 15.2, | 2.5, 23, | I |
| SCH, | C13, | 1, | −16.7, | 15.2, | −3.6, 20, | I |
| SCH, | O3, | 1, | −17.4, | 14.2, | −3.6, 25, | I |
| SCH, | C14, | 1, | −15.5, | 15.3, | −4.5, 25, | I |
| SCH, | C15, | 1, | −15.7, | 16.3, | −5.6, 29, | I |
| SCH, | N3, | 1, | −14.7, | 16.5, | −6.5, 34, | I |
| SCH, | C16, | 1, | −13.6, | 15.7, | −6.5, 35, | I |
| SCH, | C17, | 1, | −13.4, | 14.8, | −5.5, 25, | I |
| SCH, | C18, | 1, | −14.4, | 14.6, | −4.5, 25, | I |
| SCH, | C19, | 1, | −21.0, | 15.6, | 1.3, 21, | I |
| SCH, | C20, | 1, | −21.1, | 14.6, | 2.5, 31, | I |
| SCH, | N4, | 1, | −20.8, | 13.2, | 2.2, 26, | I |
| SCH, | C21, | 1, | −19.6, | 13.0, | 1.3, 15, | I |
| SCH, | C22, | 1, | −19.7, | 14.0, | −0.0, 17, | I |
| SCH, | C23, | 1, | −21.0, | 12.4, | 3.4, 30, | I |
| SCH, | C24, | 1, | −19.9, | 11.6, | 3.9, 24, | I |
| SCH, | C25, | 1, | −20.1, | 10.8, | 5.0, 29, | I |
| SCH, | C26, | 1, | −21.4, | 10.7, | 5.6, 24, | I |
| SCH, | C27, | 1, | −22.4, | 11.4, | 5.1, 37, | I |
| SCH, | C28, | 1, | −22.3, | 12.3, | 3.9, 42, | I |
| SCH, | O4, | 1, | −23.3, | 13.0, | 3.3, 33, | I |
| SCH, | C32, | 1, | −24.6, | 13.3, | 3.8, 28, | I |
| SCH, | C33, | 1, | −24.7, | 14.9, | 4.0, 23, | I |
| SCH, | O5, | 1, | −24.9, | 15.2, | 5.4, 0, | I |
| SCH, | C34, | 1, | −25.1, | 16.5, | 5.9, 45, | I |
| SCH, | C35, | 1, | −15.1, | 12.8, | 4.8, 33, | I |
| SCH, | C36, | 1, | −14.2, | 13.6, | −3.3, 38, | I |
| SCH, | C37, | 1, | −19.3, | 16.9, | −2.3, 27, | I |
| SCH, | C38, | 1, | −19.8, | 16.6, | −3.8, 23, | I |
| SCH, | O7, | 1, | −18.8, | 17.2, | −4.6, 26, | I |
| SCH, | O6, | 1, | −19.0, | 18.3, | −2.2, 26, | I |
| SCH, | C39, | 1, | −20.9, | 17.7, | −4.2, 41, | I |

The crystalline coordinates are set forth below in the following format (1), (2), (3) . . . (8); the legend for these data is as follows:
(1) Residue name
Three letter amino acid name
SCH = schering inhibitor
WAT = water
(2) Atom name
(3) Residue Number
(4) X-coordinate
(5) Y-coordinate
(6) Z-coordinate
(7) B-factor
(8) Chain ID
Disordered residues are not represented in the table.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. A complex comprising an isolated polypeptide comprising:
   (i) amino acids 17-125 of human HDM2 as set forth in SEQ ID NO: 1;
   (ii) amino acids 17-125 of human HDM2 as set forth in SEQ ID NO: 1 comprising an F55Y mutation;
   (iii) amino acids 17-125 of human HDM2 as set forth in SEQ ID NO: 1 comprising a Y76H mutation; or
   (iv) amino acids 17-125 of human HDM2 as set forth in SEQ ID NO: 1 comprising an F55Y/Y76H double mutation; complexed with a compound.

2. The complex of claim 1 wherein said HDM2 amino acids 17-125 are:
   SQIPASEQETLVRPKPLLLKLLKSV-GAQKDTYTMKEVLYYLGQYIMTKRLYDE-KQQHIV HCSNDLLGDLFGVPSFSVKEHRKIYT-MIYRNLVVVNQQESSDSGTSVSEN (SEQ ID NO: 2).

3. A method for making the complex of claim 1 comprising contacting said polypeptide and said compound.

4. A composition comprising ammonium sulfate and a complex of claim 1 comprising:
   (a) amino acids 17-125 of human HDM2 as set forth in SEQ ID NO: 1;
   (b) amino acids 17-125 of human HDM2 as set forth in SEQ ID NO: 1 comprising an F55Y mutation;
   (c) amino acids 17-125 of human HDM2 as set forth in SEQ ID NO: 1 comprising a Y76H mutation; or
   (d) amino acids 17-125 of human HDM2 as set forth in SEQ ID NO: 1 comprising an F55Y/Y76H double mutation; complexed with a compound.

5. The composition of claim 4 wherein said HDM2 amino acids 17-125 are:
   SQIPASEQETLVRPKPLLLKLLKSV-GAQKDTYTMKEVLYYLGQYIMTKRLYDE-KQQHIV HCSNDLLGDLFGVPSFSVKEHRKIYT-MIYRNLVVVNQQESSDSGTSVSEN (SEQ ID NO: 2).

6. The composition of claim 4 wherein the polypeptide is present at a concentration of at least 10 mg/ml.

7. The composition of claim 4 having a temperature of about 22° C. or about 4° C.

8. The composition of claim 4 wherein the ammonium sulfate is at a concentration of about 0.9 M.

* * * * *